United States Patent [19]
Baba et al.

[11] Patent Number: 5,175,299
[45] Date of Patent: Dec. 29, 1992

[54] BENZOIC ACID DERIVATIVES USEFUL AS INTERMEDIATES FOR THE PREPARATION OF HERBICIDAL 4-BENZOYLPYRAZOLES

[75] Inventors: Masatoshi Baba, Wako; Takuya Kakuta; Norio Tanaka, both of Funabashi; Eiichi Oya, Narashino; Takashi Ikai, Tokyo; Tsutomu Nawamaki, Yono; Shigeomi Watanabe, Omiya, all of Japan

[73] Assignee: Nissan Chemical Industries, Ltd., Tokyo, Japan

[21] Appl. No.: 785,241

[22] Filed: Nov. 1, 1991

Related U.S. Application Data

[60] Division of Ser. No. 504,311, Apr. 4, 1990, abandoned, which is a division of Ser. No. 168,139, Mar. 14, 1988, Pat. No. 4,948,887, which is a continuation-in-part of Ser. No. 122,366, Nov. 18, 1987, Pat. No. 4,885,022.

[30] Foreign Application Priority Data

Mar. 17, 1987 [JP] Japan .................. 62-61937
Jul. 17, 1987 [JP] Japan .................. 62-179797
Sep. 30, 1987 [JP] Japan .................. 62-247601
Jan. 13, 1988 [JP] Japan .................. 63-5449

[51] Int. Cl.⁵ .............. C07D 295/96; C07C 317/46; C07C 317/44; C07C 321/28
[52] U.S. Cl. ............................. 546/248; 558/406; 560/11; 560/18; 560/83; 562/429; 562/432; 562/474; 562/442
[58] Field of Search ............ 560/11, 18, 83; 562/429, 432; 546/248

[56] References Cited

U.S. PATENT DOCUMENTS 4,230,481 10/1980 Nishiyama et al. ............. 71/92
4,557,753 12/1985 Tanaka et al. ................... 71/92
4,643,757 2/1987 Baba et al. ...................... 71/86

FOREIGN PATENT DOCUMENTS 0203428 12/1986 European Pat. Off.
2513750 10/1975 Fed. Rep. of Germany.
2122188 1/1984 United Kingdom.

Primary Examiner—Mary C. Lee
Assistant Examiner—Michael G. Ambrose
Attorney, Agent, or Firm—Oblon, Spivak, McClelland, Maier & Neustadt

[57] ABSTRACT

A pyrazole derivative having the formula

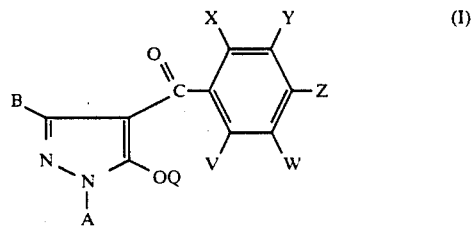

is disclosed; the groups A, B, Q, V, W, X, Y, and Z are defined in the description.

54 Claims, No Drawings

BENZOIC ACID DERIVATIVES USEFUL AS INTERMEDIATES FOR THE PREPARATION OF HERBICIDAL 4-BENZOYLPYRAZOLES

This application is a division of application Ser. No. 07/504,311 filed Apr. 4, 1990, now abandoned, which is a division of Ser. No. 07/168,139, filed Mar. 14, 1988, now U.S. Pat. No. 4,948,887, which is CIP of 07/122,366 filed Nov. 18, 1987, now U.S. Pat. No. 4,885,022.

BACKGROUND OF THE INVENTION

1. FIELD OF THE INVENTION

The present invention relates to novel 4-benzoylpyrazole derivatives and selective herbicides containing such derivatives as active ingredients, which are useful particularly as upland field herbicides.

2. DISCUSSION OF BACKGROUND

Various herbicides have been developed for practical use from extensive research and development of herbicides for many years, and such herbicides have contributed to a reduction of the labor force required for controlling weeds or to improvement of the productivity of agricultural or horticultural plants.

Even now, it is still desired to develop a new herbicide having superior herbicidal properties. In particular, it is desired to develop an agricultural or horticultural herbicide which is capable of selectively controlling weeds without adversely affecting the crop plant and at a low dose. However, conventional herbicides do not necessarily provide such desired herbicidal properties.

On the other hand, certain compounds of 4-benzoylpyrazole derivatives are known to have herbicidal activities. For example, pyrazolate (common name) and pyrazoxyfen (common name) are practically used as herbicides for paddy fields. While exhibiting excellent herbicidal activities as paddy field herbicides, these compounds are not suitable as upland herbicides since their herbicidal activities are weak against weeds of upland fields. Among 4-benzoylpyrazole derivatives, it is desired to develop a superior compound useful as an upland field herbicide.

SUMMARY OF THE INVENTION

The present invention provides a pyrazole derivative having the formula:

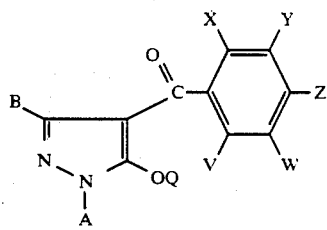

(I)

wherein A is an alkyl group having from 1 to 3 carbon atoms, an alkenyl group having from 2 to 4 carbon atoms or an alkynyl group having from 2 to 4 carbon atoms; B is a hydrogen atom, an alkyl group having from 1 to 3 carbon atoms, a halogen atom, a haloalkyl group having from 1 to 3 carbon atoms, an alkoxy group having from 1 to 3 carbon atoms, an alkylthio group having from 1 to 3 carbon atoms, an alkoxyalkyl group having from 2 to 4 carbon atoms, an alkylthioalkyl group having from 2 to 4 carbon atoms or an alkoxycarbonyl group having from 2 to 4 carbon atoms; X is an alkyl group having from 1 to 6 carbon atoms, an alkoxy group having from 1 to 6 carbon atoms, a halogen atom, a nitro group, a cyano group, a haloalkyl group having from 1 to 6 carbon atoms, an alkoxyalkyl group having from 2 to 6 carbon atoms, an alkylcarbonyl group having from 2 to 6 carbon atoms, an alkoxycarbonyl group having from 2 to 6 carbon atoms, an aminocarbonyl group substituted independently by hydrogen or alkyl having from 1 to 6 carbon atoms, a haloalkoxy group having from 1 to 6 carbon atoms, an alkylthio group having from 1 to 6 carbon atoms or an alkylthioalkyl group having from 2 to 6 carbon atoms; Y is a —COOR1 group (wherein R1 is a hydrogen atom, an alkyl group having from 1 to 6 carbon atoms, a cycloalkyl group having from 3 to 8 carbon atoms, a cycloalkylalkyl group having from 4 to 8 carbon atoms, an alkynyl group having from 3 to 6 carbon atoms, an alkenyl group having from 2 to 6 carbon atoms, a haloalkyl group having from 1 to 6 carbon atoms, a halocycloalkyl group having from 3 to 8 carbon atoms, a haloalkynyl group having from 3 to 6 carbon atoms, a haloalkenyl group having from 2 to 6 carbon atoms or a phenyl group which may be substituted by alkyl having from 1 to 3 carbon atoms, halogen, nitro or alkoxy having from 1 to 3 carbon atoms), a —COO—L—OR1 group (wherein L is an alkylene group having from 1 to 6 carbon atoms which may be substituted by alkyl having from 1 to 3 carbon atoms, and R1 is as defined above), a —COO—L—R2 group (wherein L is as defined above, and R2 is a phenyl group which may be substituted by alkyl having from 1 to 3 carbon atoms, halogen, nitro or alkoxy having from 1 to 3 carbon atoms), a —COO—M group (wherein M is a 3 to 6-membered alicyclic residue containing not more than 2 sulfur or oxygen atoms and formed by a linkage of from 1 to 4 carbon atoms), a —COO—L—M group (wherein L and M are as defined above), a COO—L—O—L—R2 group (wherein L and R2 are as defined above), a —COO—L—S(O)$_n$—R1 group (wherein L and R1 are as defined above, and n is an integer of from 0 to 2), a —CON(R3)(R4) group (wherein each of R3 and R4 is a hydrogen atom, an alkyl group having from 1 to 6 carbon atoms, a cycloalkyl group having from 3 to 8 carbon atoms, a cycloalkylalkyl group having from 4 to 8 carbon atoms, an alkoxy group having from 1 to 6 carbon atoms, an alkynyl group having from 2 to 6 carbon atoms, an alkenyl group having from 2 to 6 carbon atoms, a haloalkyl group having from 1 to 6 carbon atoms, a halocycloalkyl group having from 3 to 8 carbon atoms, a haloalkynyl group having from 2 to 6 carbon atoms, a haloalkenyl group having from 2 to 6 carbon atoms or a phenyl group which may be substituted by alkyl having from 1 to 3 carbon atoms, halogen, nitro or alkoxy having from 1 to 3 carbon atoms), a —CON—(CH$_2$)$_n$ group (wherein n is an integer of from 4 to 6), a

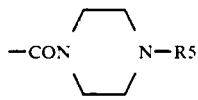

group (wherein R5 is an alkyl group having from 1 to 3 carbon atoms), a

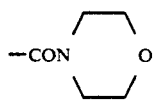

group, a —CONHSO$_2$CH$_3$ group, a —CONHSO$_2$CF$_3$ group, a —COO—L—N(R3)(R4) group (wherein L, R3 and R4 are as defined above), a —COO—L—CO—R1 group (wherein L and R1 are as defined above), a —COO—L—CO—O—R1 group (wherein L and R1 are as defined above), a —COO—L—CN group (wherein L is as defined above), a —COO—L—NO$_2$ group (wherein L is as defined above), a —COO-Si(R5)$_3$ group (wherein R5 is as defined above), a —COO—N=C(R6)(R7) group (wherein each of R6 and R7 which may be the same or different is an alkyl group having from 1 to 3 carbon atoms), a

group (wherein n is an integer of from 4 to 6), a —COO—L—O—SO$_2$—R1 group (wherein L and R1 are as defined above), a —COO—L—O—CO—R1 group (wherein L and R1 are as defined above), a —COO—L—O—L—O—R1 group (wherein L and R1 are as defined above), a —COO—L—Si(R5)$_3$ group (wherein L and R5 are as defined above), a —C(O)-S—R1 group (wherein R1 is as defined above), a —C(-S)O—R1 group (wherein R1 is as defined above), a —C(S)S—R1 group (wherein R1 is as defined above), a —L—O—R1 group (wherein L and R1 are as defined above), a —L—O—L—O—R8 group (wherein L is as defined above, and R8 is a hydrogen atom or an alkyl group having from 1 to 6 carbon atoms), a —L—O—M group (wherein L and M are as defined above), a —L—O—L—M group (wherein L and M are as defined above), a —L—NR8R9 group (wherein R8 is as defined above, and R9 is an alkyl group having from 1 to 6 carbon atoms), a —L—O—CH$_2$Ph group (wherein L is as defined above), —L—O—L—COOR9 group (wherein L and R9 are as defined above), a —L—CN group (wherein L is as defined above), a —L—S(O)-$_n$—R1 group (wherein L and R1 are as defined above, and n is an integer of from 0 to 2), a —L—S—L—O—R9 group (wherein L and R9 are as defined above), a —L—O—COR9 group (wherein L and R9 are as defined above), a L—O—SO$_2$R9 group (wherein L and R9 are as defined above), a —L—COOR8 group (wherein L and R8 are as defined above), a —CH=CHOR8 group (wherein R8 is as defined above) or a —L—O—L—CN group (wherein L is as defined above); Z is a halogen atom, a nitro group, an alkoxy group having from 1 to 3 carbon atoms, a trifluoromethyl group, a cyano group or a —S(O)$_n$R10 group (wherein R10 is an alkyl group having from 1 to 3 carbon atoms or a haloalkyl group having from 1 to 3 carbon atoms, and n is an integer of from 0 to 2); V is a hydrogen atom, a halogen atom, an alkyl group having from 1 to 4 carbon atoms or an alkoxy group having from 1 to 4 carbon atoms; W is a hydrogen atom, a halogen atom, an alkyl group having from 1 to 4 carbon atoms, a haloalkyl group having from 1 to 4 carbon atoms, an alkoxy group having from 1 to 4 carbon atoms, an alkoxyalkyl group having from 2 to 6 carbon atoms, an alkoxycarbonyl group having from 2 to 5 carbon atoms, a haloalkoxy group having from 1 to 3 carbon atoms, a nitro group, a cyano group or a —S(O)-$_n$—R group (wherein n is as defined above and R is an alkyl group having from 1 to 4 carbon atoms); Q is a hydrogen atom, an alkyl group having from 1 to 6 carbon atoms which may be substituted by halogen, an alkenyl group having from 1 to 6 carbon atoms which may be substituted by halogen, an alkynyl group having from 1 to 6 carbon atoms which may be substituted by halogen, a cyanomethyl group, a —C(O)—R11 group (wherein R11 is a phenyl group which may be substituted by the same or different substituents selected from the group consisting of alkyl having from 1 to 6 carbon atoms, alkenyl having from 1 to 6 carbon atoms, alkynyl having from 1 to 6 carbon atoms, haloalkyl having from 1 to 6 carbon atoms, haloalkenyl having from 1 to 6 carbon atoms, haloalkynyl having from 1 to 6 carbon atoms, halogen, nitro and trifluoromethyl, an alkyl group having from 1 to 6 carbon atoms, an alkoxy group having from 1 to 6 carbon atoms or a hydroxyl group), a —S(O)$_2$R11 group (wherein R11 is as defined above), a —P(O)(OR11)$_2$ group (wherein R11 is as defined above), a —L—C(O)—R11 group (wherein L and R11 are as defined above), a —L—C(O)—N(R12)(R13) (wherein L is as defined above, each of R12 and R13 is a hydrogen atom or an alkyl group having from 1 to 6 carbon atoms), a —L—R14 group (wherein L is as defined above, R14 is a phenyl group which may be substituted by the same or different substituents selected from the group consisting of halogen, nitro and trifluoromethyl, an alkyl group having from 1 to 6 carbon atoms, an alkoxy group having from 1 to 6 carbon atoms or a hydroxy group), a —L—N(R12)(R13) group (wherein L, R12 and R13 are as defined above), a —L—OR15 group (wherein R15 is a hydrogen atom, an alkyl group having from 1 to 6 carbon atoms or an alkenyl group having from 1 to 6 carbon atoms), a —L—OC(O)R16 group (wherein R16 is an alkyl group having from 1 to 6 carbon atoms or an alkoxy group having from 1 to 6 carbon atoms), a —L—S(O)$_n$R15 group (wherein R15 is as defined above, and n is an integer of 0 or 2), a —L—SC(O)R12 group (wherein R12 is as defined above),

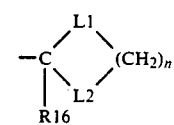

group (wherein each of L1 and L2 is a methylene group, an oxygen atom or a sulfur atom, R16 is a hydrogen atom or an alkyl group having from 1 to 3 carbon atoms, and n is an integer of 2 or 3), and a salt thereof.

The present invention also provides a selective herbicidal composition comprising a herbicidally effective amount of at least one pyrazole derivative of the formula I as defined above or its salt and an agricultural carrier or diluent.

Further, the present invention provides a method for selectively controlling weeds, which comprises applying the pyrazole derivative of the formula I as defined above or its salt to the locus to be protected.

Now, the present invention will be described in detail with reference to the preferred embodiments.

In the compound of the formula I of the present invention, A, B, X, Y, Z and Q are preferably selected from the following substituents, respectively:

A: Me, Et, n-Pr, i-Pr, CH$_2$CH=CH$_2$, CH$_2$C≡CH

B: H, Me, Et, n-Pr, i-Pr, Cl, Br, CH$_2$Cl, CF$_3$, OMe, OEt, OPr-i, SMe, CH$_2$OMe, CH$_2$SMe, CO$_2$Me, CO$_2$Et

X: Me, Et, n-Pr, i-Pr, n-Bu, i-Bu, s-Bu, t-Bu, OMe, OEt, OPr-n, OPr-i, OBu-n, OBu-i, OBu-s, OBu-t, F, Cl, Br, I, NO$_2$, CN, CH$_2$F, CHF$_2$, CF$_3$, CH$_2$CF$_3$, CH$_2$Cl, CCl$_3$, CHClMe, CH$_2$CH$_2$Cl, CHClCH$_2$Cl, CH$_2$Br, CHBrMe, CH$_2$CH$_2$Br, CH$_2$OMe, CH$_2$OEt, CH$_2$OPr-n, CH$_2$OPr-i, CH$_2$OBu-n, CH$_2$OBu-i, CH$_2$OBu-s, CH$_2$OBu-t, CHMeOMe, CHMeOEt, CHMeOPr-n, CHMeOPr-i, CHMeOBu-n, CHMeOBu-i, CHMeOBu-s, CHMeOBu-t, CH$_2$CH$_2$OMe, CH$_2$CH$_2$OEt, CH$_2$CH$_2$OPr-i, Ac, COEt, COPr-n, COPr-i, COOMe, COOEt, COOPr-i, CONHMe, CONHEt, CONMe$_2$, CONEt$_2$, CONEtMe, OCHF$_2$, OCF$_3$, OCH$_2$CF$_3$, SMe, SEt, CH$_2$SMe, CH$_2$SEt, CHMeSMe, CHMeSEt

Y: CH$_2$OH, CH$_2$OMe, CH$_2$OEt, CH$_2$OPr-n, CH$_2$OPr-i, CH$_2$OBu-n, CH$_2$OBu-i, CH$_2$OBu-s, CH$_2$OBu-t, CH$_2$OAm-n, CH$_2$OAm-i, CH$_2$OAm-t, CH$_2$OC$_6$H$_{13}$-n,

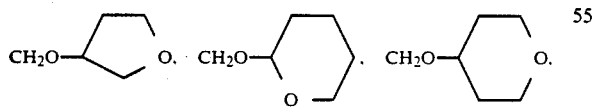

CH$_2$OCH=CH$_2$, CH$_2$OCH$_2$CH=CH$_2$, CH$_2$OCH$_2$CMe=CH$_2$, CH$_2$OCHMeCH=CH$_2$, CH$_2$OCH$_2$C≡CH, CH$_2$OCHMeC≡CH, CH$_2$OCMe$_2$C≡CH, CH$_2$OCH$_2$CH$_2$F, CH$_2$OCH$_2$CF$_3$, CH$_2$OCH$_2$CH$_2$Cl, CH$_2$OCH$_2$Cl$_3$, CH$_2$OCH$_2$CH$_2$Br,

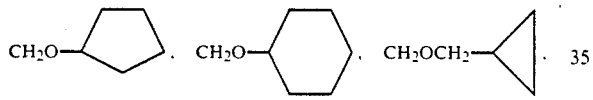

CH$_2$OCH$_2$CCl=CH$_2$,   CH$_2$OCH$_2$CCl=CHCl, CH$_2$OCH$_2$CH$_2$OMe,   CH$_2$OCH$_2$CH$_2$OEt, CH$_2$OCH$_2$CH$_2$OPr-i,

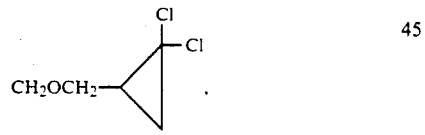

CH$_2$OPh, CH$_2$OPh-Cl-4, CH$_2$OPh-NO$_2$-4, CH$_2$NHMe, CH$_2$NHEt, CH$_2$NMe$_2$, CH$_2$NEt$_2$, CH$_2$NEtMe, CH$_2$OCH$_2$Ph, CH$_2$OCH$_2$COOMe, CH$_2$OCH$_2$COOEt, CH$_2$OCHMeCOOMe, CH$_2$OCH$_2$COOBu-t, CH$_2$OCHMeCOOEt, CH$_2$CN, CH$_2$SMe, CH$_2$SEt, CH$_2$SPr-n, CH$_2$SPr-i, CH$_2$SBn-t, CH$_2$SCH$_2$CH=CH$_2$, CH$_2$SCH$_2$C≡CH,

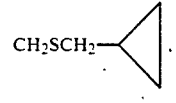

CH$_2$SCH$_2$CH$_2$Cl, CH$_2$SOMe, CH$_2$SOEt, CH$_2$SO$_2$Me, CH$_2$SO$_2$Et, CH$_2$SO$_2$Pr-n, CH$_2$SO$_2$Pr-i, CH$_2$SCH$_2$CH$_2$OMe, CH$_2$SCH$_2$CH$_2$OEt, CH$_2$SPh, CH$_2$OAc, CH$_2$OCOEt, CH$_2$OCOPr-i, CH$_2$OSO$_2$Me, CH$_2$OSO$_2$Et, CH$_2$OCH$_2$CH$_2$CN, CHMeOH, CHMeOMe, CHMeOEt, CHMeOPr-n, CHMeOPr-i, CHMeOBu-n, CHMeOBu-i, CHMeOBu-s, CHMeOBu-t,

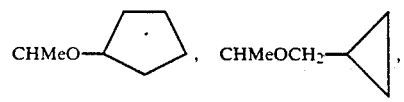

CHMeOCH=CH$_2$,         CHMeOCH$_2$CH=CH$_2$, CHMeOCH$_2$C≡CH,       CHMeOCH$_2$CF$_3$, CHMeOCH$_2$CH$_2$Cl,     CHMeOCH$_2$CCl$_3$, CHMeOCH$_2$CH$_2$Br,

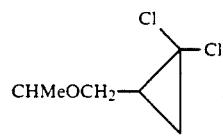

CHMeOCH$_2$CH$_2$OMe, CHMeOCH$_2$CH$_2$Et,

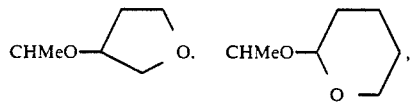

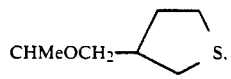

CHMeOPh, CHMeNHMe, CHMeNMe$_2$, CHMeNEt$_2$, CHMeOCH$_2$COOMe, CHMeOCH$_2$COOEt, CHMeOCHMeCOOMe, CHMeCN, CHMeSMe, CHMeSEt, CHMeSPr-n, CHMeSPr-i, CHMeSCH$_2$CH=CH$_2$, CHMeSCH$_2$C≡CH,

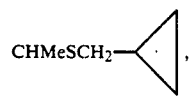

CHMeSCH$_2$CH$_2$Cl, CHMeSOMe, CHMeSOEt, CHMeSO$_2$Me, CHMeSO$_2$Et, CHMeSO$_2$Pr-i, CHMeSCH$_2$CH$_2$OMe, CHMeSPh, CHMeOAc, CHMeOCOEt, CHMeOSO$_2$Me, CHMeOSO$_2$Et, CHMeOCH$_2$CH$_2$CN, CMe$_2$OH, CMe$_2$OMe, CMe$_2$OEt, CMe$_2$OPr-n, CMe$_2$OPr-i, CMe$_2$OCH=CH$_2$, CMe$_2$OCH$_2$CH=CH$_2$, CMe$_2$OCH$_2$C≡CH, CMe$_2$OCH$_2$CH$_2$Cl, CMe$_2$OCH$_2$CH$_2$OMe,

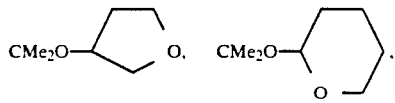

CMe₂NHMe, CMe₂NMe₂, CMe₂OCH₂COOMe, CMe₂CN, CMe₂SMe, CMe₂SEt, CMe₂SO₂Me, CMe₂SO₂Et, CMe₂OAc, CMe₂OSO₂Me, CH₂COOMe, CH₂COOEt, CH₂COOPr-i, CHMeCOOMe, CHMeCOOEt, CHMeCOOPr-i, CH₂CH₂COOMe, CH₂CH₂COOEt, CH₂CH₂COOPr-i, CH═CHOMe, CH═CHOEt, CH═CHOPr-i, COOH, COOMe, COOEt, COOPr-n, COOPr-i, COOBu-n, COOBu-s, COOBu-i, COOBu-t, COOAm-i,

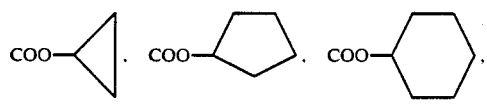

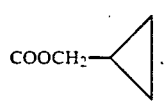

COOCH₂CH═CH₂, COOCH₂C≡CH, COOCH₂CMe═CH₂, COOCH₂CH₂Br, COOCH₂CH₂Cl COOCH₂CH₂F, COOCH₂CCl₃, COOCH₂CHF₂, COOCH₂CF₃,

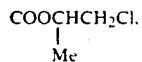

COOCH₂CCl═CH₂, COOCH₂CCl═CHCl, COOCH₂OMe, COOCH₂CH₂OMe, COOCH₂CH₂OEt, COOCH₂OEt, COOCH₂SMe, COOCH₂CH₂SMe, COOCH₂CH₂SEt, COOCH₂CH₂SCH₂CH₂Cl, COOCH₂SOMe, COOCH₂CH₂SOMe, COOCH₂CH₂OCH₂CH₂Cl, COOCH₂CH₂OCH₂CH₂Br, COOCH₂CH₂OSO₂Me, COOCH₂CH₂OSO₂Ph-Me-4, COOCH₂OCH₂CH₂OMe, COOCH₂CH₂SO₂Me, COOCH₂CH₂SO₂Et, COOCH₂SO₂Me, COOCH₂CN, COOCH₂CH₂CN, COOCH₂CH₂CH₂Cn, COOCH₂CH₂NHMe, COOCH₂CH₂NMe₂, COOCH₂NMe₂, COOCH₂CH₂NO₂, COOCH₂CH₂CH₂NO₂, COOCH₂OH,

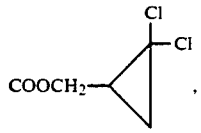

COOCH₂COMe, COOCH₂COBu-t, COOCH₂COPr-i, COOCH₂COPh, COOCH₂COOMe, COOCH₂COOEt, COOCHMeCOOMe, COOCMe₂OOMe, COOCH₂CH₂OCH₂CH═CH₂, COOCH₂CH₂OCH₂C≡CH, COOCH₂CH₂OPh, COOCH₂OPh, COOCH₂CH₂OCH₂Ph, COOCH₂SiMe₃, COOSiMe₃, COOSiEt₃, COOPh, COOPh-Cl-4, COOPh-Me-4, COOPh-OMe-4, COOPh-NO₂-4, COOCH₂Ph, COOCH₂Ph-Cl-2, COOCH₂Ph-Cl-4, COOCHMePh, COOCH₂CH₂Ph,

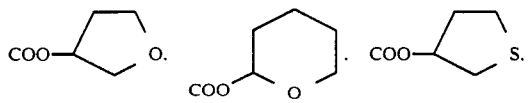

C(O)SMe, C(O)SEt, C(O)SPr-i, C(O)SPr-n, C(O)SBu-n, C(O)SBu-t, C(O)SBu-s, C(O)SBu-i, C(S)OMe, C(S)OEt, C(S)OPr-i, C(S)OPr-n, C(S)OBu-n, C(S)OBu-t, C(S)OBu-s, C(S)OBu-i, CSSMe, CSSEt, CSSPr-n, CSSPr-i, CONMe₂, CONHMe, CONEt₂, CONHEt, CONHPr-n, CONHPr-i, CONHBu-t, CONHBu-s, CONHBu-i, CONHBu-n, CONHAm-t, CONPr₂-i, CONPr₂-n, CONHPh, CONHPh-Me-4, CONHPh-NO₂-4,

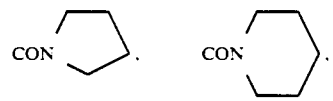

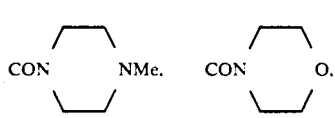

CONMeOMe, CONHCH₂CH═CH₂, CON(CH₂CH═CH₂)₂, CONHCH₂C≡CH, CON(CH₂C≡CH)₂, CONMePh, CONEtPh, CON(Me)Ph-Me-4, CONHSO₂Me, CONHSO₂CF₃, COON═CMe₂,

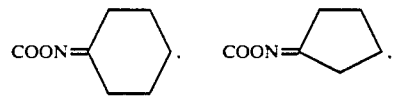

COOCH₂OCOMe, COOCH₂OCOBu-t,

Z: F, Cl, Br, I, NO₂, OMe, OEt, OPr-n, OPr-i, CF₃, CN, SMe, SOMe, SO₂Me, SCF₃, SOCF₃, SO₂CF₃

Q: H, Me, Et, n-Pr, i-Pr, n-Bu, i-Bu, s-Bu, t-Bu, CH₂CH₂Cl, CH₂CF₃, CHClMe, CH₂CH₂Br, CHClCH₂Cl, CH₂CH═CH₂, CH₂CMe═CH₂, CH₂CH═CHMe, CH₂C≡CH, CH₂CCl═CH₂, CH₂CN, CH₂Ph, CH₂Ph-Cl-2, CH₂Ph-Cl-3, CH₂Ph-Me-2,

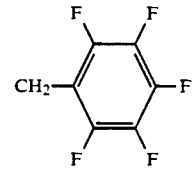

CH₂Ph-Me₂-2,4, CH₂Ph-Me-4, CHMePh, CHEtPh, CH₂Ph-NO₂-2, CH₂Ph-CF₃-3, CH₂OMe, CH₂OEt,

CH₂OH, CHMeOH, CH₂NHMe, CH₂NMe₂, CHMeNMe₂, CH₂COPh, CH₂COPh-NO₂-4, CH₂COPh-Me-4, CH₂COPh-Cl-4, CH₂COPh-Me₂-2,4, CH₂COPh-CF₃-4, CH₂Ac, CH₂COEt, CHMeAc, CH₂CO₂Me, CH₂CO₂Et, CH₂CO₂Pr-n, CH₂CO₂Pr-i, CH₂CO₂Bu-t, CH₂CO₂H, CHMe-CO₂H, CH₂CONHMe, CH₂CONMe₂, CH₂CON-HEt, CH₂CONEt₂, CH₂CONPr-n₂, CH₂OCH₂CH=CH₂, CH₂OAc, CH₂COEt, CH₂COPr-i, CH₂COBu-t, CH₂OCO₂Me, CH₂OCO₂Et, CH₂OCO₂Pr-i, CH₂OCO₂Bu-t, CH₂SMe, CH₂SEt, CH₂SCH₂CH=CH₂, CH₂SAc, CH₂SCOBu-t, CH₂SO₂Me, CH₂SO₂Et, CH₂SO₂CH₂CH=CH₂, CH₂NHCH₂CH=CH₂, CH₂NMeCH₂CH=CH₂, CH₂NHAc, CH₂NHCOEt, CH₂NHCO₂Me, CH₂NHCO₂Et, CH₂NMeCO₂Me, COPh, COPh-Me-4, COPh-NO₂-2, COPh-Cl₂-2,4, Ac, COEt, COPr-n, COPr-i, COBu-n, COBu-t, COCH₂Cl, COCHCl₂, COCCl₃, COCF₃, COCH₂OMe, COCH₂OPh, COCH₂CH=CHCH₃, CO₂Me, CO₂Et, CO₂Bu-t, CO₂Pr-i, CONHMe, CONMe₂, CONHEt, CONEt₂, CONPr-n₂, CON(CH₂CH=CH₂)₂, CONMePh,

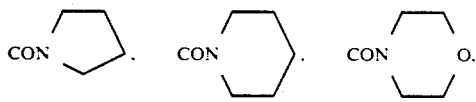

CO₂CH₂Ph, CO₂Ph, SO₂Me, SO₂Et, SO₂CH₂CH=CH₂, SO₂Ph, SO₂Ph-Me-4, SO₂Ph-Cl-4, SO₂Ph-(NO₂)₂-2,4, SO₂CF₃, P(=O) (OMe)₂, P(=O) (OEt)₂, P(=O)(OPr−n)₂, P(=O) (OPr-i)₂, P(=S) (OMe)₂, P(=S) (OEt)₂, P(=O)OMeOPh, P(=O) (OCH₂CH=CH₂)₂, P(=O)O-PhOCH₂CH=CH₂

When Q is a hydrogen atom, the compound may readily form a salt with a metal or with an organic base.

As such a metal, sodium, potassium, calcium, lithium, barium, magnesium, iron, copper, nickel or manganese may be mentioned.

As such an organic base, methylamine, dimethylamine, trimethylamine, ethylamine, diethylamine, triethylamine, n-propylamine, di-n-propylamine, i-propylamine, di-i-propylamine, n-butylamine, i-butylamine, sec-butylamine, tert-butylamine, piperidine, pyrrolidine, morpholine, pyridine, N,N-dimethylaniline or choline may be mentioned.

In the course of researches on the herbicidal properties of various organic compounds with an aim to develop useful herbicides, the present inventors have found that the above-mentioned compound of the present invention exhibits excellent herbicidal activities against narrow leaf weeds (gramineous and cyperaceous weeds) and against broad leaf weeds and no substantial phytotoxicity against useful plants e.g. crop plants such as *Zea mays* (corn), *Sorghum bicolor* (sorgo), *Triticum* spp (wheat) and *Hordeum vulgare* (barley). The present invention has been accomplished on the basis of this discovery.

The compound of the present invention exhibits strong herbicidal activities in each of soil treatment, soil incorporation treatment and foliage treatment. On the other hand, it exhibits no phytotoxicity against crop plants such as *Zea mays, Sorghum bicolor, Triticum* spp and *Hordeum vulgare* in a practical application in any of soil treatment, soil incorporation treatment and foliage treatment. Thus, the compound of the present invention has high selectivity and it is extremely effective for controlling weeds during the cultivation of these crop plants. Namely, the compound of the present invention exhibits strong herbicidal activities against noxious weeds such as *Setaria viridis* (green foxtail), *Echinochloa crus-galli* (barnyardgrass), *Amaranthus lividus* (livid amaranth), *Polygonum longisetum* (persicaria blumei gross), *Xanthium strumarium* (cocklebur), *Abutilon theophrasti* (velvet leaf) and *Cyperus esculentus* (yellow nutsedge), which develop during the cultivation of *Zea mays* or *Sorghum bicolor*. The herbicidal activities against gramineous weeds and *Cyperus esculentus* are remarkably high and extremely unique. Heretofore, during the cultivation of *Zea mays* or *Sorghum bicolor*, it has been common to employ atrazine or cyanazine as a triazine-type herbicide, or alachlor or metolachlor as an acid anilide-type herbicide. However, atrazine and cyanazine have poor herbicidal activities against gramineous weeds although they show high activities against broad leaf weeds, and their activities against *Cyperus esculentus* are very low. On the other hand, alachlor and metoachlor have poor activities against broad leaf weeds although their activities against gramineous weeds are high, and their activities against *Cyperus esculentus* are very poor. Thus, it has been difficult to eradicate all the weed species by a single application of such herbicides.

As a result of various studies, the present invention have found the compound of the present invention which exhibits excellent herbicidal effects against a wide range of weeds, and the present invention has been accomplished on the basis of this discovery. The compound of the present invention also has a feature that it exhibits no phytotoxicity against crop plants such as *Zea mays, Sorghum bicolor, Triticum* spp and *Hordeum vulgare* and thus can safely be applied to the fields for such crop plants.

Further, the compound of the present invention includes a compound which shows selectivity between *Oryza sativa* (rice) and *Echinochloa crus-galli* (barnyardgrass), and it also includes a compound having selectivity for a useful plant such as *Gossypium* spp (cotton), *Beta vulgaris* (sugar beat) or *Glycine max* (soybean).

Heretofore, it has been known that 4-benzoylpyrazole derivatives have excellent herbicidal activities. For example, pyrazolate (common name) is commercially available and widely used for practical application. However, such conventional herbicides are restricted in their application to paddy fields, and their activities are very poor in their application to upland fields. Whereas, as a result of extensive research for many years on 4-benzoylpyrazole derivatives, the present inventors have finally found that the compound of the present invention which simultaneously satisfies the various conditions for substituents in the structure as specified above, exhibits strong herbicidal activities in the application to upland fields in each of soil treatment, soil incorporation and foliage treatment. It has been found that the compound of the present invention exhibits particularly high activities against gramineous weeds and *Cyperus esculentus*.

The compound of the present invention can readily be prepared by any one of the following reactions.

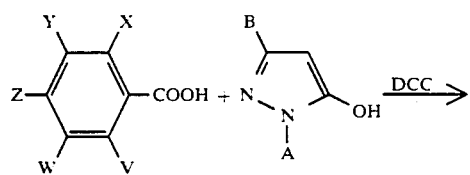 (1)

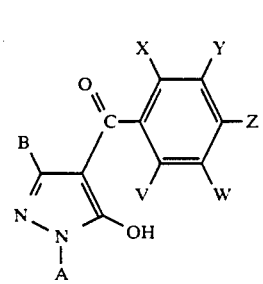

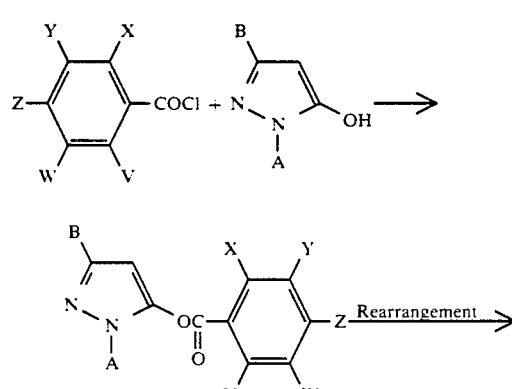 (2)

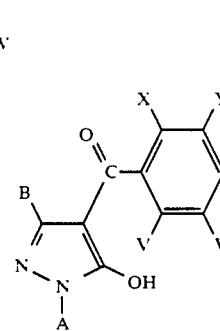

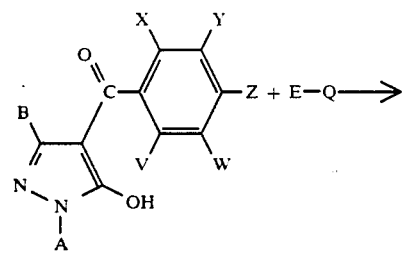 (3)

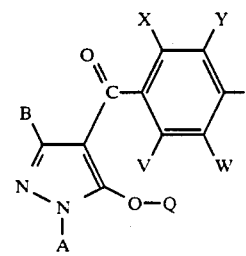

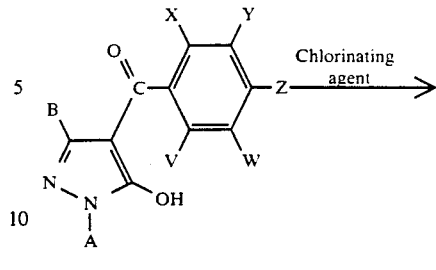 (4)

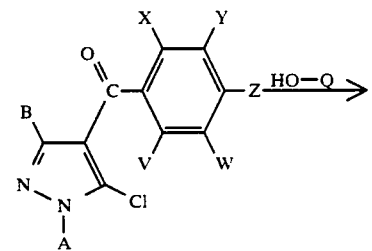

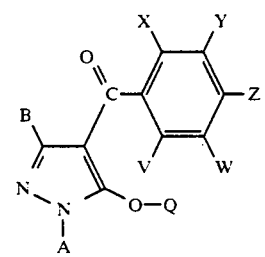

In the above formulas, A, B, X, Y, Z, Q, V and W are as defined above, E is a halogen atom, a methanesulfonyloxy group or a p-toluenesulfonyloxy group. Further,

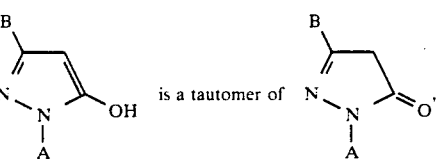

and may be represented by either formula. DCC is N,N'-dicyclohexylcarbodiimide.

Reaction scheme (1) represents a reaction wherein benzoic acid having suitable substituents and 5-hydroxypyrazole are reacted in an inert solvent in the presence of DCC and a base to obtain 4-benzoyl-5-hydroxypyrazole. DCC is used in an amount of from 1.0 to 1.5 mols per mol of the benzoic acid and pyrazole. The solvent may be any solvent so long as it is inert to the reaction. Particularly preferred is tert-butyl alcohol, tert-amyl alcohol or isopropyl alcohol. The base may not necessarily be required. However, in general, the yield can be improved by using a base. There is no particular restriction as to the base, but potassium carbonate or sodium carbonate may preferably be employed. The reaction temperature may range from room temperature to the boiling point of the solvent, but is preferably from 50° to 100° C.

The reaction time is usually from 0.5 to 20 hours.

Reaction scheme (2) shows a reaction wherein benzoyl chloride having suitable substituents and 5-hydroxypyrazole are reacted to form a benzoyl ester, which is then rearranged to a 4-benzoyl compound.

The benzoyl esterification can be accomplished in an inert solvent (such as an aromatic hydrocarbon, a fatty acid ester, a halogenated hydrocarbon, an ether, acetonitrile, dimethylsulfoxide or N,N'-dimethylformamide) or in a two phase system with such a solvent and water or in a mixture of such solvents in the presence of a suitable dehydrochlorinating agent (e.g. an inorganic base such as sodium hydroxide, potassium hydroxide or sodium hydrogencarbonate, or an organic base such as pyridine or triethylamine) at a temperature of from room temperature to 100° C. for from 10 minutes to 5 hours.

The rearrangement reaction can be accomplished by means of a Lewis acid such as anhydrous aluminum chloride or a base. As the base, potassium carbonate, calcium hydroxide or sodium carbonate may be used. The Lewis acid or base is used usually in an amount of from 1 to 10 mol times.

No solvent is required. However, in some cases, it is advantageous to use a solvent having a suitable boiling point to improve the operation efficiency or the yield. As such an advantageous example, use of dioxane or diglyme may be mentioned.

The reaction temperature is usually from 50° to 150° C., and the reaction time is usually from 15 minutes to 10 hours.

Reaction scheme (3) shows a reaction wherein 4-benzoyl-5-hydroxypyrazole is condensed with a halide, a methanesulfonic acid ester or a p-toluenesulfonic acid ester.

For this reaction, it is preferred to employ from 1 to 3 mol times of a dehydrohalogenating agent. As such a dehydrohalogenating agent, an inorganic base such as sodium hydroxide, potassium hydroxide, sodium carbonate, sodium hydrogencarbonate or potassium carbonate, or an organic base such as pyridine or triethylamine, may be mentioned.

There is no particular restriction as to the solvent so long as it is inert to the reaction. A wide range of solvents including an aromatic hydrocarbon, a fatty acid ester, a halogenated hydrocarbon, an ether, a ketone, an aliphatic hydrocarbon, acetonitrile, dimethylsulfoxide and dimethylformamide may be used.

The reaction temperature may be optionally selected within a range of from room temperature to the boiling point of the solvent. The reaction time is usually from 30 minutes to 30 hours.

Reaction scheme (4) shows a reaction wherein 4-benzoyl-5-hydroxypyrazole is converted to a 5-chloro compound by a chlorinating agent, followed by condensation with a suitable alcohol or acid.

As the chlorinating agent, phosphorus oxychloride, phosphorus pentachloride or thionyl chloride may be mentioned.

As the solvent, a wide range of solvents inert to the reaction, such as dimethylformamide, may be employed. However, the reaction can be conducted without any solvent.

The reaction temperature is preferably from 30° to 150° C., and the reaction time is usually from 30 minutes to 10 hours. In some cases, the reaction time may be shortened or the yield may be improved by an addition of a dehydrohalogenating agent.

The condensation reaction with an alcohol or acid is conducted by an addition of a dehydrohalogenating agent.

As such a dehydrohalogenating agent, a base such as sodium hydroxide, potassium hydroxide, sodium carbonate, potassium carbonate, sodium alkoxide or sodium hydride may be employed.

The solvent may be any solvent which is inert to the reaction (such as an aromatic hydrocarbon, an ether, a ketone or N,N'-dimethylformamide). The reaction temperature may be selected within a range of from room temperature to the boiling point of the solvent.

The benzoic acids or benzoyl chlorides used as the starting materials for the compounds of the present invention may readily be prepared by a proper combination of various known syntheses. For instance, compounds wherein the substituent Z in the benzene ring is —S(O)$_n$CH$_3$ can be prepared in accordance with the following reaction schemes.

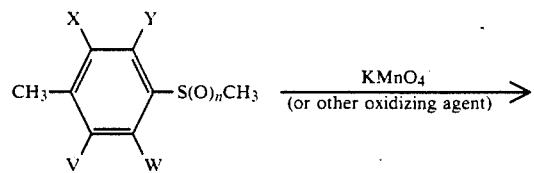

(5)

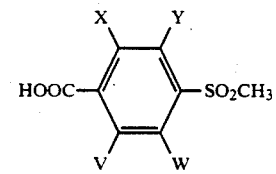

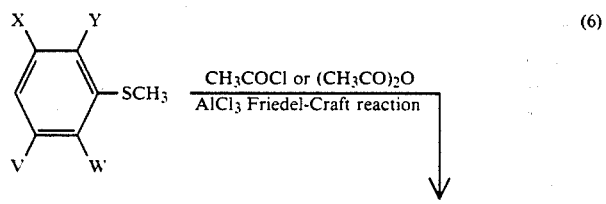

(6)

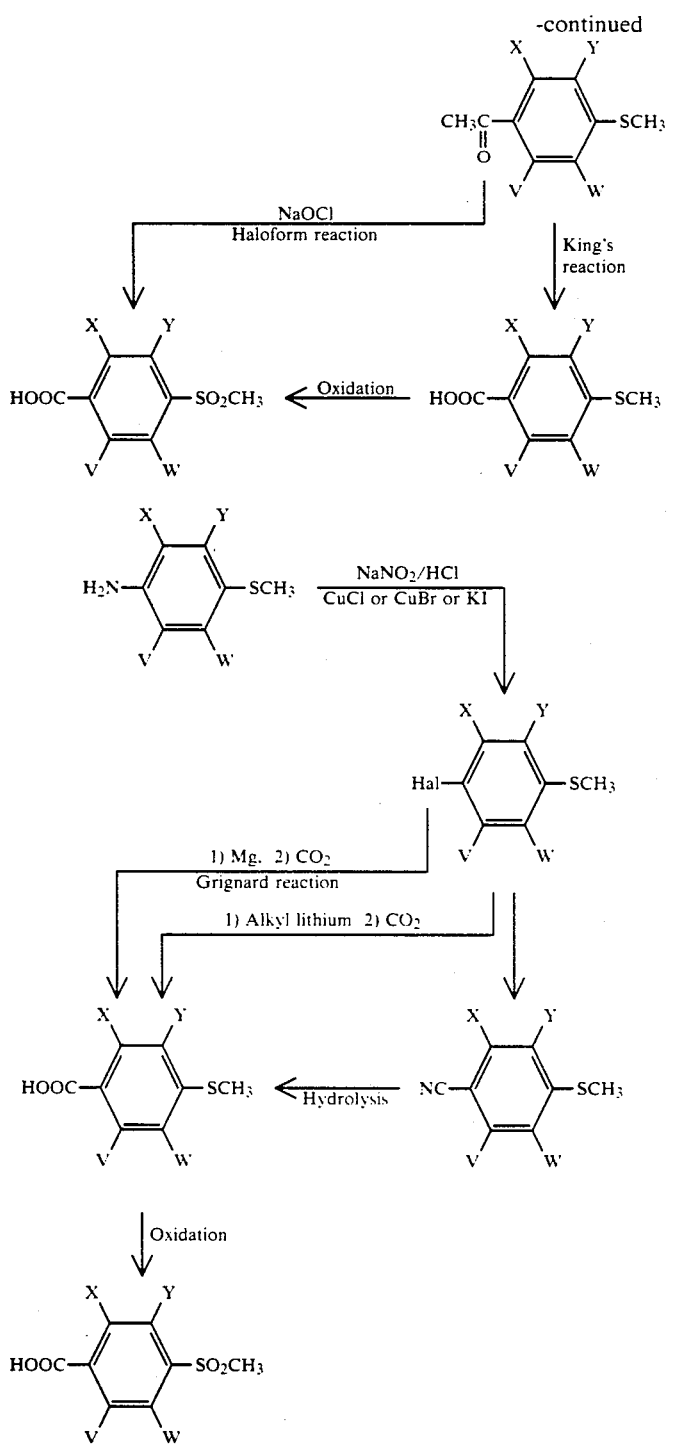

In the above formulas, X, Y, V and W are as defined above, and Hal is a halogen atom.

Now, the preparation of benzoic acids will be described in detail with reference to Reference Examples. However, it should be understood that the present invention is by no means restricted by such specific Examples.

REFERENCE EXAMPLE 1

Preparation of 4-methanesulfonyl-3-methoxymethyl-2-methyl benzoic acid and 3-methoxymethyl-2-methyl-4-methylthio benzoic acid (1) 2-Methyl-3-nitrobenzyl alcohol 39.0 g (0.2 mol) of methyl 2-methyl-3-nitrobenzoate was dissolved in 600 ml of tert-butanol, and 19.0 g of sodium borohydride was added thereto. Under refluxing, 150 ml of methanol was dropwise added thereto over a period of 1 hour. The refluxing was continued further for 1 hour to complete the reaction. The reaction mixture was left to cool, and then water was added thereto. The solvent was distilled off under reduced pressure. To the residue, water and chloroform were added, and the organic layer was separated and dried over anhydrous sodium sulfate. Then, the solvent was distilled off to obtain 30.7 g of 2-methyl-3-nitrobenzyl alcohol.

(2) 2-Methyl-3-nitrobenzyl methyl ether 30.1 g (0.18 mol) of 2-methyl-3-nitrobenzyl alcohol obtained in the preceding step was dissolved in 200 ml of benzene, and 0.2 g of tetra-n-butylammonium bromide and a 50% aqueous solution of 20.1 g of sodium hydroxide were added thereto sequentially. Then, 27.2 g of dimethyl sulfate was dropwise added thereto at room temperature. Further, the reaction was conducted for 3 hours under stirring. Water was added to the reaction solution, and the organic layer was separated and washed sequentially with water, a 2% hydrochloric acid aqueous solution, water and a saturated sodium chloride aqueous solution. Then, the solvent was distilled off to obtain 30.9 g of 2-methyl-3-nitrobenzyl methyl ether as an oily substance.

(3) 3-Methoxymethyl-2-methylaniline

To 30.7 g (0.17 mol) of the above-mentioned 2-methyl-3-nitrobenzyl methyl ether, 200 ml of methanol was added. After the compound was dissolved in methanol, 92 ml of concentrated hydrochloric acid was gradually added thereto. Then, 30.4 g of iron powder was gradually added so that the reaction temperature became at a level of not higher than 60° C., and the reaction was continued further for 1 hour.

To the reaction solution, 300 ml of water was added, and sodium hydroxide was added until the pH became higher than 8. To the slurry thus obtained, chloroform was added, and the mixture was thoroughly stirred. Then, the solid was separated by filtration, and an organic layer was separated from the filtrate.

This organic layer was washed sequentially with water and a saturated sodium chloride aqueous solution and then dried over anhydrous sodium sulfate. Further, the solvent was distilled off under reduced pressure to obtain 23.1 g of 3-methoxymethyl-2-methylaniline as an oily substance.

(4) 3-Methoxymethyl-2-methyl-4-thiocyanoaniline 22.6 g (0.15 mol) of 3-methoxymethyl-2-methylaniline was dissolved in 300 ml of methanol. Then, 36.5 g of sodium thiocyanate was added thereto to obtain a uniform solution. This solution was cooled to 0° C., and 100 ml of a saturated methanol solution of sodium bromide with 25.2 g of bromine was dropwise added thereto so that the reaction temperature did not exceed 5° C. After the dropwise addition, the mixture was stirred at a temperature of not higher than 5° C. for 1 hour and at room temperature for 1 hour to complete the reaction. The reaction solution was poured into 1 liter of water and neutralized with a 5% sodium carbonate aqueous solution. Chloroform was added to extract the oily substance. The chloroform layer was washed with water and a saturated sodium chloride aqueous solution and dried over anhydrous sodium sulfate. Then, the solvent was distilled off under reduced pressure to obtain 29.6 g of the desired product.

(5) 3-Methoxymethyl-2-methyl-4-methylthioaniline 29.1 g (0.14 mol) of 3-methoxymethyl-2-methyl-4-thiocyanoaniline was dissolved in 200 ml of ethanol and mixed with 100 ml of an aqueous solution containing 33.6 g of sodium sulfide nonahydrate at room temperature. Then, 21.9 g of methyl iodide was dropwise added thereto, and the mixture was reacted at room temperature for 3 hours. After completion of the reaction, the solvent was distilled off under reduced pressure, and water and chloroform were added to the residue. Then, the organic layer was separated and washed sequentially with water and a saturated sodium chloride aqueous solution and then dried over anhydrous sodium sulfate. The solvent was distilled off under reduced pressure to obtain 25.6 g of the desired product as an oily substance.

(6) 3'-Iodo-2'-methyl-6'-methylthiobenzyl methyl ether

To 25.6 g (0.13 mol) of 3-methoxymethyl-2-methyl-4-methylthioaniline, 100 ml of water and 33 ml of concentrated hydrochloric acid were added to convert it to an aniline hydrochloride. This solution was cooled to 0° C., and 30 ml of an aqueous solution containing 9.3 g of sodium nitrite was dropwise added thereto so that the reaction temperature did not exceed 5° C. After completion of dropwise addition, stirring was continued further for 30 minutes to complete diazotization. 100 ml of an aqueous solution containing 33 g of potassium iodide was heated to 70° C., and the aqueous solution of the diazonium salt obtained above was gradually added thereto and decomposed. The reaction solution was stirred further for 1 hour at 70° C. and then left to cool. The oil component was extracted with benzene. The benzene layer was washed sequentially with water, a saturated sodium hydrogensulfite aqueous solution, water and a saturated sodium chloride aqueous solution. Then, the solvent was distilled off under reduced pressure, and the residue was purified by column chromatography (eluent: benzene) to obtain 30.0 g of the desired product. Melting point: 56.0°-59.0° C.

(7) 3-Methoxymethyl-2-methyl-4-methylthiobenzoic acid 27.7 g (0.09 mol) of 3'-iodo-2'-methyl-6'-methylthiobenzyl methyl ether was dissolved in 100 ml of dried tetrahydrofuran, and 63 ml of a 1.5M n-butyllithium n-hexane solution was dropwise added thereto at −70° C. After the dropwise addition, the mixture was stirred for 15 minutes at the same temperature, and then dried carbon dioxide gas was thoroughly blown into the reaction solution until the heat generation of the reaction solution stopped. After the reaction, the temperature of the solution was returned to room temperature, and water and diethyl ether were added for liquid separation. The aqueous layer thus obtained was further washed twice with diethyl ether, and then concentrated hydrochloric acid was added to bring the pH<1. Precipitated crystals were collected by filtration, thoroughly washed with water and dried to obtain 14.4 g of the desired product. Melting point: 192.0°-194.0° C.

(8) 4-Methanesulfonyl-3-methoxymethyl-2-methylbenzoic acid

To 11.3 g (0.05 mol) of 3-methoxymethyl-2-methyl-4-methylthiobenzoic acid, 120 ml of acetic acid and 120 ml of a 35% hydrogen peroxide aqueous solution were added, and the mixture was reacted at 80° C. for 1 hour. After cooling, the reaction solution was poured into ice water, whereupon precipitated crystals were collected by filtration, then washed with water and dried to obtain 12.3 g of the desired product. Melting point: 129.0°-131.0° C.

REFERENCE EXAMPLE 2

Preparation of
3-methoxycarbonyl-2-methyl-4-methylthiobenzoic acid
and
4-methanesulfonyl-3-methoxycarbonyl-2-methylbenzoic acid (1) Methyl 3-amino-2-methylbenzoate 40 g of methyl 2-methyl-3-nitrobenzoate was dissolved in 120 ml of methanol, and 157 g of concentrated hydrochloric acid was added thereto. Then, 36.8 g of iron powder was gradually added while maintaining the mixture at a temperature of not higher than 60° C. The mixture was stirred at room temperature for 4 hours and then poured into 1 liter of ice water. The solution was neutralized with sodium carbonate and extracted with chloroform (after filtering off insolubles). The extract was washed with a saturated sodium chloride aqueous solution and dried over anhydrous sodium sulfate. Then, the solvent was distilled off to obtain 27.8 g of the desired product as an oily substance.

(2) Methyl 3-amino-2-methyl-6-thiocyanobenzoate

While maintaining a solution comprising 27.7 g of methyl 3-amino-2-methylbenzoate, 41.5 g of sodium thiocyanate and 250 ml of methanol at a temperature of not higher than 0° C., 100 ml of sodium bromide-saturated methanol with 28.1 g of bromine was slowly dropwise added thereto. The mixture was stirred at room temperature for 3 hours and then poured into 1 liter of ice water. The solution was neutralized with sodium carbonate and then extracted with chloroform. The extract was washed with a saturated sodium chloride aqueous solution and dried over anhydrous sodium sulfate. Then, the solvent was distilled off to obtain 34.0 g of the desired product as an oily substance.

(3) Methyl 3-amino-2-methyl-6-methylthiobenzoate

To a solution comprising 39.5 g of sodium sulfide nonahydrate and 110 ml of water, a solution comprising 32.9 g of methyl 3-amino-2-methyl-6-thiocyanobenzoate and 300 ml of ethanol was dropwise added. The mixture was stirred at room temperature for 1.5 hours, and 24.0 g of methyl iodide was dropwise added under cooling with ice. The mixture was stirred further at room temperature for 2 hours and then concentrated under reduced pressure. A saturated sodium chloride aqueous solution was added thereto, and the mixture was extracted with chloroform. The extract was dried over anhydrous sodium sulfate. Then, the solvent was distilled off to obtain 30.1 g of the desired product as an oily substance.

(4) Methyl 3-iodo-2-methyl-6-methylthiobenzoate 28 g of methyl 3-amino-2-methyl-6-methylthiobenzoate was stirred in 150 ml of concentrated hydrochloric acid at room temperature for 2 hours to convert it to a hydrochloride. Then, while maintaining the mixture at a temperature of not higher than 0° C., a solution comprising 11.9 g of sodium nitrite and 20 ml of water was dropwise added thereto to obtain a diazonium salt solution. The diazonium salt solution was dropwise added to a solution comprising 28.4 g of potassium iodide and 90 ml of water while maintaining the solution at 80° C. After completion of the dropwise addition, the mixture was stirred at 80° C. for 15 minutes and left to cool. Water was cooled thereto, and the mixture was extracted with chloroform. The extract was washed with an aqueous sodium hydrogensulfite solution and water and then dried over anhydrous sodium sulfate. The solvent was distilled off to obtain 40 g of the desired product as a crude product. The crude product was purified by silica gel column chromatography (eluted with benzene) to obtain 36.0 g of a purified product as an oily substance.

(5) 3-Methoxycarbonyl-2-methyl-4-methylthiobenzoic acid

While maintaining a solution comprising 20.0 g of methyl 3-iodo-2-methyl-6-methylthiobenzoate and 70 ml of dried tetrahydrofuran at a temperature of not higher than −60° C. under a nitrogen atmosphere, 42 ml of a 1.5M n-butyllithium n-hexane solution was dropwise added thereto. Fifteen minutes later, dried carbon dioxide gas was thoroughly blown into the mixture while maintaining it at a temperature of not higher than −50° C. After purging carbon dioxide gas with nitrogen, 12.7 g of diisopropylamine was dropwise added thereto, and the mixture was stirred until the temperature reached room temperature. The mixture was concentrated under reduced pressure. Water was added thereto and the mixture was washed with chloroform. The aqueous solution was acidified with concentrated hydrochloric acid and then extracted with chloroform. The extract was dried over anhydrous sodium sulfate. The solvent was distilled off to obtain 7.5 g of the desired product. Melting point: 178°–178.5° C.

(6) 4-Methanesulfonyl-3-methoxycarbonyl-2-methylbenzoic acid

A solution comprising 5.0 g of 3-methoxycarbonyl-2-methyl-4-methylthiobenzoic acid, 25 ml of acetic acid and 25 ml of hydrogen peroxide (35%) was stirred at 80° C. for 3 hours. After cooling, the mixture was poured into ice water and extracted with chloroform. The extract was dried over anhydrous sodium sulfate. Then, the solvent was distilled off to obtain 5.1 g of the desired product. Melting point: 151°–152° C.

REFERENCE EXAMPLE 3

Preparation of
2-chloro-3-ethylthiomethyl-4-methanesulfonylbenzoic acid (1) Methyl 3-bromomethyl-2-chloro-4-methanesulfonylbenzoate 12.1 g of methyl 2-chloro-4-methanesulfonyl-3-methylbenzoate was dissolved in 250 ml of carbon tetrachloride, and the solution was refluxed under stirring. Then, 7.5 g of bromine and 1 g of benzoyl peroxide were gradually added thereto over a period of 30 minutes, and the solution was further refluxed for 4 hours under heating. After cooling, 200 ml of chloroform was added thereto, and the mixture was washed with a 5% sodium hydrogensulfite aqueous solution. The organic layer was separated and dried over anhydrous sodium sulfate. The solvent was distilled off under reduced pressure to obtain a crude product. The crude product was washed with ethyl ether to obtain 13.2 g of crystals of the desired product. Melting point: 77°–78° C.

(2) Methyl 2-chloro-3-ethylthiomethyl-4-methanesulfonylbenzoate

To 100 ml of tetrahydrofuran, 1.3 g of ethanethiol and 1.5 g of potassium carbonate and then 4.4 g of methyl 3-bromomethyl-2-chloro-4-methanesulfonylbenzoate were added, and the mixture was stirred for 1 day at room temperature. Then, the mixture was stirred further for 1 hour at a temperature of from 50° to 60° C. After cooling, chloroform was added thereto, and the mixture was washed with a dilute potassium carbonate aqueous solution. The chloroform layer was separated and dried. Then, the solvent was distilled off to obtain 4.1 g of methyl 2-chloro-3-ethylthiomethyl-4-methanesulfonylbenzoate as an oily substance.

(3) 2-Chloro-3-ethylthiomethyl-4-methanesulfonylbenzoic acid

To a solution mixture comprising 50 ml of a 10% sodium hydroxide aqueous solution and 150 ml of methanol, 3.9 g of methyl 2-chloro-3-ethylthiomethyl-4-methanesulfonylbenzoate was added, and the mixture was stirred at room temperature for 30 minutes. Methanol was distilled off under reduced pressure, and a dilute hydrochloric acid was added to the residue for acid precipitation. The mixture was extracted with ethyl acetate, and the extract was dried. Then, the solvent was distilled off to obtain 3.5 g of the desired product. Melting point: 172°–174° C.

REFERENCE EXAMPLE 4

Preparation of 2-chloro-4-methanesulfonyl-3-methoxymethylbenzoic acid (1) Methyl 2-chloro-4-methanesulfonyl-3-methoxymethylbenzoate To a solution comprising 12.0 g of methyl 3-bromomethyl-2-chloro-4-methanesulfonylbenzoate prepared in Reference Example 3(1) and 100 ml of methanol, 50 ml of a methanol solution containing 1.7 g of sodium methoxide was added, and the mixture was stirred at room temperature overnight. The solvent was distilled off under reduced pressure. Then, dilute hydrochloric acid was added to the residue, and the mixture was extracted with chloroform. The extract was washed with water and dried over anhydrous sodium sulfate. Then, the solvent was distilled off to obtain 9.5 g of the desired product as a crude product. The crude product was purified by silica gel column chromatography (eluted with benzene) to obtain 7.5 g of a purified product as an oily substance.

(2) 2-Chloro-4-methanesulfonyl-3-methoxymethylbenzoic acid

To a solution comprising 3.0 g of methyl 2-chloro-4-methanesulfonyl-3-methoxymethylbenzoate and 20 ml of methanol, a solution comprising 0.57 g of sodium hydroxide (93%) and 2 ml of water was added, and the mixture was stirred at room temperature for 30 minutes. After an addition of 10 ml of water, the mixture was concentrated under reduced pressure. Then, dilute hydrochloric acid was added thereto, and the mixture was extracted with chloroform. The extract was dried over anhydrous sodium sulfate. Then, the solvent was distilled off to obtain 2.6 g of the desired product. Melting point: 137°–141° C.

REFERENCE EXAMPLE 5

Preparation of 2-chloro-4-methanesulfonyl-3-methoxymethylbenzoic acid (alternative method of Reference Example 4)

The desired product was prepared in the same manner as in Reference Example 1. Melting point: 137°–141° C.

The physical properties of the intermediates were as follows:
(1) 2-Chloro-3-nitrobenzyl alcohol: Oily substance
(2) 2′-Chloro-3′-nitrobenzyl methyl ether: Oily substance
(3) 2-Chloro-3-methoxymethylaniline: Oily substance
(4) 2-Chloro-3-methoxymethyl-4-thiocyanoaniline: Melting point: 90°–96° C.
(5) 2-Chloro-3-methoxymethyl-4-methylthioaniline: Oily substance
(6) 2′-Chloro-3′-iodo-6′-methylthiobenzyl methyl ether: Melting point: 53°–56° C.

REFERENCE EXAMPLE 6

Preparation of 2-chloro-4-methanesulfonyl-3-methoxycarbonyl benzoic acid

The desired product was prepared in the same manner as in Reference Example 2. Melting point 160°–162° C.

The physical properties of the intermediates were as follows:
(1) Methyl 3-amino-2-chlorobenzoate: Oily substance
(2) Methyl 3-amino-2-chloro-6-thiocyanobenzoate: Melting point: 80°–83° C.
(3) Methyl 3-amino-2-chloro-6-methylthiobenzoate: Melting point: 70°–72° C.
(4) Methyl 2-chloro-3-iodo-6-methylthiobenzoate: Oily substance
(5) 2-Chloro-3-methoxycarbonyl-4-methylthiobenzoic acid: Melting point: 176°–179° C.

REFERENCE EXAMPLE 7

Preparation of 4-methanesulfonyl-3-[(2-methoxyethyl)oxycarbonyl]-2-methylbenzoic acid The desired compound was prepared in the same manner as in Reference Example 2. Melting point: 118°–121° C.

The physical properties of the intermediates were as follows:
(1) 2-Methoxyethyl 3-amino-2-methylbenzoate: Oily substance
(2) 2-Methoxyethyl 3-amino-2-methyl-6-thiocyanobenzoate: Melting point: 79°–81° C.
(3) 2-Methoxyethyl 3-amino-2-methyl-6-methylthiobenzoate: Oily substance
(4) 2-Methoxyethyl 3-iodo-2-methyl-6-methylthiobenzoate: Oily substance
(5) 3-[(2-methoxyethyl)oxycarbonyl]-2-methyl-4-methylthiobenzoic acid: Melting point: 90°–93° C.

REFERENCE EXAMPLE 8

Preparation of 2-methyl-4-methylthio-3-n-propoxycarbonylbenzoic acid and 4-methanesulfonyl-2-methyl-3-n-propoxycarbonylbenzoic acid (1) Methyl 3-bromo-2-methyl-6-methylthiobenzoate 16.1 g of the compound of Reference Example 2(3) was stirred in 150 ml of hydrobromic acid (48%) to convert it into a hydrobromide. While maintaining the solution at a temperature of not higher than 0° C., a solution comprising 7.2 g of sodium nitrite and 20 ml of water was dropwise added to obtain a diazonium salt solution. The diazonium salt solution was dropwise added to a solution comprising 6.0 g of cuprous bromide and 7.7 g of hydrobromic acid (48%) while refluxing the solution under heating. After completion of the dropwise addition, the mixture was further refluxed for 1 hour under heating and then left to cool. Ice water was added thereto, and the mixture was extracted with chloroform. The extract was washed with an aqueous sodium hydrogensulfite solution and water and then dried over anhydrous sodium sulfate. The solvent was distilled off to obtain 19.2 g of the desired product as a crude product. The crude product was purified by silica gel column chromatography (eluted with benzene) to obtain 17.1 g of a purified product as an oily substance.

(2) 3-Bromo-2-methyl-6-methylthiobenzoic acid

To 100 ml of an ethanol solution containing 17.0 g of methyl 3-bromo-2-methyl-6-methylthiobenzoate, 16 g of a 50% sodium hydroxide aqueous solution was added, and the mixture was refluxed for 3 hours under heating. The reaction mixture was concentrated under reduced pressure. Then, water was added thereto, and the mixture was washed with chloroform. The aqueous layer was acidified with concentrated hydrochloric acid and extracted with chloroform. The extract was dried over anhydrous sodium sulfate. The solvent was distilled off to obtain 15.9 g of the desired product. Melting point: 98°–103° C.

(3) n-Propyl 3-bromo-2-methyl-6-methylthiobenzoate

Thionyl chloride was added to 15.8 g of 3-bromo-2-methyl-6-methylthiobenzoic acid. and the mixture was refluxed for 4 hours under heating. Thionyl chloride was distilled off, and 70 ml of n-propanol was added to the residue under cooling with ice. Then, a solution comprising 7.3 g of pyridine and 20 ml of n-propanol was dropwise added thereto. The mixture was stirred at room temperature overnight and then concentrated under reduced pressure. Then, ethyl acetate was added thereto, and the mixture was washed sequentially with a 5% sodium carbonate aqueous solution, 10% hydrochloric acid and water and then dried over anhydrous sodium sulfate. Then, the solvent was distilled off under reduced pressure to obtain 18 g of the desired product as a crude product. The crude product was purified by silica gel column chromatography (eluted with benzene) to obtain 16.6 g of a purified product as an oily substance.

(4) 3-Bromo-2-methyl-6-methylthiobenzoic acid

This product was prepared in the same manner as in Reference Example 2(5). Melting point: 138°–142° C.

(5) 3-Bromo-6-methanesulfonyl-2-methylbenzoic acid

This compound was prepared in the same manner as in Reference Example 2(6). Melting point: 142°–146° C.

REFERENCE EXAMPLE 9

Preparation of 2-chloro-3-isopropoxycarbonyl-4-methanesulfonylbenzoic acid

This compound was prepared from the compound of Reference Example 6(4) in the same manner as in Reference Example 8(2)–(5). Melting point: 146°–148° C.

The physical properties of the intermediates were as follows:

(1) 2-Chloro-3-iodo-6-methylthiobenzoic acid: Melting point: 155°–159° C.

(2) Isopropyl 2-chloro-3-iodo-6-methylthiobenzoate: Oily substance (3) 2-Chloro-3-isopropoxycarbonyl-4-methylthiobenzoic acid: Melting point: 114°–118° C.

REFERENCE EXAMPLE 10

Preparation of 3-(1-methoxyethyl)-2-methyl-4-methylthiobenzoic acid and 4-methanesulfonyl-3-(1-methoxyethyl)-2-methylbenzoic acid (1) 2'-Methyl-3'-nitroacetophenone To 5.4 g of metal magnesium, 5 ml of absolute ethanol and 0.5 ml of carbon tetrachloride were dropwise added under a dry nitrogen stream. Further, 130 ml of dried diethyl ether was added under refluxing, and then a solution comprising 25 ml of a diethyl ether, 35.2 g of diethyl malonate and 20 ml of ethanol was dropwise added at a rate to maintain the refluxing. After completion of the dropwise addition, refluxing was continued for 3 hours to prepare diethyl ethoxymagnesiomalonate. To the solution of diethyl ethoxymagnesiomalonate thus obtained, 150 ml of a diethyl ether solution of 40.0 g of 2-methyl-3-nitrobenzoic acid chloride prepared from 2-methyl-3-nitrobenzoic acid and thionyl chloride, was dropwise added over a period of 20 minutes under refluxing, and the reaction was continued for 2 hours. After cooling, dilute sulfuric acid was added thereto for hydrolysis. The diethyl ether layer was washed sequentially with water and a saturated sodium chloride aqueous solution. Then, the solvent was distilled off under reduced pressure, and the residue was dried to obtain a crude product of diethyl 2-(2-methyl-3-nitrobenzoyl)-malonate. To this crude product, a mixture comprising 7.5 ml of concentrated sulfuric acid, 60 ml of acetic acid and 40 ml of water was added, and the mixture was refluxed for 6 hours under heating. Then, the mixture was adjusted to pH 10 with a 20% sodium hydroxide aqueous solution. Precipitated oil component was extracted with chloroform. This chloroform layer was washed sequentially with water and a sodium chloride aqueous solution. Then, the solvent was distilled off under reduced pressure to obtain 34.0 g of the desired product. (Yield: 95%) Melting point: 53.0°–54.0° C.

(2) Preparation of 1-methyl-2'-methyl-3'-nitrobenzyl alcohol

To 50 ml of a methanol solution of 0.5 g of sodium hydroxide, 0.9 g of sodium borohydride was added at 0° C., and then 100 ml of a methanol solution of 14.3 g of 2'-methyl-3'-nitroacetophenone was dropwise added thereto. The temperature of the mixture was returned to room temperature and reacted for 1 hour. After the reaction, the reaction mixture was poured into water and extracted with benzene. The subsequent operation was conducted in a usual manner to obtain 14.3 g of the desired product as an oily substance. (Yield: 99%)

Subsequently, the synthesis was conducted in the same manner as in Reference Example 1 to obtain intermediates (3) to (9).

(3) 1-Methyl-2'-methyl-3'-nitrobenzyl methyl ether: Oily substance (4) 1-Methyl-3'-amino-2'-methylbenzyl methyl ether: Oily substance (5) 1-Methyl-3'-amino-2'-methyl-6'-thiocyanobenzyl methyl ether: Solid (6) 1-Methyl-3'-amino-2'-methyl-6'-methylthiobenzyl methyl ether: Oily substance (7) 1-Methyl-3'-iodo-2'-methyl-6'-methylthiobenzyl: Oily substance (8) 3-(1-Methoxyethyl)-2-methyl-4-methylthiobenzoic acid: Oily substance (9) 4-Methanesulfonyl-3-(1-methoxyethyl)-2-methylbenzoic acid: Melting point: 106°-109° C.

REFERENCE EXAMPLE 11

Preparation of 2,4-dichloro-3-methoxycarbonylbenzoic acid (1) 2,4-dichloro-3-nitrobenzoic acid To a solution of 25 ml of fuming nitric acid and 20 ml of sulfuric acid, 25 g of 2,4-dichlorobenzoic acid was gradually added. After completion of the heat generation, the reaction mixture was poured into ice water. Precipitated solid was washed with water and dried to obtain 23.0 g of the desired product.

(2) Methyl 2,4-dichloro-3-nitrobenzoate 23.0 g of 2,4-dichloro-3-nitrobenzoic acid and 150 ml of thionyl chloride were refluxed for 6 hours under heating. Then, thionyl chloride was distilled off to obtain crude 2,4-dichloro-3-nitrobenzoyl chloride. 200 ml of methanol was added to the crude compound and refluxed under heating. Methanol was distilled off, and then ethyl acetate was added thereto to obtain an ethyl acetate solution. The solution was washed sequentially with a 5% sodium hydroxide aqueous solution, diluted hydrochloric acid and water. After drying, the solvent was distilled off to obtain 21.8 g of the desired product. Melting point: 72°-74° C.

Subsequently, the synthesis was conducted in the same manner as in Reference Example 1 to obtain intermediates (3) and (4), and the desired product (5).

(3) Methyl 3-amino-2,4-dichlorobenzoate: Oily substance (4) Methyl 2,4-dichloro-3-iodobenzoate: Oily substance (5) 2,4-dichloro-3-methoxycarbonylbenzoic acid: Melting point: 183°-185° C.

REFERENCE EXAMPLE 12

Preparation of 2-chloro-3-cyanomethyl-4-methanesulfonyl benzoic acid (1) Methyl 2-chloro-3-cyanomethyl-4-methanesulfonylbenzoate 5.0 g of methyl 3-bromomethyl-2-chloro-4-methanesulfonylbenzoate was added to a solution of 0.4 g of 18-crown-6 and 1.9 g of potassium cyanide in 50 ml of acetonitrile. The mixture was stireed for 72 hours at room temperature. After filtering off the solid, water was added to the filtrate, and the mixture was extracted with chloroform. After washing the extract with water and drying it, the solvent was distilled off to obtain a crude product. The crude product was purified by short silica gel column chlomatography (eluent: chloroform) to obtain 4.1 g of the desired product. Melting point: 151°-155° C.

(2) 2-chloro-3-cyanomethyl-4-methanesulfonylbenzoic acid

To 4.0 g of methyl 2-chloro-3-cyanomethyl-4-methanesulfonylbenzoate and 50 ml of methanol, 5 ml of an aqueous solution containing 0.72 g of sodium hydroxide (93%) was gradually added. The mixture was stirred for 15 minutes at room temperature. Then, the reaction mixture was neutralized with diluted hydrochloric acid, methanol was distilled off under reduced pressure and the concentrated solution was extracted with chloroform. After washing the extract with water and drying it, chloroform was distilled off to obtain 0.9 g of the desired product. Melting point: 169°-172° C.

REFERENCE EXAMPLE 13

Preparation of 3-acetoxymethyl-2-chloro-4-methanesulfonyl benzoic acid (1) Methyl 3-acetoxymethyl-2-chloro-4-methanesulfonylbenzoate 50 ml of a DMF solution containing 5.0 g of methyl 3-bromomethyl-2-chloro-4-methanesulfonylbenzoate and 1.2 g of sodium acetate, was stirred for 2 hours at 100° C. After cooling, the reaction mixture was poured into ice water and extracted with chloroform. After washing the extract with water and drying it, the solvent was distilled off to obtain 4.2 g of the desired product. Melting point: 165°-168° C.

(2) 2-chloro-3-hydroxymethyl-4-methanesulfonylbenzoic acid 6 ml of an aqueous solution containing 1.3 g of sodium hydroxide (93%), was added to 3.9 g of methyl 3-acetoxymethyl-2-chloro-4-methanesulfonylbenzoate and 100 ml of methanol. The mixture was stirred for 30 minutes at room temperature. 50 ml of water was added thereto, and methanol was distilled off under reduced pressure. Then, the reaction mixture was acidified with hydrochloric acid and extracted with chloroform. The extract was concentrated to dryness to obtain 1.3 g of the desired product. Melting point: 240°-245° C.

(3) 3-acetoxymethyl-2-chloro-4-methanesulfonylbenzoic acid 1.3 g of 2-chloro-3-hydroxymethyl-4-methanesulfonyl benzoic acid and 30 ml of acetic anhydride, was refluxed for 3 hours under heating. The reaction mixture was concentrated under reduced pressure. Then, 50 ml of water was added thereto and warmed for 1 hour. Precipitated solid was collected by filtration, washed with water and dried to obtain 1.35 g of the desired product. Melting point: 219°-223° C.

REFERENCE EXAMPLE 14

Preparation of 2,4-dichloro-3-methoxymethylbenzoic acid

This compound was prepared in the same manner as in Reference Examples 3(1) and 4. Melting point: 130°-136° C.

The physical properties of the intermediates were as follows:

(1) Methyl 3-bromomethyl-2,4-dichlorobenzoate: Melting point: 55°-58° C.

(2) Methyl 2,4-dichloro-3-methoxymethylbenzoate: Oily substance

The physical properties of benzoic acids prepared in accordance with the preceding Reference Examples will be given in Tables 1 and 2 including those of the preceding Reference Examples.

TABLE 1

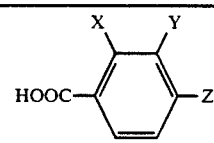

| X | Y | Z | Melting point (°C.) |
|---|---|---|---|
| Me | CH₂OMe | SMe | 192~194 |
| Me | CH₂OMe | SO₂Me | 129~131 |
| Me | CO₂Me | SMe | 178~178.5 |
| Me | CO₂Me | SO₂Me | 151~152 |
| Me | CH₂OEt | SMe | 172~175 |

TABLE 1-continued

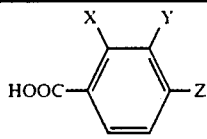

| X | Y | Z | Melting point (°C.) |
|---|---|---|---|
| Me | CH$_2$OEt | SO$_2$Me | 160~162 |
| Cl | CO$_2$Me | Cl | 183~185 |
| Me | CHMeOMe | SMe | Oily substance |
| Me | CHMeOMe | SO$_2$Me | 106~109 |
| Me | CO$_2$Pr-i | SMe | 151~153 |
| Me | CO$_2$Pr-i | SO$_2$Me | 153~155 |
| Cl | CH$_2$OMe | SO$_2$Me | 137~141 |
| Me | CH$_2$OPr-i | SMe | 134~138 |
| Me | CH$_2$OPr-i | SO$_2$Me | 159~161 |
| Me | CO$_2$CH$_2$CH$_2$OMe | SMe | 90~93 |
| Me | CO$_2$CH$_2$CH$_2$OMe | SO$_2$Me | 118~121 |
| Cl | CH$_2$SEt | SO$_2$Me | 172~174 |
| Me | CO$_2$Et | SMe | 114~120 |
| Me | CO$_2$Et | SO$_2$Me | 119.7~127.9 |
| Cl | CH$_2$OCH$_2$CH$_2$OMe | SO$_2$Me | 93~95 |
| Cl | CH$_2$N(cyclohexyl) | SO$_2$Me | Oily substance |
| Me | CO$_2$(cyclohexyl) | SMe | 169~172 |
| Me | CO$_2$(cyclohexyl) | SO$_2$Me | 129~134 |
| Me | CO$_2$Pr-n | SMe | 138~142 |
| Me | CO$_2$Pr-n | SO$_2$Me | 142~146 |
| Cl | CH$_2$OH | SO$_2$Me | 240~245 |
| Cl | CO$_2$Me | SMe | 176~179 |
| Cl | CO$_2$Me | SO$_2$Me | 160~162 |
| Cl | CO$_2$Pr-i | SMe | 114~118 |
| Cl | CO$_2$Pr-i | SO$_2$Me | 146~148 |
| OMe | CO$_2$Me | SMe | 107~109 |
| OMe | CO$_2$Me | SO$_2$Me | 113~119 |
| Me | CHEtOMe | SMe | Oily substance |
| Me | CHEtOMe | SO$_2$Me | Oily substance |
| Me | CHMeOEt | SMe | Oily substance |
| Me | CHMeOEt | SO$_2$Me | Oily substance |
| Cl | CH$_2$OCH$_2$C≡CH | SO$_2$Me | 166~169 |
| Cl | CH$_2$OCH$_2$CH=CH$_2$ | SO$_2$Me | 118~119 |
| Cl | CH$_2$OAm-n | SO$_2$Me | Oily substance |
| Me | CO$_2$Am-i | SMe | 98~105 |
| Me | CO$_2$Am-i | SO$_2$Me | 107~113 |
| Cl | CH$_2$OCH$_2$CF$_3$ | SO$_2$Me | 155~157 |
| OMe | CH$_2$OMe | SMe | 157~161 |
| OMe | CH$_2$OMe | SO$_2$Me | Oily substance |
| Me | CO$_2$CH$_2$CH$_2$Cl | SMe | 138~144 |
| Me | CO$_2$CH$_2$CH$_2$Cl | SO$_2$Me | 121~126 |
| Cl | CH$_2$CN | SO$_2$Me | 169~172 |
| Cl | CH$_2$OAc | SO$_2$Me | 219~223 |
| Cl | CH$_2$OMe | Cl | 130~136 |
| Cl | CO$_2$Et | SO$_2$Me | 156~159 |
| Cl | CH=CHOMe (trans) | SO$_2$Me | 146~149 |
| Cl | CON(Et)$_2$ | SO$_2$Me | 196~201 |

TABLE 2

| X | Y | Z | $^1$H-NMR (δ, ppm) [Solvent] |
|---|---|---|---|
| Me | CHEtOMe | SO$_2$Me | 1.19(3H, t), 1.63(3H, d), 2.78(3H, s), 3.18(3H, s), 3.35(2H, q), 5.63(1H, q), 7.81(2H, A-B q), 10.20(1H, s) [CDCl$_3$] |
| Me | CHMeOEt | SMe | 1.00(3H, t), 1.67~2.26(2H, m), 2.46(3H, s), 2.69(3H, s), 3.21(3H, s), 4.91(1H, d-d) 7.48(2H, A-Bq), 10.2(1H, s) [CDCl$_3$] |
| Me | CHMeOEt | SO$_2$Me | 1.04(3H, t), 1.60~2.20(2H, m), 2.66(3H, s), 3.23 (6H, s), 5.26(1H, d-d), 7.79(2H, A-B q) 9.0(1H, Broad s) [CDCl$_3$ + DMSO-d$_6$] |
| OMe | CH$_2$OMe | SO$_2$Me | 3.04(3H, s), 3.24(3H, s), 3.71(3H, s), 4.71(2H, s), 7.71(2H, s), 8.88(1H, Broad s) [CDCl$_3$ + DMSO-d$_6$] |

These benzoic acids can readily be led to benzoyl chlorides by chlorinating agents such as phosphorus pentachloride, thionyl chloride and sulfuryl chloride.

By using such benzoic acids or benzoyl chlorides, compounds of the present invention can be readily prepared in accordance with reaction schemes (1) to (4).

The present invention will be described in further detail with reference to Examples. However, it should be understood that the present invention is by no means restricted to such specific Examples.

EXAMPLE 1

Preparation of 1-ethyl-5-hydroxy-4-(4-methanesulfonyl-3-methoxymethyl-2-methylbenzoyl)pyrazole 1.12 g (0.01 mol) of 1-ethyl-5-hydroxypyrazole is dissolved in 30 ml of t-amyl alcohol, and then 2.59 g (0.01 mol) of 4-methanesulfonyl-3-methoxymethyl-2-methylbenzoic acid, 2.06 g (0.01 mol) of N,N'-dicyclohexylcarbodiimide and 0.69 g (0.005 mol) of anhydrous potassium carbonate were sequentially added thereto. The mixture was reacted at a temperature of from 80° to 90° C. for 8 hours under stirring. After completion of the reaction, t-amyl alcohol was distilled off under reduced pressure, and 30 ml of water was added to the residue to dissolve the soluble components. The mixture was subjected to filtration to separate out the insolubles. The aqueous solution thus obtained was washed with chloroform, and concentrated hydrochloric acid was added to adjust pH < 1. The precipitated oil component was extracted with chloroform. The solvent was distilled off under reduced pressure, and the residue was purified with silica gel column chromatography (eluent: ethyl acetate/ethanol=9/1) to obtain 2.3 g of the desired product. (Yield: 66%, melting point: 116°–118° C.)

EXAMPLE 2

Preparation of 1-ethyl-5-hydroxy-4-(4-methanesulfonyl-3-methoxycarbonyl-2-methylbenzoyl)pyrazole 1.12 g (0.01 mol) of 1-ethyl-5-hydroxypyrazole was dissolved in 30 ml of t-amyl alcohol, and 2.72 g (0.01 mol) of 4-methanesulfonyl-3-methoxycarbonyl-2-methylbenzoic acid, 2.27 g (0.011 mol) of N,N'-dicyclohexylcarbodiimide and 0.76 g (0.0055 mol) of anhydrous potassium carbonate were sequentially added thereto. The mixture was reacted at 80° C. for 6 hours under stirring. After completion of the reaction, t-amyl alcohol was distilled off under reduced pressure, and then water was added to the residue to dissolve the soluble component. The mixture was subjected to filtration to separate out the insolubles. The aqueous solution thus obtained was washed twice with chloroform, and then concentrated hydrochloric acid was added to adjust pH<1. The precipitated oil component was extracted with chloroform. The chloroform layer was washed sequentially with water and a saturated sodium chloride aqueous solution and then dried over anhydrous sodium sulfate. Then, the solvent was distilled off under reduced pressure, and the residue thus obtained was recrystallized from water/ethanol to obtain 2.26 g of the desired product. (Yield: 62%, melting point: 150°–152° C.)

EXAMPLE 3

Preparation of 5-hydroxy-(3-isopropoxycarbonyl-4-methanesulfonyl-2-methylbenzoyl)-1-methylpyrazole The operation and treatment were conducted in the same manner as in Example 1 except that 1.12 g of 1-ethyl-5-hydroxypyrazole was changed to 0.98 g of 5-hydroxy-1-methylpyrazole, and 2.72 g of 4-methanesulfonyl-3-methoxycarbonyl-2-methylbenzoic acid was changed to 3.00 g of 3-isopropoxycarbonyl-4-methanesulfonyl-2-methylbenzoic acid, to obtain 1.71 g of the desired product. (Yield: 45%, melting point: 192°–194° C.)

EXAMPLE 4

Preparation of 4-(2-chloro-3-ethylthiomethyl-4-methanesulfonylbenzoyl)-1-ethyl-5-hydroxypyrazole 3 g of 2-chloro-3-ethylthiomethyl-4-methanesulfonylbenzoic acid, 0.72 g of potassium carbonate, 50 ml of t-amyl alcohol, 1.95 g of N,N'-dicyclohexylcarbodiimide and 4.5 g of a 25% t-amyl alcohol solution of 1-ethyl-5-pyrazolone were mixed and heated under stirring for 4 hours at a temperature of from 70° to 80° C. After cooling, the mixture was distilled under reduced pressure, and 200 ml of water was added to the residue. After filtering off the insolubles, the filtrate was washed with chloroform. Hydrochloric acid was added to the aqueous layer, and the mixture was extracted with chloroform. The extract was dried, and the solvent was distilled off to obtain the desired product as a crude product. The crude product was recrystallized from ethanol to obtain 1.88 g of the purified product. (Melting point: 142°–145° C.)

EXAMPLE 5

Preparation of 4-(2-chloro-5-ethanesulfonylmethyl-4-methanesulfonylbenzoyl)-1-ethyl-5-hydroxypyrazole 0.5 g of the compound obtained in Example 4 was dissolved in a solution comprising 30 ml of $CHCl_3$ and 30 ml of THF at room temperature, and 2.2 equivalent of m-chloroperbenzoic acid was added thereto under cooling in ice bath. The mixture was gradually returned to room temperature and stirred for 1 day. The solvent was distilled off, and crystals thus obtained were collected by filtration and washed with ethyl ether to obtain 2.2 g of the desired product. (Melting point: 133°–135° C.)

EXAMPLE 6

Preparation of 4-(2-chloro-3-ethanesulfinyl-4-methanesulfonylbenzoyl)-1-ethyl-5-hydroxypyrazole 0.45 g of the compound obtained in Example 4 was dissolved in 30 ml of dioxane, and 0.21 g of sodium bromite trihydrate was added thereto. The mixture was stirred at room temperature for 30 minutes, and then water was added thereto. The mixture was extracted with chloroform. The extract was dried, and the solvent was distilled off to obtain a crude product. The crude product was purified by column chromatography (eluted with chloroform/ethanol) to obtain 0.2 g of the desired product as an oily substance.

EXAMPLE 7

Preparation of 4-(2,4-dichloro-3-methoxycarbonylbenzoyl)-1-ethyl-5-hydroxypyrazole This compound was prepared in the same manner as in Example 2. Melting point: 167°–170° C.

EXAMPLE 8

Preparation of 5-benzyloxy-4-(2,4-dichloro-3-methoxycarbonylbenzoyl)-1-ethylpyrazole A solution prepared by dissolving 0.3 g of the compound prepared in Example 7 and 0.1 g of triethylamine in 13 ml of benzene, was stirred at room temperature for 30 minutes, and then at 50° C. for 3 hours. Insoluble substances were filtered off, and then the filtrate was concentrated under reduced pressure. The concentrated product was purified by silica gel column chromatography (eluent: benzene/ethyl acetate) to obtain 0.15 g of the desired product as an oily substance.

EXAMPLE 9

Preparation of 5-hydroxy-4-(4-methanesulfonyl-3-methoxymethyl-2-methylbenzoyl)-3-methoxymethyl-1-methylpyrazole (1) 5-(4-methanesulfonyl-3-methoxymethyl-2-methylbenzoyl)oxy-3-methoxymethyl-1-methylpyrazole 1.9 g of 5-hydroxy-3-methoxymethylpyrazol was added to a mixture consisting of 8 ml of an aqueous solution containing 0.5 g of potassium hydroxide (85%) and 12 ml of chloroform, and then 4-methanesulfonyl-3-methoxymethyl-2-methylbenzoyl chloride was added thereto. The mixture was stirred for 3 hours at room temperature. Then, the reaction mixture was extracted with chloroform. The chloroform solution was washed with water and dried to obtain the desired product substantially quantitatively as an oily substance.

(2) 5-hydroxy-4-(4-methanesulfonyl-3-methoxymethyl-2-methylbenzoyl)-3-methoxymethyl-1-methylpyrazole 3.0 g of the compound obtained in step (1), 2.7 g of potassium carbonate and 8 ml of dioxane, were stirred at 120° C. for 3.5 hours. 20 ml of water was added thereto and then the mixture was left to cool. The reaction solution was washed with chloroform and acidified with hydrochloric acid. The reaction solution was extracted with chloroform, washed with water and dried to obtain 1.8 g of a crude product. The crude product was recrystallized from ethanol to obtain 1.2 g of the desired product. Melting point: 100°–104° C.

EXAMPLE 10

Preparation of 4-(3-acetoxymethyl-2-chloro-4-methanesulfonylbenzoyl)-1-ethyl-5-hydroxypyrazole This compound was prepared in the same manner as in Example 2. Melting point: 140°–144° C.

EXAMPLE 11

Preparation of 4-(2-chloro-3-hydroxymethyl-4-methanesulfonylbenzoyl)-1-ethyl-5-hydroxypyrazole To 30 ml of a methanol solution containing 0.3 g of the compound prepared in Example 10, 5 ml of an aqueous solution containing 0.1 g of sodium hydroxide (93%) was added, and the mixture was stirred for 2 hours at room temperature. Methanol was distilled off under reduced pressure. Then, hydrochloric acid was added to the residue. The precipitated product was collected by filtration to obtain 0.2 g of the desired product. Melting point: 70°–76° C.

The physical properties of the compounds prepared in the same manner as the preceding Examples will be given in Tables 3 and 4 including those of the preceding Examples.

TABLE 3

| Compound No. | A | B | X | Y | Z | Q | Melting point (°C.) |
|---|---|---|---|---|---|---|---|
| 1 | Me | H | Me | $CH_2OMe$ | $SO_2Me$ | H | Oily substance |
| 2 | Me | H | Me | $CH_2OMe$ | $SO_2Me$ | $CH_2Ph$ | Oily substance |
| 3 | Et | H | Me | $CH_2OMe$ | $SO_2Me$ | H | 116–118 |
| 4 | i-Pr | H | Me | $CH_2OMe$ | $SO_2Me$ | H | Oily substance |
| 5 | Me | H | Me | $CO_2H$ | $SO_2Me$ | H | 274–274.5 |
| 6 | Me | H | Me | $CO_2Me$ | $SO_2Me$ | H | 199–201 |
| 7 | Et | H | Me | $CO_2Me$ | $SO_2Me$ | H | 150–152 |
| 8 | Me | H | Me | $CO_2Et$ | $SO_2Me$ | H | 174–174.5 |
| 9 | Et | H | Me | $CO_2Et$ | $SO_2Me$ | H | 78–81 |
| 10 | Me | H | Me | $CO_2Pr$-i | $SO_2Me$ | H | 192–194 |
| 11 | Et | H | Me | $CO_2Pr$-i | $SO_2Me$ | H | 125–128 |
| 12 | Me | H | Cl | $CO_2Me$ | Cl | H | 123–126 |
| 13 | Me | H | Cl | $CO_2Me$ | Cl | p-Ts | Oily substance |
| 14 | Me | H | Me | $CH_2OEt$ | $SO_2Me$ | H | 178–179 |
| 15 | Et | H | Me | $CH_2OEt$ | $SO_2Me$ | H | Oily substance |
| 16 | i-Pr | H | Me | $CH_2OEt$ | $SO_2Me$ | H | Oily substance |
| 17 | Me | Me | Me | $CH_2OEt$ | $SO_2Me$ | H | Oily substance |
| 18 | Me | H | Me | $CHMeOMe$ | $SO_2Me$ | H | 238–240 |
| 19 | Et | H | Me | $CHMeOMe$ | $SO_2Me$ | H | 138–141 |
| 20 | Me | H | Cl | $CH_2OMe$ | $SO_2Me$ | H | 189–190 |
| 21 | Et | H | Cl | $CH_2OMe$ | $SO_2Me$ | H | 151–154 |
| 22 | i-Pr | H | Cl | $CH_2OMe$ | $SO_2Me$ | H | 142–144 |
| 23 | Et | H | Me | $CH_2OPr$-i | $SO_2Me$ | H | 125–127 |
| 24 | Me | H | Me | $CO_2CH_2CH_2OMe$ | $SO_2Me$ | H | 114–117 |
| 25 | Et | H | Me | $CO_2CH_2CH_2OMe$ | $SO_2Me$ | H | 122–124 |
| 26 | Me | H | Cl | $CH_2OCH_2CH_2OMe$ | $SO_2Me$ | H | 157–161 |
| 27 | Et | H | Cl | $CH_2SEt$ | $SO_2Me$ | H | 142–145 |
| 28 | Et | H | Cl | $CH_2SOEt$ | $SO_2Me$ | H | Oily substance |
| 29 | Et | H | Cl | $CH_2SO_2Et$ | $SO_2Me$ | H | 133–135 |
| 30 | Et | H | Me | $CO_2Pr$-n | $SO_2Me$ | H | Oily substance |
| 31 | Me | H | Cl | 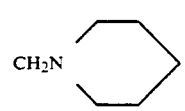 | $SO_2Me$ | H | Oily substance |
| 32 | Me | H | Me | 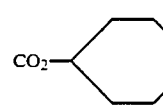 | $SO_2Me$ | H | 220–222 |
| 33 | Et | H | Me | 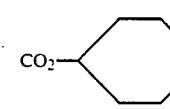 | $SO_2Me$ | H | 179–183 |
| 34 | Me | H | Cl | $CO_2Me$ | $SO_2Me$ | H | 183–185 |
| 35 | Et | H | Cl | $CO_2Me$ | $SO_2Me$ | H | 174–176 |

TABLE 3-continued

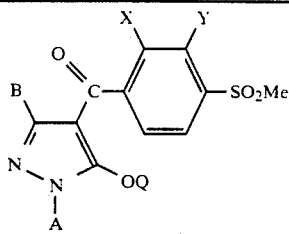

| Compound No. | A | B | X | Y | Z | Q | Melting point (°C.) |
|---|---|---|---|---|---|---|---|
| 36 | Pr-i | H | Cl | $CO_2Me$ | $SO_2Me$ | H | 138~140 |
| 37 | Et | H | Cl | $CH_2OCH_2C\equiv CH$ | $SO_2Me$ | H | 161~164 |
| 38 | Me | H | Cl | $CH_2OAm$-n | $SO_2Me$ | H | Oily substance |
| 39 | Et | H | Me | $CH_2OMe$ | $SO_2Me$ | K | 180~190 |
| 40 | Et | H | Me | $CH_2OMe$ | $SO_2Me$ | Na | 210~216 |
| 41 | Et | H | Me | $CH_2OMe$ | $SO_2Me$ | $NH_3^+$ Pr-i | 95~102 |
| 42 | Me | H | OMe | $CO_2Me$ | $SO_2Me$ | H | 195~198 |
| 43 | Me | H | Cl | $CO_2Pr$-i | $SO_2Me$ | H | 117~119 |
| 44 | Et | H | Cl | $CO_2Pr$-i | $SO_2Me$ | H | 141~143 |
| 45 | Me | H | Cl | $CH_2OCH_2CF_3$ | $SO_2Me$ | H | 167~170 |
| 46 | Et | H | Me | $CH_2OMe$ | $SO_2Me$ | 1/2 Ca | 232~242 |
| 47 | Pr-i | H | Me | $CO_2Me$ | $SO_2Me$ | H | 116~121 |
| 48 | Me | H | OMe | $CH_2OMe$ | $SO_2Me$ | H | 154~157 |
| 49 | Et | H | Me | $CO_2CH_2CH_2Cl$ | $SO_2Me$ | H | 149~152 |
| 50 | Et | H | OMe | $CO_2Me$ | $SO_2Me$ | H | 172~175 |
| 51 | Et | H | Cl | $CO_2Me$ | Cl | H | 167~170 |
| 52 | Et | H | Cl | $CO_2Me$ | Cl | $CH_2$-Ph | Oily substance |
| 53 | Pr-i | H | Cl | $CO_2Me$ | Cl | H | 144~151 |
| 54 | Pr-i | H | Cl | $CO_2Me$ | Cl | $CH_2$-Ph | 104~110 |
| 55 | Me | $CH_2OMe$ | Me | $CH_2OMe$ | $SO_2Me$ | H | 100~104 |
| 56 | Et | H | Cl | $CH_2CN$ | $SO_2Me$ | H | 235~239 |
| 57 | Et | H | Cl | $CH_2OAc$ | $SO_2Me$ | H | 140~144 |
| 58 | Et | H | Cl | $CH_2OH$ | $SO_2Me$ | H | 70~76 |
| 59 | Et | H | Me | $CO_2Me$ | SMe | H | 142~146 |
| 60 | Et | H | Cl | $CH_2OMe$ | Cl | H | 102~104 |
| 61 | Et | H | Cl | $CO_2Et$ | $SO_2Me$ | H | 100~104 |
| 62 | Et | H | Me | $CH_2OMe$ | SMe | H | Oily substance |
| 63 | Me | H | Cl | $CH_2OMe$ | Cl | H | 141~144 |
| 64 | Et | H | Cl | CH=CHOMe (trans) | $SO_2Me$ | H | 165~171 |
| 65 | Pr-i | H | Cl | $CO_2Et$ | $SO_2Me$ | H | 123~126 |
| 66 | Et | H | OMe | $CH_2OMe$ | $SO_2Me$ | H | Oily substance |
| 67 | Et | H | Me | CHMeOEt | $SO_2Me$ | H | Oily substance |
| 68 | Et | H | Me | CHEtOMe | $SO_2Me$ | H | Oily substance |
| 69 | Et | H | Cl | $CON(Et)_2$ | $SO_2Me$ | H | 94~97 |

The compounds represented by the Compound Nos. in the following Table are the same as represented by the corresponding Compound Nos. in Table 3.

TABLE 4

| Compound No. | $^1$H-NMR (δ, ppm) [Solvent] |
|---|---|
| 1 | 2.47(3H, s), 3.22(3H, s), 3.50(3H, s), 3.69(3H, s), 4.96(2H, s), 7.30(1H, s). 7.78(2H, A-Bq). 10.9(1H) [CDCl$_3$] |
| 2 | 2.41(3H, s), 3.17(3H, s), 3.50(3H, s), 4.94(2H, s), 5.53(2H, s), 7.30~8.12 (8H, m) [CDCl$_3$] |
| 3 | 1.44(3H, t), 2.48(3H, s), 3.23(3H, s), 3.51(3H, s), 4.07(2H, q), 4.98(2H, s), 7.36(1H, s), 7.82(2H, A-Bq) [CDCl$_3$] |
| 4 | 1.48(6H, d), 2.47(3H, s), 3.19(3H, s), 3.48(3H, s), 4.53(1H, m), 4.92(2H, s), 7.18(1H, s), 7.69(2H, A-Bq), 9.57(1H) [CDCl$_3$] |
| 13 | 2.43(3H, s), 3.78(3H, s), 3.94(3H, s), 7.24~7.81(7H, m) [CDCl$_3$] |
| 15 | 1.07(3H. t), 2.27(3H, s), 3.01(3H, s). 3.30~3.65(5H, m), 4.77(2H, s). 6.99(1H, s), 7.48(1H, A-B q). 8.22(1H, s) [CDCl$_3$] |
| 28 | 1.45(3H, t), 3.04(2H, q), 4.05(2H, q), 4.91(2H, q), 7.29(1H, s), 7.70(1H, s), 7.85(2H, q) [CDCl$_3$] |
| 30 | 0.91~2.03(8H, m), 2.41(3H, s), 3.20(3H, s), 3.91~4.47(4H, m), 7.36~8.08(4H, m), [CDCl$_3$] |
| 16 | 1.26(3H, t), 1.49(3H, d), 2.49(3H, s), 3.24(3H, s), 3.69(2H, q), 4.59(1H, m), 5.00(2H, s), 7.28~8.14(4H, m), [CDCl$_3$] |
| 17 | 1.27(3H, t), 1.67(3H, s), 2.42(3H, s), 3.23(3H, s), 3.63(3H, s), 3.68(2H, q), 5.02(2H, s), 7.7(1H, s), 7.75(2H, A-B q) [CDCl$_3$] |
| 62 | 1.45(3H, t), 2.49(6H, Broad s), 3.44(3H, q), 4.03(2H, q), 4.66(2H, s), 7.29(2H, q), 7.39(1H, s), |
| 66 | 1.47(3H, t), 3.29(3H, s), 3.51(3H, s) 3.82(3H, s), 4.09(2H, q), 5.00(2H, s), 7.50(1H, s), 7.84(2H, A-Bq), 7.96(1H, s) [CDCl$_3$] |
| 67 | 1.07-1.67(9H, m), 2.59(3H, s) 3.17(3H, s), 3.42(2H, t), 3.96(2H, t). 5.61(1H, q), 7.27(1H, s), 7.61(2H, A-Bq) 9.66(1H, Broad s) [CDCl$_3$] |
| 68 | 1.09(3H, t), 1.45(3H, t),. 2.55(3H, s) 3.16(3H, s), 3.27(3H, s), 3.70-4.20(4H, m), 5.13-5.36(1H, m), 7.14(1H, s), 7.60(2H, A-Bq), |

TABLE 4-continued

| Compound No. | $^1$H-NMR (δ, ppm) [Solvent] |
|---|---|
| | 9.46(1H, Broad s) [CDCl$_3$] |

Compounds which can be prepared in the same manner as the preceding Examples will be given in Table 5 including those of the preceding Examples. However, the present invention is not restricted to such compounds.

Various symbols used in Table 5 has the following meanings.

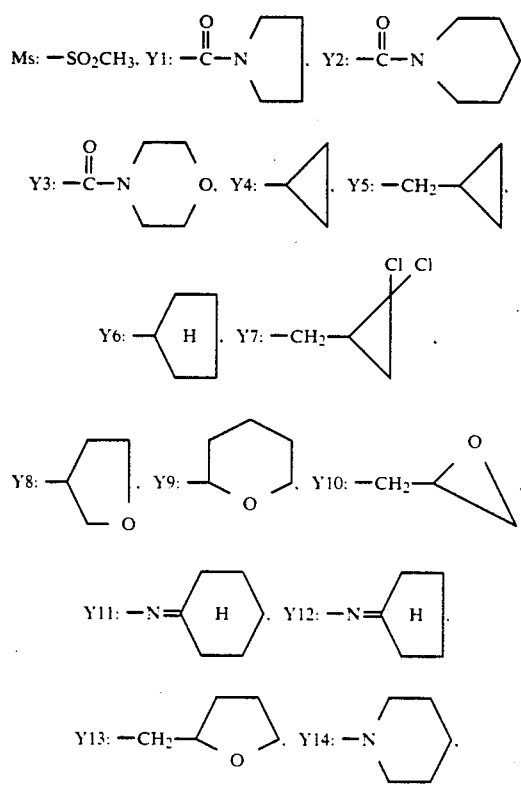

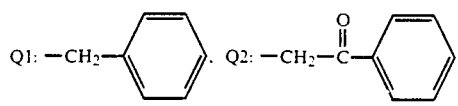

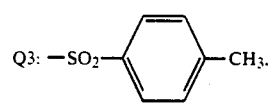

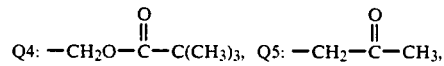

Q6: —CH$_2$CN, Q7: —CH$_2$C≡CH, Q8: —CH$_2$CH=CH$_2$,

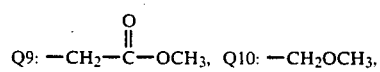

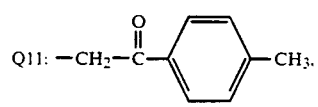

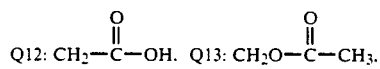

Q14: CH$_2$O—C(=O)—OCH$_3$, Q15: —CH$_2$SCH$_3$,

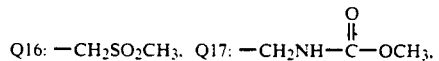

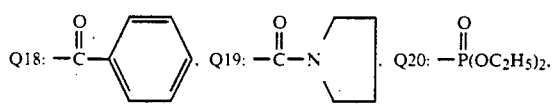

Q21: —SO$_2$CH$_3$, Q22: —SO$_2$CF$_3$

TABLE 5

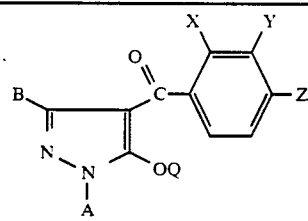

| A | B | X | Y | Z | Q |
|---|---|---|---|---|---|
| Me | H | Cl | COOMe | MeS | H |
| Me | H | Cl | COOMe | MeSO | H |
| Me | H | Cl | COOMe | Ms | H |
| Me | H | Cl | COOMe | Ms | Q1 |
| Me | H | Cl | COOMe | Ms | Q2 |
| Me | H | Cl | COOMe | Ms | Q3 |
| Me | H | Cl | COOMe | Ms | Q4 |
| Me | H | Cl | COOMe | Ms | Q5 |
| Me | H | Cl | COOMe | Ms | Q6 |
| Me | H | Cl | COOMe | Ms | Q20 |
| Me | Me | Cl | COOMe | Ms | H |
| Me | Cl | Cl | COOMe | Ms | H |
| Me | CF$_3$ | Cl | COOMe | Ms | H |

-continued

| | | | | | |
|---|---|---|---|---|---|
| Me | OMe | Cl | COOMe | Ms | H |
| Me | SMe | Cl | COOMe | Ms | H |
| Me | H | Cl | COOEt | MeS | H |
| Me | H | Cl | COOEt | MeSO | H |
| Me | H | Cl | COOEt | Ms | H |
| Me | H | Cl | COOEt | Ms | Q1 |
| Me | H | Cl | COOEt | Ms | Q18 |
| Me | H | Cl | COOEt | Ms | Q13 |
| Me | H | Cl | COOEt | Ms | Q4 |
| Me | H | Cl | COOEt | Ms | Q5 |
| Me | H | Cl | COOEt | Ms | Q6 |
| Me | H | Cl | COOEt | Ms | Q22 |
| Me | Me | Cl | COOEt | Ms | H |
| Me | Cl | Cl | COOEt | Ms | H |
| Me | CF$_3$ | Cl | COOEt | Ms | H |
| Me | OMe | Cl | COOEt | Ms | H |
| Me | SMe | Cl | COOEt | Ms | H |
| Me | H | Cl | COOCH(CH$_3$)$_2$ | MeS | H |
| Me | H | Cl | COOCH(CH$_3$)$_2$ | MeSO | H |
| Me | H | Cl | COOCH(CH$_3$)$_2$ | Ms | H |
| Me | H | Cl | COOCH(CH$_3$)$_2$ | Ms | Q7 |
| Me | H | Cl | COOCH(CH$_3$)$_2$ | Ms | Q12 |
| Me | H | Cl | COOCH(CH$_3$)$_2$ | Ms | Q9 |
| Me | H | Cl | COOCH(CH$_3$)$_2$ | Ms | Q4 |
| Me | H | Cl | COOCH(CH$_3$)$_2$ | Ms | Q5 |
| Me | H | Cl | COOCH(CH$_3$)$_2$ | Ms | Q6 |
| Me | H | Cl | COOCH(CH$_3$)$_2$ | Ms | Q17 |
| Me | Me | Cl | COOCH(CH$_3$)$_2$ | Ms | H |
| Me | Cl | Cl | COOCH(CH$_3$)$_2$ | Ms | H |
| Me | CF$_3$ | Cl | COOCH(CH$_3$)$_2$ | Ms | H |
| Me | OMe | Cl | COOCH(CH$_3$)$_2$ | Ms | H |
| Me | SMe | Cl | COOCH(CH$_3$)$_2$ | Ms | H |
| Me | H | Cl | COOMe | Cl | H |
| Me | H | Cl | COOMe | Cl | Q1 |
| Me | H | Cl | COOMe | Cl | Q2 |
| Me | H | Cl | COOMe | Cl | Q3 |
| Me | H | Cl | COOEt | Cl | H |
| Me | H | Cl | COOEt | Cl | Q1 |
| Me | H | Cl | COOEt | Cl | Q2 |
| Me | H | Cl | COOEt | Cl | Q3 |
| Me | H | Cl | COOCH(CH$_3$)$_2$ | Cl | H |
| Me | H | Cl | COOCH(CH$_3$)$_2$ | Cl | Q1 |
| Me | H | Cl | COOCH(CH$_3$)$_2$ | Cl | Q2 |
| Me | H | Cl | COOCH(CH$_3$)$_2$ | Cl | Q3 |
| Me | H | Cl | CON(CH$_3$)$_2$ | MeS | H |
| Me | H | Cl | CON(CH$_3$)$_2$ | MeSO | H |
| Me | H | Cl | CON(CH$_3$)$_2$ | Ms | H |
| Me | H | Cl | CON(CH$_3$)$_2$ | Ms | Q1 |
| Me | H | Cl | CON(CH$_3$)$_2$ | Ms | Q18 |
| Me | H | Cl | CON(CH$_3$)$_2$ | Ms | Q13 |
| Me | H | Cl | CON(CH$_3$)$_2$ | Ms | Q4 |
| Me | H | Cl | CON(CH$_3$)$_2$ | Ms | Q5 |
| Me | H | Cl | CON(CH$_3$)$_2$ | Ms | Q6 |
| Me | H | Cl | CON(CH$_3$)$_2$ | Ms | Q22 |
| Me | Me | Cl | CON(CH$_3$)$_2$ | Ms | H |
| Me | Cl | Cl | CON(CH$_3$)$_2$ | Ms | H |
| Me | CF$_3$ | Cl | CON(CH$_3$)$_2$ | Ms | H |
| Me | OMe | Cl | CON(CH$_3$)$_2$ | Ms | H |
| Me | SMe | Cl | CON(CH$_3$)$_2$ | Ms | H |
| Me | H | Cl | CON(CH$_3$)$_2$ | Cl | H |
| Me | H | Cl | CON(CH$_3$)$_2$ | Cl | Q1 |
| Me | H | Cl | CON(CH$_3$)$_2$ | Cl | Q2 |
| Me | H | Cl | CON(CH$_3$)$_2$ | Cl | Q3 |
| Me | H | Cl | COOC$_4$H$_9$ | Ms | H |
| Me | H | Cl | COOC$_4$H$_9$ | Cl | H |
| Me | H | Cl | COOCH$_2$CH(CH$_3$)$_2$ | Ms | H |
| Me | H | Cl | COOCH$_2$CH(CH$_3$)$_2$ | Cl | H |
| Me | H | Cl | COOCH(CH$_3$)C$_2$H$_5$ | Ms | H |
| Me | H | Cl | COOCH(CH$_3$)C$_2$H$_5$ | Cl | H |
| Me | H | Cl | COOC(CH$_3$)$_3$ | Ms | H |
| Me | H | Cl | COOC(CH$_3$)$_3$ | Cl | H |
| Me | H | Cl | CONHMe | Ms | H |
| Me | H | Cl | CONHMe | Cl | H |
| Me | H | Cl | CONHEt | Ms | H |
| Me | H | Cl | CONHEt | Cl | H |
| Me | H | Cl | CONHCH(CH$_3$)$_2$ | Ms | H |
| Me | H | Cl | CONHCH(CH$_3$)$_2$ | Cl | H |
| Me | H | Cl | CONHC(CH$_3$)$_3$ | Ms | H |
| Me | H | Cl | CONHC(CH$_3$)$_3$ | Cl | H |
| Me | H | Cl | CONHC$_4$H$_9$ | Ms | H |
| Me | H | Cl | CONHC$_4$H$_9$ | Cl | H |
| Me | H | Cl | CONHCH$_2$CH(CH$_3$)$_2$ | Ms | H |
| Me | H | Cl | CONHCH$_2$CH(CH$_3$)$_2$ | Cl | H |

-continued

| | | | | | |
|---|---|---|---|---|---|
| Me | H | Cl | CONHCH(CH₃)C₂H₅ | Ms | H |
| Me | H | Cl | CONHCH(CH₃)C₂H₅ | Cl | H |
| Me | H | Cl | CONEt₂ | Ms | H |
| Me | H | Cl | CONEt₂ | Cl | H |
| Me | H | Cl | CON[CH(CH₃)₂]₂ | Ms | H |
| Me | H | Cl | CON[CH(CH₃)₂]₂ | Cl | H |
| Me | H | Cl | Y1 | Ms | H |
| Me | H | Cl | Y1 | Cl | H |
| Me | H | Cl | Y2 | Ms | H |
| Me | H | Cl | Y2 | Cl | H |
| Me | H | Cl | Y3 | Ms | H |
| Me | H | Cl | Y3 | Cl | H |
| Me | H | Cl | COOPh | Ms | H |
| Me | H | Cl | COOPh | Cl | H |
| Me | H | Cl | COOCH₂Ph | Ms | H |
| Me | H | Cl | COOCH₂Ph | Cl | H |
| Me | H | Cl | COOCH₂CH=CH₂ | Ms | H |
| Me | H | Cl | COOCH₂CH=CH₂ | Cl | H |
| Me | H | Cl | COOCH₂C≡CH₂ | Ms | H |
| Me | H | Cl | COOCH₂C≡CH₂ | Cl | H |
| Me | H | Cl | C(O)SMe | Ms | H |
| Me | H | Cl | C(O)SMe | Cl | H |
| Me | H | Cl | C(O)SEt | Ms | H |
| Me | H | Cl | C(O)SEt | Cl | H |
| Me | H | Cl | C(O)SCH(CH₃)₂ | Ms | H |
| Me | H | Cl | C(O)SCH(CH₃)₂ | Cl | H |
| Me | H | Cl | C(O)SC₃H₇ | Ms | H |
| Me | H | Cl | C(O)SC₃H₇ | Cl | H |
| Me | H | Cl | C(S)OMe | Ms | H |
| Me | H | Cl | C(S)OMe | Cl | H |
| Me | H | Cl | C(S)OEt | Ms | H |
| Me | H | Cl | C(S)OEt | Cl | H |
| Me | H | Cl | C(S)OCH(CH₃)₂ | Ms | H |
| Me | H | Cl | C(S)OCH(CH₃)₂ | Cl | H |
| Me | H | Cl | C(S)SC₃H₇ | Ms | H |
| Me | H | Cl | C(S)SC₃H₇ | Cl | H |
| Me | H | Cl | C(S)SMe | Ms | H |
| Me | H | Cl | C(S)SMe | Cl | H |
| Me | H | Cl | C(S)SEt | Ms | H |
| Me | H | Cl | C(S)SEt | Cl | H |
| Me | H | Cl | C(S)SCH(CH₃)₂ | Ms | H |
| Me | H | Cl | C(S)SCH(CH₃)₂ | Cl | H |
| Me | H | Cl | C(S)SC₃H₇ | Ms | H |
| Me | H | Cl | C(S)SC₃H₇ | Cl | H |
| Me | H | Me | COOMe | MeS | H |
| Me | H | Me | COOMe | MeSO | H |
| Me | H | Me | COOMe | Ms | H |
| Me | H | Me | COOMe | Ms | Q1 |
| Me | H | Me | COOMe | Ms | Q2 |
| Me | H | Me | COOMe | Ms | Q3 |
| Me | H | Me | COOMe | Ms | Q4 |
| Me | H | Me | COOMe | Ms | Q5 |
| Me | H | Me | COOMe | Ms | Q6 |
| Me | H | Me | COOMe | Ms | Q20 |
| Me | Me | Me | COOMe | Ms | H |
| Me | Cl | Me | COOMe | Ms | H |
| Me | CF₃ | Me | COOMe | Ms | H |
| Me | OMe | Me | COOMe | Ms | H |
| Me | SMe | Me | COOMe | Ms | H |
| Me | H | Me | COOEt | MeS | H |
| Me | H | Me | COOEt | MeSO | H |
| Me | H | Me | COOEt | Ms | H |
| Me | H | Me | COOEt | Ms | Q1 |
| Me | H | Me | COOEt | Ms | Q18 |
| Me | H | Me | COOEt | Ms | Q13 |
| Me | H | Me | COOEt | Ms | Q4 |
| Me | H | Me | COOEt | Ms | Q5 |
| Me | H | Me | COOEt | Ms | Q6 |
| Me | H | Me | COOEt | Ms | Q22 |
| Me | Me | Me | COOEt | Ms | H |
| Me | Cl | Me | COOEt | Ms | H |
| Me | CF₃ | Me | COOEt | Ms | H |
| Me | OMe | Me | COOEt | Ms | H |
| Me | SMe | Me | COOEt | Ms | H |
| Me | H | Me | COOCH(CH₃)₂ | MeS | H |
| Me | H | Me | COOCH(CH₃)₂ | MeSO | H |
| Me | H | Me | COOCH(CH₃)₂ | Ms | H |
| Me | H | Me | COOCH(CH₃)₂ | Ms | Q7 |
| Me | H | Me | COOCH(CH₃)₂ | Ms | Q12 |
| Me | H | Me | COOCH(CH₃)₂ | Ms | Q9 |
| Me | H | Me | COOCH(CH₃)₂ | Ms | Q4 |
| Me | H | Me | COOCH(CH₃)₂ | Ms | Q5 |
| Me | H | Me | COOCH(CH₃)₂ | Ms | Q6 |

-continued

| | | | | | |
|---|---|---|---|---|---|
| Me | H | Me | COOCH(CH₃)₂ | Ms | Q17 |
| Me | Me | Me | COOCH(CH₃)₂ | Ms | H |
| Me | Cl | Me | COOCH(CH₃)₂ | Ms | H |
| Me | CF₃ | Me | COOCH(CH₃)₂ | Ms | H |
| Me | OMe | Me | COOCH(CH₃)₂ | Ms | H |
| Me | SMe | Me | COOCH(CH₃)₂ | Ms | H |
| Me | H | Me | COOMe | Cl | H |
| Me | H | Me | COOMe | Cl | Q1 |
| Me | H | Me | COOMe | Cl | Q2 |
| Me | H | Me | COOMe | Cl | Q3 |
| Me | H | Me | COOEt | Cl | H |
| Me | H | Me | COOEt | Cl | Q1 |
| Me | H | Me | COOEt | Cl | Q2 |
| Me | H | Me | COOEt | Cl | Q3 |
| Me | H | Me | COOCH(CH₃)₂ | Cl | H |
| Me | H | Me | COOCH(CH₃)₂ | Cl | Q1 |
| Me | H | Me | COOCH(CH₃)₂ | Cl | Q2 |
| Me | H | Me | COOCH(CH₃)₂ | Cl | Q3 |
| Me | H | Me | CON(CH₃)₂ | MeS | H |
| Me | H | Me | CON(CH₃)₂ | MeSO | H |
| Me | H | Me | CON(CH₃)₂ | Ms | H |
| Me | H | Me | CON(CH₃)₂ | Ms | Q1 |
| Me | H | Me | CON(CH₃)₂ | Ms | Q18 |
| Me | H | Me | CON(CH₃)₂ | Ms | Q13 |
| Me | H | Me | CON(CH₃)₂ | Ms | Q4 |
| Me | H | Me | CON(CH₃)₂ | Ms | Q5 |
| Me | H | Me | CON(CH₃)₂ | Ms | Q6 |
| Me | H | Me | CON(CH₃)₂ | Ms | Q22 |
| Me | Me | Me | CON(CH₃)₂ | Ms | H |
| Me | Cl | Me | CON(CH₃)₂ | Ms | H |
| Me | CF₃ | Me | CON(CH₃)₂ | Ms | H |
| Me | OMe | Me | CON(CH₃)₂ | Ms | H |
| Me | SMe | Me | CON(CH₃)₂ | Ms | H |
| Me | H | Me | CON(CH₃)₂ | Cl | H |
| Me | H | Me | CON(CH₃)₂ | Cl | Q1 |
| Me | H | Me | CON(CH₃)₂ | Cl | Q2 |
| Me | H | Me | CON(CH₃)₂ | Cl | Q3 |
| Me | H | Me | COOC₄H₉ | Ms | H |
| Me | H | Me | COOC₄H₉ | Cl | H |
| Me | H | Me | COOCH₂CH(CH₃)₂ | Ms | H |
| Me | H | Me | COOCH₂CH(CH₃)₂ | Cl | H |
| Me | H | Me | COOCH(CH₃)C₂H₅ | Ms | H |
| Me | H | Me | COOCH(CH₃)C₂H₅ | Cl | H |
| Me | H | Me | COOC(CH₃)₃ | Ms | H |
| Me | H | Me | COOC(CH₃)₃ | Cl | H |
| Me | H | Me | CONHMe | Ms | H |
| Me | H | Me | CONHMe | Cl | H |
| Me | H | Me | CONHEt | Ms | H |
| Me | H | Me | CONHEt | Cl | H |
| Me | H | Me | CONHCH(CH₃)₂ | Ms | H |
| Me | H | Me | CONHCH(CH₃)₂ | Cl | H |
| Me | H | Me | CONHC(CH₃)₃ | Ms | H |
| Me | H | Me | CONHC(CH₃)₃ | Cl | H |
| Me | H | Me | CONHC₄H₉ | Ms | H |
| Me | H | Me | CONHC₄H₉ | Cl | H |
| Me | H | Me | CONHCH₂CH(CH₃)₂ | Ms | H |
| Me | H | Me | CONHCH₂CH(CH₃)₂ | Cl | H |
| Me | H | Me | CONHCH(CH₃)C₂H₅ | Ms | H |
| Me | H | Me | CONHCH(CH₃)C₂H₅ | Cl | H |
| Me | H | Me | CONEt₂ | Ms | H |
| Me | H | Me | CONEt₂ | Cl | H |
| Me | H | Me | CON[CH(CH₃)₂]₂ | Ms | H |
| Me | H | Me | CON[CH(CH₃)₂]₂ | Cl | H |
| Me | H | Me | Y1 | Ms | H |
| Me | H | Me | Y1 | Cl | H |
| Me | H | Me | Y2 | Ms | H |
| Me | H | Me | Y2 | Cl | H |
| Me | H | Me | Y3 | Ms | H |
| Me | H | Me | Y3 | Cl | H |
| Me | H | Me | COOPh | Ms | H |
| Me | H | Me | COOPh | Cl | H |
| Me | H | Me | COOCH₂Ph | Ms | H |
| Me | H | Me | COOCH₂Ph | Cl | H |
| Me | H | Me | COOCH₂CH=CH₂ | Ms | H |
| Me | H | Me | COOCH₂CH=CH₂ | Cl | H |
| Me | H | Me | COOCH₂C≡CH | Ms | H |
| Me | H | Me | COOCH₂C≡CH | Cl | H |
| Me | H | Me | C(O)SMe | Ms | H |
| Me | H | Me | C(O)SMe | Cl | H |
| Me | H | Me | C(O)SEt | Ms | H |
| Me | H | Me | C(O)SEt | Cl | H |
| Me | H | Me | C(O)SCH(CH₃)₂ | Ms | H |
| Me | H | Me | C(O)SCH(CH₃)₂ | Cl | H |

-continued

| | | | | | |
|---|---|---|---|---|---|
| Me | H | Me | C(O)SC₃H₇ | Ms | H |
| Me | H | Me | C(O)SC₃H₇ | Cl | H |
| Me | H | Me | C(S)OMe | Ms | H |
| Me | H | Me | C(S)OMe | Cl | H |
| Me | H | Me | C(S)OEt | Ms | H |
| Me | H | Me | C(S)OEt | Cl | H |
| Me | H | Me | C(S)OCH(CH₃)₂ | Ms | H |
| Me | H | Me | C(S)OCH(CH₃)₂ | Cl | H |
| Me | H | Me | C(S)SC₃H₇ | Ms | H |
| Me | H | Me | C(S)SC₃H₇ | Cl | H |
| Me | H | Me | C(S)SMe | Ms | H |
| Me | H | Me | C(S)SMe | Cl | H |
| Me | H | Me | C(S)SEt | Ms | H |
| Me | H | Me | C(S)SEt | Cl | H |
| Me | H | Me | C(S)SCH(CH₃)₂ | Ms | H |
| Me | H | Me | C(S)SCH(CH₃)₂ | Cl | H |
| Me | H | Me | C(S)SC₃H₇ | Ms | H |
| Me | H | Me | C(S)SC₃H₇ | Cl | H |
| Me | H | OMe | COOMe | MeS | H |
| Me | H | OMe | COOMe | MeSO | H |
| Me | H | OMe | COOMe | Ms | H |
| Me | H | OMe | COOMe | Ms | Q1 |
| Me | H | OMe | COOMe | Ms | Q2 |
| Me | H | OMe | COOMe | Ms | Q3 |
| Me | H | OMe | COOMe | Ms | Q4 |
| Me | H | OMe | COOMe | Ms | Q5 |
| Me | H | OMe | COOMe | Ms | Q6 |
| Me | H | OMe | COOMe | Ms | Q20 |
| Me | Me | OMe | COOMe | Ms | H |
| Me | Cl | OMe | COOMe | Ms | H |
| Me | CF₃ | OMe | COOMe | Ms | H |
| Me | OMe | OMe | COOMe | Ms | H |
| Me | SMe | OMe | COOMe | Ms | H |
| Me | H | OMe | COOEt | MeS | H |
| Me | H | OMe | COOEt | MeSO | H |
| Me | H | OMe | COOEt | Ms | H |
| Me | H | OMe | COOEt | Ms | Q1 |
| Me | H | OMe | COOEt | Ms | Q18 |
| Me | H | OMe | COOEt | Ms | Q13 |
| Me | H | OMe | COOEt | Ms | Q5 |
| Me | H | OMe | COOEt | Ms | Q6 |
| Me | H | OMe | COOEt | Ms | Q22 |
| Me | Me | OMe | COOEt | Ms | H |
| Me | Cl | OMe | COOEt | Ms | H |
| Me | CF₃ | OMe | COOEt | Ms | H |
| Me | OMe | OMe | COOEt | Ms | H |
| Me | SMe | OMe | COOEt | Ms | H |
| Me | H | OMe | COOCH(CH₃)₂ | MeS | H |
| Me | H | OMe | COOCH(CH₃)₂ | MeSO | H |
| Me | H | OMe | COOCH(CH₃)₂ | Ms | H |
| Me | H | OMe | COOCH(CH₃)₂ | Ms | Q7 |
| Me | H | OMe | COOCH(CH₃)₂ | Ms | Q12 |
| Me | H | OMe | COOCH(CH₃)₂ | Ms | Q9 |
| Me | H | OMe | COOCH(CH₃)₂ | Ms | Q4 |
| Me | H | OMe | COOCH(CH₃)₂ | Ms | Q5 |
| Me | H | OMe | COOCH(CH₃)₂ | Ms | Q6 |
| Me | H | OMe | COOCH(CH₃)₂ | Ms | Q17 |
| Me | Me | OMe | COOCH(CH₃)₂ | Ms | H |
| Me | Cl | OMe | COOCH(CH₃)₂ | Ms | H |
| Me | CF₃ | OMe | COOCH(CH₃)₂ | Ms | H |
| Me | OMe | OMe | COOCH(CH₃)₂ | Ms | H |
| Me | SMe | OMe | COOCH(CH₃)₂ | Ms | H |
| Me | H | OMe | COOMe | Cl | H |
| Me | H | OMe | COOMe | Cl | Q1 |
| Me | H | OMe | COOMe | Cl | Q2 |
| Me | H | OMe | COOMe | Cl | Q3 |
| Me | H | OMe | COOEt | Cl | H |
| Me | H | OMe | COOEt | Cl | Q1 |
| Me | H | OMe | COOEt | Cl | Q2 |
| Me | H | OMe | COOEt | Cl | Q3 |
| Me | H | OMe | COOCH(CH₃)₂ | Cl | H |
| Me | H | OMe | COOCH(CH₃)₂ | Cl | Q1 |
| Me | H | OMe | COOCH(CH₃)₂ | Cl | Q2 |
| Me | H | OMe | COOCH(CH₃)₂ | Cl | Q3 |
| Me | H | OMe | CON(CH₃)₂ | MeS | H |
| Me | H | OMe | CON(CH₃)₂ | MeSO | H |
| Me | H | OMe | CON(CH₃)₂ | Ms | H |
| Me | H | OMe | CON(CH₃)₂ | Ms | Q1 |
| Me | H | OMe | CON(CH₃)₂ | Ms | Q18 |
| Me | H | OMe | CON(CH₃)₂ | Ms | Q13 |
| Me | H | OMe | CON(CH₃)₂ | Ms | Q4 |
| Me | H | OMe | CON(CH₃)₂ | Ms | Q5 |
| Me | H | OMe | CON(CH₃)₂ | Ms | Q6 |

-continued

| | | | | | |
|---|---|---|---|---|---|
| Me | H | OMe | CON(CH$_3$)$_2$ | Ms | Q22 |
| Me | Me | OMe | CON(CH$_3$)$_2$ | Ms | H |
| Me | Cl | OMe | CON(CH$_3$)$_2$ | Ms | H |
| Me | CF$_3$ | OMe | CON(CH$_3$)$_2$ | Ms | H |
| Me | OMe | OMe | CON(CH$_3$)$_2$ | Ms | H |
| Me | SMe | OMe | CON(CH$_3$)$_2$ | Ms | H |
| Me | H | OMe | CON(CH$_3$)$_2$ | Cl | H |
| Me | H | OMe | CON(CH$_3$)$_2$ | Cl | Q1 |
| Me | H | OMe | CON(CH$_3$)$_2$ | Cl | Q2 |
| Me | H | OMe | CON(CH$_3$)$_2$ | Cl | Q3 |
| Me | H | OMe | COOC$_4$H$_9$ | Ms | H |
| Me | H | OMe | COOC$_4$H$_9$ | Cl | H |
| Me | H | OMe | COOCH$_2$CH(CH$_3$)$_2$ | Ms | H |
| Me | H | OMe | COOCH$_2$CH(CH$_3$)$_2$ | Cl | H |
| Me | H | OMe | COOCH(CH$_3$)C$_2$H$_5$ | Ms | H |
| Me | H | OMe | COOCH(CH$_3$)C$_2$H$_5$ | Cl | H |
| Me | H | OMe | COOC(CH$_3$)$_3$ | Ms | H |
| Me | H | OMe | COOC(CH$_3$)$_3$ | Cl | H |
| Me | H | OMe | CONHMe | Ms | H |
| Me | H | OMe | CONHMe | Cl | H |
| Me | H | OMe | CONHEt | Ms | H |
| Me | H | OMe | CONHEt | Cl | H |
| Me | H | OMe | CONHCH(CH$_3$)$_2$ | Ms | H |
| Me | H | OMe | CONHCH(CH$_3$)$_2$ | Cl | H |
| Me | H | OMe | CONHC(CH$_3$)$_3$ | Ms | H |
| Me | H | OMe | CONHC(CH$_3$)$_3$ | Cl | H |
| Me | H | OMe | CONHC$_4$H$_9$ | Ms | H |
| Me | H | OMe | CONHC$_4$H$_9$ | Cl | H |
| Me | H | OMe | CONHCH$_2$CH(CH$_3$)$_2$ | Ms | H |
| Me | H | OMe | CONHCH$_2$CH(CH$_3$)$_2$ | Cl | H |
| Me | H | OMe | CONHCH(CH$_3$)C$_2$H$_5$ | Ms | H |
| Me | H | OMe | CONHCH(CH$_3$)C$_2$H$_5$ | Cl | H |
| Me | H | OMe | CONEt$_2$ | Ms | H |
| Me | H | OMe | CONEt$_2$ | Cl | H |
| Me | H | OMe | CON[CH(CH$_3$)$_2$]$_2$ | Ms | H |
| Me | H | OMe | CON[CH(CH$_3$)$_2$]$_2$ | Cl | H |
| Me | H | OMe | Y1 | Ms | H |
| Me | H | OMe | Y1 | Cl | H |
| Me | H | OMe | Y2 | Ms | H |
| Me | H | OMe | Y2 | Cl | H |
| Me | H | OMe | Y3 | Ms | H |
| Me | H | OMe | Y3 | Cl | H |
| Me | H | OMe | COOPh | Ms | H |
| Me | H | OMe | COOPh | Cl | H |
| Me | H | OMe | COOCH$_2$Ph | Ms | H |
| Me | H | OMe | COOCH$_2$Ph | Cl | H |
| Me | H | OMe | COOCH$_2$CH=CH$_2$ | Ms | H |
| Me | H | OMe | COOCH$_2$CH=CH$_2$ | Cl | H |
| Me | H | OMe | COOCH$_2$C≡CH | Ms | H |
| Me | H | OMe | COOCH$_2$C≡CH | Cl | H |
| Me | H | OMe | C(O)SMe | Ms | H |
| Me | H | OMe | C(O)SMe | Cl | H |
| Me | H | OMe | C(O)SEt | Ms | H |
| Me | H | OMe | C(O)SEt | Cl | H |
| Me | H | OMe | C(O)SCH(CH$_3$)$_2$ | Ms | H |
| Me | H | OMe | C(O)SCH(CH$_3$)$_2$ | Cl | H |
| Me | H | OMe | C(O)SC$_3$H$_7$ | Ms | H |
| Me | H | OMe | C(O)SC$_3$H$_7$ | Cl | H |
| Me | H | OMe | C(S)OMe | Ms | H |
| Me | H | OMe | C(S)OMe | Cl | H |
| Me | H | OMe | C(S)OEt | Ms | H |
| Me | H | OMe | C(S)OEt | Cl | H |
| Me | H | OMe | C(S)OCH(CH$_3$)$_2$ | Ms | H |
| Me | H | OMe | C(S)OCH(CH$_3$)$_2$ | Cl | H |
| Me | H | OMe | C(S)SC$_3$H$_7$ | Ms | H |
| Me | H | OMe | C(S)SMe | Ms | H |
| Me | H | OMe | C(S)SMe | Cl | H |
| Me | H | OMe | C(S)SEt | Ms | H |
| Me | H | OMe | C(S)SEt | Cl | H |
| Me | H | OMe | C(S)SCH(CH$_3$)$_2$ | Ms | H |
| Me | H | OMe | C(S)SCH(CH$_3$)$_2$ | Cl | H |
| Me | H | OMe | C(S)SC$_3$H$_7$ | Ms | H |
| Me | H | OMe | C(S)SC$_3$H$_7$ | Cl | H |
| Me | H | Br | COOMe | Ms | H |
| Me | H | Br | COOMe | Cl | H |
| Me | H | Br | COOEt | Ms | H |
| Me | H | Br | COOEt | Cl | H |
| Me | H | Br | COOCH(CH$_3$)$_2$ | Ms | H |
| Me | H | Br | COOCH(CH$_3$)$_2$ | Cl | H |
| Me | H | Br | CON(CH$_3$)$_2$ | Ms | H |
| Me | H | Br | CON(CH$_3$)$_2$ | Cl | H |
| Me | H | Br | CONHMe | Ms | H |

-continued

| | | | | | |
|---|---|---|---|---|---|
| Me | H | Br | CONHEt | Ms | H |
| Me | H | Br | CONHC$_3$H$_7$ | Ms | H |
| Me | H | Br | CONHCH(CH$_3$)$_2$ | Ms | H |
| Me | H | Br | CONHC(CH$_3$)$_3$ | Ms | H |
| Me | H | Br | CONEt$_2$ | Ms | H |
| Me | H | Br | CONHC(CH$_3$)$_3$ | Ms | H |
| Me | H | Br | CONHC$_4$H$_9$ | Ms | H |
| Me | H | Br | CONHC$_4$H$_9$ | Ms | H |
| Me | H | Br | CON[CH(CH$_3$)$_2$]$_2$ | Ms | H |
| Me | H | Br | Y1 | Ms | H |
| Me | H | Br | Y2 | Ms | H |
| Me | H | Br | COOPh | Ms | H |
| Me | H | Br | COOCH$_2$Ph | Ms | H |
| Me | H | Br | COOCH$_2$CH=CH$_2$ | Ms | H |
| Me | H | Br | COOCH$_2$C≡CH | Ms | H |
| Me | H | OEt | COOMe | Ms | H |
| Me | H | OEt | COOMe | Cl | H |
| Me | H | OEt | COOEt | Ms | H |
| Me | H | OEt | COOEt | Cl | H |
| Me | H | OEt | COOCH(CH$_3$)$_2$ | Ms | H |
| Me | H | OEt | COOCH(CH$_3$)$_2$ | Cl | H |
| Me | H | OEt | CON(CH$_3$)$_2$ | Ms | H |
| Me | H | OEt | CON(CH$_3$)$_2$ | Cl | H |
| Me | H | OEt | CONHMe | Ms | H |
| Me | H | OEt | CONHEt | Ms | H |
| Me | H | OEt | CONHC$_3$H$_7$ | Ms | H |
| Me | H | OEt | CONHCH(CH$_3$)$_2$ | Ms | H |
| Me | H | OEt | CONHC(CH$_3$)$_3$ | Ms | H |
| Me | H | OEt | CONEt$_2$ | Ms | H |
| Me | H | OEt | CONHC(CH$_3$)$_3$ | Ms | H |
| Me | H | OEt | CONHC$_4$H$_9$ | Ms | H |
| Me | H | OEt | CONHC$_4$H$_9$ | Ms | H |
| Me | H | OEt | CON[CH(CH$_3$)$_2$]$_2$ | Ms | H |
| Me | H | OEt | Y1 | Ms | H |
| Me | H | OEt | Y2 | Ms | H |
| Me | H | OEt | COOPh | Ms | H |
| Me | H | OEt | COOCH$_2$Ph | Ms | H |
| Me | H | OEt | COOCH$_2$CH=CH$_2$ | Ms | H |
| Me | H | OEt | COOCH$_2$C≡CH | Ms | H |
| Me | H | OCH(CH$_3$)$_2$ | COOMe | Ms | H |
| Me | H | OCH(CH$_3$)$_2$ | COOMe | Cl | H |
| Me | H | OCH(CH$_3$)$_2$ | COOEt | Ms | H |
| Me | H | OCH(CH$_3$)$_2$ | COOEt | Cl | H |
| Me | H | OCH(CH$_3$)$_2$ | COOCH(CH$_3$)$_2$ | Ms | H |
| Me | H | OCH(CH$_3$)$_2$ | COOCH(CH$_3$)$_2$ | Cl | H |
| Me | H | OCH(CH$_3$)$_2$ | CON(CH$_3$)$_2$ | Ms | H |
| Me | H | OCH(CH$_3$)$_2$ | CON(CH$_3$)$_2$ | Cl | H |
| Me | H | OCH(CH$_3$)$_2$ | CONHMe | Ms | H |
| Me | H | OCH(CH$_3$)$_2$ | CONHEt | Ms | H |
| Me | H | OCH(CH$_3$)$_2$ | CONHC$_3$H$_7$ | Ms | H |
| Me | H | OCH(CH$_3$)$_2$ | CONHCH(CH$_3$)$_2$ | Ms | H |
| Me | H | OCH(CH$_3$)$_2$ | CONHC(CH$_3$)$_3$ | Ms | H |
| Me | H | OCH(CH$_3$)$_2$ | CONEt$_2$ | Ms | H |
| Me | H | OCH(CH$_3$)$_2$ | CONHC(CH$_3$)$_3$ | Ms | H |
| Me | H | OCH(CH$_3$)$_2$ | CONHC$_4$H$_9$ | Ms | H |
| Me | H | OCH(CH$_3$)$_2$ | CONHC$_4$H$_9$ | Ms | H |
| Me | H | OCH(CH$_3$)$_2$ | CON[CH(CH$_3$)$_2$]$_2$ | Ms | H |
| Me | H | OCH(CH$_3$)$_2$ | Y1 | Ms | H |
| Me | H | OCH(CH$_3$)$_2$ | Y2 | Ms | H |
| Me | H | OCH(CH$_3$)$_2$ | COOPh | Ms | H |
| Me | H | OCH(CH$_3$)$_2$ | COOCH$_2$Ph | Ms | H |
| Me | H | OCH(CH$_3$)$_2$ | COOCH$_2$CH=CH$_2$ | Ms | H |
| Me | H | OCH(CH$_3$)$_2$ | COOCH$_2$C≡CH | Ms | H |
| Me | H | CH$_2$OCH$_3$ | COOMe | Ms | H |
| Me | H | CH$_2$OCH$_3$ | COOMe | Cl | H |
| Me | H | CH$_2$OCH$_3$ | COOEt | Ms | H |
| Me | H | CH$_2$OCH$_3$ | COOEt | Cl | H |
| Me | H | CH$_2$OCH$_3$ | COOCH(CH$_3$)$_2$ | Ms | H |
| Me | H | CH$_2$OCH$_3$ | COOCH(CH$_3$)$_2$ | Cl | H |
| Me | H | CH$_2$OCH$_3$ | CON(CH$_3$)$_2$ | Ms | H |
| Me | H | CH$_2$OCH$_3$ | CON(CH$_3$)$_2$ | Cl | H |
| Me | H | CH$_2$OCH$_3$ | CONHMe | Ms | H |
| Me | H | CH$_2$OCH$_3$ | CONHEt | Ms | H |
| Me | H | CH$_2$OCH$_3$ | CONHC$_3$H$_7$ | Ms | H |
| Me | H | CH$_2$OCH$_3$ | CONHCH(CH$_3$)$_2$ | Ms | H |
| Me | H | CH$_2$OCH$_3$ | CONHC(CH$_3$)$_3$ | Ms | H |
| Me | H | CH$_2$OCH$_3$ | CONEt$_2$ | Ms | H |
| Me | H | CH$_2$OCH$_3$ | CONHC(CH$_3$)$_3$ | Ms | H |
| Me | H | CH$_2$OCH$_3$ | CONHC$_4$H$_9$ | Ms | H |
| Me | H | CH$_2$OCH$_3$ | CONHC$_4$H$_9$ | Ms | H |
| Me | H | CH$_2$OCH$_3$ | CON[CH(CH$_3$)$_2$]$_2$ | Ms | H |
| Me | H | CH$_2$OCH$_3$ | Y1 | Ms | H |
| Me | H | CH$_2$OCH$_3$ | Y2 | Ms | H |

-continued

| | | | | | |
|---|---|---|---|---|---|
| Me | H | CH$_2$OCH$_3$ | COOPh | Ms | H |
| Me | H | CH$_2$OCH$_3$ | COOCH$_2$Ph | Ms | H |
| Me | H | CH$_2$OCH$_3$ | COOCH$_2$CH=CH$_2$ | Ms | H |
| Me | H | CH$_2$OCH$_3$ | COOCH$_2$C≡CH | Ms | H |
| Et | H | Cl | COOMe | MeS | H |
| Et | H | Cl | COOMe | MeSO | H |
| Et | H | Cl | COOMe | Ms | H |
| Et | H | Cl | COOMe | Ms | Q1 |
| Et | H | Cl | COOMe | Ms | Q2 |
| Et | H | Cl | COOMe | Ms | Q3 |
| Et | H | Cl | COOMe | Ms | Q4 |
| Et | H | Cl | COOMe | Ms | Q5 |
| Et | H | Cl | COOMe | Ms | Q6 |
| Et | H | Cl | COOMe | Ms | Q20 |
| Et | Me | Cl | COOMe | Ms | H |
| Et | Cl | Cl | COOMe | Ms | H |
| Et | CF$_3$ | Cl | COOMe | Ms | H |
| Et | OMe | Cl | COOMe | Ms | H |
| Et | SMe | Cl | COOMe | Ms | H |
| Et | H | Cl | COOEt | MeS | H |
| Et | H | Cl | COOEt | MeSO | H |
| Et | H | Cl | COOEt | Ms | H |
| Et | H | Cl | COOEt | Ms | Q1 |
| Et | H | Cl | COOEt | Ms | Q18 |
| Et | H | Cl | COOEt | Ms | Q13 |
| Et | H | Cl | COOEt | Ms | Q4 |
| Et | H | Cl | COOEt | Ms | Q5 |
| Et | H | Cl | COOEt | Ms | Q6 |
| Et | H | Cl | COOEt | Ms | Q22 |
| Et | Me | Cl | COOEt | Ms | H |
| Et | Cl | Cl | COOEt | Ms | H |
| Et | CF$_3$ | Cl | COOEt | Ms | H |
| Et | OMe | Cl | COOEt | Ms | H |
| Et | SMe | Cl | COOEt | Ms | H |
| Et | H | Cl | COOCH(CH$_3$)$_2$ | MeS | H |
| Et | H | Cl | COOCH(CH$_3$)$_2$ | MeSO | H |
| Et | H | Cl | COOCH(CH$_3$)$_2$ | Ms | H |
| Et | H | Cl | COOCH(CH$_3$)$_2$ | Ms | Q7 |
| Et | H | Cl | COOCH(CH$_3$)$_2$ | Ms | Q12 |
| Et | H | Cl | COOCH(CH$_3$)$_2$ | Ms | Q9 |
| Et | H | Cl | COOCH(CH$_3$)$_2$ | Ms | Q4 |
| Et | H | Cl | COOCH(CH$_3$)$_2$ | Ms | Q5 |
| Et | H | Cl | COOCH(CH$_3$)$_2$ | Ms | Q6 |
| Et | H | Cl | COOCH(CH$_3$)$_2$ | Ms | Q17 |
| Et | Me | Cl | COOCH(CH$_3$)$_2$ | Ms | H |
| Et | Cl | Cl | COOCH(CH$_3$)$_2$ | Ms | H |
| Et | CF$_3$ | Cl | COOCH(CH$_3$)$_2$ | Ms | H |
| Et | OMe | Cl | COOCH(CH$_3$)$_2$ | Ms | H |
| Et | SMe | Cl | COOCH(CH$_3$)$_2$ | Ms | H |
| Et | H | Cl | COOMe | Cl | H |
| Et | H | Cl | COOMe | Cl | Q1 |
| Et | H | Cl | COOMe | Cl | Q2 |
| Et | H | Cl | COOMe | Cl | Q3 |
| Et | H | Cl | COOEt | Cl | H |
| Et | H | Cl | COOEt | Cl | Q1 |
| Et | H | Cl | COOEt | Cl | Q2 |
| Et | H | Cl | COOEt | Cl | Q3 |
| Et | H | Cl | COOCH(CH$_3$)$_2$ | Cl | H |
| Et | H | Cl | COOCH(CH$_3$)$_2$ | Cl | Q1 |
| Et | H | Cl | COOCH(CH$_3$)$_2$ | Cl | Q2 |
| Et | H | Cl | COOCH(CH$_3$)$_2$ | Cl | Q3 |
| Et | H | Cl | CON(CH$_3$)$_2$ | MeS | H |
| Et | H | Cl | CON(CH$_3$)$_2$ | MeSO | H |
| Et | H | Cl | CON(CH$_3$)$_2$ | Ms | H |
| Et | H | Cl | CON(CH$_3$)$_2$ | Ms | Q1 |
| Et | H | Cl | CON(CH$_3$)$_2$ | Ms | Q18 |
| Et | H | Cl | CON(CH$_3$)$_2$ | Ms | Q13 |
| Et | H | Cl | CON(CH$_3$)$_2$ | Ms | Q4 |
| Et | H | Cl | CON(CH$_3$)$_2$ | Ms | Q5 |
| Et | H | Cl | CON(CH$_3$)$_2$ | Ms | Q6 |
| Et | H | Cl | CON(CH$_3$)$_2$ | Ms | Q22 |
| Et | Me | Cl | CON(CH$_3$)$_2$ | Ms | H |
| Et | Cl | Cl | CON(CH$_3$)$_2$ | Ms | H |
| Et | CF$_3$ | Cl | CON(CH$_3$)$_2$ | Ms | H |
| Et | OMe | Cl | CON(CH$_3$)$_2$ | Ms | H |
| Et | SMe | Cl | CON(CH$_3$)$_2$ | Ms | H |
| Et | H | Cl | CON(CH$_3$)$_2$ | Cl | H |
| Et | H | Cl | CON(CH$_3$)$_2$ | Cl | Q1 |
| Et | H | Cl | CON(CH$_3$)$_2$ | Cl | Q2 |
| Et | H | Cl | CON(CH$_3$)$_2$ | Cl | Q3 |
| Et | H | Cl | COOC$_4$H$_9$ | Ms | H |
| Et | H | Cl | COOC$_4$H$_9$ | Cl | H |
| Et | H | Cl | COOCH$_2$CH(CH$_3$)$_2$ | Ms | H |

-continued

| | | | | | |
|---|---|---|---|---|---|
| Et | H | Cl | COOCH$_2$CH(CH$_3$)$_2$ | Cl | H |
| Et | H | Cl | COOCH(CH$_3$)C$_2$H$_5$ | Ms | H |
| Et | H | Cl | COOCH(CH$_3$)C$_2$H$_5$ | Cl | H |
| Et | H | Cl | COOCH(CH$_3$)$_3$ | Ms | H |
| Et | H | Cl | COOCH(CH$_3$)$_3$ | Cl | H |
| Et | H | Cl | CONHMe | Ms | H |
| Et | H | Cl | CONHMe | Cl | H |
| Et | H | Cl | CONHEt | Ms | H |
| Et | H | Cl | CONHEt | Cl | H |
| Et | H | Cl | CONHCH(CH$_3$)$_2$ | Ms | H |
| Et | H | Cl | CONHCH(CH$_3$)$_2$ | Cl | H |
| Et | H | Cl | CONHC(CH$_3$)$_3$ | Ms | H |
| Et | H | Cl | CONHC(CH$_3$)$_3$ | Cl | H |
| Et | H | Cl | CONHC$_4$H$_9$ | Ms | H |
| Et | H | Cl | CONHC$_4$H$_9$ | Cl | H |
| Et | H | Cl | CONHCH$_2$CH(CH$_3$)$_2$ | Ms | H |
| Et | H | Cl | CONHCH$_2$CH(CH$_3$)$_2$ | Cl | H |
| Et | H | Cl | CONHCH(CH$_3$)C$_2$H$_5$ | Ms | H |
| Et | H | Cl | CONHCH(CH$_3$)C$_2$H$_5$ | Cl | H |
| Et | H | Cl | CONEt$_2$ | Ms | H |
| Et | H | Cl | CONEt$_2$ | Cl | H |
| Et | H | Cl | CON[CH(CH$_3$)$_2$]$_2$ | Ms | H |
| Et | H | Cl | CON[CH(CH$_3$)$_2$]$_2$ | Cl | H |
| Et | H | Cl | Y1 | Ms | H |
| Et | H | Cl | Y1 | Cl | H |
| Et | H | Cl | Y2 | Ms | H |
| Et | H | Cl | Y2 | Cl | H |
| Et | H | Cl | Y3 | Ms | H |
| Et | H | Cl | Y3 | Cl | H |
| Et | H | Cl | COOPh | Ms | H |
| Et | H | Cl | COOPh | Cl | H |
| Et | H | Cl | COOCH$_2$Ph | Ms | H |
| Et | H | Cl | COOCH$_2$Ph | Cl | H |
| Et | H | Cl | COOCH$_2$CH=CH$_2$ | Ms | H |
| Et | H | Cl | COOCH$_2$CH=CH$_2$ | Cl | H |
| Et | H | Cl | COOCH$_2$C≡CH | Ms | H |
| Et | H | Cl | COOCH$_2$C≡CH | Cl | H |
| Et | H | Cl | C(O)SMe | Ms | H |
| Et | H | Cl | C(O)SMe | Cl | H |
| Et | H | Cl | C(O)SEt | Ms | H |
| Et | H | Cl | C(O)SEt | Cl | H |
| Et | H | C | C(O)SCH(CH$_3$)$_2$ | Ms | H |
| Et | H | C | C(O)SCH(CH$_3$)$_2$ | Cl | H |
| Et | H | Cl | C(O)SC$_3$H$_7$ | Ms | H |
| Et | H | Cl | C(O)SC$_3$H$_7$ | Cl | H |
| Et | H | Cl | C(S)OMe | Ms | H |
| Et | H | Cl | C(S)OMe | Cl | H |
| Et | H | Cl | C(S)OEt | Ms | H |
| Et | H | Cl | C(S)OEt | Cl | H |
| Et | H | Cl | C(S)OCH(CH$_3$)$_2$ | Ms | H |
| Et | H | Cl | C(S)OCH(CH$_3$)$_2$ | Cl | H |
| Et | H | Cl | C(S)SC$_3$H$_7$ | Ms | H |
| Et | H | Cl | C(S)SC$_3$H$_7$ | Cl | H |
| Et | H | Cl | C(S)SMe | Ms | H |
| Et | H | Cl | C(S)SMe | Cl | H |
| Et | H | Cl | C(S)SEt | Ms | H |
| Et | H | Cl | C(S)SEt | Cl | H |
| Et | H | Cl | C(S)SCH(CH$_3$)$_2$ | Ms | H |
| Et | H | Cl | C(S)SCH(CH$_3$)$_2$ | Cl | H |
| Et | H | Cl | C(S)SC$_3$H$_7$ | Ms | H |
| Et | H | Cl | C(S)SC$_3$H$_7$ | Cl | H |
| Et | H | Me | COOMe | MeS | H |
| Et | H | Me | COOMe | MeSO | H |
| Et | H | Me | COOMe | Ms | H |
| Et | H | Me | COOMe | Ms | Q1 |
| Et | H | Me | COOMe | Ms | Q2 |
| Et | H | Me | COOMe | Ms | Q3 |
| Et | H | Me | COOMe | Ms | Q4 |
| Et | H | Me | COOMe | Ms | Q5 |
| Et | H | Me | COOMe | Ms | Q6 |
| Et | H | Me | COOMe | Ms | Q20 |
| Et | Me | Me | COOMe | Ms | H |
| Et | Cl | Me | COOMe | Ms | H |
| Et | CF$_3$ | Me | COOMe | Ms | H |
| Et | OMe | Me | COOMe | Ms | H |
| Et | SMe | Me | COOMe | Ms | H |
| Et | H | Me | COOEt | MeS | H |
| Et | H | Me | COOEt | MeSO | H |
| Et | H | Me | COOEt | Ms | H |
| Et | H | Me | COOEt | Ms | Q1 |
| Et | H | Me | COOEt | Ms | Q18 |
| Et | H | Me | COOEt | Ms | Q13 |
| Et | H | Me | COOEt | Ms | Q4 |

-continued

| | | | | | |
|---|---|---|---|---|---|
| Et | H | Me | COOEt | Ms | Q5 |
| Et | H | Me | COOEt | Ms | Q6 |
| Et | H | Me | COOEt | Ms | Q22 |
| Et | Me | Me | COOEt | Ms | H |
| Et | Cl | Me | COOEt | Ms | H |
| Et | CF$_3$ | Me | COOEt | Ms | H |
| Et | OMe | Me | COOEt | Ms | H |
| Et | SMe | Me | COOEt | Ms | H |
| Et | H | Me | COOCH(CH$_3$)$_2$ | MeS | H |
| Et | H | Me | COOCH(CH$_3$)$_2$ | MeSO | H |
| Et | H | Me | COOCH(CH$_3$)$_2$ | Ms | H |
| Et | H | Me | COOCH(CH$_3$)$_2$ | Ms | Q7 |
| Et | H | Me | COOCH(CH$_3$)$_2$ | Ms | Q12 |
| Et | H | Me | COOCH(CH$_3$)$_2$ | Ms | Q9 |
| Et | H | Me | COOCH(CH$_3$)$_2$ | Ms | Q4 |
| Et | H | Me | COOCH(CH$_3$)$_2$ | Ms | Q5 |
| Et | H | Me | COOCH(CH$_3$)$_2$ | Ms | Q6 |
| Et | H | Me | COOCH(CH$_3$)$_2$ | Ms | Q17 |
| Et | Me | Me | COOCH(CH$_3$)$_2$ | Ms | H |
| Et | Cl | Me | COOCH(CH$_3$)$_2$ | Ms | H |
| Et | CF$_3$ | Me | COOCH(CH$_3$)$_2$ | Ms | H |
| Et | OMe | Me | COOCH(CH$_3$)$_2$ | Ms | H |
| Et | SMe | Me | COOCH(CH$_3$)$_2$ | Ms | H |
| Et | H | Me | COOMe | Cl | H |
| Et | H | Me | COOMe | Cl | Q1 |
| Et | H | Me | COOMe | Cl | Q2 |
| Et | H | Me | COOMe | Cl | Q3 |
| Et | H | Me | COOEt | Cl | H |
| Et | H | Me | COOEt | Cl | Q1 |
| Et | H | Me | COOEt | Cl | Q2 |
| Et | H | Me | COOEt | Cl | Q3 |
| Et | H | Me | COOCH(CH$_3$)$_2$ | Cl | H |
| Et | H | Me | COOCH(CH$_3$)$_2$ | Cl | Q1 |
| Et | H | Me | COOCH(CH$_3$)$_2$ | Cl | Q2 |
| Et | H | Me | COOCH(CH$_3$)$_2$ | Cl | Q3 |
| Et | H | Me | CON(CH$_3$)$_2$ | MeS | H |
| Et | H | Me | CON(CH$_3$)$_2$ | MeSO | H |
| Et | H | Me | CON(CH$_3$)$_2$ | Ms | H |
| Et | H | Me | CON(CH$_3$)$_2$ | Ms | Q1 |
| Et | H | Me | CON(CH$_3$)$_2$ | Ms | Q18 |
| Et | H | Me | CON(CH$_3$)$_2$ | Ms | Q13 |
| Et | H | Me | CON(CH$_3$)$_2$ | Ms | Q4 |
| Et | H | Me | CON(CH$_3$)$_2$ | Ms | Q5 |
| Et | H | Me | CON(CH$_3$)$_2$ | Ms | Q6 |
| Et | H | Me | CON(CH$_3$)$_2$ | Ms | Q22 |
| Et | Me | Me | CON(CH$_3$)$_2$ | Ms | H |
| Et | Cl | Me | CON(CH$_3$)$_2$ | Ms | H |
| Et | CF$_3$ | Me | CON(CH$_3$)$_2$ | Ms | H |
| Et | OMe | Me | CON(CH$_3$)$_2$ | Ms | H |
| Et | SMe | Me | CON(CH$_3$)$_2$ | Ms | H |
| Et | H | Me | CON(CH$_3$)$_2$ | Cl | H |
| Et | H | Me | CON(CH$_3$)$_2$ | Cl | Q1 |
| Et | H | Me | CON(CH$_3$)$_2$ | Cl | Q2 |
| Et | H | Me | CON(CH$_3$)$_2$ | Cl | Q3 |
| Et | H | Me | COOC$_4$H$_9$ | Ms | H |
| Et | H | Me | COOC$_4$H$_9$ | Cl | H |
| Et | H | Me | COOCH$_2$CH(CH$_3$)$_2$ | Ms | H |
| Et | H | Me | COOCH$_2$CH(CH$_3$)$_2$ | Cl | H |
| Et | H | Me | COOCH(CH$_3$C$_2$H$_5$) | Ms | H |
| Et | H | Me | COOCH(CH$_3$C$_2$H$_5$) | Cl | H |
| Et | H | Me | COOC(CH$_3$)$_3$ | Ms | H |
| Et | H | Me | COOC(CH$_3$)$_3$ | Cl | H |
| Et | H | Me | CONHMe | Ms | H |
| Et | H | Me | CONHMe | Cl | H |
| Et | H | Me | CONHEt | Ms | H |
| Et | H | Me | CONHEt | Cl | H |
| Et | H | Me | CONHCH(CH$_3$)$_2$ | Ms | H |
| Et | H | Me | CONHCH(CH$_3$)$_2$ | Cl | H |
| Et | H | Me | CONHC(CH$_3$)$_3$ | Ms | H |
| Et | H | Me | CONHC(CH$_3$)$_3$ | Cl | H |
| Et | H | Me | CONHC$_4$H$_9$ | Ms | H |
| Et | H | Me | CONHC$_4$H$_9$ | Cl | H |
| Et | H | Me | CONHCH$_2$CH(CH$_3$)$_2$ | Ms | H |
| Et | H | Me | CONHCH$_2$CH(CH$_3$)$_2$ | Cl | H |
| Et | H | Me | CONHCH(CH$_3$)C$_2$H$_5$ | Ms | H |
| Et | H | Me | CONHCH(CH$_3$)C$_2$H$_5$ | Cl | H |
| Et | H | Me | CONEt$_2$ | Ms | H |
| Et | H | Me | CONEt$_2$ | Cl | H |
| Et | H | Me | CON[CH(CH$_3$)$_2$]$_2$ | Ms | H |
| Et | H | Me | CON[CH(CH$_3$)$_2$]$_2$ | Cl | H |
| Et | H | Me | Y1 | Ms | H |
| Et | H | Me | Y1 | Cl | H |
| Et | H | Me | Y2 | Ms | H |

-continued

| | | | | | |
|---|---|---|---|---|---|
| Et | H | Me | Y2 | Cl | H |
| Et | H | Me | Y3 | Ms | H |
| Et | H | Me | Y3 | Cl | H |
| Et | H | Me | COOPh | Ms | H |
| Et | H | Me | COOPh | Cl | H |
| Et | H | Me | COOCH$_2$Ph | Ms | H |
| Et | H | Me | COOCH$_2$Ph | Cl | H |
| Et | H | Me | COOCH$_2$CH=CH$_2$ | Ms | H |
| Et | H | Me | COOCH$_2$CH=CH$_2$ | Cl | H |
| Et | H | Me | COOCH$_2$C≡CH | Ms | H |
| Et | H | Me | COOCH$_2$C≡CH | Cl | H |
| Et | H | Me | C(O)SMe | Ms | H |
| Et | H | Me | C(O)SMe | Cl | H |
| Et | H | Me | C(O)SEt | Ms | H |
| Et | H | Me | C(O)SEt | Cl | H |
| Et | H | Me | C(O)SCH(CH$_3$)$_2$ | Ms | H |
| Et | H | Me | C(O)SCH(CH$_3$)$_2$ | Cl | H |
| Et | H | Me | C(O)SC$_3$H$_7$ | Ms | H |
| Et | H | Me | C(O)SC$_3$H$_7$ | Cl | H |
| Et | H | Me | C(S)OMe | Ms | H |
| Et | H | Me | C(S)OMe | Cl | H |
| Et | H | Me | C(S)OEt | Ms | H |
| Et | H | Me | C(S)OEt | Cl | H |
| Et | H | Me | C(S)OCH(CH$_3$)$_2$ | Ms | H |
| Et | H | Me | C(S)OCH(CH$_3$)$_2$ | Cl | H |
| Et | H | Me | C(S)SC$_3$H$_7$ | Ms | H |
| Et | H | Me | C(S)SC$_3$H$_7$ | Cl | H |
| Et | H | Me | C(S)SMe | Ms | H |
| Et | H | Me | C(S)SMe | Cl | H |
| Et | H | Me | C(S)SEt | Ms | H |
| Et | H | Me | C(S)SEt | Cl | H |
| Et | H | Me | C(S)SCH(CH$_3$)$_2$ | Ms | H |
| Et | H | Me | C(S)SCH(CH$_3$)$_2$ | Cl | H |
| Et | H | Me | C(S)SC$_3$H$_7$ | Ms | H |
| Et | H | Me | C(S)SC$_3$H$_7$ | Cl | H |
| Et | H | OMe | COOMe | MeS | H |
| Et | H | OMe | COOMe | MeSO | H |
| Et | H | OMe | COOMe | Ms | H |
| Et | H | OMe | COOMe | Ms | Q1 |
| Et | H | OMe | COOMe | Ms | Q2 |
| Et | H | OMe | COOMe | Ms | Q3 |
| Et | H | OMe | COOMe | Ms | Q4 |
| Et | H | OMe | COOMe | Ms | Q5 |
| Et | H | OMe | COOMe | Ms | Q6 |
| Et | H | OMe | COOMe | Ms | Q20 |
| Et | Me | OMe | COOMe | Ms | H |
| Et | Cl | OMe | COOMe | Ms | H |
| Et | CF$_3$ | OMe | COOMe | Ms | H |
| Et | OMe | OMe | COOMe | Ms | H |
| Et | SMe | OMe | COOMe | Ms | H |
| Et | H | OMe | COOEt | MeS | H |
| Et | H | OMe | COOEt | MeSO | H |
| Et | H | OMe | COOEt | Ms | H |
| Et | H | OMe | COOEt | Ms | Q1 |
| Et | H | OMe | COOEt | Ms | Q18 |
| Et | H | OMe | COOEt | Ms | Q13 |
| Et | H | OMe | COOEt | Ms | Q4 |
| Et | H | OMe | COOEt | Ms | Q5 |
| Et | H | OMe | COOEt | Ms | Q6 |
| Et | H | OMe | COOEt | Ms | Q22 |
| Et | Me | OMe | COOEt | Ms | H |
| Et | Cl | OMe | COOEt | Ms | H |
| Et | CF$_3$ | OMe | COOEt | Ms | H |
| Et | OMe | OMe | COOEt | Ms | H |
| Et | SMe | OMe | COOEt | Ms | H |
| Et | H | OMe | COOCH(CH$_3$)$_2$ | MeS | H |
| Et | H | OMe | COOCH(CH$_3$)$_2$ | MeSO | H |
| Et | H | OMe | COOCH(CH$_3$)$_2$ | Ms | H |
| Et | H | OMe | COOCH(CH$_3$)$_2$ | Ms | Q7 |
| Et | H | OMe | COOCH(CH$_3$)$_2$ | Ms | Q12 |
| Et | H | OMe | COOCH(CH$_3$)$_2$ | Ms | Q9 |
| Et | H | OMe | COOCH(CH$_3$)$_2$ | Ms | Q4 |
| Et | H | OMe | COOCH(CH$_3$)$_2$ | Ms | Q5 |
| Et | H | OMe | COOCH(CH$_3$)$_2$ | Ms | Q6 |
| Et | H | OMe | COOCH(CH$_3$)$_2$ | Ms | Q17 |
| Et | Me | OMe | COOCH(CH$_3$)$_2$ | Ms | H |
| Et | Cl | OMe | COOCH(CH$_3$)$_2$ | Ms | H |
| Et | CF$_3$ | OMe | COOCH(CH$_3$)$_2$ | Ms | H |
| Et | OMe | OMe | COOCH(CH$_3$)$_2$ | Ms | H |
| Et | SMe | OMe | COOCH(CH$_3$)$_2$ | Ms | H |
| Et | H | OMe | COOMe | Cl | H |
| Et | H | OMe | COOMe | Cl | Q1 |
| Et | H | OMe | COOMe | Cl | Q2 |

-continued

| | | | | | |
|---|---|---|---|---|---|
| Et | H | OMe | COOMe | Cl | Q3 |
| Et | H | OMe | COOEt | Cl | H |
| Et | H | OMe | COOEt | Cl | Q1 |
| Et | H | OMe | COOEt | Cl | Q2 |
| Et | H | OMe | COOEt | Cl | Q3 |
| Et | H | OMe | COOCH(CH$_3$)$_2$ | Cl | H |
| Et | H | OMe | COOCH(CH$_3$)$_2$ | Cl | Q1 |
| Et | H | OMe | COOCH(CH$_3$)$_2$ | Cl | Q2 |
| Et | H | OMe | COOCH(CH$_3$)$_2$ | Cl | Q3 |
| Et | H | OMe | CON(CH$_3$)$_2$ | MeS | H |
| Et | H | OMe | CON(CH$_3$)$_2$ | MeSO | H |
| Et | H | OMe | CON(CH$_3$)$_2$ | Ms | H |
| Et | H | OMe | CON(CH$_3$)$_2$ | Ms | Q1 |
| Et | H | OMe | CON(CH$_3$)$_2$ | Ms | Q18 |
| Et | H | OMe | CON(CH$_3$)$_2$ | Ms | Q13 |
| Et | H | OMe | CON(CH$_3$)$_2$ | Ms | Q4 |
| Et | H | OMe | CON(CH$_3$)$_2$ | Ms | Q5 |
| Et | H | OMe | CON(CH$_3$)$_2$ | Ms | Q6 |
| Et | H | OMe | CON(CH$_3$)$_2$ | Ms | Q22 |
| Et | Me | OMe | CON(CH$_3$)$_2$ | Ms | H |
| Et | Cl | OMe | CON(CH$_3$)$_2$ | Ms | H |
| Et | CF$_3$ | OMe | CON(CH$_3$)$_2$ | Ms | H |
| Et | OMe | OMe | CON(CH$_3$)$_2$ | Ms | H |
| Et | SMe | OMe | CON(CH$_3$)$_2$ | Ms | H |
| Et | H | OMe | CON(CH$_3$)$_2$ | Cl | H |
| Et | H | OMe | CON(CH$_3$)$_2$ | Cl | Q1 |
| Et | H | OMe | CON(CH$_3$)$_2$ | Cl | Q2 |
| Et | H | OMe | CON(CH$_3$)$_2$ | Cl | Q3 |
| Et | H | OMe | COOC$_4$H$_9$ | Ms | H |
| Et | H | OMe | COOC$_4$H$_9$ | Cl | H |
| Et | H | OMe | COOCH$_2$CH(CH$_3$)$_2$ | Ms | H |
| Et | H | OMe | COOCH$_2$CH(CH$_3$)$_2$ | Cl | H |
| Et | H | OMe | COOCH(CH$_3$)C$_2$H$_5$ | Ms | H |
| Et | H | OMe | COOCH(CH$_3$)C$_2$H$_5$ | Cl | H |
| Et | H | OMe | COOC(CH$_3$)$_3$ | Ms | H |
| Et | H | OMe | COOC(CH$_3$)$_3$ | Cl | H |
| Et | H | OMe | CONHMe | Ms | H |
| Et | H | OMe | CONHMe | Cl | H |
| Et | H | OMe | CONHEt | Ms | H |
| Et | H | OMe | CONHEt | Cl | H |
| Et | H | OMe | CONHCH(CH$_3$)$_2$ | Ms | H |
| Et | H | OMe | CONHCH(CH$_3$)$_2$ | Cl | H |
| Et | H | OMe | CONHC(CH$_3$)$_3$ | Ms | H |
| Et | H | OMe | CONHC(CH$_3$)$_3$ | Cl | H |
| Et | H | OMe | CONHC$_4$H$_9$ | Ms | H |
| Et | H | OMe | CONHC$_4$H$_9$ | Cl | H |
| Et | H | OMe | CONHCH$_2$CH(CH$_3$)$_2$ | Ms | H |
| Et | H | OMe | CONHCH$_2$CH(CH$_3$)$_2$ | Cl | H |
| Et | H | OMe | CONHCH(CH$_3$)C$_2$H$_5$ | Ms | H |
| Et | H | OMe | CONHCH(CH$_3$)C$_2$H$_5$ | Cl | H |
| Et | H | OMe | CONEt$_2$ | Ms | H |
| Et | H | OMe | CONEt$_2$ | Cl | H |
| Et | H | OMe | CON[CH(CH$_3$)$_2$]$_2$ | Ms | H |
| Et | H | OMe | CON[CH(CH$_3$)$_2$]$_2$ | Cl | H |
| Et | H | OMe | Y1 | Ms | H |
| Et | H | OMe | Y1 | Cl | H |
| Et | H | OMe | Y2 | Ms | H |
| Et | H | OMe | Y2 | Cl | H |
| Et | H | OMe | Y3 | Ms | H |
| Et | H | OMe | Y3 | Cl | H |
| Et | H | OMe | COOPh | Ms | H |
| Et | H | OMe | COOPh | Cl | H |
| Et | H | OMe | COOCH$_2$Ph | Ms | H |
| Et | H | OMe | COOCH$_2$Ph | Cl | H |
| Et | H | OMe | COOCH$_2$CH=CH$_2$ | Ms | H |
| Et | H | OMe | COOCH$_2$CH=CH$_2$ | Cl | H |
| Et | H | OMe | COOCH$_2$C≡CH | Ms | H |
| Et | H | OMe | COOCH$_2$C≡CH | Cl | H |
| Et | H | OMe | C(O)SMe | Ms | H |
| Et | H | OMe | C(O)SMe | Cl | H |
| Et | H | OMe | C(O)SEt | Ms | H |
| Et | H | OMe | C(O)SEt | Cl | H |
| Et | H | OMe | C(O)SCH(CH$_3$)$_2$ | Ms | H |
| Et | H | OMe | C(O)SCH(CH$_3$)$_2$ | Cl | H |
| Et | H | OMe | C(O)SC$_3$H$_7$ | Ms | H |
| Et | H | OMe | C(O)SC$_3$H$_7$ | Cl | H |
| Et | H | OMe | C(S)OMe | Ms | H |
| Et | H | OMe | C(S)OMe | Cl | H |
| Et | H | OMe | C(S)OEt | Ms | H |
| Et | H | OMe | C(S)OEt | Cl | H |
| Et | H | OMe | C(S)OCH(CH$_3$)$_2$ | Ms | H |
| Et | H | OMe | C(S)OCH(CH$_3$)$_2$ | Cl | H |
| Et | H | OMe | C(S)SC$_3$H$_7$ | Ms | H |

-continued

| | | | | | |
|---|---|---|---|---|---|
| Et | H | OMe | C(S)SC$_3$H$_7$ | Cl | H |
| Et | H | OMe | C(S)SMe | Ms | H |
| Et | H | OMe | C(S)SMe | Cl | H |
| Et | H | OMe | C(S)SEt | Ms | H |
| Et | H | OMe | C(S)SEt | Cl | H |
| Et | H | OMe | C(S)SCH(CH$_3$)$_2$ | Ms | H |
| Et | H | OMe | C(S)SCH(CH$_3$)$_2$ | Cl | H |
| Et | H | OMe | C(S)SC$_3$H$_7$ | Ms | H |
| Et | H | OMe | C(S)SC$_3$H$_7$ | Cl | H |
| Et | H | Br | COOMe | Ms | H |
| Et | H | Br | COOMe | Cl | H |
| Et | H | Br | COOEt | Ms | H |
| Et | H | Br | COOEt | Cl | H |
| Et | H | Br | COOCH(CH$_3$)$_2$ | Ms | H |
| Et | H | Br | COOCH(CH$_3$)$_2$ | Cl | H |
| Et | H | Br | CON(CH$_3$)$_2$ | Ms | H |
| Et | H | Br | CON(CH$_3$)$_2$ | Cl | H |
| Et | H | Br | CONHMe | Ms | H |
| Et | H | Br | CONHEt | Ms | H |
| Et | H | Br | CONHC$_3$H$_7$ | Ms | H |
| Et | H | Br | CONHCH(CH$_3$)$_2$ | Ms | H |
| Et | H | Br | CONHC(CH$_3$)$_3$ | Ms | H |
| Et | H | Br | CONEt$_2$ | Ms | H |
| Et | H | Br | CONHC(CH$_3$)$_3$ | Ms | H |
| Et | H | Br | CONHC$_4$H$_9$ | Ms | H |
| Et | H | Br | CONHC$_4$H$_9$ | Ms | H |
| Et | H | Br | CON[CH(CH$_3$)$_2$]$_2$ | Ms | H |
| Et | H | Br | Y1 | Ms | H |
| Et | H | Br | Y2 | Ms | H |
| Et | H | Br | COOPh | Ms | H |
| Et | H | Br | COOCH$_2$Ph | Ms | H |
| Et | H | Br | COOCH$_2$CH=CH$_2$ | Ms | H |
| Et | H | Br | COOCH$_2$C≡CH | Ms | H |
| Et | H | OEt | COOMe | Ms | H |
| Et | H | OEt | COOMe | Cl | H |
| Et | H | OEt | COOEt | Ms | H |
| Et | H | OEt | COOEt | Cl | H |
| Et | H | OEt | COOCH(CH$_3$)$_2$ | Ms | H |
| Et | H | OEt | COOCH(CH$_3$)$_2$ | Cl | H |
| Et | H | OEt | CON(CH$_3$)$_2$ | Ms | H |
| Et | H | OEt | CON(CH$_3$)$_2$ | Cl | H |
| Et | H | OEt | CONHMe | Ms | H |
| Et | H | OEt | CONHEt | Ms | H |
| Et | H | OEt | CONHC$_3$H$_7$ | Ms | H |
| Et | H | OEt | CONHCH(CH$_3$)$_2$ | Ms | H |
| Et | H | OEt | CONHC(CH$_3$)$_3$ | Ms | H |
| Et | H | OEt | CONEt$_2$ | Ms | H |
| Et | H | OEt | CONHC(CH$_3$)$_3$ | Ms | H |
| Et | H | OEt | CONHC$_4$H$_9$ | Ms | H |
| Et | H | OEt | CONHC$_4$H$_9$ | Ms | H |
| Et | H | OEt | CON[CH(CH$_3$)$_2$]$_2$ | Ms | H |
| Et | H | OEt | Y1 | Ms | H |
| Et | H | OEt | Y2 | Ms | H |
| Et | H | OEt | COOPh | Ms | H |
| Et | H | OEt | COOCH$_2$Ph | Ms | H |
| Et | H | OEt | COOCH$_2$CH=CH$_2$ | Ms | H |
| Et | H | OEt | COOCH$_2$C≡CH | Ms | H |
| Et | H | OCH(CH$_3$)$_2$ | COOMe | Ms | H |
| Et | H | OCH(CH$_3$)$_2$ | COOMe | Cl | H |
| Et | H | OCH(CH$_3$)$_2$ | COOEt | Ms | H |
| Et | H | OCH(CH$_3$)$_2$ | COOEt | Cl | H |
| Et | H | OCH(CH$_3$)$_2$ | COOCH(CH$_3$)$_2$ | Ms | H |
| Et | H | OCH(CH$_3$)$_2$ | COOCH(CH$_3$)$_2$ | Cl | H |
| Et | H | OCH(CH$_3$)$_2$ | CON(CH$_3$)$_2$ | Ms | H |
| Et | H | OCH(CH$_3$)$_2$ | CON(CH$_3$)$_2$ | Cl | H |
| Et | H | OCH(CH$_3$)$_2$ | CONHMe | Ms | H |
| Et | H | OCH(CH$_3$)$_2$ | CONHEt | Ms | H |
| Et | H | OCH(CH$_3$)$_2$ | CONHC$_3$H$_7$ | Ms | H |
| Et | H | OCH(CH$_3$)$_2$ | CONHCH(CH$_3$)$_2$ | Ms | H |
| Et | H | OCH(CH$_3$)$_2$ | CONHC(CH$_3$)$_3$ | Ms | H |
| Et | H | OCH(CH$_3$)$_2$ | CONEt$_2$ | Ms | H |
| Et | H | OCH(CH$_3$)$_2$ | CONHC(CH$_3$)$_3$ | Ms | H |
| Et | H | OCH(CH$_3$)$_2$ | CONHC$_4$H$_9$ | Ms | H |
| i-Pr | H | OMe | COOMe | Cl | Q3 |
| i-Pr | H | OMe | COOEt | Cl | H |
| i-Pr | H | OMe | COOEt | Cl | Q1 |
| i-Pr | H | OMe | COOEt | Cl | Q2 |
| i-Pr | H | OMe | COOEt | Cl | Q3 |
| i-Pr | H | OMe | COOCH(CH$_3$)$_2$ | Cl | H |
| i-Pr | H | OMe | COOCH(CH$_3$)$_2$ | Cl | Q1 |
| i-Pr | H | OMe | COOCH(CH$_3$)$_2$ | Cl | Q2 |
| i-Pr | H | OMe | COOCH(CH$_3$)$_2$ | Cl | Q3 |
| i-Pr | H | OMe | CON(CH$_3$)$_2$ | MeS | H |

-continued

| | | | | | |
|---|---|---|---|---|---|
| i-Pr | H | OMe | CON(CH₃)₂ | MeSO | H |
| i-Pr | H | OMe | CON(CH₃)₂ | Ms | H |
| i-Pr | H | OMe | CON(CH₃)₂ | Ms | Q1 |
| i-Pr | H | OMe | CON(CH₃)₂ | Ms | Q18 |
| i-Pr | H | OMe | CON(CH₃)₂ | Ms | Q13 |
| i-Pr | H | OMe | CON(CH₃)₂ | Ms | Q4 |
| i-Pr | H | OMe | CON(CH₃)₂ | Ms | Q5 |
| i-Pr | H | OMe | CON(CH₃)₂ | Ms | Q6 |
| i-Pr | H | OMe | CON(CH₃)₂ | Ms | Q22 |
| i-Pr | Me | OMe | CON(CH₃)₂ | Ms | H |
| i-Pr | Cl | OMe | CON(CH₃)₂ | Ms | H |
| i-Pr | CF₃ | OMe | CON(CH₃)₂ | Ms | H |
| i-Pr | OMe | OMe | CON(CH₃)₂ | Ms | H |
| i-Pr | SMe | OMe | CON(CH₃)₂ | Ms | H |
| i-Pr | H | OMe | CON(CH₃)₂ | Cl | H |
| i-Pr | H | OMe | CON(CH₃)₂ | Cl | Q1 |
| i-Pr | H | OMe | CON(CH₃)₂ | Cl | Q2 |
| i-Pr | H | OMe | CON(CH₃)₂ | Cl | Q3 |
| i-Pr | H | OMe | COOC₄H₉ | Ms | H |
| i-Pr | H | OMe | COOC₄H₉ | Cl | H |
| i-Pr | H | OMe | COOCH₂CH(CH₃)₂ | Ms | H |
| i-Pr | H | OMe | COOCH₂CH(CH₃)₂ | Cl | H |
| i-Pr | H | OMe | COOCH(CH₃)C₂H₅ | Ms | H |
| i-Pr | H | OMe | COOCH(CH₃)C₂H₅ | Cl | H |
| i-Pr | H | OMe | COOC(CH₃)₃ | Ms | H |
| i-Pr | H | OMe | COOC(CH₃)₃ | Cl | H |
| i-Pr | H | OMe | CONHMe | Ms | H |
| i-Pr | H | OMe | CONHMe | Cl | H |
| i-Pr | H | OMe | CONHEt | Ms | H |
| i-Pr | H | OMe | CONHEt | Cl | H |
| i-Pr | H | Cl | COOMe | Ms | Q6 |
| i-Pr | H | Cl | COOMe | Ms | Q20 |
| i-Pr | Me | Cl | COOMe | Ms | H |
| i-Pr | Cl | Cl | COOMe | Ms | H |
| i-Pr | CF₃ | Cl | COOMe | Ms | H |
| i-Pr | OMe | Cl | COOMe | Ms | H |
| i-Pr | SMe | Cl | COOMe | Ms | H |
| i-Pr | H | Cl | COOEt | MeS | H |
| i-Pr | H | Cl | COOEt | MeSO | H |
| i-Pr | H | Cl | COOEt | Ms | H |
| i-Pr | H | Cl | COOEt | Ms | Q1 |
| i-Pr | H | Cl | COOEt | Ms | Q18 |
| i-Pr | H | Cl | COOEt | Ms | Q13 |
| i-Pr | H | Cl | COOEt | Ms | Q4 |
| i-Pr | H | Cl | COOEt | Ms | Q5 |
| i-Pr | H | Cl | COOEt | Ms | Q6 |
| i-Pr | H | Cl | COOEt | Ms | Q22 |
| i-Pr | Me | Cl | COOEt | Ms | H |
| i-Pr | Cl | Cl | COOEt | Ms | H |
| i-Pr | CF₃ | Cl | COOEt | Ms | H |
| i-Pr | OMe | Cl | COOEt | Ms | H |
| i-Pr | SMe | Cl | COOEt | Ms | H |
| i-Pr | H | Cl | COOCH(CH₃)₂ | MeS | H |
| i-Pr | H | Cl | COOCH(CH₃)₂ | MeSO | H |
| i-Pr | H | Cl | COOCH(CH₃)₂ | Ms | H |
| i-Pr | H | Cl | COOCH(CH₃)₂ | Ms | Q7 |
| i-Pr | H | Cl | COOCH(CH₃)₂ | Ms | Q12 |
| i-Pr | H | Cl | COOCH(CH₃)₂ | Ms | Q9 |
| i-Pr | H | Cl | COOCH(CH₃)₂ | Ms | Q4 |
| i-Pr | H | Cl | COOCH(CH₃)₂ | Ms | Q5 |
| i-Pr | H | Cl | COOCH(CH₃)₂ | Ms | Q6 |
| i-Pr | H | Cl | COOCH(CH₃)₂ | Ms | Q17 |
| i-Pr | Me | Cl | COOCH(CH₃)₂ | Ms | H |
| i-Pr | Cl | Cl | COOCH(CH₃)₂ | Ms | H |
| i-Pr | CF₃ | Cl | COOCH(CH₃)₂ | Ms | H |
| i-Pr | OMe | Cl | COOCH(CH₃)₂ | Ms | H |
| i-Pr | SMe | Cl | COOCH(CH₃)₂ | Ms | H |
| i-Pr | H | Cl | COOMe | Cl | H |
| i-Pr | H | Cl | COOMe | Cl | Q1 |
| i-Pr | H | Cl | COOMe | Cl | Q2 |
| i-Pr | H | Cl | COOMe | Cl | Q3 |
| i-Pr | H | Cl | COOEt | Cl | H |
| i-Pr | H | Cl | COOEt | Cl | Q1 |
| i-Pr | H | Cl | COOEt | Cl | Q2 |
| i-Pr | H | Cl | COOEt | Cl | Q3 |
| i-Pr | H | Cl | COOCH(CH₃)₂ | Cl | H |
| i-Pr | H | Cl | COOCH(CH₃)₂ | Cl | Q1 |
| i-Pr | H | Cl | COOCH(CH₃)₂ | Cl | Q2 |
| i-Pr | H | Cl | COOCH(CH₃)₂ | Cl | Q3 |
| i-Pr | H | Cl | CON(CH₃)₂ | MeS | H |
| i-Pr | H | Cl | CON(CH₃)₂ | MeSO | H |
| i-Pr | H | Cl | CON(CH₃)₂ | Ms | H |
| i-Pr | H | Cl | CON(CH₃)₂ | Ms | Q1 |

-continued

| | | | | | |
|---|---|---|---|---|---|
| i-Pr | H | Cl | CON(CH$_3$)$_2$ | Ms | Q18 |
| i-Pr | H | Cl | CON(CH$_3$)$_2$ | Ms | Q13 |
| i-Pr | H | Cl | CON(CH$_3$)$_2$ | Ms | Q4 |
| i-Pr | H | Cl | CON(CH$_3$)$_2$ | Ms | Q5 |
| i-Pr | H | Cl | CON(CH$_3$)$_2$ | Ms | Q6 |
| i-Pr | H | Cl | CON(CH$_3$)$_2$ | Ms | Q22 |
| i-Pr | Me | Cl | CON(CH$_3$)$_2$ | Ms | H |
| i-Pr | Cl | Cl | CON(CH$_3$)$_2$ | Ms | H |
| i-Pr | CF$_3$ | Cl | CON(CH$_3$)$_2$ | Ms | H |
| i-Pr | OMe | Cl | CON(CH$_3$)$_2$ | Ms | H |
| i-Pr | SMe | Cl | CON(CH$_3$)$_2$ | Ms | H |
| i-Pr | H | Cl | CON(CH$_3$)$_2$ | Cl | H |
| i-Pr | H | Cl | CON(CH$_3$)$_2$ | Cl | Q1 |
| i-Pr | H | Cl | CON(CH$_3$)$_2$ | Cl | Q2 |
| i-Pr | H | Cl | CON(CH$_3$)$_2$ | Cl | Q3 |
| i-Pr | H | Cl | COOC$_4$H$_9$ | Ms | H |
| i-Pr | H | Cl | COOC$_4$H$_9$ | Cl | H |
| i-Pr | H | Cl | COOCH$_2$CH(CH$_3$)$_2$ | Ms | H |
| i-Pr | H | Cl | COOCH$_2$CH(CH$_3$)$_2$ | Cl | H |
| i-Pr | H | Cl | COOCH(CH$_3$)C$_2$H$_5$ | Ms | H |
| i-Pr | H | Cl | COOCH(CH$_3$)C$_2$H$_5$ | Cl | H |
| i-Pr | H | Cl | COOC(CH$_3$)$_3$ | Ms | H |
| i-Pr | H | Cl | COOC(CH$_3$)$_3$ | Cl | H |
| i-Pr | H | Cl | CONHMe | Ms | H |
| i-Pr | H | Cl | CONHMe | Cl | H |
| i-Pr | H | Cl | CONHEt | Ms | H |
| i-Pr | H | Cl | CONHEt | Cl | H |
| i-Pr | H | Cl | CONHCH(CH$_3$)$_2$ | Ms | H |
| i-Pr | H | Cl | CONHCH(CH$_3$)$_2$ | Cl | H |
| i-Pr | H | Cl | CONHC(CH$_3$)$_3$ | Ms | H |
| i-Pr | H | Cl | CONHC(CH$_3$)$_3$ | Cl | H |
| i-Pr | H | Cl | CONHC$_4$H$_9$ | Ms | H |
| i-Pr | H | Cl | CONHC$_4$H$_9$ | Cl | H |
| i-Pr | H | Cl | CONHCH$_2$CH(CH$_3$)$_2$ | Ms | H |
| i-Pr | H | Cl | CONHCH$_2$CH(CH$_3$)$_2$ | Cl | H |
| i-Pr | H | Cl | CONHCH(CH$_3$)C$_2$H$_5$ | Ms | H |
| i-Pr | H | Cl | CONHCH(CH$_3$)C$_2$H$_5$ | Cl | H |
| i-Pr | H | Cl | CONEt$_2$ | Ms | H |
| i-Pr | H | Cl | CONEt$_2$ | Cl | H |
| i-Pr | H | Cl | CON[CH(CH$_3$)$_2$]$_2$ | Ms | H |
| i-Pr | H | Cl | CON[CH(CH$_3$)$_2$]$_2$ | Cl | H |
| i-Pr | H | Cl | Y1 | Ms | H |
| i-Pr | H | Cl | Y1 | Cl | H |
| i-Pr | H | Cl | Y2 | Ms | H |
| i-Pr | H | Cl | Y2 | Cl | H |
| i-Pr | H | Cl | Y3 | Ms | H |
| i-Pr | H | Cl | Y3 | Cl | H |
| i-Pr | H | Cl | COOPh | Ms | H |
| i-Pr | H | Cl | COOPh | Cl | H |
| i-Pr | H | Cl | COOCH$_2$Ph | Ms | H |
| i-Pr | H | Cl | COOCH$_2$Ph | Cl | H |
| i-Pr | H | Cl | COOCH$_2$CH=CH$_2$ | Ms | H |
| i-Pr | H | Cl | COOCH$_2$CH=CH$_2$ | Cl | H |
| i-Pr | H | Cl | COOCH$_2$C≡CH | Ms | H |
| i-Pr | H | Cl | COOCH$_2$C≡CH | Cl | H |
| i-Pr | H | Cl | C(O)SMe | Ms | H |
| i-Pr | H | Cl | C(O)SMe | Cl | H |
| i-Pr | H | Cl | C(O)SEt | Ms | H |
| i-Pr | H | Cl | C(O)SEt | Cl | H |
| i-Pr | H | Cl | C(O)SCH(CH$_3$)$_2$ | Ms | H |
| i-Pr | H | Cl | C(O)SCH(CH$_3$)$_2$ | Cl | H |
| i-Pr | H | Cl | C(O)SC$_3$H$_7$ | Ms | H |
| i-Pr | H | Cl | C(O)SC$_3$H$_7$ | Cl | H |
| i-Pr | H | Cl | C(S)OMe | Ms | H |
| i-Pr | H | Cl | C(S)OMe | Cl | H |
| i-Pr | H | Cl | C(S)OEt | Ms | H |
| i-Pr | H | Cl | C(S)OEt | Cl | H |
| i-Pr | H | Cl | C(S)OCH(CH$_3$)$_2$ | Ms | H |
| i-Pr | H | Cl | C(S)OCH(CH$_3$)$_2$ | Cl | H |
| i-Pr | H | Cl | C(S)SC$_3$H$_7$ | Ms | H |
| i-Pr | H | Cl | C(S)SC$_3$H$_7$ | Cl | H |
| i-Pr | H | Cl | C(S)SMe | Ms | H |
| i-Pr | H | Cl | C(S)SMe | Cl | H |
| i-Pr | H | Cl | C(S)SEt | Ms | H |
| i-Pr | H | Cl | C(S)SEt | Cl | H |
| i-Pr | H | Cl | C(S)SCH(CH$_3$)$_2$ | Ms | H |
| i-Pr | H | Cl | C(S)SCH(CH$_3$)$_2$ | Cl | H |
| i-Pr | H | Cl | C(S)SC$_3$H$_7$ | Ms | H |
| i-Pr | H | Cl | C(S)SC$_3$H$_7$ | Cl | H |
| i-Pr | H | Me | COOMe | MeS | H |
| i-Pr | H | Me | COOMe | MeSO | H |
| i-Pr | H | Me | COOMe | Ms | H |
| i-Pr | H | Me | COOMe | Ms | Q1 |

-continued

| | | | | | |
|---|---|---|---|---|---|
| i-Pr | H | Me | COOMe | Ms | Q2 |
| i-Pr | H | Me | COOMe | Ms | Q3 |
| i-Pr | H | Me | COOMe | Ms | Q4 |
| i-Pr | H | Me | COOMe | Ms | Q5 |
| i-Pr | H | Me | COOMe | Ms | Q6 |
| i-Pr | H | Me | COOMe | Ms | Q20 |
| i-Pr | Me | Me | COOMe | Ms | H |
| i-Pr | Cl | Me | COOMe | Ms | H |
| i-Pr | CF$_3$ | Me | COOMe | Ms | H |
| i-Pr | OMe | Me | COOMe | Ms | H |
| i-Pr | SMe | Me | COOMe | Ms | H |
| i-Pr | H | Me | COOEt | MeS | H |
| i-Pr | H | Me | COOEt | MeSO | H |
| i-Pr | H | Me | COOEt | Ms | H |
| i-Pr | H | Me | COOEt | Ms | Q1 |
| i-Pr | H | Me | COOEt | Ms | Q18 |
| i-Pr | H | Me | COOEt | Ms | Q13 |
| i-Pr | H | Me | COOEt | Ms | Q4 |
| i-Pr | H | Me | COOEt | Ms | Q5 |
| i-Pr | H | Me | COOEt | Ms | Q6 |
| i-Pr | H | Me | COOEt | Ms | Q22 |
| i-Pr | Me | Me | COOEt | Ms | H |
| i-Pr | Cl | Me | COOEt | Ms | H |
| i-Pr | CF$_3$ | Me | COOEt | Ms | H |
| i-Pr | OMe | Me | COOEt | Ms | H |
| i-Pr | SMe | Me | COOEt | Ms | H |
| i-Pr | H | Me | COOCH(CH$_3$)$_2$ | MeS | H |
| i-Pr | H | Me | COOCH(CH$_3$)$_2$ | MeSO | H |
| i-Pr | H | Me | COOCH(CH$_3$)$_2$ | Ms | H |
| i-Pr | H | Me | COOCH(CH$_3$)$_2$ | Ms | Q7 |
| i-Pr | H | Me | COOCH(CH$_3$)$_2$ | Ms | Q12 |
| i-Pr | H | Me | COOCH(CH$_3$)$_2$ | Ms | Q9 |
| i-Pr | H | Me | COOCH(CH$_3$)$_2$ | Ms | Q4 |
| i-Pr | H | Me | COOCH(CH$_3$)$_2$ | Ms | Q5 |
| i-Pr | H | Me | COOCH(CH$_3$)$_2$ | Ms | Q6 |
| i-Pr | H | Me | COOCH(CH$_3$)$_2$ | Ms | Q17 |
| i-Pr | Me | Me | COOCH(CH$_3$)$_2$ | Ms | H |
| i-Pr | Cl | Me | COOCH(CH$_3$)$_2$ | Ms | H |
| i-Pr | CF$_3$ | Me | COOCH(CH$_3$)$_2$ | Ms | H |
| i-Pr | OMe | Me | COOCH(CH$_3$)$_2$ | Ms | H |
| i-Pr | SMe | Me | COOCH(CH$_3$)$_2$ | Ms | H |
| i-Pr | H | Me | COOMe | Cl | H |
| i-Pr | H | Me | COOMe | Cl | Q1 |
| i-Pr | H | Me | COOMe | Cl | Q2 |
| i-Pr | H | Me | COOMe | Cl | Q3 |
| i-Pr | H | Me | COOEt | Cl | H |
| i-Pr | H | Me | COOEt | Cl | Q1 |
| i-Pr | H | Me | COOEt | Cl | Q2 |
| i-Pr | H | Me | COOEt | Cl | Q3 |
| i-Pr | H | Me | COOCH(CH$_3$)$_2$ | Cl | H |
| i-Pr | H | Me | COOCH(CH$_3$)$_2$ | Cl | Q1 |
| i-Pr | H | Me | COOCH(CH$_3$)$_2$ | Cl | Q2 |
| i-Pr | H | Me | COOCH(CH$_3$)$_2$ | Cl | Q3 |
| i-Pr | H | Me | CON(CH$_3$)$_2$ | MeS | H |
| i-Pr | H | Me | CON(CH$_3$)$_2$ | MeSO | H |
| i-Pr | H | Me | CON(CH$_3$)$_2$ | Ms | H |
| i-Pr | H | Me | CON(CH$_3$)$_2$ | Ms | Q1 |
| i-Pr | H | Me | CON(CH$_3$)$_2$ | Ms | Q18 |
| i-Pr | H | Me | CON(CH$_3$)$_2$ | Ms | Q13 |
| i-Pr | H | Me | CON(CH$_3$)$_2$ | Ms | Q4 |
| i-Pr | H | Me | CON(CH$_3$)$_2$ | Ms | Q5 |
| i-Pr | H | Me | CON(CH$_3$)$_2$ | Ms | Q6 |
| i-Pr | H | Me | CON(CH$_3$)$_2$ | Ms | Q22 |
| i-Pr | Me | Me | CON(CH$_3$)$_2$ | Ms | H |
| i-Pr | Cl | Me | CON(CH$_3$)$_2$ | Ms | H |
| i-Pr | CF$_3$ | Me | CON(CH$_3$)$_2$ | Ms | H |
| i-Pr | OMe | Me | CON(CH$_3$)$_2$ | Ms | H |
| i-Pr | SMe | Me | CON(CH$_3$)$_2$ | Ms | H |
| i-Pr | H | Me | CON(CH$_3$)$_2$ | Cl | H |
| i-Pr | H | Me | CON(CH$_3$)$_2$ | Cl | Q1 |
| i-Pr | H | Me | CON(CH$_3$)$_2$ | Cl | Q2 |
| i-Pr | H | Me | CON(CH$_3$)$_2$ | Cl | Q3 |
| i-Pr | H | Me | COOC$_4$H$_9$ | Ms | H |
| i-Pr | H | Me | COOC$_4$H$_9$ | Cl | H |
| i-Pr | H | Me | COOCH$_2$CH(CH$_3$)$_2$ | Ms | H |
| i-Pr | H | Me | COOCH$_2$CH(CH$_3$)$_2$ | Cl | H |
| i-Pr | H | Me | COOCH(CH$_3$)C$_2$H$_5$ | Ms | H |
| i-Pr | H | Me | COOCH(CH$_3$)C$_2$H$_5$ | Cl | H |
| i-Pr | H | Me | COOC(CH$_3$)$_3$ | Ms | H |
| i-Pr | H | Me | COOC(CH$_3$)$_3$ | Cl | H |
| i-Pr | H | Me | CONHMe | Ms | H |
| i-Pr | H | Me | CONHMe | Cl | H |
| i-Pr | H | Me | CONHEt | Ms | H |

-continued

| | | | | | |
|---|---|---|---|---|---|
| i-Pr | H | Me | CONHEt | Cl | H |
| i-Pr | H | Me | CONHCH(CH$_3$)$_2$ | Ms | H |
| i-Pr | H | Me | CONHCH(CH$_3$)$_2$ | Cl | H |
| i-Pr | H | Me | CONHC(CH$_3$)$_3$ | Ms | H |
| i-Pr | H | Me | CONHC(CH$_3$)$_3$ | Cl | H |
| i-Pr | H | Me | CONHC$_4$H$_9$ | Ms | H |
| i-Pr | H | Me | CONHC$_4$H$_9$ | Cl | H |
| i-Pr | H | Me | CONHCH$_2$CH(CH$_3$)$_2$ | Ms | H |
| i-Pr | H | Me | CONHCH$_2$CH(CH$_3$)$_2$ | Cl | H |
| i-Pr | H | Me | CONHCH(CH$_3$)C$_2$H$_5$ | Ms | H |
| i-Pr | H | Me | CONHCH(CH$_3$)C$_2$H$_5$ | Cl | H |
| i-Pr | H | Me | CONEt$_2$ | Ms | H |
| i-Pr | H | Me | CONEt$_2$ | Cl | H |
| i-Pr | H | Me | CON[CH(CH$_3$)$_2$]$_2$ | Ms | H |
| i-Pr | H | Me | CON[CH(CH$_3$)$_2$]$_2$ | Cl | H |
| i-Pr | H | Me | Y1 | Ms | H |
| i-Pr | H | Me | Y1 | Cl | H |
| i-Pr | H | Me | Y2 | Ms | H |
| i-Pr | H | Me | Y2 | Cl | H |
| i-Pr | H | Me | Y3 | Ms | H |
| i-Pr | H | Me | Y3 | Cl | H |
| i-Pr | H | Me | COOPh | Ms | H |
| i-Pr | H | Me | COOPh | Cl | H |
| i-Pr | H | Me | COOCH$_2$Ph | Ms | H |
| i-Pr | H | Me | COOCH$_2$Ph | Cl | H |
| i-Pr | H | Me | COOCH$_2$CH=CH$_2$ | Ms | H |
| i-Pr | H | Me | COOCH$_2$CH=CH$_2$ | Cl | H |
| i-Pr | H | Me | COOCH$_2$C≡CH | Ms | H |
| i-Pr | H | Me | COOCH$_2$C≡CH | Cl | H |
| i-Pr | H | Me | C(O)SMe | Ms | H |
| i-Pr | H | Me | C(O)SMe | Cl | H |
| i-Pr | H | Me | C(O)SEt | Ms | H |
| i-Pr | H | Me | C(O)SEt | Cl | H |
| i-Pr | H | Me | C(O)SCH(CH$_3$)$_2$ | Ms | H |
| i-Pr | H | Me | C(O)SCH(CH$_3$)$_2$ | Cl | H |
| i-Pr | H | Me | C(O)SC$_3$H$_7$ | Ms | H |
| i-Pr | H | Me | C(O)SC$_3$H$_7$ | Cl | H |
| i-Pr | H | Me | C(S)OMe | Ms | H |
| i-Pr | H | Me | C(S)OMe | Cl | H |
| i-Pr | H | Me | C(S)OEt | Ms | H |
| i-Pr | H | Me | C(S)OEt | Cl | H |
| i-Pr | H | Me | C(S)OCH(CH$_3$)$_2$ | Ms | H |
| i-Pr | H | Me | C(S)OCH(CH$_3$)$_2$ | Cl | H |
| i-Pr | H | Me | C(S)SC$_3$H$_7$ | Ms | H |
| i-Pr | H | Me | C(S)SC$_3$H$_7$ | Cl | H |
| i-Pr | H | Me | C(S)SMe | Ms | H |
| i-Pr | H | Me | C(S)SMe | Cl | H |
| i-Pr | H | Me | C(S)SEt | Ms | H |
| i-Pr | H | Me | C(S)SEt | Cl | H |
| i-Pr | H | Me | C(S)SCH(CH$_3$)$_2$ | Ms | H |
| i-Pr | H | Me | C(S)SCH(CH$_3$)$_2$ | Cl | H |
| i-Pr | H | Me | C(S)SC$_3$H$_7$ | Ms | H |
| i-Pr | H | Me | C(S)SC$_3$H$_7$ | Cl | H |
| i-Pr | H | OMe | COOMe | MeS | H |
| i-Pr | H | OMe | COOMe | MeSO | H |
| i-Pr | H | OMe | COOMe | Ms | H |
| i-Pr | H | OMe | COOMe | Ms | Q1 |
| i-Pr | H | OMe | COOMe | Ms | Q2 |
| i-Pr | H | OMe | COOMe | Ms | Q3 |
| i-Pr | H | OMe | COOMe | Ms | Q4 |
| i-Pr | H | OMe | COOMe | Ms | Q5 |
| i-Pr | H | OMe | COOMe | Ms | Q6 |
| i-Pr | H | OMe | COOMe | Ms | Q20 |
| i-Pr | Me | OMe | COOMe | Ms | H |
| i-Pr | Cl | OMe | COOMe | Ms | H |
| i-Pr | CF$_3$ | OMe | COOMe | Ms | H |
| i-Pr | OMe | OMe | COOMe | Ms | H |
| i-Pr | SMe | OMe | COOMe | Ms | H |
| i-Pr | H | OMe | COOEt | MeS | H |
| i-Pr | H | OMe | COOEt | MeSO | H |
| i-Pr | H | OMe | COOEt | Ms | H |
| i-Pr | H | OMe | COOEt | Ms | Q1 |
| i-Pr | H | OMe | COOEt | Ms | Q18 |
| i-Pr | H | OMe | COOEt | Ms | Q13 |
| i-Pr | H | OMe | COOEt | Ms | Q4 |
| i-Pr | H | OMe | COOEt | Ms | Q5 |
| i-Pr | H | OMe | COOEt | Ms | Q6 |
| i-Pr | H | OMe | COOEt | Ms | Q22 |
| i-Pr | Me | OMe | COOEt | Ms | H |
| i-Pr | Cl | OMe | COOEt | Ms | H |
| i-Pr | CF$_3$ | OMe | COOEt | Ms | H |
| i-Pr | OMe | OMe | COOEt | Ms | H |
| i-Pr | SMe | OMe | COOEt | Ms | H |

-continued

| | | | | | |
|---|---|---|---|---|---|
| i-Pr | H | OMe | COOCH(CH₃)₂ | MeS | H |
| i-Pr | H | OMe | COOCH(CH₃)₂ | MeSO | H |
| i-Pr | H | OMe | COOCH(CH₃)₂ | Ms | H |
| i-Pr | H | OMe | COOCH(CH₃)₂ | Ms | Q7 |
| i-Pr | H | OMe | COOCH(CH₃)₂ | Ms | Q12 |
| i-Pr | H | OMe | COOCH(CH₃)₂ | Ms | Q9 |
| i-Pr | H | OMe | COOCH(CH₃)₂ | Ms | Q4 |
| i-Pr | H | OMe | COOCH(CH₃)₂ | Ms | Q5 |
| i-Pr | H | OMe | COOCH(CH₃)₂ | Ms | Q6 |
| i-Pr | H | OMe | COOCH(CH₃)₂ | Ms | Q17 |
| i-Pr | Me | OMe | COOCH(CH₃)₂ | Ms | H |
| i-Pr | Cl | OMe | COOCH(CH₃)₂ | Ms | H |
| i-Pr | CF₃ | OMe | COOCH(CH₃)₂ | Ms | H |
| i-Pr | OMe | OMe | COOCH(CH₃)₂ | Ms | H |
| i-Pr | SMe | OMe | COOCH(CH₃)₂ | Ms | H |
| i-Pr | H | OMe | COOMe | Cl | H |
| i-Pr | H | OMe | COOMe | Cl | Q1 |
| i-Pr | H | OMe | COOMe | Cl | Q2 |
| i-Pr | H | OMe | COOMe | Cl | Q3 |
| i-Pr | H | OMe | COOEt | Cl | H |
| i-Pr | H | OMe | COOEt | Cl | Q1 |
| i-Pr | H | OMe | COOEt | Cl | Q2 |
| i-Pr | H | OMe | COOEt | Cl | Q3 |
| i-Pr | H | OMe | COOCH(CH₃)₂ | Cl | H |
| i-Pr | H | OMe | COOCH(CH₃)₂ | Cl | Q1 |
| i-Pr | H | OMe | COOCH(CH₃)₂ | Cl | Q2 |
| i-Pr | H | OMe | COOCH(CH₃)₂ | Cl | Q3 |
| i-Pr | H | OMe | CON(CH₃)₂ | MeS | H |
| i-Pr | H | OMe | CON(CH₃)₂ | MeSO | H |
| i-Pr | H | OMe | CON(CH₃)₂ | Ms | H |
| i-Pr | H | OMe | CON(CH₃)₂ | Ms | Q1 |
| i-Pr | H | OMe | CON(CH₃)₂ | Ms | Q18 |
| i-Pr | H | OMe | CON(CH₃)₂ | Ms | Q13 |
| i-Pr | H | OMe | CON(CH₃)₂ | Ms | Q4 |
| i-Pr | H | OMe | CON(CH₃)₂ | Ms | Q5 |
| i-Pr | H | OMe | CON(CH₃)₂ | Ms | Q6 |
| i-Pr | H | OMe | CON(CH₃)₂ | Ms | Q22 |
| i-Pr | Me | OMe | CON(CH₃)₂ | Ms | H |
| i-Pr | Cl | OMe | CON(CH₃)₂ | Ms | H |
| i-Pr | CF₃ | OMe | CON(CH₃)₂ | Ms | H |
| i-Pr | OMe | OMe | CON(CH₃)₂ | Ms | H |
| i-Pr | SMe | OMe | CON(CH₃)₂ | Ms | H |
| i-Pr | H | OMe | CON(CH₃)₂ | Cl | H |
| i-Pr | H | OMe | CON(CH₃)₂ | Cl | Q1 |
| i-Pr | H | OMe | CON(CH₃)₂ | Cl | Q2 |
| i-Pr | H | OMe | CON(CH₃)₂ | Cl | Q3 |
| i-Pr | H | OMe | COOC₄H₉ | Ms | H |
| i-Pr | H | OMe | COOC₄H₉ | Cl | H |
| i-Pr | H | OMe | COOCH₂CH(CH₃)₂ | Ms | H |
| i-Pr | H | OMe | COOCH₂CH(CH₃)₂ | Cl | H |
| i-Pr | H | OMe | COOCH(CH₃)C₂H₅ | Ms | H |
| i-Pr | H | OMe | COOCH(CH₃)C₂H₅ | Cl | H |
| i-Pr | H | OMe | COOC(CH₃)₃ | Ms | H |
| i-Pr | H | OMe | COOC(CH₃)₃ | Cl | H |
| i-Pr | H | OMe | CONHMe | Ms | H |
| i-Pr | H | OMe | CONHMe | Cl | H |
| i-Pr | H | OMe | CONHEt | Ms | H |
| i-Pr | H | OMe | CONHEt | Cl | H |
| i-Pr | H | OMe | CONHCH(CH₃)₂ | Ms | H |
| i-Pr | H | OMe | CONHCH(CH₃)₂ | Cl | H |
| i-Pr | H | OMe | CONHC(CH₃)₃ | Ms | H |
| i-Pr | H | OMe | CONHC(CH₃)₃ | Cl | H |
| i-Pr | H | OMe | CONHC₄H₉ | Ms | H |
| i-Pr | H | OMe | CONHC₄H₉ | Cl | H |
| i-Pr | H | OMe | CONHCH₂CH(CH₃)₂ | Ms | H |
| i-Pr | H | OMe | CONHCH₂CH(CH₃)₂ | Cl | H |
| i-Pr | H | OMe | CONHCH(CH₃)C₂H₅ | Ms | H |
| i-Pr | H | OMe | CONHCH(CH₃)C₂H₅ | Cl | H |
| i-Pr | H | OMe | CONEt₂ | Ms | H |
| i-Pr | H | OMe | CONEt₂ | Cl | H |
| i-Pr | H | OMe | CON[CH(CH₃)₂]₂ | Ms | H |
| i-Pr | H | OMe | CON[CH(CH₃)₂]₂ | Cl | H |
| i-Pr | H | OMe | Y1 | Ms | H |
| i-Pr | H | OMe | Y1 | Cl | H |
| i-Pr | H | OMe | Y2 | Ms | H |
| i-Pr | H | OMe | Y2 | Cl | H |
| i-Pr | H | OMe | Y3 | Ms | H |
| i-Pr | H | OMe | Y3 | Cl | H |
| i-Pr | H | OMe | COOPh | Ms | H |
| i-Pr | H | OMe | COOPh | Cl | H |
| i-Pr | H | OMe | COOCH₂Ph | Ms | H |
| i-Pr | H | OMe | COOCH₂Ph | Cl | H |
| i-Pr | H | OMe | COOCH₂CH=CH₂ | Ms | H |

-continued

| | | | | | |
|---|---|---|---|---|---|
| i-Pr | H | OMe | COOCH$_2$CH=CH$_2$ | Cl | H |
| i-Pr | H | OMe | COOCH$_2$C≡CH | Ms | H |
| i-Pr | H | OMe | COOCH$_2$C≡CH | Cl | H |
| i-Pr | H | OMe | C(O)SMe | Ms | H |
| i-Pr | H | OMe | C(O)SMe | Cl | H |
| i-Pr | H | OMe | C(O)SEt | Ms | H |
| i-Pr | H | OMe | C(O)SEt | Cl | H |
| i-Pr | H | OMe | C(O)SCH(CH$_3$)$_2$ | Ms | H |
| i-Pr | H | OMe | C(O)SCH(CH$_3$)$_2$ | Cl | H |
| i-Pr | H | OMe | C(O)SC$_3$H$_7$ | Ms | H |
| i-Pr | H | OMe | C(O)SC$_3$H$_7$ | Cl | H |
| i-Pr | H | OMe | C(S)OMe | Ms | H |
| i-Pr | H | OMe | C(S)OMe | Cl | H |
| i-Pr | H | OMe | C(S)OEt | Ms | H |
| i-Pr | H | OMe | C(S)OEt | Cl | H |
| i-Pr | H | OMe | C(S)OCH(CH$_3$)$_2$ | Ms | H |
| i-Pr | H | OMe | C(S)OCH(CH$_3$)$_2$ | Cl | H |
| i-Pr | H | OMe | C(S)SC$_3$H$_7$ | Ms | H |
| i-Pr | H | OMe | C(S)SC$_3$H$_7$ | Cl | H |
| i-Pr | H | OMe | C(S)SMe | Ms | H |
| i-Pr | H | OMe | C(S)SMe | Cl | H |
| i-Pr | H | OMe | C(S)SEt | Ms | H |
| i-Pr | H | OMe | C(S)SEt | Cl | H |
| i-Pr | H | OMe | C(S)SCH(CH$_3$)$_2$ | Ms | H |
| i-Pr | H | OMe | C(S)SCH(CH$_3$)$_2$ | Cl | H |
| i-Pr | H | OMe | C(S)SC$_3$H$_7$ | Ms | H |
| i-Pr | H | OMe | C(S)SC$_3$H$_7$ | Cl | H |
| i-Pr | H | Br | COOMe | Ms | H |
| i-Pr | H | Br | COOMe | Cl | H |
| i-Pr | H | Br | COOEt | Ms | H |
| i-Pr | H | Br | COOEt | Cl | H |
| i-Pr | H | Br | COOCH(CH$_3$)$_2$ | Ms | H |
| i-Pr | H | Br | COOCH(CH$_3$)$_2$ | Cl | H |
| i-Pr | H | Br | CON(CH$_3$)$_2$ | Ms | H |
| i-Pr | H | Br | CON(CH$_3$)$_2$ | Cl | H |
| i-Pr | H | Br | CONHMe | Ms | H |
| i-Pr | H | Br | CONHEt | Ms | H |
| i-Pr | H | Br | CONHC$_3$H$_7$ | Ms | H |
| i-Pr | H | Br | CONHCH(CH$_3$)$_2$ | Ms | H |
| i-Pr | H | Br | CONHC(CH$_3$)$_3$ | Ms | H |
| i-Pr | H | Br | CONEt$_2$ | Ms | H |
| i-Pr | H | Br | CONHC(CH$_3$)$_3$ | Ms | H |
| i-Pr | H | Br | CONHC$_4$H$_9$ | Ms | H |
| i-Pr | H | Br | CONHC$_4$H$_9$ | Ms | H |
| i-Pr | H | Br | CON[CH(CH$_3$)$_2$]$_2$ | Ms | H |
| i-Pr | H | Br | Y1 | Ms | H |
| i-Pr | H | Br | Y2 | Ms | H |
| i-Pr | H | Br | COOPh | Ms | H |
| i-Pr | H | Br | COOCH$_2$Ph | Ms | H |
| i-Pr | H | Br | COOCH$_2$CH=CH$_2$ | Ms | H |
| i-Pr | H | Br | COOCH$_2$C≡CH | Ms | H |
| i-Pr | H | OEt | COOMe | Ms | H |
| i-Pr | H | OEt | COOMe | Cl | H |
| i-Pr | H | OEt | COOEt | Ms | H |
| i-Pr | H | OEt | COOEt | Cl | H |
| i-Pr | H | OEt | COOCH(CH$_2$)$_2$ | Ms | H |
| i-Pr | H | OEt | COOCH(CH$_2$)$_2$ | Cl | H |
| i-Pr | H | OEt | CON(CH$_3$)$_2$ | Ms | H |
| i-Pr | H | OEt | CON(CH$_3$)$_2$ | Cl | H |
| i-Pr | H | OEt | CONHMe | Ms | H |
| i-Pr | H | OEt | CONHEt | Ms | H |
| i-Pr | H | OEt | CONHC$_3$H$_7$ | Ms | H |
| i-Pr | H | OEt | CONHCH(CH$_3$)$_2$ | Ms | H |
| i-Pr | H | OEt | CONEt$_2$ | Ms | H |
| i-Pr | H | OEt | CONHC(CH$_3$)$_3$ | Ms | H |
| i-Pr | H | OEt | CONHC$_4$H$_9$ | Ms | H |
| i-Pr | H | OEt | CONHC$_4$H$_9$ | Ms | H |
| i-Pr | H | OEt | CON[CH(CH$_3$)$_2$]$_2$ | Ms | H |
| i-Pr | H | OEt | Y1 | Ms | H |
| i-Pr | H | OEt | Y2 | Ms | H |
| i-Pr | H | OEt | COOPh | Ms | H |
| i-Pr | H | OEt | COOCH$_2$Ph | Ms | H |
| i-Pr | H | OEt | COOCH$_2$CH=CH$_2$ | Ms | H |
| i-Pr | H | OEt | COOCH$_2$C≡CH | Ms | H |
| i-Pr | H | OCH(CH$_3$)$_2$ | COOMe | Ms | H |
| i-Pr | H | OCH(CH$_3$)$_2$ | COOMe | Cl | H |
| i-Pr | H | OCH(CH$_3$)$_2$ | COOEt | Ms | H |
| i-Pr | H | OCH(CH$_3$)$_2$ | COOEt | Cl | H |
| i-Pr | H | OCH(CH$_3$)$_2$ | COOCH(CH$_3$)$_2$ | Ms | H |
| i-Pr | H | OCH(CH$_3$)$_2$ | COOCH(CH$_3$)$_2$ | Cl | H |
| i-Pr | H | OCH(CH$_3$)$_2$ | CON(CH$_3$)$_2$ | Ms | H |
| i-Pr | H | OCH(CH$_3$)$_2$ | CON(CH$_3$)$_2$ | Cl | H |

-continued

| | | | | | |
|---|---|---|---|---|---|
| i-Pr | H | OCH(CH$_3$)$_2$ | CONHMe | Ms | H |
| i-Pr | H | OCH(CH$_3$)$_2$ | CONHEt | Ms | H |
| i-Pr | H | OCH(CH$_3$)$_2$ | CONHC$_3$H$_7$ | Ms | 7 |
| i-Pr | H | OCH(CH$_3$)$_2$ | CONHCH(CH$_3$)$_2$ | Ms | H |
| i-Pr | H | OCH(CH$_3$)$_2$ | CONHC(CH$_3$)$_3$ | Ms | H |
| i-Pr | H | OCH(CH$_3$)$_2$ | CONEt$_2$ | Ms | H |
| i-Pr | H | OCH(CH$_3$)$_2$ | CONHC(CH$_3$)$_3$ | Ms | H |
| i-Pr | H | OCH(CH$_3$)$_2$ | CONHC$_4$H$_9$ | Ms | H |
| i-Pr | H | OCH(CH$_3$)$_2$ | CONHC$_4$H$_9$ | Ms | H |
| i-Pr | H | OCH(CH$_3$)$_2$ | CON[CH(CH$_3$)$_2$]$_2$ | Ms | H |
| i-Pr | H | OCH(CH$_3$)$_2$ | Y1 | Ms | H |
| i-Pr | H | OCH(CH$_3$)$_2$ | Y2 | Ms | H |
| i-Pr | H | OCH(CH$_3$)$_2$ | COOPh | Ms | H |
| i-Pr | H | OCH(CH$_3$)$_2$ | COOCH$_2$Ph | Ms | H |
| i-Pr | H | OCH(CH$_3$)$_2$ | COOCH$_2$CH=CH$_2$ | Ms | H |
| i-Pr | H | OCH(CH$_3$)$_2$ | COOCH$_2$C≡CH | Ms | H |
| i-Pr | H | CH$_2$OCH$_3$ | COOMe | Ms | H |
| i-Pr | H | CH$_2$OCH$_3$ | COOMe | Cl | H |
| i-Pr | H | CH$_2$OCH$_3$ | COOEt | Ms | H |
| i-Pr | H | CH$_2$OCH$_3$ | COOEt | Cl | H |
| i-Pr | H | CH$_2$OCH$_3$ | COOCH(CH$_3$)$_2$ | Ms | H |
| i-Pr | H | CH$_2$OCH$_3$ | COOCH(CH$_3$)$_2$ | Cl | H |
| i-Pr | H | CH$_2$OCH$_3$ | CON(CH$_3$)$_2$ | Ms | H |
| i-Pr | H | CH$_2$OCH$_3$ | CON(CH$_3$)$_2$ | Cl | H |
| i-Pr | H | CH$_2$OCH$_3$ | CONHMe | Ms | H |
| i-Pr | H | CH$_2$OCH$_3$ | CONHEt | Ms | H |
| i-Pr | H | CH$_2$OCH$_3$ | CONHC$_3$H$_7$ | Ms | H |
| i-Pr | H | CH$_2$OCH$_3$ | CONHCH(CH$_3$)$_2$ | Ms | H |
| i-Pr | H | CH$_2$OCH$_3$ | CONHC(CH$_3$)$_3$ | Ms | H |
| i-Pr | H | CH$_2$OCH$_3$ | CONEt$_2$ | Ms | H |
| i-Pr | H | CH$_2$OCH$_3$ | CONHC(CH$_3$)$_3$ | Ms | H |
| i-Pr | H | CH$_2$OCH$_3$ | CONHC$_4$H$_9$ | Ms | H |
| i-Pr | H | CH$_2$OCH$_3$ | CONHC$_4$H$_9$ | Ms | H |
| i-Pr | H | CH$_2$OCH$_3$ | CON[CH(CH$_3$)$_2$]$_2$ | Ms | H |
| i-Pr | H | CH$_2$OCH$_3$ | Y1 | Ms | H |
| i-Pr | H | CH$_2$OCH$_3$ | Y2 | Ms | H |
| i-Pr | H | CH$_2$OCH$_3$ | COOPh | Ms | H |
| i-Pr | H | CH$_2$OCH$_3$ | COOCH$_2$Ph | Ms | H |
| i-Pr | H | CH$_2$OCH$_3$ | COOCH$_2$CH=CH$_2$ | Ms | H |
| i-Pr | H | CH$_2$OCH$_3$ | COOCH$_2$C≡CH | Ms | H |
| Me | H | NO$_2$ | COOMe | Ms | H |
| Me | H | NO$_2$ | COOEt | Ms | H |
| Me | H | NO$_2$ | COOCH(CH$_3$)$_2$ | Ms | H |
| Me | H | NO$_2$ | CONMe$_2$ | Ms | H |
| Me | H | NO$_2$ | CONEt$_2$ | Ms | H |
| Me | H | NO$_2$ | COOC$_3$H$_7$ | Ms | H |
| Me | H | NO$_2$ | Y1 | Ms | H |
| Me | H | NO$_2$ | Y2 | Ms | H |
| Me | H | NO$_2$ | Y3 | Ms | H |
| Me | H | NO$_2$ | COOPh | Ms | H |
| Me | H | NO$_2$ | COOCH$_2$Ph | Ms | H |
| Me | H | NO$_2$ | COOCH$_2$CH=CH$_2$ | Ms | H |
| Me | H | CF$_3$ | COOMe | Ms | H |
| Me | H | CF$_3$ | COOEt | Ms | H |
| Me | H | CF$_3$ | COOCH(CH$_3$)$_2$ | Ms | H |
| Me | H | CF$_3$ | CONMe$_2$ | Ms | H |
| Me | H | CF$_3$ | CONEt$_2$ | Ms | H |
| Me | H | CF$_3$ | COOC$_3$H$_7$ | Ms | H |
| Me | H | CF$_3$ | Y1 | Ms | H |
| Me | H | CF$_3$ | Y2 | Ms | H |
| Me | H | CF$_3$ | Y3 | Ms | H |
| Me | H | CF$_3$ | COOPh | Ms | H |
| Me | H | CF$_3$ | COOCH$_2$Ph | Ms | H |
| Me | H | CF$_3$ | COOCH$_2$CH=CH$_2$ | Ms | H |
| Me | H | CN | COOMe | Ms | H |
| Me | H | CN | COOEt | Ms | H |
| Me | H | CN | COOCH(CH$_3$)$_2$ | Ms | H |
| Me | H | CN | CONMe$_2$ | Ms | H |
| Me | H | CN | CONEt$_2$ | Ms | H |
| Me | H | CN | COOC$_3$H$_7$ | Ms | H |
| Me | H | CN | Y1 | Ms | H |
| Me | H | CN | Y2 | Ms | H |
| Me | H | CN | Y3 | Ms | H |
| Me | H | CN | COOPh | Ms | H |
| Me | H | CN | COOCH$_2$Ph | Ms | H |
| Me | H | CN | COOCH$_2$CH=CH$_2$ | Ms | H |
| Me | H | CH$_2$OEt | COOMe | Ms | H |
| Me | H | CH$_2$OEt | COOEt | Ms | H |
| Me | H | CH$_2$OEt | COOCH(CH$_3$)$_2$ | Ms | H |
| Me | H | CH$_2$OEt | CONMe$_2$ | Ms | H |
| Me | H | CH$_2$OEt | CONEt$_2$ | Ms | H |
| Me | H | CH$_2$OEt | COOC$_3$H$_7$ | Ms | H |
| Me | H | CH$_2$OEt | Y1 | Ms | H |

-continued

| | | | | | |
|---|---|---|---|---|---|
| Me | H | CH₂OEt | Y2 | Ms | H |
| Me | H | CH₂OEt | Y3 | Ms | H |
| Me | H | CH₂OEt | COOPh | Ms | H |
| Me | H | CH₂OEt | COOCH₂Ph | Ms | H |
| Me | H | CH₂OEt | COOCH₂CH=CH₂ | Ms | H |
| Me | H | Et | COOMe | Ms | H |
| Me | H | Et | COOEt | Ms | H |
| Me | H | Et | COOCH(CH₃)₂ | Ms | H |
| Me | H | Et | CONMe₂ | Ms | H |
| Me | H | Et | CONEt₂ | Ms | H |
| Me | H | Et | COOC₃H₇ | Ms | H |
| Me | H | Et | Y1 | Ms | H |
| Me | H | Et | Y2 | Ms | H |
| Me | H | Et | Y3 | Ms | H |
| Me | H | Et | COOPh | Ms | H |
| Me | H | Et | COOCH₂Ph | Ms | H |
| Me | H | Et | COOCH₂CH=CH₂ | Ms | H |
| Me | H | i-Pr | COOMe | Ms | H |
| Me | H | i-Pr | COOEt | Ms | H |
| Me | H | i-Pr | COOCH(CH₃)₂ | Ms | H |
| Me | H | i-Pr | CONMe₂ | Ms | H |
| Me | H | i-Pr | CONEt₂ | Ms | H |
| Me | H | i-Pr | COOC₃H₇ | Ms | H |
| Me | H | i-Pr | Y1 | Ms | H |
| Me | H | i-Pr | Y2 | Ms | H |
| Me | H | i-Pr | Y3 | Ms | H |
| Me | H | i-Pr | COOPh | Ms | H |
| Me | H | i-Pr | COOCH₂Ph | Ms | H |
| Me | H | i-Pr | COOCH₂CH=CH₂ | Ms | H |
| Me | H | n-Pr | COOMe | Ms | H |
| Me | H | n-Pr | COOEt | Ms | H |
| Me | H | n-Pr | COOCH(CH₃)₂ | Ms | H |
| Me | H | n-Pr | CONMe₂ | Ms | H |
| Me | H | n-Pr | CONEt₂ | Ms | H |
| Me | H | n-Pr | COOC₃H₇ | Ms | H |
| Me | H | n-Pr | Y1 | Ms | H |
| Me | H | n-Pr | Y2 | Ms | H |
| Me | H | n-Pr | Y3 | Ms | H |
| Me | H | n-Pr | COOPh | Ms | H |
| Me | H | n-Pr | COOCH₂Ph | Ms | H |
| Me | H | n-Pr | COOCH₂CH=CH₂ | Ms | H |
| Me | H | I | COOMe | Ms | H |
| Me | H | I | COOEt | Ms | H |
| Me | H | I | COOCH(CH₃)₂ | Ms | H |
| Me | H | I | CONMe₂ | Ms | H |
| Me | H | I | CONEt₂ | Ms | H |
| Me | H | I | COOC₃H₇ | Ms | H |
| Me | H | I | Y1 | Ms | H |
| Me | H | I | Y2 | Ms | H |
| Me | H | I | Y3 | Ms | H |
| Me | H | I | COOPh | Ms | H |
| Me | H | I | COOCH₂Ph | Ms | H |
| Me | H | I | COOCH₂CH=CH₂ | Ms | H |
| Et | H | NO₂ | COOMe | Ms | H |
| Et | H | NO₂ | COOEt | Ms | H |
| Et | H | NO₂ | COOCH(CH₃)₂ | Ms | H |
| Et | H | NO₂ | CONMe₂ | Ms | H |
| Et | H | NO₂ | CONEt₂ | Ms | H |
| Et | H | NO₂ | COOC₃H₇ | Ms | H |
| Et | H | NO₂ | Y1 | Ms | H |
| Et | H | NO₂ | Y2 | Ms | H |
| Et | H | NO₂ | Y3 | Ms | H |
| Et | H | NO₂ | COOPh | Ms | H |
| Et | H | NO₂ | COOCH₂Ph | Ms | H |
| Et | H | NO₂ | COOCH₂CH=CH₂ | Ms | H |
| Et | H | CF₃ | COOMe | Ms | H |
| Et | H | CF₃ | COOEt | Ms | H |
| Et | H | CF₃ | COOCH(CH₃)₂ | Ms | H |
| Et | H | CF₃ | CONMe₂ | Ms | H |
| Et | H | CF₃ | CONEt₂ | Ms | H |
| Et | H | CF₃ | COOC₃H₇ | Ms | H |
| Et | H | CF₃ | Y1 | Ms | H |
| Et | H | CF₃ | Y2 | Ms | H |
| Et | H | CF₃ | Y3 | Ms | H |
| Et | H | CF₃ | COOPh | Ms | H |
| Et | H | CF₃ | COOCH₂Ph | Ms | H |
| Et | H | CF₃ | COOCH₂CH=CH₂ | Ms | H |
| Et | H | CN | COOMe | Ms | H |
| Et | H | CN | COOEt | Ms | H |
| Et | H | CN | COOCH(CH₃)₂ | Ms | H |
| Et | H | CN | CONMe₂ | Ms | H |
| Et | H | CN | CONEt₂ | Ms | H |
| Et | H | CN | COOC₃H₇ | Ms | H |

-continued

| | | | | | |
|---|---|---|---|---|---|
| Et | H | CN | Y1 | Ms | H |
| Et | H | CN | Y2 | Ms | H |
| Et | H | CN | Y3 | Ms | H |
| Et | H | CN | COOPh | Ms | H |
| Et | H | CN | COOCH$_2$Ph | Ms | H |
| Et | H | CN | COOCH$_2$CH=CH$_2$ | Ms | H |
| Et | H | CH$_2$OEt | COOMe | Ms | H |
| Et | H | CH$_2$OEt | COOEt | Ms | H |
| Et | H | CH$_2$OEt | COOCH(CH$_3$)$_2$ | Ms | H |
| Et | H | CH$_2$OEt | CONMe$_2$ | Ms | H |
| Et | H | CH$_2$OEt | CONEt$_2$ | Ms | H |
| Et | H | CH$_2$OEt | COOC$_3$H$_7$ | Ms | H |
| Et | H | CH$_2$OEt | Y1 | Ms | H |
| Et | H | CH$_2$OEt | Y2 | Ms | H |
| Et | H | CH$_2$OEt | Y3 | Ms | H |
| Et | H | CH$_2$OEt | COOPh | Ms | H |
| Et | H | CH$_2$OEt | COOCH$_2$Ph | Ms | H |
| Et | H | CH$_2$OEt | COOCH$_2$CH=CH$_2$ | Ms | H |
| Et | H | Et | COOMe | Ms | H |
| Et | H | Et | COOEt | Ms | H |
| Et | H | Et | COOCH(CH$_3$)$_2$ | Ms | H |
| Et | H | Et | CONMe$_2$ | Ms | H |
| Et | H | Et | CONEt$_2$ | Ms | H |
| Et | H | Et | COOC$_3$H$_7$ | Ms | H |
| Et | H | Et | Y1 | Ms | H |
| Et | H | Et | Y2 | Ms | H |
| Et | H | Et | Y3 | Ms | H |
| Et | H | Et | COOPh | Ms | H |
| Et | H | Et | COOCH$_2$Ph | Ms | H |
| Et | H | Et | COOCH$_2$CH=CH$_2$ | Ms | H |
| Et | H | i-Pr | COOMe | Ms | H |
| Et | H | i-Pr | COOEt | Ms | H |
| Et | H | i-Pr | COOCH(CH$_3$)$_2$ | Ms | H |
| Et | H | i-Pr | CONMe$_2$ | Ms | H |
| Et | H | i-Pr | CONEt$_2$ | Ms | H |
| Et | H | i-Pr | COOC$_3$H$_7$ | Ms | H |
| Et | H | i-Pr | Y1 | Ms | H |
| Et | H | i-Pr | Y2 | Ms | H |
| Et | H | i-Pr | Y3 | Ms | H |
| Et | H | i-Pr | COOPh | Ms | H |
| Et | H | i-Pr | COOCH$_2$Ph | Ms | H |
| Et | H | i-Pr | COOCH$_2$CH=CH$_2$ | Ms | H |
| Et | H | n-Pr | COOMe | Ms | H |
| Et | H | n-Pr | COOEt | Ms | H |
| Et | H | n-Pr | COOCH(CH$_3$)$_2$ | Ms | H |
| Et | H | n-Pr | CONMe$_2$ | Ms | H |
| Et | H | n-Pr | CONEt$_2$ | Ms | H |
| Et | H | n-Pr | COOC$_3$H$_7$ | Ms | H |
| Et | H | n-Pr | Y1 | Ms | H |
| Et | H | n-Pr | Y2 | Ms | H |
| Et | H | n-Pr | Y3 | Ms | H |
| Et | H | n-Pr | COOPh | Ms | H |
| Et | H | n-Pr | COOCH$_2$Ph | Ms | H |
| Et | H | n-Pr | COOCH$_2$CH=CH$_2$ | Ms | H |
| Et | H | I | COOMe | Ms | H |
| Et | H | I | COOEt | Ms | H |
| Et | H | I | COOCH(CH$_3$)$_2$ | Ms | H |
| Et | H | I | CONMe$_2$ | Ms | H |
| Et | H | I | CONEt$_2$ | Ms | H |
| Et | H | I | COOC$_3$H$_7$ | Ms | H |
| Et | H | I | Y1 | Ms | H |
| Et | H | I | Y2 | Ms | H |
| Et | H | I | Y3 | Ms | H |
| Et | H | I | COOPh | Ms | H |
| Et | H | I | COOCH$_2$Ph | Ms | H |
| Et | H | I | COOCH$_2$CH=CH$_2$ | Ms | H |
| i-Pr | H | NO$_2$ | COOMe | Ms | H |
| i-Pr | H | NO$_2$ | COOEt | Ms | H |
| i-Pr | H | NO$_2$ | COOCH(CH$_3$)$_2$ | Ms | H |
| i-Pr | H | NO$_2$ | CONMe$_2$ | Ms | H |
| i-Pr | H | NO$_2$ | CONEt$_2$ | Ms | H |
| i-Pr | H | NO$_2$ | COOC$_3$H$_7$ | Ms | H |
| i-Pr | H | NO$_2$ | Y1 | Ms | H |
| i-Pr | H | NO$_2$ | Y2 | Ms | H |
| i-Pr | H | NO$_2$ | Y3 | Ms | H |
| i-Pr | H | NO$_2$ | COOPh | Ms | H |
| i-Pr | H | NO$_2$ | COOCH$_2$Ph | Ms | H |
| i-Pr | H | NO$_2$ | COOCH$_2$CH=CH$_2$ | Ms | H |
| i-Pr | H | CF$_3$ | COOMe | Ms | H |
| i-Pr | H | CF$_3$ | COOEt | Ms | H |
| i-Pr | H | CF$_3$ | COOCH(CH$_3$)$_2$ | Ms | H |
| i-Pr | H | CF$_3$ | CONMe$_2$ | Ms | H |
| i-Pr | H | CF$_3$ | CONEt$_2$ | Ms | H |

-continued

| | | | | | |
|---|---|---|---|---|---|
| i-Pr | H | CF₃ | COOC₃H₇ | Ms | H |
| i-Pr | H | CF₃ | Y1 | Ms | H |
| i-Pr | H | CF₃ | Y2 | Ms | H |
| i-Pr | H | CF₃ | Y3 | Ms | H |
| i-Pr | H | CF₃ | COOPh | Ms | H |
| i-Pr | H | CF₃ | COOCH₂Ph | Ms | H |
| i-Pr | H | CF₃ | COOCH₂CH=CH₂ | Ms | H |
| i-Pr | H | CN | COOMe | Ms | H |
| i-Pr | H | CN | COOEt | Ms | H |
| i-Pr | H | CN | COOCH(CH₃)₂ | Ms | H |
| i-Pr | H | CN | CONMe₂ | Ms | H |
| i-Pr | H | CN | CONEt₂ | Ms | H |
| i-Pr | H | CN | COOC₃H₇ | Ms | H |
| i-Pr | H | CN | Y1 | Ms | H |
| i-Pr | H | CN | Y2 | Ms | H |
| i-Pr | H | CN | Y3 | Ms | H |
| i-Pr | H | CN | COOPh | Ms | H |
| i-Pr | H | CN | COOCH₂Ph | Ms | H |
| i-Pr | H | CN | COOCH₂CH=CH₂ | Ms | H |
| i-Pr | H | CH₂OEt | COOMe | Ms | H |
| i-Pr | H | CH₂OEt | COOEt | Ms | H |
| i-Pr | H | CH₂OEt | COOCH(CH₃)₂ | Ms | H |
| i-Pr | H | CH₂OEt | CONMe₂ | Ms | H |
| i-Pr | H | CH₂OEt | CONEt₂ | Ms | H |
| i-Pr | H | CH₂OEt | COOC₃H₇ | Ms | H |
| i-Pr | H | CH₂OEt | Y1 | Ms | H |
| i-Pr | H | CH₂OEt | Y2 | Ms | H |
| i-Pr | H | CH₂OEt | Y3 | Ms | H |
| i-Pr | H | CH₂OEt | COOPh | Ms | H |
| i-Pr | H | CH₂OEt | COOCH₂Ph | Ms | H |
| i-Pr | H | CH₂OEt | COOCH₂CH=CH₂ | Ms | H |
| i-Pr | H | Et | COOMe | Ms | H |
| i-Pr | H | Et | COOEt | Ms | H |
| i-Pr | H | Et | COOCH(CH₃)₂ | Ms | H |
| i-Pr | H | Et | CONMe₂ | Ms | H |
| i-Pr | H | Et | CONEt₂ | Ms | H |
| i-Pr | H | Et | COOC₃H₇ | Ms | H |
| i-Pr | H | Et | Y1 | Ms | H |
| i-Pr | H | Et | Y2 | Ms | H |
| i-Pr | H | Et | Y3 | Ms | H |
| i-Pr | H | Et | COOPh | Ms | H |
| i-Pr | H | Et | COOCH₂Ph | Ms | H |
| i-Pr | H | Et | COOCH₂CH=CH₂ | Ms | H |
| i-Pr | H | i-Pr | COOMe | Ms | H |
| i-Pr | H | i-Pr | COOEt | Ms | H |
| i-Pr | H | i-Pr | COOCH(CH₃)₂ | Ms | H |
| i-Pr | H | i-Pr | CONMe₂ | Ms | H |
| i-Pr | H | i-Pr | CONEt₂ | Ms | H |
| i-Pr | H | i-Pr | COOC₃H₇ | Ms | H |
| i-Pr | H | i-Pr | Y1 | Ms | H |
| i-Pr | H | i-Pr | Y2 | Ms | H |
| i-Pr | H | i-Pr | Y3 | Ms | H |
| i-Pr | H | i-Pr | COOPh | Ms | H |
| i-Pr | H | i-Pr | COOCH₂Ph | Ms | H |
| i-Pr | H | i-Pr | COOCH₂CH=CH₂ | Ms | H |
| i-Pr | H | n-Pr | COOMe | Ms | H |
| i-Pr | H | n-Pr | COOEt | Ms | H |
| i-Pr | H | n-Pr | COOCH(CH₃)₂ | Ms | H |
| i-Pr | H | n-Pr | CONMe₂ | Ms | H |
| i-Pr | H | n-Pr | CONEt₂ | Ms | H |
| i-Pr | H | n-Pr | COOC₃H₇ | Ms | H |
| i-Pr | H | n-Pr | Y1 | Ms | H |
| i-Pr | H | n-Pr | Y2 | Ms | H |
| i-Pr | H | n-Pr | Y3 | Ms | H |
| i-Pr | H | n-Pr | COOPh | Ms | H |
| i-Pr | H | n-Pr | COOCH₂Ph | Ms | H |
| i-Pr | H | n-Pr | COOCH₂CH=CH₂ | Ms | H |
| i-Pr | H | I | COOMe | Ms | H |
| i-Pr | H | I | COOEt | Ms | H |
| i-Pr | H | I | COOCH(CH₃)₂ | Ms | H |
| i-Pr | H | I | CONMe₂ | Ms | H |
| i-Pr | H | I | CONEt₂ | Ms | H |
| i-Pr | H | I | COOC₃H₇ | Ms | H |
| i-Pr | H | I | Y1 | Ms | H |
| i-Pr | H | I | Y2 | Ms | H |
| i-Pr | H | I | Y3 | Ms | H |
| i-Pr | H | I | COOPh | Ms | H |
| i-Pr | H | I | COOCH₂Ph | Ms | H |
| i-Pr | H | I | COOCH₂CH=CH₂ | Ms | H |
| allyl | H | NO₂ | COOMe | Ms | H |
| allyl | H | NO₂ | COOEt | Ms | H |
| allyl | H | NO₂ | COOCH(CH₃)₂ | Ms | H |
| allyl | H | NO₂ | CONMe₂ | Ms | H |

-continued

| | | | | | |
|---|---|---|---|---|---|
| allyl | H | NO$_2$ | CONEt$_2$ | Ms | H |
| allyl | H | NO$_2$ | COOC$_3$H$_7$ | Ms | H |
| allyl | H | NO$_2$ | Y1 | Ms | H |
| allyl | H | NO$_2$ | Y2 | Ms | H |
| allyl | H | NO$_2$ | Y3 | Ms | H |
| allyl | H | NO$_2$ | COOPh | Ms | H |
| allyl | H | NO$_2$ | COOCH$_2$Ph | Ms | H |
| allyl | H | NO$_2$ | COOCH$_2$CH=CH$_2$ | Ms | H |
| allyl | H | CF$_3$ | COOMe | Ms | H |
| allyl | H | CF$_3$ | COOEt | Ms | H |
| allyl | H | CF$_3$ | COOCH(CH$_3$)$_2$ | Ms | H |
| allyl | H | CF$_3$ | CONMe$_2$ | Ms | H |
| allyl | H | CF$_3$ | CONEt$_2$ | Ms | H |
| allyl | H | CF$_3$ | COOC$_3$H$_7$ | Ms | H |
| allyl | H | CF$_3$ | Y1 | Ms | H |
| allyl | H | CF$_3$ | Y2 | Ms | H |
| allyl | H | CF$_3$ | Y3 | Ms | H |
| allyl | H | CF$_3$ | COOPh | Ms | H |
| allyl | H | CF$_3$ | COOCH$_2$Ph | Ms | H |
| allyl | H | CF$_3$ | COOCH$_2$CH=CH$_2$ | Ms | H |
| allyl | H | CN | COOMe | Ms | H |
| allyl | H | CN | COOEt | Ms | H |
| allyl | H | CN | COOCH(CH$_3$)$_2$ | Ms | H |
| allyl | H | CN | CONMe$_2$ | Ms | H |
| allyl | H | CN | CONEt$_2$ | Ms | H |
| allyl | H | CN | COOC$_3$H$_7$ | Ms | H |
| allyl | H | CN | Y1 | Ms | H |
| allyl | H | CN | Y2 | Ms | H |
| allyl | H | CN | Y3 | Ms | H |
| allyl | H | CN | COOPh | Ms | H |
| allyl | H | CN | COOCH$_2$Ph | Ms | H |
| allyl | H | CN | COOCH$_2$CH=CH$_2$ | Ms | H |
| allyl | H | CH$_2$OEt | COOMe | Ms | H |
| allyl | H | CH$_2$OEt | COOEt | Ms | H |
| allyl | H | CH$_2$OEt | COOCH(CH$_3$)$_2$ | Ms | H |
| allyl | H | CH$_2$OEt | CONMe$_2$ | Ms | H |
| allyl | H | CH$_2$OEt | CONEt$_2$ | Ms | H |
| allyl | H | CH$_2$OEt | COOC$_3$H$_7$ | Ms | H |
| allyl | H | CH$_2$OEt | Y1 | Ms | H |
| allyl | H | CH$_2$OEt | Y2 | Ms | H |
| allyl | H | CH$_2$OEt | Y3 | Ms | H |
| allyl | H | CH$_2$OEt | COOPh | Ms | H |
| allyl | H | CH$_2$OEt | COOCH$_2$Ph | Ms | H |
| allyl | H | CH$_2$OEt | COOCH$_2$CH=CH$_2$ | Ms | H |
| allyl | H | Et | COOMe | Ms | H |
| allyl | H | Et | COOEt | Ms | H |
| allyl | H | Et | COOCH(CH$_3$)$_2$ | Ms | H |
| allyl | H | Et | CONMe$_2$ | Ms | H |
| allyl | H | Et | CONEt$_2$ | Ms | H |
| allyl | H | Et | COOC$_3$H$_7$ | Ms | H |
| allyl | H | Et | Y1 | Ms | H |
| allyl | H | Et | Y2 | Ms | H |
| allyl | H | Et | Y3 | Ms | H |
| allyl | H | Et | COOPh | Ms | H |
| allyl | H | Et | COOCH$_2$Ph | Ms | H |
| allyl | H | Et | COOCH$_2$CH=CH$_2$ | Ms | H |
| allyl | H | i-Pr | COOMe | Ms | H |
| allyl | H | i-Pr | COOEt | Ms | H |
| allyl | H | i-Pr | COOCH(CH$_3$)$_2$ | Ms | H |
| allyl | H | i-Pr | CONMe$_2$ | Ms | H |
| allyl | H | i-Pr | CONEt$_2$ | Ms | H |
| allyl | H | i-Pr | COOC$_3$H$_7$ | Ms | H |
| allyl | H | i-Pr | Y1 | Ms | H |
| allyl | H | i-Pr | Y2 | Ms | H |
| allyl | H | i-Pr | Y3 | Ms | H |
| allyl | H | i-Pr | COOPh | Ms | H |
| allyl | H | i-Pr | COOCH$_2$Ph | Ms | H |
| allyl | H | i-Pr | COOCH$_2$CH=CH$_2$ | Ms | H |
| allyl | H | n-Pr | COOMe | Ms | H |
| allyl | H | n-Pr | COOEt | Ms | H |
| allyl | H | n-Pr | COOCH(CH$_3$)$_2$ | Ms | H |
| allyl | H | n-Pr | CONMe$_2$ | Ms | H |
| allyl | H | n-Pr | CONEt$_2$ | Ms | H |
| allyl | H | n-Pr | COOC$_3$H$_7$ | Ms | H |
| allyl | H | n-Pr | Y1 | Ms | H |
| allyl | H | n-Pr | Y2 | Ms | H |
| allyl | H | n-Pr | Y3 | Ms | H |
| allyl | H | n-Pr | COOPh | Ms | H |
| allyl | H | n-Pr | COOCH$_2$Ph | Ms | H |
| allyl | H | n-Pr | COOCH$_2$CH=CH$_2$ | Ms | H |
| allyl | H | I | COOMe | Ms | H |
| allyl | H | I | COOEt | Ms | H |
| allyl | H | I | COOCH(CH$_3$)$_2$ | Ms | H |

-continued

| | | | | | |
|---|---|---|---|---|---|
| allyl | H | I | CONMe$_2$ | Ms | H |
| allyl | H | I | CONEt$_2$ | Ms | H |
| allyl | H | I | COOC$_3$H$_7$ | Ms | H |
| allyl | H | I | Y1 | Ms | H |
| allyl | H | I | Y2 | Ms | H |
| allyl | H | I | Y3 | Ms | H |
| allyl | H | I | COOPh | Ms | H |
| allyl | H | I | COOCH$_2$Ph | Ms | H |
| allyl | H | I | COOCH$_2$CH=CH$_2$ | Ms | H |
| allyl | H | Me | COOH | Ms | H |
| allyl | H | Cl | COOH | Ms | H |
| Me | H | Me | COOH | Ms | H |
| Me | H | Cl | COOH | Ms | H |
| Et | H | Me | COOH | Ms | H |
| Et | H | Cl | COOH | Ms | H |
| i-Pr | H | Me | COOH | Ms | H |
| i-Pr | H | Cl | COOH | Ms | H |
| Me | H | COOMe | CH$_2$OCH$_2$CH=CH$_2$ | Ms | H |
| Me | H | COOMe | CH$_2$OCH$_2$C≡CH | Ms | H |
| Me | H | COOMe | SCH$_3$ | Ms | H |
| Me | H | COOMe | CH$_2$OH | Ms | H |
| Me | H | COOMe | CH$_2$SCH$_3$ | Ms | H |
| Et | H | COOMe | CH$_2$OCH$_2$CH=CH$_2$ | Ms | H |
| Et | H | COOMe | CH$_2$OCH$_2$C≡CH | Ms | H |
| Et | H | COOMe | SCH$_3$ | Ms | H |
| Et | H | COOMe | CH$_2$OH | Ms | H |
| Et | H | COOMe | CH$_2$SCH$_3$ | Ms | H |
| i-Pr | H | COOMe | CH$_2$OCH$_2$CH=CH$_2$ | Ms | H |
| i-Pr | H | COOMe | CH$_2$OCH$_2$C≡CH | Ms | H |
| i-Pr | H | COOMe | SCH$_3$ | Ms | H |
| i-Pr | H | COOMe | CH$_2$OH | Ms | H |
| i-Pr | H | COOMe | CH$_2$SCH$_3$ | Ms | H |
| Me | H | COOEt | CH$_2$OCH$_2$CH=CH$_2$ | Ms | H |
| Me | H | COOEt | CH$_2$OCH$_2$C≡CH | Ms | H |
| Me | H | COOEt | SCH$_3$ | Ms | H |
| Me | H | COOEt | CH$_2$OH | Ms | H |
| Me | H | COOEt | CH$_2$SCH$_3$ | Ms | H |
| Et | H | COOEt | CH$_2$OCH$_2$CH=CH$_2$ | Ms | H |
| Et | H | COOEt | CH$_2$OCH$_2$C≡CH | Ms | H |
| Et | H | COOEt | SCH$_3$ | Ms | H |
| Et | H | COOEt | CH$_2$OH | Ms | H |
| Et | H | COOEt | CH$_2$SCH$_3$ | Ms | H |
| i-Pr | H | COOEt | CH$_2$OCH$_2$CH=CH$_2$ | Ms | H |
| i-Pr | H | COOEt | CH$_2$OCH$_2$C≡CH | Ms | H |
| i-Pr | H | COOEt | SCH$_3$ | Ms | H |
| i-Pr | H | COOEt | CH$_2$OH | Ms | H |
| i-Pr | H | COOEt | CH$_2$SCH$_3$ | Ms | H |
| Me | H | Me | COOY4 | Ms | H |
| Me | H | Me | COOY5 | Ms | H |
| Me | H | Me | COOY6 | Ms | H |
| Me | H | Me | COOCH$_2$CH$_2$Cl | Ms | H |
| Me | H | Me | COOCH$_2$CF$_3$ | Ms | H |
| Me | H | Me | COOCH$_2$CCl=CH$_2$ | Ms | H |
| Me | H | Me | COOCH$_2$CH$_2$OCH$_3$ | Ms | H |
| Me | H | Me | COOCH$_2$SCH$_3$ | Ms | H |
| Me | H | Me | COOCH$_2$CH$_2$OCH$_2$CH$_2$Cl | Ms | H |
| Me | H | Me | COOCH$_2$CH$_2$OMs | Ms | H |
| Me | H | Me | COOCH$_2$OCH$_2$CH$_2$OCH$_3$ | Ms | H |
| Me | H | Me | COOCH$_2$CH$_2$Ms | Ms | H |
| Me | H | Me | COOCH$_2$CH$_2$CN | Ms | H |
| Me | H | Me | COOCH$_2$CH$_2$NHCH$_2$ | Ms | H |
| Me | H | Me | COOCH$_2$CH$_2$OH | Ms | H |
| Me | H | Me | COOCH$_2$CH$_2$NO$_2$ | Ms | H |
| Me | H | Me | COOY7 | Ms | H |
| Me | H | Me | COOCH$_2$COCH$_3$ | Ms | H |
| Me | H | Me | COOCH$_2$CO$_2$CH$_3$ | Ms | H |
| Me | H | Me | COOCH(CH$_3$)COOEt | Ms | H |
| Me | H | Me | COOCH$_2$CH$_2$OPh | Ms | H |
| Me | H | Me | COOCH$_2$CH$_2$OCH$_2$Ph | Ms | H |
| Me | H | Me | COOPh-4-CH$_3$ | Ms | H |
| Me | H | Me | COOPh-4-Cl | Ms | H |
| Me | H | Me | COOPh-4-NO$_2$ | Ms | H |
| Me | H | Me | COOCH$_2$SiMe$_3$ | Ms | H |
| Me | H | Me | COOY8 | Ms | H |
| Me | H | Me | COOCH$_2$Y8 | Ms | H |
| Me | H | Me | COOY9 | Ms | H |
| Me | H | Me | COOY10 | Ms | H |
| Me | H | Me | CONHSO$_2$CH$_3$ | Ms | H |
| Me | H | Me | CONHSO$_2$CF$_3$ | Ms | H |
| Me | H | Cl | COOY4 | Ms | H |
| Me | H | Cl | COOY5 | Ms | H |
| Me | H | Cl | COOY6 | Ms | H |
| Me | H | Cl | COOCH$_2$CH$_2$Cl | Ms | H |

-continued

| | | | | | | |
|---|---|---|---|---|---|---|
| Me | H | Cl | COOCH$_2$CF$_3$ | Ms | H | |
| Me | H | Cl | COOCH$_2$CCl=CH$_2$ | Ms | H | |
| Me | H | Cl | COOCH$_2$CH$_2$OCH$_3$ | Ms | H | |
| Me | H | Cl | COOCH$_2$SCH$_3$ | Ms | H | |
| Me | H | Cl | COOCH$_2$CH$_2$OCH$_2$CH$_2$Cl | Ms | H | |
| Me | H | Cl | COOCH$_2$CH$_2$OMs | Ms | H | |
| Me | H | Cl | COOCH$_2$OCH$_2$CH$_2$OCH$_3$ | Ms | H | |
| Me | H | Cl | COOCH$_2$CH$_2$Ms | Ms | H | |
| Me | H | Cl | COOCH$_2$CH$_2$CN | Ms | H | |
| Me | H | Cl | COOCH$_2$CH$_2$NHCH$_2$ | Ms | H | |
| Me | H | Cl | COOCH$_2$CH$_2$OH | Ms | H | |
| Me | H | Cl | COOCH$_2$CH$_2$CH$_2$NO$_2$ | Ms | H | |
| Me | H | Cl | COOY7 | Ms | H | |
| Me | H | Cl | COOCH$_2$COCH$_3$ | Ms | H | |
| Me | H | Cl | COOCH$_2$CO$_2$CH$_3$ | Ms | H | |
| Me | H | Cl | COOCH(CH$_3$)COOEt | Ms | H | |
| Me | H | Cl | COOCH$_2$CH$_2$OPh | Ms | H | |
| Me | H | Cl | COOCH$_2$CH$_2$OCH$_2$Ph | Ms | H | |
| Me | H | Cl | COOPh-4-CH$_3$ | Ms | H | |
| Me | H | Cl | COOPh-4-Cl | Ms | H | |
| Me | H | Cl | COOPh-4-NO$_2$ | Ms | H | |
| Me | H | Cl | COOCH$_2$SiMe$_3$ | Ms | H | |
| Me | H | Cl | COOY8 | Ms | H | |
| Me | H | Cl | COOCH$_2$Y8 | Ms | H | |
| Me | H | Cl | COOY9 | Ms | H | |
| Me | H | Cl | COOY10 | Ms | H | |
| Me | H | Cl | CONHSO$_2$CH$_3$ | Ms | H | |
| Me | H | Cl | CONHSO$_2$CF$_3$ | Ms | H | |
| Me | H | OMe | COOY4 | Ms | H | |
| Me | H | OMe | COOY5 | Ms | H | |
| Me | H | OMe | COOY6 | Ms | H | |
| Me | H | OMe | COOCH$_2$CH$_2$Cl | Ms | H | |
| Me | H | OMe | COOCH$_2$CF$_3$ | Ms | H | |
| Me | H | OMe | COOCH$_2$CCl=CH$_2$ | Ms | H | |
| Me | H | OMe | COOCH$_2$CH$_2$OCH$_3$ | Ms | H | |
| Me | H | OMe | COOCH$_2$SCH$_3$ | Ms | H | |
| Me | H | OMe | COOCH$_2$CH$_2$OCH$_2$CH$_2$Cl | Ms | H | |
| Me | H | OMe | COOCH$_2$CH$_2$OMs | Ms | H | |
| Me | H | OMe | COOCH$_2$OCH$_2$CH$_2$OCH$_3$ | Ms | H | |
| Me | H | OMe | COOCH$_2$CH$_2$Ms | Ms | H | |
| Me | H | OMe | COOCH$_2$CH$_2$CN | Ms | H | |
| Me | H | OMe | COOCH$_2$CH$_2$NHCH$_2$ | Ms | H | |
| Me | H | OMe | COOCH$_2$CH$_2$OH | Ms | H | |
| Me | H | OMe | COOCH$_2$CH$_2$CH$_2$NO$_2$ | Ms | H | |
| Me | H | OMe | COOY7 | Ms | H | |
| Me | H | OMe | COOCH$_2$COCH$_3$ | Ms | H | |
| Me | H | OMe | COOCH$_2$CO$_2$CH$_3$ | Ms | H | |
| Me | H | OMe | COOCH(CH$_3$)COOEt | Ms | H | |
| Me | H | OMe | COOCH$_2$CH$_2$OPh | Ms | H | |
| Me | H | OMe | COOCH$_2$CH$_2$OCH$_2$Ph | Ms | H | |
| Me | H | OMe | COOPh-4-CH$_3$ | Ms | H | |
| Me | H | OMe | COOPh-4-Cl | Ms | H | |
| Me | H | OMe | COOPh-4-NO$_2$ | Ms | H | |
| Me | H | OMe | COOCH$_2$SiMe$_3$ | Ms | H | |
| Me | H | OMe | COOY8 | Ms | H | |
| Me | H | OMe | COOCH$_2$Y8 | Ms | H | |
| Me | H | OMe | COOY9 | Ms | H | |
| Me | H | OMe | COOY10 | Ms | H | |
| Me | H | OMe | CONHSO$_2$CH$_3$ | Ms | H | |
| Me | H | OMe | CONHSO$_2$CF$_3$ | Ms | H | |
| Et | H | Me | COOY4 | Ms | H | |
| Et | H | Me | COOY5 | Ms | H | |
| Et | H | Me | COOY6 | Ms | H | |
| Et | H | Me | COOCH$_2$CH$_2$Cl | Ms | H | |
| Et | H | Me | COOCH$_2$CF$_3$ | Ms | H | |
| Et | H | Me | COOCH$_2$CCl=CH$_2$ | Ms | H | |
| Et | H | Me | COOCH$_2$CH$_2$OCH$_3$ | Ms | H | |
| Et | H | Me | COOCH$_2$SCH$_3$ | Ms | H | |
| Et | H | Me | COOCH$_2$CH$_2$OCH$_2$CH$_2$Cl | Ms | H | |
| Et | H | Me | COOCH$_2$CH$_2$OMs | Ms | H | |
| Et | H | Me | COOCH$_2$OCH$_2$CH$_2$OCH$_3$ | Ms | H | |
| Et | H | Me | COOCH$_2$CH$_2$Ms | Ms | H | |
| Et | H | Me | COOCH$_2$CH$_2$CN | Ms | H | |
| Et | H | Me | COOCH$_2$CH$_2$NHCH$_2$ | Ms | H | |
| Et | H | Me | COOCH$_2$CH$_2$OH | Ms | H | |
| Et | H | Me | COOCH$_2$CH$_2$CH$_2$NO$_2$ | Ms | H | |
| Et | H | Me | COOY7 | Ms | H | |
| Et | H | Me | COOCH$_2$COCH$_3$ | Ms | H | |
| Et | H | Me | COOCH$_2$CO$_2$CH$_3$ | Ms | H | |
| Et | H | Me | COOCH(CH$_3$)COOEt | Ms | H | |
| Et | H | Me | COOCH$_2$CH$_2$OPh | Ms | H | |
| Et | H | Me | COOCH$_2$CH$_2$OCH$_2$Ph | Ms | H | |
| Et | H | Me | COOPh-4-CH$_3$ | Ms | H | |

-continued

| | | | | | |
|---|---|---|---|---|---|
| Et | H | Me | COOPh-4-Cl | Ms | H |
| Et | H | Me | COOPh-4-NO$_2$ | Ms | H |
| Et | H | Me | COOCH$_2$SiMe$_3$ | Ms | H |
| Et | H | Me | COOY8 | Ms | H |
| Et | H | Me | COOCH$_2$Y8 | Ms | H |
| Et | H | Me | COOY9 | Ms | H |
| Et | H | Me | COOY10 | Ms | H |
| Et | H | Me | CONHSO$_2$CH$_3$ | Ms | H |
| Et | H | Me | CONHSO$_2$CF$_3$ | Ms | H |
| Et | H | Cl | COOY4 | Ms | H |
| Et | H | Cl | COOY5 | Ms | H |
| Et | H | Cl | COOY6 | Ms | H |
| Et | H | Cl | COOCH$_2$CH$_2$Cl | Ms | H |
| Et | H | Cl | COOCH$_2$CF$_3$ | Ms | H |
| Et | H | Cl | COOCH$_2$CCl=CH$_2$ | Ms | H |
| Et | H | Cl | COOCH$_2$CH$_2$OCH$_3$ | Ms | H |
| Et | H | Cl | COOCH$_2$SCH$_3$ | Ms | H |
| Et | H | Cl | COOCH$_2$CH$_2$OCH$_2$CH$_2$Cl | Ms | H |
| Et | H | Cl | COOCH$_2$CH$_2$OMs | Ms | H |
| Et | H | Cl | COOCH$_2$OCH$_2$CH$_2$OCH$_3$ | Ms | H |
| Et | H | Cl | COOCH$_2$CH$_2$Ms | Ms | H |
| Et | H | Cl | COOCH$_2$CH$_2$CN | Ms | H |
| Et | H | Cl | COOCH$_2$CH$_2$NHCH$_2$ | Ms | H |
| Et | H | Cl | COOCH$_2$CH$_2$OH | Ms | H |
| Et | H | Cl | COOCH$_2$CH$_2$CH$_2$NO$_2$ | Ms | H |
| Et | H | Cl | COOY7 | Ms | H |
| Et | H | Cl | COOCH$_2$COCH$_3$ | Ms | H |
| Et | H | Cl | COOCH$_2$CO$_2$CH$_3$ | Ms | H |
| Et | H | Cl | COOCH(CH$_3$)COOEt | Ms | H |
| Et | H | Cl | COOCH$_2$CH$_2$OPh | Ms | H |
| Et | H | Cl | COOCH$_2$CH$_2$OCH$_2$Ph | Ms | H |
| Et | H | Cl | COOPh-4-CH$_3$ | Ms | H |
| Et | H | Cl | COOPh-4-Cl | Ms | H |
| Et | H | Cl | COOPh-4-NO$_2$ | Ms | H |
| Et | H | Cl | COOCH$_2$SiMe$_3$ | Ms | H |
| Et | H | Cl | COOY8 | Ms | H |
| Et | H | Cl | COOCH$_2$Y8 | Ms | H |
| Et | H | Cl | COOY9 | Ms | H |
| Et | H | Cl | COOY10 | Ms | H |
| Et | H | Cl | CONHSO$_2$CH$_3$ | Ms | H |
| Et | H | Cl | CONHSO$_2$CF$_3$ | Ms | H |
| Et | H | OMe | COOY4 | Ms | H |
| Et | H | OMe | COOY5 | Ms | H |
| Et | H | OMe | COOY6 | Ms | H |
| Et | H | OMe | COOCH$_2$CH$_2$Cl | Ms | H |
| Et | H | OMe | COOCH$_2$CF$_3$ | Ms | H |
| Et | H | OMe | COOCH$_2$CCl=CH$_2$ | Ms | H |
| Et | H | OMe | COOCH$_2$CH$_2$OCH$_3$ | Ms | H |
| Et | H | OMe | COOCH$_2$SCH$_3$ | Ms | H |
| Et | H | OMe | COOCH$_2$CH$_2$OCH$_2$CH$_2$Cl | Ms | H |
| Et | H | OMe | COOCH$_2$CH$_2$OMs | Ms | H |
| Et | H | OMe | COOCH$_2$OCH$_2$CH$_2$OCH$_3$ | Ms | H |
| Et | H | OMe | COOCH$_2$CH$_2$Ms | Ms | H |
| Et | H | OMe | COOCH$_2$CH$_2$CN | Ms | H |
| Et | H | OMe | COOCH$_2$CH$_2$NHCH$_2$ | Ms | H |
| Et | H | OMe | COOCH$_2$CH$_2$OH | Ms | H |
| Et | H | OMe | COOCH$_2$CH$_2$CH$_2$NO$_2$ | Ms | H |
| Et | H | OMe | COOY7 | Ms | H |
| Et | H | OMe | COOCH$_2$COCH$_3$ | Ms | H |
| Et | H | OMe | COOCH$_2$CO$_2$CH$_3$ | Ms | H |
| Et | H | OMe | COOCH(CH$_3$)COOEt | Ms | H |
| Et | H | OMe | COOCH$_2$CH$_2$OPh | Ms | H |
| Et | H | OMe | COOCH$_2$CH$_2$OCH$_2$Ph | Ms | H |
| Et | H | OMe | COOPh-4-CH$_3$ | Ms | H |
| Et | H | OMe | COOPh-4-Cl | Ms | H |
| Et | H | OMe | COOPh-4-NO$_2$ | Ms | H |
| Et | H | OMe | COOCH$_2$SiMe$_3$ | Ms | H |
| Et | H | OMe | COOY8 | Ms | H |
| Et | H | OMe | COOCH$_2$Y8 | Ms | H |
| Et | H | OMe | COOY9 | Ms | H |
| Et | H | OMe | COOY10 | Ms | H |
| Et | H | OMe | CONHSO$_2$CH$_3$ | Ms | H |
| Et | H | OMe | CONHSO$_2$CF$_3$ | Ms | H |
| i-Pr | H | Me | COOY4 | Ms | H |
| i-Pr | H | Me | COOY5 | Ms | H |
| i-Pr | H | Me | COOY6 | Ms | H |
| i-Pr | H | Me | COOCH$_2$CH$_2$Cl | Ms | H |
| i-Pr | H | Me | COOCH$_2$CF$_3$ | Ms | H |
| i-Pr | H | Me | COOCH$_2$CCl=CH$_2$ | Ms | H |
| i-Pr | H | Me | COOCH$_2$CH$_2$OCH$_3$ | Ms | H |
| i-Pr | H | Me | COOCH$_2$SCH$_3$ | Ms | H |
| i-Pr | H | Me | COOCH$_2$CH$_2$OCH$_2$CH$_2$Cl | Ms | H |
| i-Pr | H | Me | COOCH$_2$CH$_2$OMs | Ms | H |

-continued

| | | | | | |
|---|---|---|---|---|---|
| i-Pr | H | Me | COOCH$_2$OCH$_2$CH$_2$OCH$_3$ | Ms | H |
| i-Pr | H | Me | COOCH$_2$CH$_2$Ms | Ms | H |
| i-Pr | H | Me | COOCH$_2$CH$_2$CN | Ms | H |
| i-Pr | H | Me | COOCH$_2$CH$_2$NHCH$_2$ | Ms | H |
| i-Pr | H | Me | COOCH$_2$CH$_2$OH | Ms | H |
| i-Pr | H | Me | COOCH$_2$CH$_2$CH$_2$NO$_2$ | Ms | H |
| i-Pr | H | Me | COOY7 | Ms | H |
| i-Pr | H | Me | COOCH$_2$COCH$_3$ | Ms | H |
| i-Pr | H | Me | COOCH$_2$CO$_2$CH$_3$ | Ms | H |
| i-Pr | H | Me | COOCH(CH$_3$)COOEt | Ms | H |
| i-Pr | H | Me | COOCH$_2$CH$_2$OPh | Ms | H |
| i-Pr | H | Me | COOCH$_2$CH$_2$OCH$_2$Ph | Ms | H |
| i-Pr | H | Me | COOPh-4-CH$_3$ | Ms | H |
| i-Pr | H | Me | COOPh-4-Cl | Ms | H |
| i-Pr | H | Me | COOPh-4-NO$_2$ | Ms | H |
| i-Pr | H | Me | COOCH$_2$SiMe$_3$ | Ms | H |
| i-Pr | H | Me | COOY8 | Ms | H |
| i-Pr | H | Me | COOCH$_2$Y8 | Ms | H |
| i-Pr | H | Me | COOY9 | Ms | H |
| i-Pr | H | Me | COOY10 | Ms | H |
| i-Pr | H | Me | CONHSO$_2$CH$_3$ | Ms | H |
| i-Pr | H | Me | CONHSO$_2$CF$_3$ | Ms | H |
| i-Pr | H | Cl | COOY4 | Ms | H |
| i-Pr | H | Cl | COOY5 | Ms | H |
| i-Pr | H | Cl | COOY6 | Ms | H |
| i-Pr | H | Cl | COOCH$_2$CH$_2$Cl | Ms | H |
| i-Pr | H | Cl | COOCH$_2$CF$_3$ | Ms | H |
| i-Pr | H | Cl | COOCH$_2$CCl=CH$_2$ | Ms | H |
| i-Pr | H | Cl | COOCH$_2$CH$_2$OCH$_3$ | Ms | H |
| i-Pr | H | Cl | COOCH$_2$SCH$_3$ | Ms | H |
| i-Pr | H | Cl | COOCH$_2$CH$_2$OCH$_2$CH$_2$Cl | Ms | H |
| i-Pr | H | Cl | COOCH$_2$CH$_2$OMs | Ms | H |
| i-Pr | H | Cl | COOCH$_2$OCH$_2$CH$_2$OCH$_3$ | Ms | H |
| i-Pr | H | Cl | COOCH$_2$CH$_2$Ms | Ms | H |
| i-Pr | H | Cl | COOCH$_2$CH$_2$CN | Ms | H |
| i-Pr | H | Cl | COOCH$_2$CH$_2$NHCH$_2$ | Ms | H |
| i-Pr | H | Cl | COOCH$_2$CH$_2$OH | Ms | H |
| i-Pr | H | Cl | COOCH$_2$CH$_2$CH$_2$NO$_2$ | Ms | H |
| i-Pr | H | Cl | COOY7 | Ms | H |
| i-Pr | H | Cl | COOCH$_2$COCH$_3$ | Ms | H |
| i-Pr | H | Cl | COOCH$_2$CO$_2$CH$_3$ | Ms | H |
| i-Pr | H | Cl | COOCH(CH$_3$)COOEt | Ms | H |
| i-Pr | H | Cl | COOCH$_2$CH$_2$OPh | Ms | H |
| i-Pr | H | Cl | COOCH$_2$CH$_2$OCH$_2$Ph | Ms | H |
| i-Pr | H | Cl | COOPh-4-CH$_3$ | Ms | H |
| i-Pr | H | Cl | COOPh-4-Cl | Ms | H |
| i-Pr | H | Cl | COOPh-4-NO$_2$ | Ms | H |
| i-Pr | H | Cl | COOCH$_2$SiMe$_3$ | Ms | H |
| i-Pr | H | Cl | COOY8 | Ms | H |
| i-Pr | H | Cl | COOCH$_2$Y8 | Ms | H |
| i-Pr | H | Cl | COOY9 | Ms | H |
| i-Pr | H | Cl | COOY10 | Ms | H |
| i-Pr | H | Cl | CONHSO$_2$CH$_3$ | Ms | H |
| i-Pr | H | Cl | CONHSO$_2$CF$_3$ | Ms | H |
| i-Pr | H | OMe | COOY4 | Ms | H |
| i-Pr | H | OMe | COOY5 | Ms | H |
| i-Pr | H | OMe | COOY6 | Ms | H |
| i-Pr | H | OMe | COOCH$_2$CH$_2$Cl | Ms | H |
| i-Pr | H | OMe | COOCH$_2$CF$_3$ | Ms | H |
| i-Pr | H | OMe | COOCH$_2$CCl=CH$_2$ | Ms | H |
| i-Pr | H | OMe | COOCH$_2$CH$_2$OCH$_3$ | Ms | H |
| i-Pr | H | OMe | COOCH$_2$SCH$_3$ | Ms | H |
| i-Pr | H | OMe | COOCH$_2$CH$_2$OCH$_2$CH$_2$Cl | Ms | H |
| i-Pr | H | OMe | COOCH$_2$CH$_2$OMs | Ms | H |
| i-Pr | H | OMe | COOCH$_2$OCH$_2$CH$_2$OCH$_3$ | Ms | H |
| i-Pr | H | OMe | COOCH$_2$CH$_2$Ms | Ms | H |
| i-Pr | H | OMe | COOCH$_2$CH$_2$CN | Ms | H |
| i-Pr | H | OMe | COOCH$_2$CH$_2$NHCH$_2$ | Ms | H |
| i-Pr | H | OMe | COOCH$_2$CH$_2$OH | Ms | H |
| i-Pr | H | OMe | COOCH$_2$CH$_2$CH$_2$NO$_2$ | Ms | H |
| i-Pr | H | OMe | COOY7 | Ms | H |
| i-Pr | H | OMe | COOCH$_2$COCH$_3$ | Ms | H |
| i-Pr | H | OMe | COOCH$_2$CO$_2$CH$_3$ | Ms | H |
| i-Pr | H | OMe | COOCH(CH$_3$)COOEt | Ms | H |
| i-Pr | H | OMe | COOCH$_2$CH$_2$OPh | Ms | H |
| i-Pr | H | OMe | COOCH$_2$CH$_2$OCH$_2$Ph | Ms | H |
| i-Pr | H | OMe | COOPh-4-CH$_3$ | Ms | H |
| i-Pr | H | OMe | COOPh-4-Cl | Ms | H |
| i-Pr | H | OMe | COOPh-4-NO$_2$ | Ms | H |
| i-Pr | H | OMe | COOCH$_2$SiMe$_3$ | Ms | H |
| i-Pr | H | OMe | COOY8 | Ms | H |
| i-Pr | H | OMe | COOCH$_2$Y8 | Ms | H |
| i-Pr | H | OMe | COOY9 | Ms | H |

-continued

| | | | | | |
|---|---|---|---|---|---|
| i-Pr | H | OMe | COOY10 | Ms | H |
| i-Pr | H | OMe | CONHSO$_2$CH$_3$ | Ms | H |
| i-Pr | H | OMe | CONHSO$_2$CF$_3$ | Ms | H |
| Me | H | Me | CON(CH$_3$)OCH$_3$ | Ms | H |
| Me | H | Me | CONHPh | Ms | H |
| Me | H | Me | COOCH$_2$COC(CH$_3$)$_3$ | Ms | H |
| Me | H | Me | COOCH$_2$COPh | Ms | H |
| Me | H | Me | COOSi(CH$_3$)$_3$ | Ms | H |
| Me | H | Me | COON=C(CH$_3$)$_2$ | Ms | H |
| Me | H | Me | COOY11 | Ms | H |
| Me | H | Me | COOY12 | Ms | H |
| Me | H | Me | COOCH$_2$OCOC(CH$_3$)$_3$ | Ms | H |
| Me | H | Me | COOCH$_2$OCOCH$_3$ | Ms | H |
| Me | H | Me | COOCH$_2$CH$_2$OCH$_2$CH=CH$_2$ | Ms | H |
| Me | H | Me | COOCH$_2$CH$_2$OCH$_2$C≡CH | Ms | H |
| Me | H | OMe | CON(CH$_3$)OCH$_3$ | Ms | H |
| Me | H | OMe | CONHPh | Ms | H |
| Me | H | OMe | COOCH$_2$COC(CH$_3$)$_3$ | Ms | H |
| Me | H | OMe | COOCH$_2$COPh | Ms | H |
| Me | H | OMe | COOSi(CH$_3$)$_3$ | Ms | H |
| Me | H | OMe | COON=C(CH$_3$)$_2$ | Ms | H |
| Me | H | OMe | COOY11 | Ms | H |
| Me | H | OMe | COOY12 | Ms | H |
| Me | H | OMe | COOCH$_2$OCOC(CH$_3$)$_3$ | Ms | H |
| Me | H | OMe | COOCH$_2$OCOCH$_3$ | Ms | H |
| Me | H | OMe | COOCH$_2$CH$_2$OCH$_2$CH=CH$_2$ | Ms | H |
| Me | H | OMe | COOCH$_2$CH$_2$OCH$_2$C≡CH | Ms | H |
| Me | H | Cl | CON(CH$_3$)OCH$_3$ | Ms | H |
| Me | H | Cl | CONHPh | Ms | H |
| Me | H | Cl | COOCH$_2$COC(CH$_3$)$_3$ | Ms | H |
| Me | H | Cl | COOCH$_2$COPh | Ms | H |
| Me | H | Cl | COOSi(CH$_3$)$_3$ | Ms | H |
| Me | H | Cl | COON=C(CH$_3$)$_2$ | Ms | H |
| Me | H | Cl | COOY11 | Ms | H |
| Me | H | Cl | COOY12 | Ms | H |
| Me | H | Cl | COOCH$_2$OCOC(CH$_3$)$_3$ | Ms | H |
| Me | H | Cl | COOCH$_2$OCOCH$_3$ | Ms | H |
| Me | H | Cl | COOCH$_2$CH$_2$OCH$_2$CH=CH$_2$ | Ms | H |
| Me | H | Cl | COOCH$_2$CH$_2$OCH$_2$C≡CH | Ms | H |
| Et | H | Me | CON(CH$_3$)OCH$_3$ | Ms | H |
| Et | H | Me | CONHPh | Ms | H |
| Et | H | Me | COOCH$_2$COC(CH$_3$)$_3$ | Ms | H |
| Et | H | Me | COOCH$_2$COPh | Ms | H |
| Et | H | Me | COOSi(CH$_3$)$_3$ | Ms | H |
| Et | H | Me | COON=C(CH$_3$)$_2$ | Ms | H |
| Et | H | Me | COOY11 | Ms | H |
| Et | H | Me | COOY12 | Ms | H |
| Et | H | Me | COOCH$_2$OCOC(CH$_3$)$_3$ | Ms | H |
| Et | H | Me | COOCH$_2$OCOCH$_3$ | Ms | H |
| Et | H | Me | COOCH$_2$CH$_2$OCH$_2$CH=CH$_2$ | Ms | H |
| Et | H | Me | COOCH$_2$CH$_2$OCH$_2$C≡CH | Ms | H |
| Et | H | OMe | CON(CH$_3$)OCH$_3$ | Ms | H |
| Et | H | OMe | CONHPh | Ms | H |
| Et | H | OMe | COOCH$_2$COC(CH$_3$)$_3$ | Ms | H |
| Et | H | OMe | COOCH$_2$COPh | Ms | H |
| Et | H | OMe | COOSi(CH$_3$)$_3$ | Ms | H |
| Et | H | OMe | COON=C(CH$_3$)$_2$ | Ms | H |
| Et | H | OMe | COOY11 | Ms | H |
| Et | H | OMe | COOY12 | Ms | H |
| Et | H | OMe | COOCH$_2$OCOC(CH$_3$)$_3$ | Ms | H |
| Et | H | OMe | COOCH$_2$OCOCH$_3$ | Ms | H |
| Et | H | OMe | COOCH$_2$CH$_2$OCH$_2$CH=CH$_2$ | Ms | H |
| Et | H | OMe | COOCH$_2$CH$_2$OCH$_2$C≡CH | Ms | H |
| Et | H | Cl | CON(CH$_3$)OCH$_3$ | Ms | H |
| Et | H | Cl | CONHPh | Ms | H |
| Et | H | Cl | COOCH$_2$COC(CH$_3$)$_3$ | Ms | H |
| Et | H | Cl | COOCH$_2$COPh | Ms | H |
| Et | H | Cl | COOSi(CH$_3$)$_3$ | Ms | H |
| Et | H | Cl | COON=C(CH$_3$)$_2$ | Ms | H |
| Et | H | Cl | COOY11 | Ms | H |
| Et | H | Cl | COOY12 | Ms | H |
| Et | H | Cl | COOCH$_2$OCOC(CH$_3$)$_3$ | Ms | H |
| Et | H | Cl | COOCH$_2$OCOCH$_3$ | Ms | H |
| Et | H | Cl | COOCH$_2$CH$_2$OCH$_2$CH=CH$_2$ | Ms | H |
| Et | H | Cl | COOCH$_2$CH$_2$OCH$_2$C≡CH | Ms | H |
| i-Pr | H | Me | CON(CH$_3$)OCH$_3$ | Ms | H |
| i-Pr | H | Me | CONHPh | Ms | H |
| i-Pr | H | Me | COOCH$_2$COC(CH$_3$)$_3$ | Ms | H |
| i-Pr | H | Me | COOCH$_2$COPh | Ms | H |
| i-Pr | H | Me | COOSi(CH$_3$)$_3$ | Ms | H |

-continued

| | | | | | |
|---|---|---|---|---|---|
| i-Pr | H | Me | COON=C(CH₃)₂ | Ms | H |
| i-Pr | H | Me | COOY11 | Ms | H |
| i-Pr | H | Me | COOY12 | Ms | H |
| i-Pr | H | Me | COOCH₂OCOC(CH₃)₃ | Ms | H |
| i-Pr | H | Me | COOCH₂OCOCH₃ | Ms | H |
| i-Pr | H | Me | COOCH₂CH₂OCH₂CH=CH₂ | Ms | H |
| i-Pr | H | Me | COOCH₂CH₂OCH₂C≡CH | Ms | H |
| i-Pr | H | OMe | CON(CH₃)OCH₃ | Ms | H |
| i-Pr | H | OMe | CONHPh | Ms | H |
| i-Pr | H | OMe | COOCH₂COC(CH₃)₃ | Ms | H |
| i-Pr | H | OMe | COOCH₂COPh | Ms | H |
| i-Pr | H | OMe | COOSi(CH₃)₃ | Ms | H |
| i-Pr | H | OMe | COON=C(CH₃)₂ | Ms | H |
| i-Pr | H | OMe | COOY11 | Ms | H |
| i-Pr | H | OMe | COOY12 | Ms | H |
| i-Pr | H | OMe | COOCH₂OCOC(CH₃)₃ | Ms | H |
| i-Pr | H | OMe | COOCH₂OCOCH₃ | Ms | H |
| i-Pr | H | OMe | COOCH₂CH₂OCH₂CH=CH₂ | Ms | H |
| i-Pr | H | OMe | COOCH₂CH₂OCH₂C≡CH | Ms | H |
| i-Pr | H | Cl | CON(CH₃)OCH₃ | Ms | H |
| i-Pr | H | Cl | CONHPh | Ms | H |
| i-Pr | H | Cl | COOCH₂COC(CH₃)₃ | Ms | H |
| i-Pr | H | Cl | COOCH₂COPh | Ms | H |
| i-Pr | H | Cl | COOSi(CH₃)₃ | Ms | H |
| i-Pr | H | Cl | COON=C(CH₃)₂ | Ms | H |
| i-Pr | H | Cl | COOY11 | Ms | H |
| i-Pr | H | Cl | COOY12 | Ms | H |
| i-Pr | H | Cl | COOCH₂OCOC(CH₃)₃ | Ms | H |
| i-Pr | H | Cl | COOCH₂OCOCH₃ | Ms | H |
| i-Pr | H | Cl | COOCH₂CH₂OCH₂CH=CH₂ | Ms | H |
| i-Pr | H | Cl | COOCH₂CH₂OCH₂C≡CH | Ms | H |
| Me | H | Me | CH₂OH | Ms | H |
| Me | H | Me | CH₂OMe | Ms | H |
| Me | H | Me | CH₂OMe | Cl | H |
| Me | H | Me | CH₂OMe | MeS | H |
| Me | H | Me | CH₂OMe | MeSO | H |
| Me | H | Me | CH₂OMe | Ms | Q1 |
| Me | H | Me | CH₂OMe | MeS | Q1 |
| Me | H | Me | CH₂OMe | MeSO | Q1 |
| Me | H | Me | CH₂OMe | Ms | Q2 |
| Me | H | Me | CH₂OMe | MeS | Q2 |
| Me | H | Me | CH₂OMe | MeSO | Q2 |
| Me | H | Me | CH₂OMe | Ms | Q3 |
| Me | H | Me | CH₂OMe | MeS | Q3 |
| Me | H | Me | CH₂OMe | MeSO | Q3 |
| Me | H | Me | CH₂OMe | Ms | Q4 |
| Me | H | Me | CH₂OMe | Ms | Q5 |
| Me | H | Me | CH₂OMe | Ms | Q6 |
| Me | H | Me | CH₂OMe | Ms | Q7 |
| Me | H | Me | CH₂OMe | Ms | Q8 |
| Me | H | Me | CH₂OMe | Ms | Q9 |
| Me | H | Me | CH₂OEt | Ms | H |
| Me | H | Me | CH₂OEt | Cl | H |
| Me | H | Me | CH₂OEt | MeS | H |
| Me | H | Me | CH₂OEt | MeSO | H |
| Me | H | Me | CH₂OEt | Ms | Q1 |
| Me | H | Me | CH₂OEt | MeS | Q1 |
| Me | H | Me | CH₂OEt | MeSO | Q1 |
| Me | H | Me | CH₂OEt | Ms | Q2 |
| Me | H | Me | CH₂OEt | MeS | Q2 |
| Me | H | Me | CH₂OEt | MeSO | Q2 |
| Me | H | Me | CH₂OEt | Ms | Q3 |
| Me | H | Me | CH₂OEt | MeS | Q3 |
| Me | H | Me | CH₂OEt | MeSO | Q3 |
| Me | H | Me | CH₂OEt | Ms | Q4 |
| Me | H | Me | CH₂OEt | Ms | Q5 |
| Me | H | Me | CH₂OEt | Ms | Q6 |
| Me | H | Me | CH₂OEt | Ms | Q7 |
| Me | H | Me | CH₂OEt | Ms | Q8 |
| Me | H | Me | CH₂OEt | Ms | Q9 |
| Me | H | Me | CH₂OPr-i | Ms | H |
| Me | H | Me | CH₂OPr-i | Cl | H |
| Me | H | Me | CH₂OPr-i | MeS | H |
| Me | H | Me | CH₂OPr-i | MeSO | H |
| Me | H | Me | CH₂OPr-i | Ms | Q1 |
| Me | H | Me | CH₂OPr-i | Ms | Q2 |
| Me | H | Me | CH₂OPr-i | Ms | Q3 |
| Me | H | Me | CH₂OPr-n | Ms | H |
| Me | H | Me | CH₂OPr-n | Cl | H |
| Me | H | Me | CH₂OPr-n | MeS | H |
| Me | H | Me | CH₂OPr-n | MeSO | H |
| Me | H | Me | CH₂OCH=CH₂ | Ms | H |
| Me | H | Me | CH₂OCH=CH₂ | Cl | H |

-continued

| | | | | | |
|---|---|---|---|---|---|
| Me | H | Me | CH₂OCH=CH₂ | MeS | H |
| Me | H | Me | CH₂OCH=CH₂ | MeSO | H |
| Me | H | Me | CH₂OCH₂CH=CH₂ | Ms | H |
| Me | H | Me | CH₂OCH₂CH=CH₂ | Cl | H |
| Me | H | Me | CH₂OCH₂CH=CH₂ | MeS | H |
| Me | H | Me | CH₂OCH₂CH=CH₂ | MeSO | H |
| Me | H | Me | CH₂OCH₂C≡CH | Ms | H |
| Me | H | Me | CH₂OCH₂C≡CH | Cl | H |
| Me | H | Me | CH₂OCH₂C≡CH | MeS | H |
| Me | H | Me | CH₂OCH₂C≡CH | MeSO | H |
| Me | H | Me | CH₂OCH₂CH₂Cl | Ms | H |
| Me | H | Me | CH₂OCH₂CH₂Cl | Cl | H |
| Me | H | Me | CH₂OCH₂CH₂Cl | MeS | H |
| Me | H | Me | CH₂OCH₂CH₂Cl | MeSO | H |
| Me | H | Me | CH₂OCH₂CH₂Br | Ms | H |
| Me | H | Me | CH₂OCH₂CH₂CN | Ms | H |
| Me | H | Me | CH₂OAm-n | Ms | H |
| Me | H | Me | CH₂O—Y5 | Ms | H |
| Me | H | Me | CHMeOH | Ms | H |
| Me | H | Me | CHMeOMe | Ms | H |
| Me | H | Me | CHMeOMe | Cl | H |
| Me | H | Me | CHMeOMe | MeS | H |
| Me | H | Me | CHMeOMe | MeSO | H |
| Me | H | Me | CHMeOMe | Ms | Q1 |
| Me | H | Me | CHMeOMe | Ms | Q2 |
| Me | H | Me | CHMeOMe | Ms | Q3 |
| Me | H | Me | CHMeOEt | Ms | H |
| Me | H | Me | CHMeOEt | Cl | H |
| Me | H | Me | CHMeOEt | MeS | H |
| Me | H | Me | CHMeOEt | MeSO | H |
| Me | H | Me | CHMeOEt | Ms | Q1 |
| Me | H | Me | CHMeOEt | Ms | Q2 |
| Me | H | Me | CHMeOEt | Ms | Q3 |
| Me | H | Me | CHMeOPr-i | Ms | H |
| Me | H | Me | CHMeOPr-i | Cl | H |
| Me | H | Me | CHMeOPr-i | MeS | H |
| Me | H | Me | CHMeOPr-i | MeSO | H |
| Me | H | Me | CHMeOPr-n | Ms | H |
| Me | H | Me | CHMeOCH=CH₂ | Ms | H |
| Me | H | Me | CHMeOCH=CH₂ | Ms | H |
| Me | H | Me | CHMeOCH₂CH=CH₂ | Ms | H |
| Me | H | Me | CHMeOCH₂C≡CH | Ms | H |
| Me | H | Me | CHMeOCH₂CH₂Cl | Ms | H |
| Me | H | Me | CHMeO—Y5 | Ms | H |
| Me | H | Me | CMe₂OH | Ms | H |
| Me | H | Me | CMe₂OMe | Ms | H |
| Me | H | Me | CMe₂OMe | Cl | H |
| Me | H | Me | CMe₂OMe | MeS | H |
| Me | H | Me | CMe₂OMe | MeSO | H |
| Me | H | Me | CMe₂OEt | Ms | H |
| Me | H | Me | CMe₂OEt | Cl | H |
| Me | H | Me | CMe₂OEt | MeS | H |
| Me | H | Me | CMe₂OEt | MeSO | H |
| Me | H | Me | CMe₂OPr-i | Ms | H |
| Me | H | Me | CH₂CH₂OMe | Ms | H |
| Me | H | Me | CH₂CH₂OMe | Cl | H |
| Me | H | Me | CH₂CH₂OMe | MeS | H |
| Me | H | Me | CH₂CH₂OMe | MeSO | H |
| Me | H | Me | CH₂CH₂OEt | Ms | H |
| Me | H | Me | CH₂CH₂OEt | Cl | H |
| Me | H | Me | CH₂CH₂OEt | MeS | H |
| Me | H | Me | CH₂CH₂OEt | MeSO | H |
| Me | H | Me | CH₂CH₂OPr-i | Ms | H |
| Me | H | Me | CH₂CH₂OPr-i | Cl | H |
| Me | H | Me | CH₂CH₂OPr-i | MeS | H |
| Me | H | Me | CH₂CH₂OPr-i | MeSO | H |
| Me | H | Me | CHEtOH | Ms | H |
| Me | H | Me | CHEtOMe | Ms | H |
| Me | H | Me | CHEtOMe | Cl | H |
| Me | H | Me | CHEtOMe | MeS | H |
| Me | H | Me | CHEtOMe | MeSO | H |
| Me | H | Me | CHEtOEt | Ms | H |
| Me | H | Me | CHEtOPr-i | Ms | H |
| Me | H | Me | CH₂OCH₂CH₂OMe | Ms | H |
| Me | H | Me | CH₂OCH₂CH₂OMe | Cl | H |
| Me | H | Me | CH₂OCH₂CH₂OMe | MeS | H |
| Me | H | Me | CH₂OCH₂CH₂OMe | MeSO | H |
| Me | H | Me | CH₂OCH₂CH₂OEt | Ms | H |
| Me | H | Me | CHMeOCH₂CH₂OMe | Ms | H |
| Me | H | Me | CH₂O—Y8 | Ms | H |
| Me | H | Me | CH₂O—Y9 | Ms | H |
| Me | H | Me | CH₂O—Y10 | Ms | H |
| Me | H | Me | CHMeO—Y8 | Ms | H |

-continued

| | | | | | |
|---|---|---|---|---|---|
| Me | H | Me | CHMeO—Y9 | Ms | H |
| Me | H | Me | CHMeO—Y10 | Ms | H |
| Me | H | Me | CH$_2$O—Y13 | Ms | H |
| Me | H | Me | CHMeO—Y13 | Ms | H |
| Me | H | Me | CH$_2$NHMe | Ms | H |
| Me | H | Me | CH$_2$NMe$_2$ | Ms | H |
| Me | H | Me | CH$_2$NEtMe | Ms | H |
| Me | H | Me | CH$_2$NEt$_2$ | Ms | H |
| Me | H | Me | CH$_2$—Y14 | Ms | H |
| Me | H | Me | CHMeNMe$_2$ | Ms | H |
| Me | H | Me | CH$_2$CH$_2$NMe$_2$ | Ms | H |
| Me | H | Me | CH$_2$OCH$_2$Ph | Ms | H |
| Me | H | Me | CHMeOCH$_2$Ph | Ms | H |
| Me | H | Me | CH$_2$OCH$_2$CO$_2$Me | Ms | H |
| Me | H | Me | CH$_2$OCH$_2$CO$_2$Et | Ms | H |
| Me | H | Me | CH$_2$OCHMeCO$_2$Me | Ms | H |
| Me | H | Me | CH$_2$CN | Ms | H |
| Me | H | Me | CHMeCN | Ms | H |
| Me | H | Me | CH$_2$SMe | Ms | H |
| Me | H | Me | CH$_2$SMe | Cl | H |
| Me | H | Me | CH$_2$SMe | MeS | H |
| Me | H | Me | CH$_2$SMe | MeSO | H |
| Me | H | Me | CH$_2$SEt | Ms | H |
| Me | H | Me | CH$_2$SEt | Cl | H |
| Me | H | Me | CH$_2$SEt | MeS | H |
| Me | H | Me | CH$_2$SEt | MeSO | H |
| Me | H | Me | CH$_2$SOMe | Ms | H |
| Me | H | Me | CH$_2$SOEt | Ms | H |
| Me | H | Me | CH$_2$SO$_2$Me | Ms | H |
| Me | H | Me | CH$_2$SO$_2$Me | Cl | H |
| Me | H | Me | CH$_2$SO$_2$Me | MeS | H |
| Me | H | Me | CH$_2$SO$_2$Me | MeSO | H |
| Me | H | Me | CH$_2$SO$_2$Et | Ms | H |
| Me | H | Me | CH$_2$SO$_2$Et | Cl | H |
| Me | H | Me | CH$_2$SO$_2$Et | MeS | H |
| Me | H | Me | CH$_2$SO$_2$Et | MeSO | H |
| Me | H | Me | CHMeSMe | Ms | H |
| Me | H | Me | CHMeSEt | Ms | H |
| Me | H | Me | CHMeSO$_2$Me | Ms | H |
| Me | H | Me | CHMeSO$_2$Et | Ms | H |
| Me | H | Me | CH$_2$SCH$_2$CH$_2$OMe | Ms | H |
| Me | H | Me | CH$_2$OCOMe | Ms | H |
| Me | H | Me | CH$_2$OCOEt | Ms | H |
| Me | H | Me | CHMeOCOMe | Ms | H |
| Me | H | Me | CH$_2$OSO$_2$Me | Ms | H |
| Me | H | Me | CH$_2$OSO$_2$Et | Ms | H |
| Me | H | Me | CHMeOSO$_2$Me | Ms | H |
| Et | H | Me | CH$_2$OH | Ms | H |
| Et | H | Me | CH$_2$OMe | Ms | H |
| Et | H | Me | CH$_2$OMe | Cl | H |
| Et | H | Me | CH$_2$OMe | MeS | H |
| Et | H | Me | CH$_2$OMe | MeSO | H |
| Et | H | Me | CH$_2$OMe | Ms | Q1 |
| Et | H | Me | CH$_2$OMe | MeS | Q1 |
| Et | H | Me | CH$_2$OMe | MeSO | Q1 |
| Et | H | Me | CH$_2$OMe | Ms | Q2 |
| Et | H | Me | CH$_2$OMe | MeS | Q2 |
| Et | H | Me | CH$_2$OMe | MeSO | Q2 |
| Et | H | Me | CH$_2$OMe | Ms | Q3 |
| Et | H | Me | CH$_2$OMe | MeS | Q3 |
| Et | H | Me | CH$_2$OMe | MeSO | Q3 |
| Et | H | Me | CH$_2$OMe | Ms | Q4 |
| Et | H | Me | CH$_2$OMe | Ms | Q5 |
| Et | H | Me | CH$_2$OMe | Ms | Q6 |
| Et | H | Me | CH$_2$OMe | Ms | Q7 |
| Et | H | Me | CH$_2$OMe | Ms | Q8 |
| Et | H | Me | CH$_2$OMe | Ms | Q9 |
| Et | H | Me | CH$_2$OEt | Ms | H |
| Et | H | Me | CH$_2$OEt | Cl | H |
| Et | H | Me | CH$_2$OEt | MeS | H |
| Et | H | Me | CH$_2$OEt | MeSO | H |
| Et | H | Me | CH$_2$OEt | Ms | Q1 |
| Et | H | Me | CH$_2$OEt | MeS | Q1 |
| Et | H | Me | CH$_2$OEt | MeSO | Q1 |
| Et | H | Me | CH$_2$OEt | Ms | Q2 |
| Et | H | Me | CH$_2$OEt | MeS | Q2 |
| Et | H | Me | CH$_2$OEt | MeSO | Q2 |
| Et | H | Me | CH$_2$OEt | Ms | Q3 |
| Et | H | Me | CH$_2$OEt | MeS | Q3 |
| Et | H | Me | CH$_2$OEt | MeSO | Q3 |
| Et | H | Me | CH$_2$OEt | Ms | Q4 |
| Et | H | Me | CH$_2$OEt | Ms | Q5 |
| Et | H | Me | CH$_2$OEt | Ms | Q6 |

-continued

| | | | | | |
|---|---|---|---|---|---|
| Et | H | Me | CH₂OEt | Ms | Q7 |
| Et | H | Me | CH₂OEt | Ms | Q8 |
| Et | H | Me | CH₂OEt | Ms | Q9 |
| Et | H | Me | CH₂OPr-i | Ms | H |
| Et | H | Me | CH₂OPr-i | Cl | H |
| Et | H | Me | CH₂OPr-i | MeS | H |
| Et | H | Me | CH₂OPr-i | MeSO | H |
| Et | H | Me | CH₂OPr-i | Ms | Q1 |
| Et | H | Me | CH₂OPr-i | Ms | Q2 |
| Et | H | Me | CH₂OPr-i | Ms | Q3 |
| Et | H | Me | CH₂OPr-n | Ms | H |
| Et | H | Me | CH₂OPr-n | Cl | H |
| Et | H | Me | CH₂OPr-n | MeS | H |
| Et | H | Me | CH₂OPr-n | MeSO | H |
| Et | H | Me | CH₂OCH=CH₂ | Ms | H |
| Et | H | Me | CH₂OCH=CH₂ | Cl | H |
| Et | H | Me | CH₂OCH=CH₂ | MeS | H |
| Et | H | Me | CH₂OCH=CH₂ | MeSO | H |
| Et | H | Me | CH₂OCH₂CH=CH₂ | Ms | H |
| Et | H | Me | CH₂OCH₂CH=CH₂ | Cl | H |
| Et | H | Me | CH₂OCH₂CH=CH₂ | MeS | H |
| Et | H | Me | CH₂OCH₂CH=CH₂ | MeSO | H |
| Et | H | Me | CH₂OCH₂C≡CH | Ms | H |
| Et | H | Me | CH₂OCH₂C≡CH | Cl | H |
| Et | H | Me | CH₂OCH₂C≡CH | MeS | H |
| Et | H | Me | CH₂OCH₂C≡CH | MeSO | H |
| Et | H | Me | CH₂OCH₂CH₂Cl | Ms | H |
| Et | H | Me | CH₂OCH₂CH₂Cl | Cl | H |
| Et | H | Me | CH₂OCH₂CH₂Cl | MeS | H |
| Et | H | Me | CH₂OCH₂CH₂Cl | MeSO | H |
| Et | H | Me | CH₂OCH₂CH₂Br | Ms | H |
| Et | H | Me | CH₂OCH₂CH₂CN | Ms | H |
| Et | H | Me | CH₂OAm-n | Ms | H |
| Et | H | Me | CH₂O—Y5 | Ms | H |
| Et | H | Me | CHMeOH | Ms | H |
| Et | H | Me | CHMeOMe | Ms | H |
| Et | H | Me | CHMeOMe | Cl | H |
| Et | H | Me | CHMeOMe | MeS | H |
| Et | H | Me | CHMeOMe | MeSO | H |
| Et | H | Me | CHMeOMe | Ms | Q1 |
| Et | H | Me | CHMeOMe | Ms | Q2 |
| Et | H | Me | CHMeOMe | Ms | Q3 |
| Et | H | Me | CHMeOEt | Ms | H |
| Et | H | Me | CHMeOEt | Cl | H |
| Et | H | Me | CHMeOEt | MeS | H |
| Et | H | Me | CHMeOEt | MeSO | H |
| Et | H | Me | CHMeOEt | Ms | Q1 |
| Et | H | Me | CHMeOEt | Ms | Q2 |
| Et | H | Me | CHMeOEt | Ms | Q3 |
| Et | H | Me | CHMeOPr-i | Ms | H |
| Et | H | Me | CHMeOPr-i | Cl | H |
| Et | H | Me | CHMeOPr-i | MeS | H |
| Et | H | Me | CHMeOPr-i | MeSO | H |
| Et | H | Me | CHMeOPr-n | Ms | H |
| Et | H | Me | CHMeOCH=CH₂ | Ms | H |
| Et | H | Me | CHMeOCH=CH₂ | Ms | H |
| Et | H | Me | CHMeOCH₂CH=CH₂ | Ms | H |
| Et | H | Me | CHMeOCH₂C≡CH | Ms | H |
| Et | H | Me | CHMeOCH₂CH₂Cl | Ms | H |
| Et | H | Me | CHMeO—Y5 | Ms | H |
| Et | H | Me | CMe₂OH | Ms | H |
| Et | H | Me | CMe₂OMe | Ms | H |
| Et | H | Me | CMe₂OMe | Cl | H |
| Et | H | Me | CMe₂OMe | MeS | H |
| Et | H | Me | CHe₂OMe | MeSO | H |
| Et | H | Me | CMe₂OEt | Ms | H |
| Et | H | Me | CMe₂OEt | Cl | H |
| Et | H | Me | CMe₂OEt | MeS | H |
| Et | H | Me | CMe₂OEt | MeSO | H |
| Et | H | Me | CMe₂OPr-i | Ms | H |
| Et | H | Me | CH₂CH₂OMe | Ms | H |
| Et | H | Me | CH₂CH₂OMe | Cl | H |
| Et | H | Me | CH₂CH₂OMe | MeS | H |
| Et | H | Me | CH₂CH₂OMe | MeSO | H |
| Et | H | Me | CH₂CH₂OEt | Ms | H |
| Et | H | Me | CH₂CH₂OEt | Cl | H |
| Et | H | Me | CH₂CH₂OEt | MeS | H |
| Et | H | Me | CH₂CH₂OEt | MeSO | H |
| Et | H | Me | CH₂CH₂OPr-i | Ms | H |
| Et | H | Me | CH₂CH₂OPr-i | Cl | H |
| Et | H | Me | CH₂CH₂OPr-i | MeS | H |
| Et | H | Me | CH₂CH₂OPr-i | MeSO | H |
| Et | H | Me | CHEtOH | Ms | H |

-continued

| | | | | | |
|---|---|---|---|---|---|
| Et | H | Me | CHEtOMe | Ms | H |
| Et | H | Me | CHEtOMe | Cl | H |
| Et | H | Me | CHEtOMe | MeS | H |
| Et | H | Me | CHEtOMe | MeSO | H |
| Et | H | Me | CHEtOEt | Ms | H |
| Et | H | Me | CHEtOPr-i | Ms | H |
| Et | H | Me | CH$_2$OCH$_2$CH$_2$OMe | Ms | H |
| Et | H | Me | CH$_2$OCH$_2$CH$_2$OMe | Cl | H |
| Et | H | Me | CH$_2$OCH$_2$CH$_2$OMe | MeS | H |
| Et | H | Me | CH$_2$OCH$_2$CH$_2$OMe | MeSO | H |
| Et | H | Me | CH$_2$OCH$_2$CH$_2$OEt | Ms | H |
| Et | H | Me | CHMeOCH$_2$CH$_2$OMe | Ms | H |
| Et | H | Me | CH$_2$O—Y8 | Ms | H |
| Et | H | Me | CH$_2$O—Y9 | Ms | H |
| Et | H | Me | CH$_2$O—Y10 | Ms | H |
| Et | H | Me | CHMeO—Y8 | Ms | H |
| Et | H | Me | CHMeO—Y9 | Ms | H |
| Et | H | Me | CHMeO—Y10 | Ms | H |
| Et | H | Me | CH$_2$O—Y13 | Ms | H |
| Et | H | Me | CHMeO—Y13 | Ms | H |
| Et | H | Me | CH$_2$NHMe | Ms | H |
| Et | H | Me | CH$_2$NMe$_2$ | Ms | H |
| Et | H | Me | CH$_2$NEtMe | Ms | H |
| Et | H | Me | CH$_2$NEt$_2$ | Ms | H |
| Et | H | Me | CH$_2$—Y14 | Ms | H |
| Et | H | Me | CHMeNMe$_2$ | Ms | H |
| Et | H | Me | CH$_2$CH$_2$NMe$_2$ | Ms | H |
| Et | H | Me | CH$_2$OCH$_2$Ph | Ms | H |
| Et | H | Me | CHMeOCH$_2$Ph | Ms | H |
| Et | H | Me | CH$_2$OCH$_2$CO$_2$Me | Ms | H |
| Et | H | Me | CH$_2$OCH$_2$CO$_2$Et | Ms | H |
| Et | H | Me | CH$_2$OCHMeCO$_2$Me | Ms | H |
| Et | H | Me | CH$_2$CN | Ms | H |
| Et | H | Me | CHMeCN | Ms | H |
| Et | H | Me | CH$_2$SMe | Ms | H |
| Et | H | Me | CH$_2$SMe | Cl | H |
| Et | H | Me | CH$_2$SMe | MeS | H |
| Et | H | Me | CH$_2$SMe | MeSO | H |
| Et | H | Me | CH$_2$SEt | Ms | H |
| Et | H | Me | CH$_2$SEt | Cl | H |
| Et | H | Me | CH$_2$SEt | MeS | H |
| Et | H | Me | CH$_2$SEt | MeSO | H |
| Et | H | Me | CH$_2$SOMe | Ms | H |
| Et | H | Me | CH$_2$SOEt | Ms | H |
| Et | H | Me | CH$_2$SO$_2$Me | Ms | H |
| Et | H | Me | CH$_2$SO$_2$Me | Cl | H |
| Et | H | Me | CH$_2$SO$_2$Me | MeS | H |
| Et | H | Me | CH$_2$SO$_2$Me | MeSO | H |
| Et | H | Me | CH$_2$SO$_2$Et | Ms | H |
| Et | H | Me | CH$_2$SO$_2$Et | Cl | H |
| Et | H | Me | CH$_2$SO$_2$Et | MeS | H |
| Et | H | Me | CH$_2$SO$_2$Et | MeSO | H |
| Et | H | Me | CHMeSMe | Ms | H |
| Et | H | Me | CHMeSEt | Ms | H |
| Et | H | Me | CHMeSO$_2$Me | Ms | H |
| Et | H | Me | CHMeSO$_2$Et | Ms | H |
| Et | H | Me | CH$_2$SCH$_2$CH$_2$OMe | Ms | H |
| Et | H | Me | CH$_2$OCOMe | Ms | H |
| Et | H | Me | CH$_2$OCOEt | Ms | H |
| Et | H | Me | CHMeOCOMe | Ms | H |
| Et | H | Me | CH$_2$OSO$_2$Me | Ms | H |
| Et | H | Me | CH$_2$OSO$_2$Et | Ms | H |
| Et | H | Me | CHMeOSO$_2$Me | Ms | H |
| Pr-i | H | Me | CH$_2$OH | Ms | H |
| Pr-i | H | Me | CH$_2$OMe | Ms | H |
| Pr-i | H | Me | CH$_2$OMe | Cl | H |
| Pr-i | H | Me | CH$_2$OMe | MeS | H |
| Pr-i | H | Me | CH$_2$OMe | MeSO | H |
| Pr-i | H | Me | CH$_2$OMe | Ms | Q1 |
| Pr-i | H | Me | CH$_2$OMe | MeS | Q1 |
| Pr-i | H | Me | CH$_2$OMe | MeSO | Q1 |
| Pr-i | H | Me | CH$_2$OMe | Ms | Q2 |
| Pr-i | H | Me | CH$_2$OMe | MeS | Q2 |
| Pr-i | H | Me | CH$_2$OMe | MeSO | Q2 |
| Pr-i | H | Me | CH$_2$OMe | Ms | Q3 |
| Pr-i | H | Me | CH$_2$OMe | MeS | Q3 |
| Pr-i | H | Me | CH$_2$OMe | MeSO | Q3 |
| Pr-i | H | Me | CH$_2$OMe | Ms | Q4 |
| Pr-i | H | Me | CH$_2$OMe | Ms | Q5 |
| Pr-i | H | Me | CH$_2$OMe | Ms | Q6 |
| Pr-i | H | Me | CH$_2$OMe | Ms | Q7 |
| Pr-i | H | Me | CH$_2$OMe | Ms | Q8 |
| Pr-i | H | Me | CH$_2$OMe | Ms | Q9 |

-continued

| | | | | | |
|---|---|---|---|---|---|
| Pr-i | H | Me | CH₂OEt | Ms | H |
| Pr-i | H | Me | CH₂OEt | Cl | H |
| Pr-i | H | Me | CH₂OEt | MeS | H |
| Pr-i | H | Me | CH₂OEt | MeSO | H |
| Pr-i | H | Me | CH₂OEt | Ms | Q1 |
| Pr-i | H | Me | CH₂OEt | MeS | Q1 |
| Pr-i | H | Me | CH₂OEt | MeSO | Q1 |
| Pr-i | H | Me | CH₂OEt | Ms | Q2 |
| Pr-i | H | Me | CH₂OEt | MeS | Q2 |
| Pr-i | H | Me | CH₂OEt | MeSO | Q2 |
| Pr-i | H | Me | CH₂OEt | Ms | Q3 |
| Pr-i | H | Me | CH₂OEt | MeS | Q3 |
| Pr-i | H | Me | CH₂OEt | MeSO | Q3 |
| Pr-i | H | Me | CH₂OEt | Ms | Q4 |
| Pr-i | H | Me | CH₂OEt | Ms | Q5 |
| Pr-i | H | Me | CH₂OEt | Ms | Q6 |
| Pr-i | H | Me | CH₂OEt | Ms | Q7 |
| Pr-i | H | Me | CH₂OEt | Ms | Q8 |
| Pr-i | H | Me | CH₂OEt | Ms | Q9 |
| Pr-i | H | Me | CH₂OPr-i | Ms | H |
| Pr-i | H | Me | CH₂OPr-i | Cl | H |
| Pr-i | H | Me | CH₂OPr-i | MeS | H |
| Pr-i | H | Me | CH₂OPr-i | MeSO | H |
| Pr-i | H | Me | CH₂OPr-i | Ms | Q1 |
| Pr-i | H | Me | CH₂OPr-i | Ms | Q2 |
| Pr-i | H | Me | CH₂OPr-i | Ms | Q3 |
| Pr-i | H | Me | CH₂OPr-n | Ms | H |
| Pr-i | H | Me | CH₂OPr-n | Cl | H |
| Pr-i | H | Me | CH₂OPr-n | MeS | H |
| Pr-i | H | Me | CH₂OPr-n | MeSO | H |
| Pr-i | H | Me | CH₂OCH=CH₂ | Ms | H |
| Pr-i | H | Me | CH₂OCH=CH₂ | Cl | H |
| Pr-i | H | Me | CH₂OCH=CH₂ | MeS | H |
| Pr-i | H | Me | CH₂OCH=CH₂ | MeSO | H |
| Pr-i | H | Me | CH₂OCH₂CH=CH₂ | Ms | H |
| Pr-i | H | Me | CH₂OCH₂CH=CH₂ | Cl | H |
| Pr-i | H | Me | CH₂OCH₂CH=CH₂ | MeS | H |
| Pr-i | H | Me | CH₂OCH₂CH=CH₂ | MeSO | H |
| Pr-i | H | Me | CH₂OCH₂C≡CH | Ms | H |
| Pr-i | H | Me | CH₂OCH₂C≡CH | Cl | H |
| Pr-i | H | Me | CH₂OCH₂C≡CH | MeS | H |
| Pr-i | H | Me | CH₂OCH₂C≡CH | MeSO | H |
| Pr-i | H | Me | CH₂OCH₂CH₂Cl | Ms | H |
| Pr-i | H | Me | CH₂OCH₂CH₂Cl | Cl | H |
| Pr-i | H | Me | CH₂OCH₂CH₂Cl | MeS | H |
| Pr-i | H | Me | CH₂OCH₂CH₂Cl | MeSO | H |
| Pr-i | H | Me | CH₂OCH₂CH₂Br | Ms | H |
| Pr-i | H | Me | CH₂OCH₂CH₂CN | Ms | H |
| Pr-i | H | Me | CH₂OAm-n | Ms | H |
| Pr-i | H | Me | CH₂O—Y5 | Ms | H |
| Pr-i | H | Me | CHMeOH | Ms | H |
| Pr-i | H | Me | CHMeOMe | Ms | H |
| Pr-i | H | Me | CHMeOMe | Cl | H |
| Pr-i | H | Me | CHMeOMe | MeS | H |
| Pr-i | H | Me | CHMeOMe | MeSO | H |
| Pr-i | H | Me | CHMeOMe | Ms | Q1 |
| Pr-i | H | Me | CHMeOMe | Ms | Q2 |
| Pr-i | H | Me | CHMeOMe | Ms | Q3 |
| Pr-i | H | Me | CHMeOEt | Ms | H |
| Pr-i | H | Me | CHMeOEt | Cl | H |
| Pr-i | H | Me | CHMeOEt | MeS | H |
| Pr-i | H | Me | CHMeOEt | MeSO | H |
| Pr-i | H | Me | CHMeOEt | Ms | Q1 |
| Pr-i | H | Me | CHMeOEt | Ms | Q2 |
| Pr-i | H | Me | CHMeOEt | Ms | Q3 |
| Pr-i | H | Me | CHMeOPr-i | Ms | H |
| Pr-i | H | Me | CHMeOPr-i | Cl | H |
| Pr-i | H | Me | CHMeOPr-i | MeS | H |
| Pr-i | H | Me | CHMeOPr-i | MeSO | H |
| Pr-i | H | Me | CHMeOPr-n | Ms | H |
| Pr-i | H | Me | CHMeOCH=CH₂ | Ms | H |
| Pr-i | H | Me | CHMeOCH=CH₂ | Ms | H |
| Pr-i | H | Me | CHMeOCH₂CH=CH₂ | Ms | H |
| Pr-i | H | Me | CHMeOCH₂C≡CH | Ms | H |
| Pr-i | H | Me | CHMeOCH₂CH₂Cl | Ms | H |
| Pr-i | H | Me | CHMeO—Y5 | Ms | H |
| Pr-i | H | Me | CMe₂OH | Ms | H |
| Pr-i | H | Me | CMe₂OMe | Ms | H |
| Pr-i | H | Me | CMe₂OMe | Cl | H |
| Pr-i | H | Me | CMe₂OMe | MeS | H |
| Pr-i | H | Me | CMe₂OMe | MeSO | H |
| Pr-i | H | Me | CMe₂OEt | Ms | H |
| Pr-i | H | Me | CMe₂OEt | Cl | H |

-continued

| | | | | | |
|---|---|---|---|---|---|
| Pr-i | H | Me | CMe$_2$OEt | MeS | H |
| Pr-i | H | Me | CMe$_2$OEt | MeSO | H |
| Pr-i | H | Me | CMe$_2$OPr-i | Ms | H |
| Pr-i | H | Me | CH$_2$CH$_2$OMe | Ms | H |
| Pr-i | H | Me | CH$_2$CH$_2$OMe | Cl | H |
| Pr-i | H | Me | CH$_2$CH$_2$OMe | MeS | H |
| Pr-i | H | Me | CH$_2$CH$_2$OMe | MeSO | H |
| Pr-i | H | Me | CH$_2$CH$_2$OEt | Ms | H |
| Pr-i | H | Me | CH$_2$CH$_2$OEt | Cl | H |
| Pr-i | H | Me | CH$_2$CH$_2$OEt | MeS | H |
| Pr-i | H | Me | CH$_2$CH$_2$OEt | MeSO | H |
| Pr-i | H | Me | CH$_2$CH$_2$OPr-i | Ms | H |
| Pr-i | H | Me | CH$_2$CH$_2$OPr-i | Cl | H |
| Pr-i | H | Me | CH$_2$CH$_2$OPr-i | MeS | H |
| Pr-i | H | Me | CH$_2$CH$_2$OPr-i | MeSO | H |
| Pr-i | H | Me | CHEtOH | Ms | H |
| Pr-i | H | Me | CHEtOMe | Ms | H |
| Pr-i | H | Me | CHEtOMe | Cl | H |
| Pr-i | H | Me | CHEtOMe | MeS | H |
| Pr-i | H | Me | CHEtOMe | MeSO | H |
| Pr-i | H | Me | CHEtOEt | Ms | H |
| Pr-i | H | Me | CHEtOPr-i | Ms | H |
| Pr-i | H | Me | CH$_2$OCH$_2$CH$_2$OMe | Ms | H |
| Pr-i | H | Me | CH$_2$OCH$_2$CH$_2$OMe | Cl | H |
| Pr-i | H | Me | CH$_2$OCH$_2$CH$_2$OMe | MeS | H |
| Pr-i | H | Me | CH$_2$OCH$_2$CH$_2$OMe | MeSO | H |
| Pr-i | H | Me | CH$_2$OCH$_2$CH$_2$OEt | Ms | H |
| Pr-i | H | Me | CHMeOCH$_2$CH$_2$OMe | Ms | H |
| Pr-i | H | Me | CH$_2$O—Y8 | Ms | H |
| Pr-i | H | Me | CH$_2$O—Y9 | Ms | H |
| Pr-i | H | Me | CH$_2$O—Y10 | Ms | H |
| Pr-i | H | Me | CHMeO—Y8 | Ms | H |
| Pr-i | H | Me | CHMeO—Y9 | Ms | H |
| Pr-i | H | Me | CHMeO—Y10 | Ms | H |
| Pr-i | H | Me | CH$_2$O—Y13 | Ms | H |
| Pr-i | H | Me | CHMeO—Y13 | Ms | H |
| Pr-i | H | Me | CH$_2$NHMe | Ms | H |
| Pr-i | H | Me | CH$_2$NMe$_2$ | Ms | H |
| Pr-i | H | Me | CH$_2$NEtMe | Ms | H |
| Pr-i | H | Me | CH$_2$NEt$_2$ | Ms | H |
| Pr-i | H | Me | CH$_2$—Y14 | Ms | H |
| Pr-i | H | Me | CHMeNMe$_2$ | Ms | H |
| Pr-i | H | Me | CH$_2$CH$_2$NMe$_2$ | Ms | H |
| Pr-i | H | Me | CH$_2$OCH$_2$Ph | Ms | H |
| Pr-i | H | Me | CHMeOCH$_2$Ph | Ms | H |
| Pr-i | H | Me | CH$_2$OCH$_2$CO$_2$Me | Ms | H |
| Pr-i | H | Me | CH$_2$OCH$_2$CO$_2$Et | Ms | H |
| Pr-i | H | Me | CH$_2$OCHMeCO$_2$Me | Ms | H |
| Pr-i | H | Me | CH$_2$CN | Ms | H |
| Pr-i | H | Me | CHMeCN | Ms | H |
| Pr-i | H | Me | CH$_2$SMe | Ms | H |
| Pr-i | H | Me | CH$_2$SMe | Cl | H |
| Pr-i | H | Me | CH$_2$SMe | MeS | H |
| Pr-i | H | Me | CH$_2$SMe | MeSO | H |
| Pr-i | H | Me | CH$_2$SEt | Ms | H |
| Pr-i | H | Me | CH$_2$SEt | Cl | H |
| Pr-i | H | Me | CH$_2$SEt | MeS | H |
| Pr-i | H | Me | CH$_2$SEt | MeSO | H |
| Pr-i | H | Me | CH$_2$SOMe | Ms | H |
| Pr-i | H | Me | CH$_2$SOEt | Ms | H |
| Pr-i | H | Me | CH$_2$SO$_2$Me | Ms | H |
| Pr-i | H | Me | CH$_2$SO$_2$Me | Cl | H |
| Pr-i | H | Me | CH$_2$SO$_2$Me | MeS | H |
| Pr-i | H | Me | CH$_2$SO$_2$Me | MeSO | H |
| Pr-i | H | Me | CH$_2$SO$_2$Et | Ms | H |
| Pr-i | H | Me | CH$_2$SO$_2$Et | Cl | H |
| Pr-i | H | Me | CH$_2$SO$_2$Et | MeS | H |
| Pr-i | H | Me | CH$_2$SO$_2$Et | MeSO | H |
| Pr-i | H | Me | CHMeSMe | Ms | H |
| Pr-i | H | Me | CHMeSEt | Ms | H |
| Pr-i | H | Me | CHMeSO$_2$Me | Ms | H |
| Pr-i | H | Me | CHMeSO$_2$Et | Ms | H |
| Pr-i | H | Me | CH$_2$SCH$_2$CH$_2$OMe | Ms | H |
| Pr-i | H | Me | CH$_2$OCOMe | Ms | H |
| Pr-i | H | Me | CH$_2$OCOEt | Ms | H |
| Pr-i | H | Me | CHMeOCOMe | Ms | H |
| Pr-i | H | Me | CH$_2$OSO$_2$Me | Ms | H |
| Pr-i | H | Me | CH$_2$OSO$_2$Et | Ms | H |
| Pr-i | H | Me | CHMeOSO$_2$Me | Ms | H |
| Me | H | Cl | CH$_2$OH | Ms | H |
| Me | H | Cl | CH$_2$OMe | Ms | H |
| Me | H | Cl | CH$_2$OMe | Cl | H |
| Me | H | Cl | CH$_2$OMe | MeS | H |

-continued

| | | | | | |
|---|---|---|---|---|---|
| Me | H | Cl | CH₂OMe | MeSO | H |
| Me | H | Cl | CH₂OMe | Ms | Q1 |
| Me | H | Cl | CH₂OMe | MeS | Q1 |
| Me | H | Cl | CH₂OMe | MeSO | Q1 |
| Me | H | Cl | CH₂OMe | Ms | Q2 |
| Me | H | Cl | CH₂OMe | MeS | Q2 |
| Me | H | Cl | CH₂OMe | MeSO | Q2 |
| Me | H | Cl | CH₂OMe | Ms | Q3 |
| Me | H | Cl | CH₂OMe | MeS | Q3 |
| Me | H | Cl | CH₂OMe | MeSO | Q3 |
| Me | H | Cl | CH₂OMe | Ms | Q4 |
| Me | H | Cl | CH₂OMe | Ms | Q5 |
| Me | H | Cl | CH₂OMe | Ms | Q6 |
| Me | H | Cl | CH₂OMe | Ms | Q7 |
| Me | H | Cl | CH₂OMe | Ms | Q8 |
| Me | H | Cl | CH₂OMe | Ms | Q9 |
| Me | H | Cl | CH₂OEt | Ms | H |
| Me | H | Cl | CH₂OEt | Cl | H |
| Me | H | Cl | CH₂OEt | MeS | H |
| Me | H | Cl | CH₂OEt | MeSO | H |
| Me | H | Cl | CH₂OEt | Ms | Q1 |
| Me | H | Cl | CH₂OEt | MeS | Q1 |
| Me | H | Cl | CH₂OEt | MeSO | Q1 |
| Me | H | Cl | CH₂OEt | Ms | Q2 |
| Me | H | Cl | CH₂OEt | MeS | Q2 |
| Me | H | Cl | CH₂OEt | MeSO | Q2 |
| Me | H | Cl | CH₂OEt | Ms | Q3 |
| Me | H | Cl | CH₂OEt | MeS | Q3 |
| Me | H | Cl | CH₂OEt | MeSO | Q3 |
| Me | H | Cl | CH₂OEt | Ms | Q4 |
| Me | H | Cl | CH₂OEt | Ms | Q5 |
| Me | H | Cl | CH₂OEt | Ms | Q6 |
| Me | H | Cl | CH₂OEt | Ms | Q7 |
| Me | H | Cl | CH₂OEt | Ms | Q8 |
| Me | H | Cl | CH₂OEt | Ms | Q9 |
| Me | H | Cl | CH₂OPr-i | Ms | H |
| Me | H | Cl | CH₂OPr-i | Cl | H |
| Me | H | Cl | CH₂OPr-i | MeS | H |
| Me | H | Cl | CH₂OPr-i | MeSO | H |
| Me | H | Cl | CH₂OPr-i | Ms | Q1 |
| Me | H | Cl | CH₂OPr-i | Ms | Q2 |
| Me | H | Cl | CH₂OPr-i | Ms | Q3 |
| Me | H | Cl | CH₂OPr-n | Ms | H |
| Me | H | Cl | CH₂OPr-n | Cl | H |
| Me | H | Cl | CH₂OPr-n | MeS | H |
| Me | H | Cl | CH₂OPr-n | MeSO | H |
| Me | H | Cl | CH₂OCH=CH₂ | Ms | H |
| Me | H | Cl | CH₂OCH=CH₂ | Cl | H |
| Me | H | Cl | CH₂OCH=CH₂ | MeS | H |
| Me | H | Cl | CH₂OCH=CH₂ | MeSO | H |
| Me | H | Cl | CH₂OCH₂CH=CH₂ | Ms | H |
| Me | H | Cl | CH₂OCH₂CH=CH₂ | Cl | H |
| Me | H | Cl | CH₂OCH₂CH=CH₂ | MeS | H |
| Me | H | Cl | CH₂OCH₂CH=CH₂ | MeSO | H |
| Me | H | Cl | CH₂OCH₂C≡CH | Ms | H |
| Me | H | Cl | CH₂OCH₂C≡CH | Cl | H |
| Me | H | Cl | CH₂OCH₂C≡CH | MeS | H |
| Me | H | Cl | CH₂OCH₂C≡CH | MeSO | H |
| Me | H | Cl | CH₂OCH₂CH₂Cl | Ms | H |
| Me | H | Cl | CH₂OCH₂CH₂Cl | Cl | H |
| Me | H | Cl | CH₂OCH₂CH₂Cl | MeS | H |
| Me | H | Cl | CH₂OCH₂CH₂Cl | MeSO | H |
| Me | H | Cl | CH₂OCH₂CH₂Br | Ms | H |
| Me | H | Cl | CH₂OCH₂CH₂CN | Ms | H |
| Me | H | Cl | CH₂OAm-n | Ms | H |
| Me | H | Cl | CH₂O—Y5 | Ms | H |
| Me | H | Cl | CHMeOH | Ms | H |
| Me | H | Cl | CHMeOMe | Ms | H |
| Me | H | Cl | CHMeOMe | Cl | H |
| Me | H | Cl | CHMeOMe | MeS | H |
| Me | H | Cl | CHMeOMe | MeSO | H |
| Me | H | Cl | CHMeOMe | Ms | Q1 |
| Me | H | Cl | CHMeOMe | Ms | Q2 |
| Me | H | Cl | CHMeOMe | Ms | Q3 |
| Me | H | Cl | CHMeOEt | Ms | H |
| Me | H | Cl | CHMeOEt | Cl | H |
| Me | H | Cl | CHMeOEt | MeS | H |
| Me | H | Cl | CHMeOEt | MeSO | H |
| Me | H | Cl | CHMeOEt | Ms | Q1 |
| Me | H | Cl | CHMeOEt | Ms | Q2 |
| Me | H | Cl | CHMeOEt | Ms | Q3 |
| Me | H | Cl | CHMeOPr-i | Ms | H |
| Me | H | Cl | CHMeOPr-i | Cl | H |

-continued

| | | | | | |
|---|---|---|---|---|---|
| Me | H | Cl | CHMeOPr-i | MeS | H |
| Me | H | Cl | CHMeOPr-i | MeSO | H |
| Me | H | Cl | CHMeOPr-n | Ms | H |
| Me | H | Cl | CHMeOCH=CH$_2$ | Ms | H |
| Me | H | Cl | CHMeOCH=CH$_2$ | Ms | H |
| Me | H | Cl | CHMeOCH$_2$CH=CH$_2$ | Ms | H |
| Me | H | Cl | CHMeOCH$_2$C≡CH | Ms | H |
| Me | H | Cl | CHMeOCH$_2$CH$_2$Cl | Ms | H |
| Me | H | Cl | CHMeO—Y5 | Ms | H |
| Me | H | Cl | CMe$_2$OH | Ms | H |
| Me | H | Cl | CMe$_2$OMe | Ms | H |
| Me | H | Cl | CMe$_2$OMe | Cl | H |
| Me | H | Cl | CMe$_2$OMe | MeS | H |
| Me | H | Cl | CMe$_2$OMe | MeSO | H |
| Me | H | Cl | CMe$_2$OEt | Ms | H |
| Me | H | Cl | CMe$_2$OEt | Cl | H |
| Me | H | Cl | CMe$_2$OEt | MeS | H |
| Me | H | Cl | CMe$_2$OEt | MeSO | H |
| Me | H | Cl | CMe$_2$OPr-i | Ms | H |
| Me | H | Cl | CH$_2$CH$_2$OMe | Ms | H |
| Me | H | Cl | CH$_2$CH$_2$OMe | Cl | H |
| Me | H | Cl | CH$_2$CH$_2$OMe | MeS | H |
| Me | H | Cl | CH$_2$CH$_2$OMe | MeSO | H |
| Me | H | Cl | CH$_2$CH$_2$OEt | Ms | H |
| Me | H | Cl | CH$_2$CH$_2$OEt | Cl | H |
| Me | H | Cl | CH$_2$CH$_2$OEt | MeS | H |
| Me | H | Cl | CH$_2$CH$_2$OEt | MeSO | H |
| Me | H | Cl | CH$_2$CH$_2$OPr-i | Ms | H |
| Me | H | Cl | CH$_2$CH$_2$OPr-i | Cl | H |
| Me | H | Cl | CH$_2$CH$_2$OPr-i | MeS | H |
| Me | H | Cl | CH$_2$CH$_2$OPr-i | MeSO | H |
| Me | H | Cl | CHEtOH | Ms | H |
| Me | H | Cl | CHEtOMe | Ms | H |
| Me | H | Cl | CHEtOMe | Cl | H |
| Me | H | Cl | CHEtOMe | MeS | H |
| Me | H | Cl | CHEtOMe | MeSO | H |
| Me | H | Cl | CHEtOEt | Ms | H |
| Me | H | Cl | CHEtOPr-i | Ms | H |
| Me | H | Cl | CH$_2$OCH$_2$CH$_2$OMe | Ms | H |
| Me | H | Cl | CH$_2$OCH$_2$CH$_2$OMe | Cl | H |
| Me | H | Cl | CH$_2$OCH$_2$CH$_2$OMe | MeS | H |
| Me | H | Cl | CH$_2$OCH$_2$CH$_2$OMe | MeSO | H |
| Me | H | Cl | CH$_2$OCH$_2$CH$_2$OEt | Ms | H |
| Me | H | Cl | CHMeOCH$_2$CH$_2$OMe | Ms | H |
| Me | H | Cl | CH$_2$O—Y8 | Ms | H |
| Me | H | Cl | CH$_2$O—Y9 | Ms | H |
| Me | H | Cl | CH$_2$O—Y10 | Ms | H |
| Me | H | Cl | CHMeO—Y8 | Ms | H |
| Me | H | Cl | CHMeO—Y9 | Ms | H |
| Me | H | Cl | CHMeO—Y10 | Ms | H |
| Me | H | Cl | CH$_2$O—Y13 | Ms | H |
| Me | H | Cl | CHMeO—Y13 | Ms | H |
| Me | H | Cl | CH$_2$NHMe | Ms | H |
| Me | H | Cl | CH$_2$NMe$_2$ | Ms | H |
| Me | H | Cl | CH$_2$NEtMe | Ms | H |
| Me | H | Cl | CH$_2$NEt$_2$ | Ms | H |
| Me | H | Cl | CH$_2$—Y14 | Ms | H |
| Me | H | Cl | CHMeNMe$_2$ | Ms | H |
| Me | H | Cl | CH$_2$CH$_2$NMe$_2$ | Ms | H |
| Me | H | Cl | CH$_2$OCH$_2$Ph | Ms | H |
| Me | H | Cl | CHMeOCH$_2$Ph | Ms | H |
| Me | H | Cl | CH$_2$OCH$_2$CO$_2$Me | Ms | H |
| Me | H | Cl | CH$_2$OCH$_2$CO$_2$Et | Ms | H |
| Me | H | Cl | CH$_2$OCHMeCO$_2$Me | Ms | H |
| Me | H | Cl | CH$_2$CN | Ms | H |
| Me | H | Cl | CHMeCN | Ms | H |
| Me | H | Cl | CH$_2$SMe | Ms | H |
| Me | H | Cl | CH$_2$SMe | Cl | H |
| Me | H | Cl | CH$_2$SMe | MeS | H |
| Me | H | Cl | CH$_2$SMe | MeSO | H |
| Me | H | Cl | CH$_2$SEt | Ms | H |
| Me | H | Cl | CH$_2$SEt | Cl | H |
| Me | H | Cl | CH$_2$SEt | MeS | H |
| Me | H | Cl | CH$_2$SEt | MeSO | H |
| Me | H | Cl | CH$_2$SOMe | Ms | H |
| Me | H | Cl | CH$_2$SOEt | Ms | H |
| Me | H | Cl | CH$_2$SO$_2$Me | Ms | H |
| Me | H | Cl | CH$_2$SO$_2$Me | Cl | H |
| Me | H | Cl | CH$_2$SO$_2$Me | MeS | H |
| Me | H | Cl | CH$_2$SO$_2$Me | MeSO | H |
| Me | H | Cl | CH$_2$SO$_2$Et | Ms | H |
| Me | H | Cl | CH$_2$SO$_2$Et | Cl | H |
| Me | H | Cl | CH$_2$SO$_2$Et | MeS | H |

-continued

| | | | | | |
|---|---|---|---|---|---|
| Me | H | Cl | CH$_2$SO$_2$Et | MeSO | H |
| Me | H | Cl | CHMeSMe | Ms | H |
| Me | H | Cl | CHMeSEt | Ms | H |
| Me | H | Cl | CHMeSO$_2$Me | Ms | H |
| Me | H | Cl | CHMeSO$_2$Et | Ms | H |
| Me | H | Cl | CH$_2$SCH$_2$CH$_2$OMe | Ms | H |
| Me | H | Cl | CH$_2$OCOMe | Ms | H |
| Me | H | Cl | CH$_2$OCOEt | Ms | H |
| Me | H | Cl | CHMeOCOMe | Ms | H |
| Me | H | Cl | CH$_2$OSO$_2$Me | Ms | H |
| Me | H | Cl | CH$_2$OSO$_2$Et | Ms | H |
| Me | H | Cl | CHMeOSO$_2$Me | Ms | H |
| Et | H | Cl | CH$_2$OH | Ms | H |
| Et | H | Cl | CH$_2$OMe | Ms | H |
| Et | H | Cl | CH$_2$OMe | Cl | H |
| Et | H | Cl | CH$_2$OMe | MeS | H |
| Et | H | Cl | CH$_2$OMe | MeSO | H |
| Et | H | Cl | CH$_2$OMe | Ms | Q1 |
| Et | H | Cl | CH$_2$OMe | MeS | Q1 |
| Et | H | Cl | CH$_2$OMe | MeSO | Q1 |
| Et | H | Cl | CH$_2$OMe | Ms | Q2 |
| Et | H | Cl | CH$_2$OMe | MeS | Q2 |
| Et | H | Cl | CH$_2$OMe | MeSO | Q2 |
| Et | H | Cl | CH$_2$OMe | Ms | Q3 |
| Et | H | Cl | CH$_2$OMe | MeS | Q3 |
| Et | H | Cl | CH$_2$OMe | MeSO | Q3 |
| Et | H | Cl | CH$_2$OMe | Ms | Q4 |
| Et | H | Cl | CH$_2$OMe | Ms | Q5 |
| Et | H | Cl | CH$_2$OMe | Ms | Q6 |
| Et | H | Cl | CH$_2$OMe | Ms | Q7 |
| Et | H | Cl | CH$_2$OMe | Ms | Q8 |
| Et | H | Cl | CH$_2$OMe | Ms | Q9 |
| Et | H | Cl | CH$_2$OEt | Ms | H |
| Et | H | Cl | CH$_2$OEt | Cl | H |
| Et | H | Cl | CH$_2$OEt | MeS | H |
| Et | H | Cl | CH$_2$OEt | MeSO | H |
| Et | H | Cl | CH$_2$OEt | Ms | Q1 |
| Et | H | Cl | CH$_2$OEt | MeS | Q1 |
| Et | H | Cl | CH$_2$OEt | MeSO | Q1 |
| Et | H | Cl | CH$_2$OEt | Ms | Q2 |
| Et | H | Cl | CH$_2$OEt | MeS | Q2 |
| Et | H | Cl | CH$_2$OEt | MeSO | Q2 |
| Et | H | Cl | CH$_2$OEt | Ms | Q3 |
| Et | H | Cl | CH$_2$OEt | MeS | Q3 |
| Et | H | Cl | CH$_2$OEt | MeSO | Q3 |
| Et | H | Cl | CH$_2$OEt | Ms | Q4 |
| Et | H | Cl | CH$_2$OEt | Ms | Q5 |
| Et | H | Cl | CH$_2$OEt | Ms | Q6 |
| Et | H | Cl | CH$_2$OEt | Ms | Q7 |
| Et | H | Cl | CH$_2$OEt | Ms | Q8 |
| Et | H | Cl | CH$_2$OEt | Ms | Q9 |
| Et | H | Cl | CH$_2$OPr-i | Ms | H |
| Et | H | Cl | CH$_2$OPr-i | Cl | H |
| Et | H | Cl | CH$_2$OPr-i | MeS | H |
| Et | H | Cl | CH$_2$OPr-i | MeSO | H |
| Et | H | Cl | CH$_2$OPr-i | Ms | Q1 |
| Et | H | Cl | CH$_2$OPr-i | Ms | Q2 |
| Et | H | Cl | CH$_2$OPr-i | Ms | Q3 |
| Et | H | Cl | CH$_2$OPr-n | Ms | H |
| Et | H | Cl | CH$_2$OPr-n | Cl | H |
| Et | H | Cl | CH$_2$OPr-n | MeS | H |
| Et | H | Cl | CH$_2$OPr-n | MeSO | H |
| Et | H | Cl | CH$_2$OCH=CH$_2$ | Ms | H |
| Et | H | Cl | CH$_2$OCH=CH$_2$ | Cl | H |
| Et | H | Cl | CH$_2$OCH=CH$_2$ | MeS | H |
| Et | H | Cl | CH$_2$OCH=CH$_2$ | MeSO | H |
| Et | H | Cl | CH$_2$OCH$_2$CH=CH$_2$ | Ms | H |
| Et | H | Cl | CH$_2$OCH$_2$CH=CH$_2$ | Cl | H |
| Et | H | Cl | CH$_2$OCH$_2$CH=CH$_2$ | MeS | H |
| Et | H | Cl | CH$_2$OCH$_2$CH=CH$_2$ | MeSO | H |
| Et | H | Cl | CH$_2$OCH$_2$C≡CH | Ms | H |
| Et | H | Cl | CH$_2$OCH$_2$C≡CH | Cl | H |
| Et | H | Cl | CH$_2$OCH$_2$C≡CH | MeS | H |
| Et | H | Cl | CH$_2$OCH$_2$C≡CH | MeSO | H |
| Et | H | Cl | CH$_2$OCH$_2$CH$_2$Cl | Ms | H |
| Et | H | Cl | CH$_2$OCH$_2$CH$_2$Cl | Cl | H |
| Et | H | Cl | CH$_2$OCH$_2$CH$_2$Cl | MeS | H |
| Et | H | Cl | CH$_2$OCH$_2$CH$_2$Cl | MeSO | H |
| Et | H | Cl | CH$_2$OCH$_2$CH$_2$Br | Ms | H |
| Et | H | Cl | CH$_2$OCH$_2$CH$_2$CN | Ms | H |
| Et | H | Cl | CH$_2$OAm-n | Ms | H |
| Et | H | Cl | CH$_2$O—Y5 | Ms | H |
| Et | H | Cl | CHMeOH | Ms | H |

-continued

| | | | | | |
|---|---|---|---|---|---|
| Et | H | Cl | CHMeOMe | Ms | H |
| Et | H | Cl | CHMeOMe | Cl | H |
| Et | H | Cl | CHMeOMe | MeS | H |
| Et | H | Cl | CHMeOMe | MeSO | H |
| Et | H | Cl | CHMeOMe | Ms | Q1 |
| Et | H | Cl | CHMeOMe | Ms | Q2 |
| Et | H | Cl | CHMeOMe | Ms | Q3 |
| Et | H | Cl | CHMeOEt | Ms | H |
| Et | H | Cl | CHMeOEt | Cl | H |
| Et | H | Cl | CHMeOEt | MeS | H |
| Et | H | Cl | CHMeOEt | MeSO | H |
| Et | H | Cl | CHMeOEt | Ms | Q1 |
| Et | H | Cl | CHMeOEt | Ms | Q2 |
| Et | H | Cl | CHMeOEt | Ms | Q3 |
| Et | H | Cl | CHMeOPr-i | Ms | H |
| Et | H | Cl | CHMeOPr-i | Cl | H |
| Et | H | Cl | CHMeOPr-i | MeS | H |
| Et | H | Cl | CHMeOPr-i | MeSO | H |
| Et | H | Cl | CHMeOPr-n | Ms | H |
| Et | H | Cl | CHMeOCH=CH$_2$ | Ms | H |
| Et | H | Cl | CHMeOCH=CH$_2$ | Ms | H |
| Et | H | Cl | CHMeOCH$_2$CH=CH$_2$ | Ms | H |
| Et | H | Cl | CHMeOCH$_2$C≡CH | Ms | H |
| Et | H | Cl | CHMeOCH$_2$CH$_2$Cl | Ms | H |
| Et | H | Cl | CHMeO—Y5 | Ms | H |
| Et | H | Cl | CMe$_2$OH | Ms | H |
| Et | H | Cl | CMe$_2$OMe | Ms | H |
| Et | H | Cl | CMe$_2$OMe | Cl | H |
| Et | H | Cl | CMe$_2$OMe | MeS | H |
| Et | H | Cl | CMe$_2$OMe | MeSO | H |
| Et | H | Cl | CMe$_2$OEt | Ms | H |
| Et | H | Cl | CMe$_2$OEt | Cl | H |
| Et | H | Cl | CMe$_2$OEt | MeS | H |
| Et | H | Cl | CMe$_2$OEt | MeSO | H |
| Et | H | Cl | CMe$_2$OPr-i | Ms | H |
| Et | H | Cl | CH$_2$CH$_2$OMe | Ms | H |
| Et | H | Cl | CH$_2$CH$_2$OMe | Cl | H |
| Et | H | Cl | CH$_2$CH$_2$OMe | MeS | H |
| Et | H | Cl | CH$_2$CH$_2$OMe | MeSO | H |
| Et | H | Cl | CH$_2$CH$_2$OEt | Ms | H |
| Et | H | Cl | CH$_2$CH$_2$OEt | Cl | H |
| Et | H | Cl | CH$_2$CH$_2$OEt | MeS | H |
| Et | H | Cl | CH$_2$CH$_2$OEt | MeSO | H |
| Et | H | Cl | CH$_2$CH$_2$OPr-i | Ms | H |
| Et | H | Cl | CH$_2$CH$_2$OPr-i | Cl | H |
| Et | H | Cl | CH$_2$CH$_2$OPr-i | MeS | H |
| Et | H | Cl | CH$_2$CH$_2$OPr-i | MeSO | H |
| Et | H | Cl | CHEtOH | Ms | H |
| Et | H | Cl | CHEtOMe | Ms | H |
| Et | H | Cl | CHEtOMe | Cl | H |
| Et | H | Cl | CHEtOMe | MeS | H |
| Et | H | Cl | CHEtOMe | MeSO | H |
| Et | H | Cl | CHEtOEt | Ms | H |
| Et | H | Cl | CHEtOPr-i | Ms | H |
| Et | H | Cl | CH$_2$OCH$_2$CH$_2$OMe | Ms | H |
| Et | H | Cl | CH$_2$OCH$_2$CH$_2$OMe | Cl | H |
| Et | H | Cl | CH$_2$OCH$_2$CH$_2$OMe | MeS | H |
| Et | H | Cl | CH$_2$OCH$_2$CH$_2$OMe | MeSO | H |
| Et | H | Cl | CH$_2$OCH$_2$CH$_2$OEt | Ms | H |
| Et | H | Cl | CHMeOCH$_2$CH$_2$OMe | Ms | H |
| Et | H | Cl | CH$_2$O—Y8 | Ms | H |
| Et | H | Cl | CH$_2$O—Y9 | Ms | H |
| Et | H | Cl | CH$_2$O—Y10 | Ms | H |
| Et | H | Cl | CHMeO—Y8 | Ms | H |
| Et | H | Cl | CHMeO—Y9 | Ms | H |
| Et | H | Cl | CHMeO—Y10 | Ms | H |
| Et | H | Cl | CH$_2$O—Y13 | Ms | H |
| Et | H | Cl | CHMeO—Y13 | Ms | H |
| Et | H | Cl | CH$_2$NHMe | Ms | H |
| Et | H | Cl | CH$_2$NMe$_2$ | Ms | H |
| Et | H | Cl | CH$_2$NEtMe | Ms | H |
| Et | H | Cl | CH$_2$NEt$_2$ | Ms | H |
| Et | H | Cl | CH$_2$—Y14 | Ms | H |
| Et | H | Cl | CHMeNMe$_2$ | Ms | H |
| Et | H | Cl | CH$_2$CH$_2$NMe$_2$ | Ms | H |
| Et | H | Cl | CH$_2$OCH$_2$Ph | Ms | H |
| Et | H | Cl | CHMeOCH$_2$Ph | Ms | H |
| Et | H | Cl | CH$_2$OCH$_2$CO$_2$Me | Ms | H |
| Et | H | Cl | CH$_2$OCH$_2$CO$_2$Et | Ms | H |
| Et | H | Cl | CH$_2$OCHMeCO$_2$Me | Ms | H |
| Et | H | Cl | CH$_2$CN | Ms | H |
| Et | H | Cl | CHMeCN | Ms | H |
| Et | H | Cl | CH$_2$SMe | Ms | H |

-continued

| | | | | | |
|---|---|---|---|---|---|
| Et | H | Cl | CH$_2$SMe | Cl | H |
| Et | H | Cl | CH$_2$SMe | MeS | H |
| Et | H | Cl | CH$_2$SMe | MeSO | H |
| Et | H | Cl | CH$_2$SEt | Ms | H |
| Et | H | Cl | CH$_2$SEt | Cl | H |
| Et | H | Cl | CH$_2$SEt | MeS | H |
| Et | H | Cl | CH$_2$SEt | MeSO | H |
| Et | H | Cl | CH$_2$SOMe | Ms | H |
| Et | H | Cl | CH$_2$SOEt | Ms | H |
| Et | H | Cl | CH$_2$SO$_2$Me | Ms | H |
| Et | H | Cl | CH$_2$SO$_2$Me | Cl | H |
| Et | H | Cl | CH$_2$SO$_2$Me | MeS | H |
| Et | H | Cl | CH$_2$SO$_2$Me | MeSO | H |
| Et | H | Cl | CH$_2$SO$_2$Et | Ms | H |
| Et | H | Cl | CH$_2$SO$_2$Et | Cl | H |
| Et | H | Cl | CH$_2$SO$_2$Et | MeS | H |
| Et | H | Cl | CH$_2$SO$_2$Et | MeSO | H |
| Et | H | Cl | CHMeSMe | Ms | H |
| Et | H | Cl | CHMeSEt | Ms | H |
| Et | H | Cl | CHMeSO$_2$Me | Ms | H |
| Et | H | Cl | CHMeSO$_2$Et | Ms | H |
| Et | H | Cl | CH$_2$SCH$_2$CH$_2$OMe | Ms | H |
| Et | H | Cl | CH$_2$OCOMe | Ms | H |
| Et | H | Cl | CH$_2$OCOEt | Ms | H |
| Et | H | Cl | CHMeOCOMe | Ms | H |
| Et | H | Cl | CH$_2$OSO$_2$Me | Ms | H |
| Et | H | Cl | CH$_2$OSO$_2$Et | Ms | H |
| Et | H | Cl | CHMeOSO$_2$Me | Ms | H |
| Pr-i | H | Cl | CH$_2$OH | Ms | H |
| Pr-i | H | Cl | CH$_2$OMe | Ms | H |
| Pr-i | H | Cl | CH$_2$OMe | Cl | H |
| Pr-i | H | Cl | CH$_2$OMe | MeS | H |
| Pr-i | H | Cl | CH$_2$OMe | MeSO | H |
| Pr-i | H | Cl | CH$_2$OMe | Ms | Q1 |
| Pr-i | H | Cl | CH$_2$OMe | MeS | Q1 |
| Pr-i | H | Cl | CH$_2$OMe | MeSO | Q1 |
| Pr-i | H | Cl | CH$_2$OMe | Ms | Q2 |
| Pr-i | H | Cl | CH$_2$OMe | MeS | Q2 |
| Pr-i | H | Cl | CH$_2$OMe | MeSO | Q2 |
| Pr-i | H | Cl | CH$_2$OMe | Ms | Q3 |
| Pr-i | H | Cl | CH$_2$OMe | MeS | Q3 |
| Pr-i | H | Cl | CH$_2$OMe | MeSO | Q3 |
| Pr-i | H | Cl | CH$_2$OMe | Ms | Q4 |
| Pr-i | H | Cl | CH$_2$OMe | Ms | Q5 |
| Pr-i | H | Cl | CH$_2$OMe | Ms | Q6 |
| Pr-i | H | Cl | CH$_2$OMe | Ms | Q7 |
| Pr-i | H | Cl | CH$_2$OMe | Ms | Q8 |
| Pr-i | H | Cl | CH$_2$OMe | Ms | Q9 |
| Pr-i | H | Cl | CH$_2$OEt | Ms | H |
| Pr-i | H | Cl | CH$_2$OEt | Cl | H |
| Pr-i | H | Cl | CH$_2$OEt | MeS | H |
| Pr-i | H | Cl | CH$_2$OEt | MeSO | H |
| Pr-i | H | Cl | CH$_2$OEt | Ms | Q1 |
| Pr-i | H | Cl | CH$_2$OEt | MeS | Q1 |
| Pr-i | H | Cl | CH$_2$OEt | MeSO | Q1 |
| Pr-i | H | Cl | CH$_2$OEt | Ms | Q2 |
| Pr-i | H | Cl | CH$_2$OEt | MeS | Q2 |
| Pr-i | H | Cl | CH$_2$OEt | MeSO | Q2 |
| Pr-i | H | Cl | CH$_2$OEt | Ms | Q3 |
| Pr-i | H | Cl | CH$_2$OEt | MeS | Q3 |
| Pr-i | H | Cl | CH$_2$OEt | MeSO | Q3 |
| Pr-i | H | Cl | CH$_2$OEt | Ms | Q4 |
| Pr-i | H | Cl | CH$_2$OEt | Ms | Q5 |
| Pr-i | H | Cl | CH$_2$OEt | Ms | Q6 |
| Pr-i | H | Cl | CH$_2$OEt | Ms | Q7 |
| Pr-i | H | Cl | CH$_2$OEt | Ms | Q8 |
| Pr-i | H | Cl | CH$_2$OEt | Ms | Q9 |
| Pr-i | H | Cl | CH$_2$OPr-i | Ms | H |
| Pr-i | H | Cl | CH$_2$OPr-i | Cl | H |
| Pr-i | H | Cl | CH$_2$OPr-i | MeS | H |
| Pr-i | H | Cl | CH$_2$OPr-i | MeSO | H |
| Pr-i | H | Cl | CH$_2$OPr-i | Ms | Q1 |
| Pr-i | H | Cl | CH$_2$OPr-i | Ms | Q2 |
| Pr-i | H | Cl | CH$_2$OPr-i | Ms | Q3 |
| Pr-i | H | Cl | CH$_2$OPr-n | Ms | H |
| Pr-i | H | Cl | CH$_2$OPr-n | Cl | H |
| Pr-i | H | Cl | CH$_2$OPr-n | MeS | H |
| Pr-i | H | Cl | CH$_2$OPr-n | MeSO | H |
| Pr-i | H | Cl | CH$_2$OCH=CH$_2$ | Ms | H |
| Pr-i | H | Cl | CH$_2$OCH=CH$_2$ | Cl | H |
| Pr-i | H | Cl | CH$_2$OCH=CH$_2$ | MeS | H |
| Pr-i | H | Cl | CH$_2$OCH=CH$_2$ | MeSO | H |
| Pr-i | H | Cl | CH$_2$OCH$_2$CH=CH$_2$ | Ms | H |

-continued

| | | | | | |
|---|---|---|---|---|---|
| Pr-i | H | Cl | CH$_2$OCH$_2$CH=CH$_2$ | Cl | H |
| Pr-i | H | Cl | CH$_2$OCH$_2$CH=CH$_2$ | MeS | H |
| Pr-i | H | Cl | CH$_2$OCH$_2$CH=CH$_2$ | MeSO | H |
| Pr-i | H | Cl | CH$_2$OCH$_2$C≡CH | Ms | H |
| Pr-i | H | Cl | CH$_2$OCH$_2$C≡CH | Cl | H |
| Pr-i | H | Cl | CH$_2$OCH$_2$C≡CH | MeS | H |
| Pr-i | H | Cl | CH$_2$OCH$_2$C≡CH | MeSO | H |
| Pr-i | H | Cl | CH$_2$OCH$_2$CH$_2$Cl | Ms | H |
| Pr-i | H | Cl | CH$_2$OCH$_2$CH$_2$Cl | Cl | H |
| Pr-i | H | Cl | CH$_2$OCH$_2$CH$_2$Cl | MeS | H |
| Pr-i | H | Cl | CH$_2$OCH$_2$CH$_2$Cl | MeSO | H |
| Pr-i | H | Cl | CH$_2$OCH$_2$CH$_2$Br | Ms | H |
| Pr-i | H | Cl | CH$_2$OCH$_2$CH$_2$CN | Ms | H |
| Pr-i | H | Cl | CH$_2$OAm-n | Ms | H |
| Pr-i | H | Cl | CH$_2$O—Y5 | Ms | H |
| Pr-i | H | Cl | CHMeOH | Ms | H |
| Pr-i | H | Cl | CHMeOMe | Ms | H |
| Pr-i | H | Cl | CHMeOMe | Cl | H |
| Pr-i | H | Cl | CHMeOMe | MeS | H |
| Pr-i | H | Cl | CHMeOMe | MeSO | H |
| Pr-i | H | Cl | CHMeOMe | Ms | Q1 |
| Pr-i | H | Cl | CHMeOMe | Ms | Q2 |
| Pr-i | H | Cl | CHMeOMe | Ms | Q3 |
| Pr-i | H | Cl | CHMeOEt | Ms | H |
| Pr-i | H | Cl | CHMeOEt | Cl | H |
| Pr-i | H | Cl | CHMeOEt | MeS | H |
| Pr-i | H | Cl | CHMeOEt | MeSO | H |
| Pr-i | H | Cl | CHMeOEt | Ms | Q1 |
| Pr-i | H | Cl | CHMeOEt | Ms | Q2 |
| Pr-i | H | Cl | CHMeOEt | Ms | Q3 |
| Pr-i | H | Cl | CHMeOPr-i | Ms | H |
| Pr-i | H | Cl | CHMeOPr-i | Cl | H |
| Pr-i | H | Cl | CHMeOPr-i | MeS | H |
| Pr-i | H | Cl | CHMeOPr-i | MeSO | H |
| Pr-i | H | Cl | CHMeOPr-n | Ms | H |
| Pr-i | H | Cl | CHMeOCH=CH$_2$ | Ms | H |
| Pr-i | H | Cl | CHMeOCH=CH$_2$ | Ms | H |
| Pr-i | H | Cl | CHMeOCH$_2$CH=CH$_2$ | Ms | H |
| Pr-i | H | Cl | CHMeOCH$_2$C≡CH | Ms | H |
| Pr-i | H | Cl | CHMeOCH$_2$CH$_2$Cl | Ms | H |
| Pr-i | H | Cl | CHMeO—Y5 | Ms | H |
| Pr-i | H | Cl | CMe$_2$OH | Ms | H |
| Pr-i | H | Cl | CMe$_2$OMe | Ms | H |
| Pr-i | H | Cl | CMe$_2$OMe | Cl | H |
| Pr-i | H | Cl | CMe$_2$OMe | MeS | H |
| Pr-i | H | Cl | CMe$_2$OMe | MeSO | H |
| Pr-i | H | Cl | CMe$_2$OEt | Ms | H |
| Pr-i | H | Cl | CMe$_2$OEt | Cl | H |
| Pr-i | H | Cl | CMe$_2$OEt | MeS | H |
| Pr-i | H | Cl | CMe$_2$OEt | MeSO | H |
| Pr-i | H | Cl | CMe$_2$OPr-i | Ms | H |
| Pr-i | H | Cl | CH$_2$CH$_2$OMe | Ms | H |
| Pr-i | H | Cl | CH$_2$CH$_2$OMe | Cl | H |
| Pr-i | H | Cl | CH$_2$CH$_2$OMe | MeS | H |
| Pr-i | H | Cl | CH$_2$CH$_2$OMe | MeSO | H |
| Pr-i | H | Cl | CH$_2$CH$_2$OEt | Ms | H |
| Pr-i | H | Cl | CH$_2$CH$_2$OEt | Cl | H |
| Pr-i | H | Cl | CH$_2$CH$_2$OEt | MeS | H |
| Pr-i | H | Cl | CH$_2$CH$_2$OEt | MeSO | H |
| Pr-i | H | Cl | CH$_2$CH$_2$OPr-i | Ms | H |
| Pr-i | H | Cl | CH$_2$CH$_2$OPr-i | Cl | H |
| Pr-i | H | Cl | CH$_2$CH$_2$OPr-i | MeS | H |
| Pr-i | H | Cl | CH$_2$CH$_2$OPr-i | MeSO | H |
| Pr-i | H | Cl | CHEtOH | Ms | H |
| Pr-i | H | Cl | CHEtOMe | Ms | H |
| Pr-i | H | Cl | CHEtOMe | Cl | H |
| Pr-i | H | Cl | CHEtOMe | MeS | H |
| Pr-i | H | Cl | CHEtOMe | MeSO | H |
| Pr-i | H | Cl | CHEtOEt | Ms | H |
| Pr-i | H | Cl | CHEtOPr-i | Ms | H |
| Pr-i | H | Cl | CH$_2$OCH$_2$CH$_2$OMe | Ms | H |
| Pr-i | H | Cl | CH$_2$OCH$_2$CH$_2$OMe | Cl | H |
| Pr-i | H | Cl | CH$_2$OCH$_2$CH$_2$OMe | MeS | H |
| Pr-i | H | Cl | CH$_2$OCH$_2$CH$_2$OMe | MeSO | H |
| Pr-i | H | Cl | CH$_2$OCH$_2$CH$_2$OEt | Ms | H |
| Pr-i | H | Cl | CHMeOCH$_2$CH$_2$OMe | Ms | H |
| Pr-i | H | Cl | CH$_2$O—Y8 | Ms | H |
| Pr-i | H | Cl | CH$_2$O—Y9 | Ms | H |
| Pr-i | H | Cl | CH$_2$O—Y10 | Ms | H |
| Pr-i | H | Cl | CHMeO—Y8 | Ms | H |
| Pr-i | H | Cl | CHMeO—Y9 | Ms | H |
| Pr-i | H | Cl | CHMeO—Y10 | Ms | H |
| Pr-i | H | Cl | CH$_2$O—Y13 | Ms | H |

-continued

| | | | | | |
|---|---|---|---|---|---|
| Pr-i | H | Cl | CHMeO—Y13 | Ms | H |
| Pr-i | H | Cl | CH₂NHMe | Ms | H |
| Pr-i | H | Cl | CH₂NMe₂ | Ms | H |
| Pr-i | H | Cl | CH₂NEtMe | Ms | H |
| Pr-i | H | Cl | CH₂NEt₂ | Ms | H |
| Pr-i | H | Cl | CH₂—Y14 | Ms | H |
| Pr-i | H | Cl | CHMeNMe₂ | Ms | H |
| Pr-i | H | Cl | CH₂CH₂NMe₂ | Ms | H |
| Pr-i | H | Cl | CH₂OCH₂Ph | Ms | H |
| Pr-i | H | Cl | CHMeOCH₂Ph | Ms | H |
| Pr-i | H | Cl | CH₂OCH₂CO₂Me | Ms | H |
| Pr-i | H | Cl | CH₂OCH₂CO₂Et | Ms | H |
| Pr-i | H | Cl | CH₂OCHMeCO₂Me | Ms | H |
| Pr-i | H | Cl | CH₂CN | Ms | H |
| Pr-i | H | Cl | CHMeCN | Ms | H |
| Pr-i | H | Cl | CH₂SMe | Ms | H |
| Pr-i | H | Cl | CH₂SMe | Cl | H |
| Pr-i | H | Cl | CH₂SMe | MeS | H |
| Pr-i | H | Cl | CH₂SMe | MeSO | H |
| Pr-i | H | Cl | CH₂SEt | Ms | H |
| Pr-i | H | Cl | CH₂SEt | Cl | H |
| Pr-i | H | Cl | CH₂SEt | MeS | H |
| Pr-i | H | Cl | CH₂SEt | MeSO | H |
| Pr-i | H | Cl | CH₂SOMe | Ms | H |
| Pr-i | H | Cl | CH₂SOEt | Ms | H |
| Pr-i | H | Cl | CH₂SO₂Me | Ms | H |
| Pr-i | H | Cl | CH₂SO₂Me | Cl | H |
| Pr-i | H | Cl | CH₂SO₂Me | MeS | H |
| Pr-i | H | Cl | CH₂SO₂Me | MeSO | H |
| Pr-i | H | Cl | CH₂SO₂Et | Ms | H |
| Pr-i | H | Cl | CH₂SO₂Et | Cl | H |
| Pr-i | H | Cl | CH₂SO₂Et | MeS | H |
| Pr-i | H | Cl | CH₂SO₂Et | MeSO | H |
| Pr-i | H | Cl | CHMeSMe | Ms | H |
| Pr-i | H | Cl | CHMeSEt | Ms | H |
| Pr-i | H | Cl | CHMeSO₂Me | Ms | H |
| Pr-i | H | Cl | CHMeSO₂Et | Ms | H |
| Pr-i | H | Cl | CH₂SCH₂CH₂OMe | Ms | H |
| Pr-i | H | Cl | CH₂OCOMe | Ms | H |
| Pr-i | H | Cl | CH₂OCOEt | Ms | H |
| Pr-i | H | Cl | CHMeOCOMe | Ms | H |
| Pr-i | H | Cl | CH₂OSO₂Me | Ms | H |
| Pr-i | H | Cl | CH₂OSO₂Et | Ms | H |
| Pr-i | H | Cl | CHMeOSO₂Me | Ms | H |
| Me | H | MeO | CH₂OH | Ms | H |
| Me | H | MeO | CH₂OMe | Ms | H |
| Me | H | MeO | CH₂OMe | Cl | H |
| Me | H | MeO | CH₂OMe | MeS | H |
| Me | H | MeO | CH₂OMe | MeSO | H |
| Me | H | MeO | CH₂OMe | Ms | Q1 |
| Me | H | MeO | CH₂OMe | MeS | Q1 |
| Me | H | MeO | CH₂OMe | MeSO | Q1 |
| Me | H | MeO | CH₂OMe | Ms | Q2 |
| Me | H | MeO | CH₂OMe | MeS | Q2 |
| Me | H | MeO | CH₂OMe | MeSO | Q2 |
| Me | H | MeO | CH₂OMe | Ms | Q3 |
| Me | H | MeO | CH₂OMe | MeS | Q3 |
| Me | H | MeO | CH₂OMe | MeSO | Q3 |
| Me | H | MeO | CH₂OMe | Ms | Q4 |
| Me | H | MeO | CH₂OMe | Ms | Q5 |
| Me | H | MeO | CH₂OMe | Ms | Q6 |
| Me | H | MeO | CH₂OMe | Ms | Q7 |
| Me | H | MeO | CH₂OMe | Ms | Q8 |
| Me | H | MeO | CH₂OMe | Ms | Q9 |
| Me | H | MeO | CH₂OEt | Ms | H |
| Me | H | MeO | CH₂OEt | Cl | H |
| Me | H | MeO | CH₂OEt | MeS | H |
| Me | H | MeO | CH₂OEt | MeSO | H |
| Me | H | MeO | CH₂OEt | Ms | Q1 |
| Me | H | MeO | CH₂OEt | MeS | Q1 |
| Me | H | MeO | CH₂OEt | MeSO | Q1 |
| Me | H | MeO | CH₂OEt | Ms | Q2 |
| Me | H | MeO | CH₂OEt | MeS | Q2 |
| Me | H | MeO | CH₂OEt | MeSO | Q2 |
| Me | H | MeO | CH₂OEt | Ms | Q3 |
| Me | H | MeO | CH₂OEt | MeS | Q3 |
| Me | H | MeO | CH₂OEt | MeSO | Q3 |
| Me | H | MeO | CH₂OEt | Ms | Q4 |
| Me | H | MeO | CH₂OEt | Ms | Q5 |
| Me | H | MeO | CH₂OEt | Ms | Q6 |
| Me | H | MeO | CH₂OEt | Ms | Q7 |
| Me | H | MeO | CH₂OEt | Ms | Q8 |
| Me | H | MeO | CH₂OEt | Ms | Q9 |

-continued

| | | | | | |
|---|---|---|---|---|---|
| Me | H | MeO | CH$_2$OPr-i | Ms | H |
| Me | H | MeO | CH$_2$OPr-i | Cl | H |
| Me | H | MeO | CH$_2$OPr-i | MeS | H |
| Me | H | MeO | CH$_2$OPr-i | MeSO | H |
| Me | H | MeO | CH$_2$OPr-i | Ms | Q1 |
| Me | H | MeO | CH$_2$OPr-i | Ms | Q2 |
| Me | H | MeO | CH$_2$OPr-i | Ms | Q3 |
| Me | H | MeO | CH$_2$OPr-n | Ms | H |
| Me | H | MeO | CH$_2$OPr-n | Cl | H |
| Me | H | MeO | CH$_2$OPr-n | MeS | H |
| Me | H | MeO | CH$_2$OPr-n | MeSO | H |
| Me | H | MeO | CH$_2$OCH=CH$_2$ | Ms | H |
| Me | H | MeO | CH$_2$OCH=CH$_2$ | Cl | H |
| Me | H | MeO | CH$_2$OCH=CH$_2$ | MeS | H |
| Me | H | MeO | CH$_2$OCH=CH$_2$ | MeSO | H |
| Me | H | MeO | CH$_2$OCH$_2$CH=CH$_2$ | Ms | H |
| Me | H | MeO | CH$_2$OCH$_2$CH=CH$_2$ | Cl | H |
| Me | H | MeO | CH$_2$OCH$_2$CH=CH$_2$ | MeS | H |
| Me | H | MeO | CH$_2$OCH$_2$CH=CH$_2$ | MeSO | H |
| Me | H | MeO | CH$_2$OCH$_2$C≡CH | Ms | H |
| Me | H | MeO | CH$_2$OCH$_2$C≡CH | Cl | H |
| Me | H | MeO | CH$_2$OCH$_2$C≡CH | MeS | H |
| Me | H | MeO | CH$_2$OCH$_2$C≡CH | MeSO | H |
| Me | H | MeO | CH$_2$OCH$_2$CH$_2$Cl | Ms | H |
| Me | H | MeO | CH$_2$OCH$_2$CH$_2$Cl | Cl | H |
| Me | H | MeO | CH$_2$OCH$_2$CH$_2$Cl | MeS | H |
| Me | H | MeO | CH$_2$OCH$_2$CH$_2$Cl | MeSO | H |
| Me | H | MeO | CH$_2$O—Y5 | Ms | H |
| Me | H | MeO | CHMeOH | Ms | H |
| Me | H | MeO | CHMeOMe | Ms | H |
| Me | H | MeO | CHMeOMe | Cl | H |
| Me | H | MeO | CHMeOMe | MeS | H |
| Me | H | MeO | CHMeOMe | MeSO | H |
| Me | H | MeO | CHMeOMe | Ms | Q1 |
| Me | H | MeO | CHMeOMe | Ms | Q2 |
| Me | H | MeO | CHMeOMe | Ms | Q3 |
| Me | H | MeO | CHMeOEt | Ms | H |
| Me | H | MeO | CHMeOEt | Cl | H |
| Me | H | MeO | CHMeOEt | MeS | H |
| Me | H | MeO | CHMeOEt | MeSO | H |
| Me | H | MeO | CHMeOEt | Ms | Q1 |
| Me | H | MeO | CHMeOEt | Ms | Q2 |
| Me | H | MeO | CHMeOEt | Ms | Q3 |
| Me | H | MeO | CHMeOPr-i | Ms | H |
| Me | H | MeO | CHMeOPr-i | Cl | H |
| Me | H | MeO | CHMeOPr-i | MeS | H |
| Me | H | MeO | CHMeOPr-i | MeSO | H |
| Me | H | MeO | CHMeOPr-n | Ms | H |
| Me | H | MeO | CHMeOCH=CH$_2$ | Ms | H |
| Me | H | MeO | CHMeOCH$_2$CH=CH$_2$ | Ms | H |
| Me | H | MeO | CHMeOCH$_2$C≡CH | Ms | H |
| Me | H | MeO | CHMeOCH$_2$CH$_2$Cl | Ms | H |
| Me | H | MeO | CHMeO—Y5 | Ms | H |
| Me | H | MeO | CMe$_2$OH | Ms | H |
| Me | H | MeO | CMe$_2$OMe | Ms | H |
| Me | H | MeO | CMe$_2$OMe | Cl | H |
| Me | H | MeO | CMe$_2$OMe | MeS | H |
| Me | H | MeO | CMe$_2$OMe | MeSO | H |
| Me | H | MeO | CMe$_2$OEt | Ms | H |
| Me | H | MeO | CMe$_2$OEt | Cl | H |
| Me | H | MeO | CMe$_2$OEt | MeS | H |
| Me | H | MeO | CMe$_2$OEt | MeSO | H |
| Me | H | MeO | CHe$_2$OPr-i | Ms | H |
| Me | H | MeO | CH$_2$CH$_2$OMe | Ms | H |
| Me | H | MeO | CH$_2$CH$_2$OMe | Cl | H |
| Me | H | MeO | CH$_2$CH$_2$OMe | MeS | H |
| Me | H | MeO | CH$_2$CH$_2$OMe | MeSO | H |
| Me | H | MeO | CH$_2$CH$_2$OEt | Ms | H |
| Me | H | MeO | CH$_2$CH$_2$OEt | Cl | H |
| Me | H | MeO | CH$_2$CH$_2$OEt | MeS | H |
| Me | H | MeO | CH$_2$CH$_2$OEt | MeSO | H |
| Me | H | MeO | CH$_2$CH$_2$OPr-i | Ms | H |
| Me | H | MeO | CH$_2$CH$_2$OPr-i | Cl | H |
| Me | H | MeO | CH$_2$CH$_2$OPr-i | MeS | H |
| Me | H | MeO | CH$_2$CH$_2$OPr-i | MeSO | H |
| Me | H | MeO | CHEtOH | Ms | H |
| Me | H | MeO | CHEtOMe | Ms | H |
| Me | H | MeO | CHEtOMe | Cl | H |
| Me | H | MeO | CHEtOMe | MeS | H |
| Me | H | MeO | CHEtOMe | MeSO | H |
| Me | H | MeO | CHEtOEt | Ms | H |
| Me | H | MeO | CHEtOPr-i | Ms | H |

-continued

| | | | | | |
|---|---|---|---|---|---|
| Me | H | MeO | CH$_2$OCH$_2$CH$_2$OMe | Ms | H |
| Me | H | MeO | CH$_2$OCH$_2$CH$_2$OMe | Cl | H |
| Me | H | MeO | CH$_2$OCH$_2$CH$_2$OMe | MeS | H |
| Me | H | MeO | CH$_2$OCH$_2$CH$_2$OMe | MeSO | H |
| Me | H | MeO | CH$_2$OCH$_2$CH$_2$OEt | Ms | H |
| Me | H | MeO | CHMeOCH$_2$CH$_2$OMe | Ms | H |
| Me | H | MeO | CH$_2$O—Y8 | Ms | H |
| Me | H | MeO | CH$_2$O—Y9 | Ms | H |
| Me | H | MeO | CH$_2$O—Y10 | Ms | H |
| Me | H | MeO | CHMeO—Y8 | Ms | H |
| Me | H | MeO | CHMeO—Y9 | Ms | H |
| Me | H | MeO | CHMeO—Y10 | Ms | H |
| Me | H | MeO | CH$_2$O—Y13 | Ms | H |
| Me | H | MeO | CHMeO—Y13 | Ms | H |
| Me | H | MeO | CH$_2$NHMe | Ms | H |
| Me | H | MeO | CH$_2$NMe$_2$ | Ms | H |
| Me | H | MeO | CH$_2$NEtMe | Ms | H |
| Me | H | MeO | CH$_2$NEt$_2$ | Ms | H |
| Me | H | MeO | CH$_2$—Y14 | Ms | H |
| Me | H | MeO | CHMeNMe$_2$ | Ms | H |
| Me | H | MeO | CH$_2$CH$_2$NMe$_2$ | Ms | H |
| Me | H | MeO | CH$_2$OCH$_2$Ph | Ms | H |
| Me | H | MeO | CHMeOCH$_2$Ph | Ms | H |
| Me | H | MeO | CH$_2$OCH$_2$CO$_2$Me | Ms | H |
| Me | H | MeO | CH$_2$OCH$_2$CO$_2$Et | Ms | H |
| Me | H | MeO | CH$_2$OCHMeCO$_2$Me | Ms | H |
| Me | H | MeO | CH$_2$CN | Ms | H |
| Me | H | MeO | CHMeCN | Ms | H |
| Me | H | MeO | CH$_2$SMe | Ms | H |
| Me | H | MeO | CH$_2$SMe | Cl | H |
| Me | H | MeO | CH$_2$SMe | MeS | H |
| Me | H | MeO | CH$_2$SMe | MeSO | H |
| Me | H | MeO | CH$_2$SEt | Ms | H |
| Me | H | MeO | CH$_2$SEt | Cl | H |
| Me | H | MeO | CH$_2$SEt | MeS | H |
| Me | H | MeO | CH$_2$SEt | MeSO | H |
| Me | H | MeO | CH$_2$SOMe | Ms | H |
| Me | H | MeO | CH$_2$SOEt | Ms | H |
| Me | H | MeO | CH$_2$SO$_2$Me | Ms | H |
| Me | H | MeO | CH$_2$SO$_2$Me | Cl | H |
| Me | H | MeO | CH$_2$SO$_2$Me | MeS | H |
| Me | H | MeO | CH$_2$SO$_2$Me | MeSO | H |
| Me | H | MeO | CH$_2$SO$_2$Et | Ms | H |
| Me | H | MeO | CH$_2$SO$_2$Et | Cl | H |
| Me | H | MeO | CH$_2$SO$_2$Et | MeS | H |
| Me | H | MeO | CH$_2$SO$_2$Et | MeSO | H |
| Me | H | MeO | CHMeSMe | Ms | H |
| Me | H | MeO | CHMeSEt | Ms | H |
| Me | H | MeO | CHMeSO$_2$Me | Ms | H |
| Me | H | MeO | CHMeSO$_2$Et | Ms | H |
| Me | H | MeO | CH$_2$SCH$_2$CH$_2$OMe | Ms | H |
| Me | H | MeO | CH$_2$OCOMe | Ms | H |
| Me | H | MeO | CH$_2$OCOEt | Ms | H |
| Me | H | MeO | CHMeOCOMe | Ms | H |
| Me | H | MeO | CH$_2$OSO$_2$Me | Ms | H |
| Me | H | MeO | CH$_2$OSO$_2$Et | Ms | H |
| Me | H | MeO | CHMeOSO$_2$Me | Ms | H |
| Et | H | MeO | CH$_2$OH | Ms | H |
| Et | H | MeO | CH$_2$OMe | Ms | H |
| Et | H | MeO | CH$_2$OMe | Cl | H |
| Et | H | MeO | CH$_2$OMe | MeS | H |
| Et | H | MeO | CH$_2$OMe | MeSO | H |
| Et | H | MeO | CH$_2$OMe | Ms | Q1 |
| Et | H | MeO | CH$_2$OMe | MeS | Q1 |
| Et | H | MeO | CH$_2$OMe | MeSO | Q1 |
| Et | H | MeO | CH$_2$OMe | Ms | Q2 |
| Et | H | MeO | CH$_2$OMe | MeS | Q2 |
| Et | H | MeO | CH$_2$OMe | MeSO | Q2 |
| Et | H | MeO | CH$_2$OMe | Ms | Q3 |
| Et | H | MeO | CH$_2$OMe | MeS | Q3 |
| Et | H | MeO | CH$_2$OMe | MeSO | Q3 |
| Et | H | MeO | CH$_2$OMe | Ms | Q4 |
| Et | H | MeO | CH$_2$OMe | Ms | Q5 |
| Et | H | MeO | CH$_2$OMe | Ms | Q6 |
| Et | H | MeO | CH$_2$OMe | Ms | Q7 |
| Et | H | MeO | CH$_2$OMe | Ms | Q8 |
| Et | H | MeO | CH$_2$OMe | Ms | Q9 |
| Et | H | MeO | CH$_2$OEt | Ms | H |
| Et | H | MeO | CH$_2$OEt | Cl | H |
| Et | H | MeO | CH$_2$OEt | MeS | H |
| Et | H | MeO | CH$_2$OEt | MeSO | H |
| Et | H | MeO | CH$_2$OEt | Ms | Q1 |
| Et | H | MeO | CH$_2$OEt | MeS | Q1 |

-continued

| | | | | | |
|---|---|---|---|---|---|
| Et | H | MeO | CH₂OEt | MeSO | Q1 |
| Et | H | MeO | CH₂OEt | Ms | Q2 |
| Et | H | MeO | CH₂OEt | MeS | Q2 |
| Et | H | MeO | CH₂OEt | MeSO | Q2 |
| Et | H | MeO | CH₂OEt | Ms | Q3 |
| Et | H | MeO | CH₂OEt | MeS | Q3 |
| Et | H | MeO | CH₂OEt | MeSO | Q3 |
| Et | H | MeO | CH₂OEt | Ms | Q4 |
| Et | H | MeO | CH₂OEt | Ms | Q5 |
| Et | H | MeO | CH₂OEt | Ms | Q6 |
| Et | H | MeO | CH₂OEt | Ms | Q7 |
| Et | H | MeO | CH₂OEt | Ms | Q8 |
| Et | H | MeO | CH₂OEt | Ms | Q9 |
| Et | H | MeO | CH₂OPr-i | Ms | H |
| Et | H | MeO | CH₂OPr-i | Cl | H |
| Et | H | MeO | CH₂OPr-i | MeS | H |
| Et | H | MeO | CH₂OPr-i | MeSO | H |
| Et | H | MeO | CH₂OPr-i | Ms | Q1 |
| Et | H | MeO | CH₂OPr-i | Ms | Q2 |
| Et | H | MeO | CH₂OPr-i | Ms | Q3 |
| Et | H | MeO | CH₂OPr-n | Ms | H |
| Et | H | MeO | CH₂OPr-n | Cl | H |
| Et | H | MeO | CH₂OPr-n | MeS | H |
| Et | H | MeO | CH₂OPr-n | MeSO | H |
| Et | H | MeO | CH₂OCH=CH₂ | Ms | H |
| Et | H | MeO | CH₂OCH=CH₂ | Cl | H |
| Et | H | MeO | CH₂OCH=CH₂ | MeS | H |
| Et | H | MeO | CH₂OCH=CH₂ | MeSO | H |
| Et | H | MeO | CH₂OCH₂CH=CH₂ | Ms | H |
| Et | H | MeO | CH₂OCH₂CH=CH₂ | Cl | H |
| Et | H | MeO | CH₂OCH₂CH=CH₂ | MeS | H |
| Et | H | MeO | CH₂OCH₂CH=CH₂ | MeSO | H |
| Et | H | MeO | CH₂OCH₂C≡CH | Ms | H |
| Et | H | MeO | CH₂OCH₂C≡CH | Cl | H |
| Et | H | MeO | CH₂OCH₂C≡CH | MeS | H |
| Et | H | MeO | CH₂OCH₂C≡CH | MeSO | H |
| Et | H | MeO | CH₂OCH₂CH₂Cl | Ms | H |
| Et | H | MeO | CH₂OCH₂CH₂Cl | Cl | H |
| Et | H | MeO | CH₂OCH₂CH₂Cl | MeS | H |
| Et | H | MeO | CH₂OCH₂CH₂Cl | MeSO | H |
| Et | H | MeO | CH₂O—Y5 | Ms | H |
| Et | H | MeO | CHMeOH | Ms | H |
| Et | H | MeO | CHMeOMe | Ms | H |
| Et | H | MeO | CHMeOMe | Cl | H |
| Et | H | MeO | CHMeOMe | MeS | H |
| Et | H | MeO | CHMeOMe | MeSO | H |
| Et | H | MeO | CHMeOMe | Ms | Q1 |
| Et | H | MeO | CHMeOMe | Ms | Q2 |
| Et | H | MeO | CHMeOMe | Ms | Q3 |
| Et | H | MeO | CHMeOEt | Ms | H |
| Et | H | MeO | CHMeOEt | Cl | H |
| Et | H | MeO | CHMeOEt | MeS | H |
| Et | H | MeO | CHMeOEt | MeSO | H |
| Et | H | MeO | CHMeOEt | Ms | Q1 |
| Et | H | MeO | CHMeOEt | Ms | Q2 |
| Et | H | MeO | CHMeOEt | Ms | Q3 |
| Et | H | MeO | CHMeOPr-i | Ms | H |
| Et | H | MeO | CHMeOPr-i | Cl | H |
| Et | H | MeO | CHMeOPr-i | MeS | H |
| Et | H | MeO | CHMeOPr-i | MeSO | H |
| Et | H | MeO | CHMeOPr-n | Ms | H |
| Et | H | MeO | CHMeOCH=CH₂ | Ms | H |
| Et | H | MeO | CHMeOCH=CH₂ | Ms | H |
| Et | H | MeO | CHMeOCH₂CH=CH₂ | Ms | H |
| Et | H | MeO | CHMeOCH₂C≡CH | Ms | H |
| Et | H | MeO | CHMeOCH₂CH₂Cl | Ms | H |
| Et | H | MeO | CHMeO—Y5 | Ms | H |
| Et | H | MeO | CMe₂OH | Ms | H |
| Et | H | MeO | CMe₂OMe | Ms | H |
| Et | H | MeO | CMe₂OMe | Cl | H |
| Et | H | MeO | CMe₂OMe | MeS | H |
| Et | H | MeO | CMe₂OMe | MeSO | H |
| Et | H | MeO | CMe₂OEt | Ms | H |
| Et | H | MeO | CMe₂OEt | Cl | H |
| Et | H | MeO | CMe₂OEt | MeS | H |
| Et | H | MeO | CMe₂OEt | MeSO | H |
| Et | H | MeO | CMe₂OPr-i | Ms | H |
| Et | H | MeO | CH₂CH₂OMe | Ms | H |
| Et | H | MeO | CH₂CH₂OMe | Cl | H |
| Et | H | MeO | CH₂CH₂OMe | MeS | H |
| Et | H | MeO | CH₂CH₂OMe | MeSO | H |
| Et | H | MeO | CH₂CH₂OEt | Ms | H |
| Et | H | MeO | CH₂CH₂OEt | Cl | H |

-continued

| | | | | | |
|---|---|---|---|---|---|
| Et | H | MeO | CH$_2$CH$_2$OEt | MeS | H |
| Et | H | MeO | CH$_2$CH$_2$OEt | MeSO | H |
| Et | H | MeO | CH$_2$CH$_2$OPr-i | Ms | H |
| Et | H | MeO | CH$_2$CH$_2$OPr-i | Cl | H |
| Et | H | MeO | CH$_2$CH$_2$OPr-i | MeS | H |
| Et | H | MeO | CH$_2$CH$_2$OPr-i | MeSO | H |
| Et | H | MeO | CHEtOH | Ms | H |
| Et | H | MeO | CHEtOMe | Ms | H |
| Et | H | MeO | CHEtOMe | Cl | H |
| Et | H | MeO | CHEtOMe | MeS | H |
| Et | H | MeO | CHEtOMe | MeSO | H |
| Et | H | MeO | CHEtOEt | Ms | H |
| Et | H | MeO | CHEtOPr-i | Ms | H |
| Et | H | MeO | CH$_2$OCH$_2$CH$_2$OMe | Ms | H |
| Et | H | MeO | CH$_2$OCH$_2$CH$_2$OMe | Cl | H |
| Et | H | MeO | CH$_2$OCH$_2$CH$_2$OMe | MeS | H |
| Et | H | MeO | CH$_2$OCH$_2$CH$_2$OMe | MeSO | H |
| Et | H | MeO | CH$_2$OCH$_2$CH$_2$OEt | Ms | H |
| Et | H | MeO | CHMeOCH$_2$CH$_2$OMe | Ms | H |
| Et | H | MeO | CH$_2$O—Y8 | Ms | H |
| Et | H | MeO | CH$_2$O—Y9 | Ms | H |
| Et | H | MeO | CH$_2$O—Y10 | Ms | H |
| Et | H | MeO | CHMeO—Y8 | Ms | H |
| Et | H | MeO | CHMeO—Y9 | Ms | H |
| Et | H | MeO | CHMeO—Y10 | Ms | H |
| Et | H | MeO | CH$_2$O—Y13 | Ms | H |
| Et | H | MeO | CHMeO—Y13 | Ms | H |
| Et | H | MeO | CH$_2$NHMe | Ms | H |
| Et | H | MeO | CH$_2$NMe$_2$ | Ms | H |
| Et | H | MeO | CH$_2$NEtMe | Ms | H |
| Et | H | MeO | CH$_2$NEt$_2$ | Ms | H |
| Et | H | MeO | CH$_2$—Y14 | Ms | H |
| Et | H | MeO | CHMeNMe$_2$ | Ms | H |
| Et | H | MeO | CH$_2$CH$_2$NMe$_2$ | Ms | H |
| Et | H | MeO | CH$_2$OCH$_2$Ph | Ms | H |
| Et | H | MeO | CHMeOCH$_2$Ph | Ms | H |
| Et | H | MeO | CH$_2$OCH$_2$CO$_2$Me | Ms | H |
| Et | H | MeO | CH$_2$OCH$_2$CO$_2$Et | Ms | H |
| Et | H | MeO | CH$_2$OCHMeCO$_2$Me | Ms | H |
| Et | H | MeO | CH$_2$CN | Ms | H |
| Et | H | MeO | CHMeCN | Ms | H |
| Et | H | MeO | CH$_2$SMe | Ms | H |
| Et | H | MeO | CH$_2$SMe | Cl | H |
| Et | H | MeO | CH$_2$SMe | MeS | H |
| Et | H | MeO | CH$_2$SMe | MeSO | H |
| Et | H | MeO | CH$_2$SEt | Ms | H |
| Et | H | MeO | CH$_2$SEt | Cl | H |
| Et | H | MeO | CH$_2$SEt | MeS | H |
| Et | H | MeO | CH$_2$SEt | MeSO | H |
| Et | H | MeO | CH$_2$SOMe | Ms | H |
| Et | H | MeO | CH$_2$SOEt | Ms | H |
| Et | H | MeO | CH$_2$SO$_2$Me | Ms | H |
| Et | H | MeO | CH$_2$SO$_2$Me | Cl | H |
| Et | H | MeO | CH$_2$SO$_2$Me | MeS | H |
| Et | H | MeO | CH$_2$SO$_2$Me | MeSO | H |
| Et | H | MeO | CH$_2$SO$_2$Et | Ms | H |
| Et | H | MeO | CH$_2$SO$_2$Et | Cl | H |
| Et | H | MeO | CH$_2$SO$_2$Et | MeS | H |
| Et | H | MeO | CH$_2$SO$_2$Et | MeSO | H |
| Et | H | MeO | CHMeSMe | Ms | H |
| Et | H | MeO | CHMeSEt | Ms | H |
| Et | H | MeO | CHMeSO$_2$Me | Ms | H |
| Et | H | MeO | CHMeSO$_2$Et | Ms | H |
| Et | H | MeO | CH$_2$SCH$_2$CH$_2$OMe | Ms | H |
| Et | H | MeO | CH$_2$OCOMe | Ms | H |
| Et | H | MeO | CH$_2$OCOEt | Ms | H |
| Et | H | MeO | CHMeOCOMe | Ms | H |
| Et | H | MeO | CH$_2$OSO$_2$Me | Ms | H |
| Et | H | MeO | CH$_2$OSO$_2$Et | Ms | H |
| Et | H | MeO | CHMeOSO$_2$Me | Ms | H |
| Pr-i | H | MeO | CH$_2$OH | Ms | H |
| Pr-i | H | MeO | CH$_2$OMe | Ms | H |
| Pr-i | H | MeO | CH$_2$OMe | Cl | H |
| Pr-i | H | MeO | CH$_2$OMe | MeS | H |
| Pr-i | H | MeO | CH$_2$OMe | MeSO | H |
| Pr-i | H | MeO | CH$_2$OMe | Ms | Q1 |
| Pr-i | H | MeO | CH$_2$OMe | MeS | Q1 |
| Pr-i | H | MeO | CH$_2$OMe | MeSO | Q1 |
| Pr-i | H | MeO | CH$_2$OMe | Ms | Q2 |
| Pr-i | H | MeO | CH$_2$OMe | MeS | Q2 |
| Pr-i | H | MeO | CH$_2$OMe | MeSO | Q2 |
| Pr-i | H | MeO | CH$_2$OMe | Ms | Q3 |
| Pr-i | H | MeO | CH$_2$OMe | MeS | Q3 |

-continued

| | | | | | |
|---|---|---|---|---|---|
| Pr-i | H | MeO | CH$_2$OMe | MeSO | Q3 |
| Pr-i | H | MeO | CH$_2$OMe | Ms | Q4 |
| Pr-i | H | MeO | CH$_2$OMe | Ms | Q5 |
| Pr-i | H | MeO | CH$_2$OMe | Ms | Q6 |
| Pr-i | H | MeO | CH$_2$OMe | Ms | Q7 |
| Pr-i | H | MeO | CH$_2$OMe | Ms | Q8 |
| Pr-i | H | MeO | CH$_2$OMe | Ms | Q9 |
| Pr-i | H | MeO | CH$_2$OEt | Ms | H |
| Pr-i | H | MeO | CH$_2$OEt | Cl | H |
| Pr-i | H | MeO | CH$_2$OEt | MeS | H |
| Pr-i | H | MeO | CH$_2$OEt | MeSO | H |
| Pr-i | H | MeO | CH$_2$OEt | Ms | Q1 |
| Pr-i | H | MeO | CH$_2$OEt | MeS | Q1 |
| Pr-i | H | MeO | CH$_2$OEt | MeSO | Q1 |
| Pr-i | H | MeO | CH$_2$OEt | Ms | Q2 |
| Pr-i | H | MeO | CH$_2$OEt | MeS | Q2 |
| Pr-i | H | MeO | CH$_2$OEt | MeSO | Q2 |
| Pr-i | H | MeO | CH$_2$OEt | Ms | Q3 |
| Pr-i | H | MeO | CH$_2$OEt | MeS | Q3 |
| Pr-i | H | MeO | CH$_2$OEt | MeSO | Q3 |
| Pr-i | H | MeO | CH$_2$OEt | Ms | Q4 |
| Pr-i | H | MeO | CH$_2$OEt | Ms | Q5 |
| Pr-i | H | MeO | CH$_2$OEt | Ms | Q6 |
| Pr-i | H | MeO | CH$_2$OEt | Ms | Q7 |
| Pr-i | H | MeO | CH$_2$OEt | Ms | Q8 |
| Pr-i | H | MeO | CH$_2$OEt | Ms | Q9 |
| Pr-i | H | MeO | CH$_2$OPr-i | Ms | H |
| Pr-i | H | MeO | CH$_2$OPr-i | Cl | H |
| Pr-i | H | MeO | CH$_2$OPr-i | MeS | H |
| Pr-i | H | MeO | CH$_2$OPr-i | MeSO | H |
| Pr-i | H | MeO | CH$_2$OPr-i | Ms | Q1 |
| Pr-i | H | MeO | CH$_2$OPr-i | Ms | Q2 |
| Pr-i | H | MeO | CH$_2$OPr-i | Ms | Q3 |
| Pr-i | H | MeO | CH$_2$OPr-n | Ms | H |
| Pr-i | H | MeO | CH$_2$OPr-n | Cl | H |
| Pr-i | H | MeO | CH$_2$OPr-n | MeS | H |
| Pr-i | H | MeO | CH$_2$OPr-n | MeSO | H |
| Pr-i | H | MeO | CH$_2$OCH=CH$_2$ | Ms | H |
| Pr-i | H | MeO | CH$_2$OCH=CH$_2$ | Cl | H |
| Pr-i | H | MeO | CH$_2$OCH=CH$_2$ | MeS | H |
| Pr-i | H | MeO | CH$_2$OCH=CH$_2$ | MeSO | H |
| Pr-i | H | MeO | CH$_2$OCH$_2$CH=CH$_2$ | Ms | H |
| Pr-i | H | MeO | CH$_2$OCH$_2$CH=CH$_2$ | Cl | H |
| Pr-i | H | MeO | CH$_2$OCH$_2$CH=CH$_2$ | MeS | H |
| Pr-i | H | MeO | CH$_2$OCH$_2$CH=CH$_2$ | MeSO | H |
| Pr-i | H | MeO | CH$_2$OCH$_2$C≡CH | Ms | H |
| Pr-i | H | MeO | CH$_2$OCH$_2$C≡CH | Cl | H |
| Pr-i | H | MeO | CH$_2$OCH$_2$C≡CH | MeS | H |
| Pr-i | H | MeO | CH$_2$OCH$_2$C≡CH | MeSO | H |
| Pr-i | H | MeO | CH$_2$OCH$_2$CH$_2$Cl | Ms | H |
| Pr-i | H | MeO | CH$_2$OCH$_2$CH$_2$Cl | Cl | H |
| Pr-i | H | MeO | CH$_2$OCH$_2$CH$_2$Cl | MeS | H |
| Pr-i | H | MeO | CH$_2$OCH$_2$CH$_2$Cl | MeSO | H |
| Pr-i | H | MeO | CH$_2$O—Y5 | Ms | H |
| Pr-i | H | MeO | CHMeOH | Ms | H |
| Pr-i | H | MeO | CHMeOMe | Ms | H |
| Pr-i | H | MeO | CHMeOMe | Cl | H |
| Pr-i | H | MeO | CHMeOMe | MeS | H |
| Pr-i | H | MeO | CHMeOMe | MeSO | H |
| Pr-i | H | MeO | CHMeOMe | Ms | Q1 |
| Pr-i | H | MeO | CHMeOMe | Ms | Q2 |
| Pr-i | H | MeO | CHMeOMe | Ms | Q3 |
| Pr-i | H | MeO | CHMeOEt | Ms | H |
| Pr-i | H | MeO | CHMeOEt | Cl | H |
| Pr-i | H | MeO | CHMeOEt | MeS | H |
| Pr-i | H | MeO | CHMeOEt | MeSO | H |
| Pr-i | H | MeO | CHMeOEt | Ms | Q1 |
| Pr-i | H | MeO | CHMeOEt | Ms | Q2 |
| Pr-i | H | MeO | CHMeOEt | Ms | Q3 |
| Pr-i | H | MeO | CHMeOPr-i | Ms | H |
| Pr-i | H | MeO | CHMeOPr-i | Cl | H |
| Pr-i | H | MeO | CHMeOPr-i | MeS | H |
| Pr-i | H | MeO | CHMeOPr-i | MeSO | H |
| Pr-i | H | MeO | CHMeOPr-n | Ms | H |
| Pr-i | H | MeO | CHMeOCH=CH$_2$ | Ms | H |
| Pr-i | H | MeO | CHMeOCH=CH$_2$ | Ms | H |
| Pr-i | H | MeO | CHMeOCH$_2$CH=CH$_2$ | Ms | H |
| Pr-i | H | MeO | CHMeOCH$_2$C≡CH | Ms | H |
| Pr-i | H | MeO | CHMeOCH$_2$CH$_2$Cl | Ms | H |
| Pr-i | H | MeO | CHMeO—Y5 | Ms | H |
| Pr-i | H | MeO | CMe$_2$OH | Ms | H |
| Pr-i | H | MeO | CMe$_2$OMe | Ms | H |
| Pr-i | H | MeO | CMe$_2$OMe | Cl | H |

-continued

| | | | | | |
|---|---|---|---|---|---|
| Pr-i | H | MeO | CMe₂OMe | MeS | H |
| Pr-i | H | MeO | CMe₂OMe | MeSO | H |
| Pr-i | H | MeO | CMe₂OEt | Ms | H |
| Pr-i | H | MeO | CMe₂OEt | Cl | H |
| Pr-i | H | MeO | CMe₂OEt | MeS | H |
| Pr-i | H | MeO | CMe₂OEt | MeSO | H |
| Pr-i | H | MeO | CMe₂OPr-i | Ms | H |
| Pr-i | H | MeO | CH₂CH₂OMe | Ms | H |
| Pr-i | H | MeO | CH₂CH₂OMe | Cl | H |
| Pr-i | H | MeO | CH₂CH₂OMe | MeS | H |
| Pr-i | H | MeO | CH₂CH₂OMe | MeSO | H |
| Pr-i | H | MeO | CH₂CH₂OEt | Ms | H |
| Pr-i | H | MeO | CH₂CH₂OEt | Cl | H |
| Pr-i | H | MeO | CH₂CH₂OEt | MeS | H |
| Pr-i | H | MeO | CH₂CH₂OEt | MeSO | H |
| Pr-i | H | MeO | CH₂CH₂OPr-i | Ms | H |
| Pr-i | H | MeO | CH₂CH₂OPr-i | Cl | H |
| Pr-i | H | MeO | CH₂CH₂OPr-i | MeS | H |
| Pr-i | H | MeO | CH₂CH₂OPr-i | MeSO | H |
| Pr-i | H | MeO | CHEtOH | Ms | H |
| Pr-i | H | MeO | CHEtOMe | Ms | H |
| Pr-i | H | MeO | CHEtOMe | Cl | H |
| Pr-i | H | MeO | CHEtOMe | MeS | H |
| Pr-i | H | MeO | CHEtOMe | MeSO | H |
| Pr-i | H | MeO | CHEtOEt | Ms | H |
| Pr-i | H | MeO | CHEtOPr-i | Ms | H |
| Pr-i | H | MeO | CH₂OCH₂CH₂OMe | Ms | H |
| Pr-i | H | MeO | CH₂OCH₂CH₂OMe | Cl | H |
| Pr-i | H | MeO | CH₂OCH₂CH₂OMe | MeS | H |
| Pr-i | H | MeO | CH₂OCH₂CH₂OMe | MeSO | H |
| Pr-i | H | MeO | CH₂OCH₂CH₂OEt | Ms | H |
| Pr-i | H | MeO | CHMeOCH₂CH₂OMe | Ms | H |
| Pr-i | H | MeO | CH₂O—Y8 | Ms | H |
| Pr-i | H | MeO | CH₂O—Y9 | Ms | H |
| Pr-i | H | MeO | CH₂O—Y10 | Ms | H |
| Pr-i | H | MeO | CHMeO—Y8 | Ms | H |
| Pr-i | H | MeO | CHMeO—Y9 | Ms | H |
| Pr-i | H | MeO | CHMeO—Y10 | Ms | H |
| Pr-i | H | MeO | CH₂O—Y13 | Ms | H |
| Pr-i | H | MeO | CHMeO—Y13 | Ms | H |
| Pr-i | H | MeO | CH₂NHMe | Ms | H |
| Pr-i | H | MeO | CH₂NMe₂ | Ms | H |
| Pr-i | H | MeO | CH₂NEtMe | Ms | H |
| Pr-i | H | MeO | CH₂NEt₂ | Ms | H |
| Pr-i | H | MeO | CH₂—Y14 | Ms | H |
| Pr-i | H | MeO | CHMeNMe₂ | Ms | H |
| Pr-i | H | MeO | CH₂CH₂NMe₂ | Ms | H |
| Pr-i | H | MeO | CH₂OCH₂Ph | Ms | H |
| Pr-i | H | MeO | CHMeOCH₂Ph | Ms | H |
| Pr-i | H | MeO | CH₂OCH₂CO₂Me | Ms | H |
| Pr-i | H | MeO | CH₂OCH₂CO₂Et | Ms | H |
| Pr-i | H | MeO | CH₂OCHMeCO₂Me | Ms | H |
| Pr-i | H | MeO | CH₂CN | Ms | H |
| Pr-i | H | MeO | CHMeCN | Ms | H |
| Pr-i | H | MeO | CH₂SMe | Ms | H |
| Pr-i | H | MeO | CH₂SMe | Cl | H |
| Pr-i | H | MeO | CH₂SMe | MeS | H |
| Pr-i | H | MeO | CH₂SMe | MeSO | H |
| Pr-i | H | MeO | CH₂SEt | Ms | H |
| Pr-i | H | MeO | CH₂SEt | Cl | H |
| Pr-i | H | MeO | CH₂SEt | MeS | H |
| Pr-i | H | MeO | CH₂SEt | MeSO | H |
| Pr-i | H | MeO | CH₂SOMe | Ms | H |
| Pr-i | H | MeO | CH₂SOEt | Ms | H |
| Pr-i | H | MeO | CH₂SO₂Me | Ms | H |
| Pr-i | H | MeO | CH₂SO₂Me | Cl | H |
| Pr-i | H | MeO | CH₂SO₂Me | MeS | H |
| Pr-i | H | MeO | CH₂SO₂Me | MeSO | H |
| Pr-i | H | MeO | CH₂SO₂Et | Ms | H |
| Pr-i | H | MeO | CH₂SO₂Et | Cl | H |
| Pr-i | H | MeO | CH₂SO₂Et | MeS | H |
| Pr-i | H | MeO | CH₂SO₂Et | MeSO | H |
| Pr-i | H | MeO | CHMeSMe | Ms | H |
| Pr-i | H | MeO | CHMeSEt | Ms | H |
| Pr-i | H | MeO | CHMeSO₂Me | Ms | H |
| Pr-i | H | MeO | CHMeSO₂Et | Ms | H |
| Pr-i | H | MeO | CH₂SCH₂CH₂OMe | Ms | H |
| Pr-i | H | MeO | CH₂OCOMe | Ms | H |
| Pr-i | H | MeO | CH₂OCOEt | Ms | H |
| Pr-i | H | MeO | CHMeOCOMe | Ms | H |
| Pr-i | H | MeO | CH₂OSO₂Me | Ms | H |
| Pr-i | H | MeO | CH₂OSO₂Et | Ms | H |
| Pr-i | H | MeO | CHMeOSO₂Me | Ms | H |

-continued

| | | | | | |
|---|---|---|---|---|---|
| Me | Me | Me | CH$_2$OH | Ms | H |
| Me | Me | Me | CH$_2$OMe | Ms | H |
| Me | Me | Me | CH$_2$OMe | Cl | H |
| Me | Me | Me | CH$_2$OMe | MeS | H |
| Me | Me | Me | CH$_2$OMe | MeSO | H |
| Me | Me | Me | CH$_2$OMe | Ms | Q1 |
| Me | Me | Me | CH$_2$OMe | Cl | Q1 |
| Me | Me | Me | CH$_2$OMe | MeS | Q1 |
| Me | Me | Me | CH$_2$OMe | MeSO | Q2 |
| Me | Me | Me | CH$_2$OMe | MeS | Q2 |
| Me | Me | Me | CH$_2$OMe | MeSO | Q2 |
| Me | Me | Me | CH$_2$OMe | Ms | Q3 |
| Me | Me | Me | CH$_2$OMe | MeS | Q3 |
| Me | Me | Me | CH$_2$OMe | MeSO | Q3 |
| Me | Me | Me | CH$_2$OEt | Ms | H |
| Me | Me | Me | CH$_2$OEt | Cl | H |
| Me | Me | Me | CH$_2$OEt | MeS | H |
| Me | Me | Me | CH$_2$OEt | MeSO | H |
| Me | Me | Me | CH$_2$OEt | Ms | Q1 |
| Me | Me | Me | CH$_2$OEt | MeS | Q1 |
| Me | Me | Me | CH$_2$OEt | MeSO | Q1 |
| Me | Me | Me | CH$_2$OEt | Ms | Q2 |
| Me | Me | Me | CH$_2$OEt | MeS | Q2 |
| Me | Me | Me | CH$_2$OEt | MeSO | Q2 |
| Me | Me | Me | CH$_2$OEt | Ms | Q3 |
| Me | Me | Me | CH$_2$OEt | MeS | Q3 |
| Me | Me | Me | CH$_2$OEt | MeSO | Q3 |
| Me | Me | Me | CH$_2$OPr-i | Ms | H |
| Me | Me | Me | CH$_2$OPr-i | Cl | H |
| Me | Me | Me | CH$_2$OPr-i | MeS | H |
| Me | Me | Me | CH$_2$OPr-i | MeSO | H |
| Me | Me | Me | CH$_2$OPr-i | Ms | Q1 |
| Me | Me | Me | CH$_2$OPr-i | Ms | Q2 |
| Me | Me | Me | CH$_2$OPr-i | Ms | Q3 |
| Me | Me | Me | CH$_2$OPr-n | Ms | H |
| Me | Me | Me | CH$_2$OCH=CH$_2$ | Ms | H |
| Me | Me | Me | CH$_2$OCH$_2$CH=CH$_2$ | Ms | H |
| Me | Me | Me | CH$_2$OCH$_2$C≡CH | Ms | H |
| Me | Me | Me | CH$_2$OCH$_2$CH$_2$Cl | Ms | H |
| Me | Me | Me | CH$_2$O—Y5 | Ms | H |
| Me | Me | Me | CHMeOH | Ms | H |
| Me | Me | Me | CHMeOMe | Ms | H |
| Me | Me | Me | CHMeOMe | Cl | H |
| Me | Me | Me | CHMeOMe | MeS | H |
| Me | Me | Me | CHMeOMe | MeSO | H |
| Me | Me | Me | CHMeOMe | Ms | Q1 |
| Me | Me | Me | CHMeOMe | Ms | Q2 |
| Me | Me | Me | CHMeOMe | Ms | Q3 |
| Me | Me | Me | CHMeOEt | Ms | H |
| Me | Me | Me | CHMeOEt | Cl | H |
| Me | Me | Me | CHMeOEt | MeS | H |
| Me | Me | Me | CHMeOEt | MeSO | H |
| Me | Me | Me | CHMeOEt | Ms | Q1 |
| Me | Me | Me | CHMeOEt | Ms | Q2 |
| Me | Me | Me | CHMeOEt | Ms | Q3 |
| Me | Me | Me | CHMeOPr-i | Ms | H |
| Me | Me | Me | CHMeOPr-i | Cl | H |
| Me | Me | Me | CHMeOPr-i | MeS | H |
| Me | Me | Me | CHMeOPr-i | MeSO | H |
| Me | Me | Me | CHMeOPr-n | Ms | H |
| Me | Me | Me | CHMeOCH=CH$_2$ | Ms | H |
| Me | Me | Me | CHMeOCH=CH$_2$ | Ms | H |
| Me | Me | Me | CHMeOCH$_2$CH=CH$_2$ | Ms | H |
| Me | Me | Me | CHMeOCH$_2$C≡CH | Ms | H |
| Me | Me | Me | CHMeOCH$_2$CH$_2$Cl | Ms | H |
| Me | Me | Me | CHMeO—Y5 | Ms | H |
| Me | Me | Me | CMe$_2$OH | Ms | H |
| Me | Me | Me | CMe$_2$OMe | Ms | H |
| Me | Me | Me | CMe$_2$OEt | Ms | H |
| Me | Me | Me | CMe$_2$OPr-i | Ms | H |
| Me | Me | Me | CH$_2$CH$_2$OMe | Ms | H |
| Me | Me | Me | CH$_2$CH$_2$OEt | Ms | H |
| Me | Me | Me | CH$_2$CH$_2$OPr-i | Ms | H |
| Me | Me | Me | CHEtOH | Ms | H |
| Me | Me | Me | CHEtOMe | Ms | H |
| Me | Me | Me | CHEtOMe | Cl | H |
| Me | Me | Me | CHEtOMe | MeS | H |
| Me | Me | Me | CHEtOMe | MeSO | H |
| Me | Me | Me | CHEtOEt | Ms | H |
| Me | Me | Me | CHEtOPr-i | Ms | H |
| Me | Me | Me | CH$_2$OCH$_2$CH$_2$OMe | Ms | H |
| Me | Me | Me | CH$_2$OCH$_2$CH$_2$OMe | Cl | H |
| Me | Me | Me | CH$_2$OCH$_2$CH$_2$OMe | MeS | H |

-continued

| | | | | | |
|---|---|---|---|---|---|
| Me | Me | Me | CH$_2$OCH$_2$CH$_2$OMe | MeSO | H |
| Me | Me | Me | CH$_2$OCH$_2$CH$_2$OEt | Ms | H |
| Me | Me | Me | CHMeOCH$_2$CH$_2$OMe | Ms | H |
| Me | Me | Me | CH$_2$O—Y8 | Ms | H |
| Me | Me | Me | CH$_2$O—Y9 | Ms | H |
| Me | Me | Me | CH$_2$O—Y10 | Ms | H |
| Me | Me | Me | CHMeO—Y8 | Ms | H |
| Me | Me | Me | CHMeO—Y9 | Ms | H |
| Me | Me | Me | CHMeO—Y10 | Ms | H |
| Me | Me | Me | CH$_2$O—Y13 | Ms | H |
| Me | Me | Me | CHMeO—Y13 | Ms | H |
| Me | Me | Me | CH$_2$NMe$_2$ | Ms | H |
| Me | Me | Me | CH$_2$—Y14 | Ms | H |
| Me | Me | Me | CHMeNMe$_2$ | Ms | H |
| Me | Me | Me | CH$_2$CH$_2$NMe$_2$ | Ms | H |
| Me | Me | Me | CH$_2$OCH$_2$Ph | Ms | H |
| Me | Me | Me | CHMeOCH$_2$Ph | Ms | H |
| Me | Me | Me | CH$_2$OCH$_2$CO$_2$Me | Ms | H |
| Me | Me | Me | CH$_2$OCH$_2$CO$_2$Et | Ms | H |
| Me | Me | Me | CH$_2$OCHMeCO$_2$Me | Ms | H |
| Me | Me | Me | CH$_2$CN | Ms | H |
| Me | Me | Me | CHMeCN | Ms | H |
| Me | Me | Me | CH$_2$SMe | Ms | H |
| Me | Me | Me | CH$_2$SMe | Cl | H |
| Me | Me | Me | CH$_2$SMe | MeS | H |
| Me | Me | Me | CH$_2$SMe | MeSO | H |
| Me | Me | Me | CH$_2$SEt | Ms | H |
| Me | Me | Me | CH$_2$SEt | Cl | H |
| Me | Me | Me | CH$_2$SEt | MeS | H |
| Me | Me | Me | CH$_2$SEt | MeSO | H |
| Me | Me | Me | CH$_2$SOMe | Ms | H |
| Me | Me | Me | CH$_2$SOEt | Ms | H |
| Me | Me | Me | CH$_2$SO$_2$Me | Ms | H |
| Me | Me | Me | CH$_2$SO$_2$Me | Cl | H |
| Me | Me | Me | CH$_2$SO$_2$Me | MeS | H |
| Me | Me | Me | CH$_2$SO$_2$Me | MeSO | H |
| Me | Me | Me | CH$_2$SO$_2$Et | Ms | H |
| Me | Me | Me | CH$_2$SO$_2$Et | Cl | H |
| Me | Me | Me | CH$_2$SO$_2$Et | MeS | H |
| Me | Me | Me | CH$_2$SO$_2$Et | MeSO | H |
| Me | Me | Me | CHMeSMe | Ms | H |
| Me | Me | Me | CHMeSEt | Ms | H |
| Me | Me | Me | CHMeSO$_2$Me | Ms | H |
| Me | Me | Me | CHMeSO$_2$Et | Ms | H |
| Me | Me | Me | CH$_2$SCH$_2$CH$_2$OMe | Ms | H |
| Me | Me | Me | CH$_2$OCOMe | Ms | H |
| Me | Me | Me | CH$_2$OCOEt | Ms | H |
| Me | Me | Me | CHMeOCOMe | Ms | H |
| Me | Me | Me | CH$_2$OSO$_2$Me | Ms | H |
| Me | Me | Me | CH$_2$OSO$_2$Et | Ms | H |
| Me | Me | Me | CHMeOSO$_2$Me | Ms | H |
| Et | Me | Me | CH$_2$OH | Ms | H |
| Et | Me | Me | CH$_2$OMe | Ms | H |
| Et | Me | Me | CH$_2$OMe | Cl | H |
| Et | Me | Me | CH$_2$OMe | MeS | H |
| Et | Me | Me | CH$_2$OMe | MeSO | H |
| Et | Me | Me | CH$_2$OMe | Ms | Q1 |
| Et | Me | Me | CH$_2$OMe | Cl | Q1 |
| Et | Me | Me | CH$_2$OMe | MeS | Q1 |
| Et | Me | Me | CH$_2$OMe | MeSO | Q2 |
| Et | Me | Me | CH$_2$OMe | MeS | Q2 |
| Et | Me | Me | CH$_2$OMe | MeSO | Q2 |
| Et | Me | Me | CH$_2$OMe | Ms | Q3 |
| Et | Me | Me | CH$_2$OMe | MeS | Q3 |
| Et | Me | Me | CH$_2$OMe | MeSO | Q3 |
| Et | Me | Me | CH$_2$OEt | Ms | H |
| Et | Me | Me | CH$_2$OEt | Cl | H |
| Et | Me | Me | CH$_2$OEt | MeS | H |
| Et | Me | Me | CH$_2$OEt | MeSO | H |
| Et | Me | Me | CH$_2$OEt | Ms | Q1 |
| Et | Me | Me | CH$_2$OEt | MeS | Q1 |
| Et | Me | Me | CH$_2$OEt | MeSO | Q1 |
| Et | Me | Me | CH$_2$OEt | Ms | Q2 |
| Et | Me | Me | CH$_2$OEt | MeS | Q2 |
| Et | Me | Me | CH$_2$OEt | MeSO | Q2 |
| Et | Me | Me | CH$_2$OEt | Ms | Q3 |
| Et | Me | Me | CH$_2$OEt | MeS | Q3 |
| Et | Me | Me | CH$_2$OEt | MeSO | Q3 |
| Et | Me | Me | CH$_2$OPr-i | Ms | H |
| Et | Me | Me | CH$_2$OPr-i | Cl | H |
| Et | Me | Me | CH$_2$OPr-i | MeS | H |
| Et | Me | Me | CH$_2$OPr-i | MeSO | H |
| Et | Me | Me | CH$_2$OPr-i | Ms | Q1 |

-continued

| | | | | | |
|---|---|---|---|---|---|
| Et | Me | Me | CH$_2$OPr-i | Ms | Q2 |
| Et | Me | Me | CH$_2$OPr-i | Ms | Q3 |
| Et | Me | Me | CH$_2$OPr-n | Ms | H |
| Et | Me | Me | CH$_2$OCH=CH$_2$ | Ms | H |
| Et | Me | Me | CH$_2$OCH$_2$CH=CH$_2$ | Ms | H |
| Et | Me | Me | CH$_2$OCH$_2$C≡CH | Ms | H |
| Et | Me | Me | CH$_2$OCH$_2$CH$_2$Cl | Ms | H |
| Et | Me | Me | CH$_2$O—Y5 | Ms | H |
| Et | Me | Me | CHMeOH | Ms | H |
| Et | Me | Me | CHMeOMe | Ms | H |
| Et | Me | Me | CHMeOMe | Cl | H |
| Et | Me | Me | CHMeOMe | MeS | H |
| Et | Me | Me | CHMeOMe | MeSO | H |
| Et | Me | Me | CHMeOMe | Ms | Q1 |
| Et | Me | Me | CHMeOMe | Ms | Q2 |
| Et | Me | Me | CHMeOMe | Ms | Q3 |
| Et | Me | Me | CHMeOEt | Ms | H |
| Et | Me | Me | CHMeOEt | Cl | H |
| Et | Me | Me | CHMeOEt | MeS | H |
| Et | Me | Me | CHMeOEt | MeSO | H |
| Et | Me | Me | CHMeOEt | Ms | Q1 |
| Et | Me | Me | CHMeOEt | Ms | Q2 |
| Et | Me | Me | CHMeOEt | Ms | Q3 |
| Et | Me | Me | CHMeOPr-i | Ms | H |
| Et | Me | Me | CHMeOPr-i | Cl | H |
| Et | Me | Me | CHMeOPr-i | MeS | H |
| Et | Me | Me | CHMeOPr-i | MeSO | H |
| Et | Me | Me | CHMeOPr-n | Ms | H |
| Et | Me | Me | CHMeOCH=CH$_2$ | Ms | H |
| Et | Me | Me | CHMeOCH=CH$_2$ | Ms | H |
| Et | Me | Me | CHMeOCH$_2$CH=CH$_2$ | Ms | H |
| Et | Me | Me | CHMeOCH$_2$C≡CH | Ms | H |
| Et | Me | Me | CHMeOCH$_2$CH$_2$Cl | Ms | H |
| Et | Me | Me | CHMeO—Y5 | Ms | H |
| Et | Me | Me | CMe$_2$OH | Ms | H |
| Et | Me | Me | CMe$_2$OMe | Ms | H |
| Et | Me | Me | CMe$_2$OEt | Ms | H |
| Et | Me | Me | CMe$_2$OPr-i | Ms | H |
| Et | Me | Me | CH$_2$CH$_2$OMe | Ms | H |
| Et | Me | Me | CH$_2$CH$_2$OEt | Ms | H |
| Et | Me | Me | CH$_2$CH$_2$OPr-i | Ms | H |
| Et | Me | Me | CHEtOH | Ms | H |
| Et | Me | Me | CHEtOMe | Ms | H |
| Et | Me | Me | CHEtOMe | Cl | H |
| Et | Me | Me | CHEtOMe | MeS | H |
| Et | Me | Me | CHEtOMe | MeSO | H |
| Et | Me | Me | CHEtOEt | Ms | H |
| Et | Me | Me | CHEtOPr-i | Ms | H |
| Et | Me | Me | CH$_2$OCH$_2$CH$_2$OMe | Ms | H |
| Et | Me | Me | CH$_2$OCH$_2$CH$_2$OMe | Cl | H |
| Et | Me | Me | CH$_2$OCH$_2$CH$_2$OMe | MeS | H |
| Et | Me | Me | CH$_2$OCH$_2$CH$_2$OMe | MeSO | H |
| Et | Me | Me | CH$_2$OCH$_2$CH$_2$OEt | Ms | H |
| Et | Me | Me | CHMeOCH$_2$CH$_2$OMe | Ms | H |
| Et | Me | Me | CH$_2$O—Y8 | Ms | H |
| Et | Me | Me | CH$_2$O—Y9 | Ms | H |
| Et | Me | Me | CH$_2$O—Y10 | Ms | H |
| Et | Me | Me | CHMeO—Y8 | Ms | H |
| Et | Me | Me | CHMeO—Y9 | Ms | H |
| Et | Me | Me | CHMeO—Y10 | Ms | H |
| Et | Me | Me | CH$_2$O—Y13 | Ms | H |
| Et | Me | Me | CHMeO—Y13 | Ms | H |
| Et | Me | Me | CH$_2$NMe$_2$ | Ms | H |
| Et | Me | Me | CH$_2$—Y14 | Ms | H |
| Et | Me | Me | CHMeNMe$_2$ | Ms | H |
| Et | Me | Me | CH$_2$CH$_2$NMe$_2$ | Ms | H |
| Et | Me | Me | CH$_2$OCH$_2$Ph | Ms | H |
| Et | Me | Me | CHMeOCH$_2$Ph | Ms | H |
| Et | Me | Me | CH$_2$OCH$_2$CO$_2$Me | Ms | H |
| Et | Me | Me | CH$_2$OCH$_2$CO$_2$Et | Ms | H |
| Et | Me | Me | CH$_2$OCHMeCO$_2$Me | Ms | H |
| Et | Me | Me | CH$_2$CN | Ms | H |
| Et | Me | Me | CHMeCN | Ms | H |
| Et | Me | Me | CH$_2$SMe | Ms | H |
| Et | Me | Me | CH$_2$SMe | Cl | H |
| Et | Me | Me | CH$_2$SMe | MeS | H |
| Et | Me | Me | CH$_2$SMe | MeSO | H |
| Et | Me | Me | CH$_2$SEt | Ms | H |
| Et | Me | Me | CH$_2$SEt | Cl | H |
| Et | Me | Me | CH$_2$SEt | MeS | H |
| Et | Me | Me | CH$_2$SEt | MeSO | H |
| Et | Me | Me | CH$_2$SOMe | Ms | H |
| Et | Me | Me | CH$_2$SOEt | Ms | H |

-continued

| | | | | | |
|---|---|---|---|---|---|
| Et | Me | Me | CH₂SO₂Me | Ms | H |
| Et | Me | Me | CH₂SO₂Me | Cl | H |
| Et | Me | Me | CH₂SO₂Me | MeS | H |
| Et | Me | Me | CH₂SO₂Me | MeSO | H |
| Et | Me | Me | CH₂SO₂Et | Ms | H |
| Et | Me | Me | CH₂SO₂Et | Cl | H |
| Et | Me | Me | CH₂SO₂Et | MeS | H |
| Et | Me | Me | CH₂SO₂Et | MeSO | H |
| Et | Me | Me | CHMeSMe | Ms | H |
| Et | Me | Me | CHMeSEt | Ms | H |
| Et | Me | Me | CHMeSO₂Me | Ms | H |
| Et | Me | Me | CHMeSO₂Et | Ms | H |
| Et | Me | Me | CH₂SCH₂CH₂OMe | Ms | H |
| Et | Me | Me | CH₂OCOMe | Ms | H |
| Et | Me | Me | CH₂OCOEt | Ms | H |
| Et | Me | Me | CHMeOCOMe | Ms | H |
| Et | Me | Me | CH₂OSO₂Me | Ms | H |
| Et | Me | Me | CH₂OSO₂Et | Ms | H |
| Et | Me | Me | CHMeOSO₂Me | Ms | H |
| Pr-i | Me | Me | CH₂OH | Ms | H |
| Pr-i | Me | Me | CH₂OMe | Ms | H |
| Pr-i | Me | Me | CH₂OMe | Cl | H |
| Pr-i | Me | Me | CH₂OMe | MeS | H |
| Pr-i | Me | Me | CH₂OMe | MeSO | H |
| Pr-i | Me | Me | CH₂OMe | Ms | Q1 |
| Pr-i | Me | Me | CH₂OMe | Cl | Q1 |
| Pr-i | Me | Me | CH₂OMe | MeS | Q1 |
| Pr-i | Me | Me | CH₂OMe | MeSO | Q2 |
| Pr-i | Me | Me | CH₂OMe | MeS | Q2 |
| Pr-i | Me | Me | CH₂OMe | MeSO | Q2 |
| Pr-i | Me | Me | CH₂OMe | Ms | Q3 |
| Pr-i | Me | Me | CH₂OMe | MeS | Q3 |
| Pr-i | Me | Me | CH₂OMe | MeSO | Q3 |
| Pr-i | Me | Me | CH₂OEt | Ms | H |
| Pr-i | Me | Me | CH₂OEt | Cl | H |
| Pr-i | Me | Me | CH₂OEt | MeS | H |
| Pr-i | Me | Me | CH₂OEt | MeSO | H |
| Pr-i | Me | Me | CH₂OEt | Ms | Q1 |
| Pr-i | Me | Me | CH₂OEt | MeS | Q1 |
| Pr-i | Me | Me | CH₂OEt | MeSO | Q1 |
| Pr-i | Me | Me | CH₂OEt | Ms | Q2 |
| Pr-i | Me | Me | CH₂OEt | MeS | Q2 |
| Pr-i | Me | Me | CH₂OEt | MeSO | Q2 |
| Pr-i | Me | Me | CH₂OEt | Ms | Q3 |
| Pr-i | Me | Me | CH₂OEt | MeS | Q3 |
| Pr-i | Me | Me | CH₂OEt | MeSO | Q3 |
| Pr-i | Me | Me | CH₂OPr-i | Ms | H |
| Pr-i | Me | Me | CH₂OPr-i | Cl | H |
| Pr-i | Me | Me | CH₂OPr-i | MeS | H |
| Pr-i | Me | Me | CH₂OPr-i | MeSO | H |
| Pr-i | Me | Me | CH₂OPr-i | Ms | Q1 |
| Pr-i | Me | Me | CH₂OPr-i | Ms | Q2 |
| Pr-i | Me | Me | CH₂OPr-i | Ms | Q3 |
| Pr-i | Me | Me | CH₂OPr-n | Ms | H |
| Pr-i | Me | Me | CH₂OCH=CH₂ | Ms | H |
| Pr-i | Me | Me | CH₂OCH₂CH=CH₂ | Ms | H |
| Pr-i | Me | Me | CH₂OCH₂C≡CH | Ms | H |
| Pr-i | Me | Me | CH₂OCH₂CH₂Cl | Ms | H |
| Pr-i | Me | Me | CH₂O—Y5 | Ms | H |
| Pr-i | Me | Me | CHMeOH | Ms | H |
| Pr-i | Me | Me | CHMeOMe | Ms | H |
| Pr-i | Me | Me | CHMeOMe | Cl | H |
| Pr-i | Me | Me | CHMeOMe | MeS | H |
| Pr-i | Me | Me | CHMeOMe | MeSO | H |
| Pr-i | Me | Me | CHMeOMe | Ms | Q1 |
| Pr-i | Me | Me | CHMeOMe | Ms | Q2 |
| Pr-i | Me | Me | CHMeOMe | Ms | Q3 |
| Pr-i | Me | Me | CHMeOEt | Ms | H |
| Pr-i | Me | Me | CHMeOEt | Cl | H |
| Pr-i | Me | Me | CHMeOEt | MeS | H |
| Pr-i | Me | Me | CHMeOEt | MeSO | H |
| Pr-i | Me | Me | CHMeOEt | Ms | Q1 |
| Pr-i | Me | Me | CHMeOEt | Ms | Q2 |
| Pr-i | Me | Me | CHMeOEt | Ms | Q3 |
| Pr-i | Me | Me | CHMeOPr-i | Ms | H |
| Pr-i | Me | Me | CHMeOPr-i | Cl | H |
| Pr-i | Me | Me | CHMeOPr-i | MeS | H |
| Pr-i | Me | Me | CHMeOPr-i | MeSO | H |
| Pr-i | Me | Me | CHMeOPr-n | Ms | H |
| Pr-i | Me | Me | CHMeOCH=CH₂ | Ms | H |
| Pr-i | Me | Me | CHMeOCH=CH₂ | Ms | H |
| Pr-i | Me | Me | CHMeOCH₂CH=CH₂ | Ms | H |
| Pr-i | Me | Me | CHMeOCH₂C≡CH | Ms | H |

-continued

| | | | | | |
|---|---|---|---|---|---|
| Pr-i | Me | Me | CHMeOCH$_2$CH$_2$Cl | Ms | H |
| Pr-i | Me | Me | CHMeO—Y5 | Ms | H |
| Pr-i | Me | Me | CMe$_2$OH | Ms | H |
| Pr-i | Me | Me | CMe$_2$OMe | Ms | H |
| Pr-i | Me | Me | CMe$_2$OEt | Ms | H |
| Pr-i | Me | Me | CMe$_2$OPr-i | Ms | H |
| Pr-i | Me | Me | CH$_2$CH$_2$OMe | Ms | H |
| Pr-i | Me | Me | CH$_2$CH$_2$OEt | Ms | H |
| Pr-i | Me | Me | CH$_2$CH$_2$OPr-i | Ms | H |
| Pr-i | Me | Me | CHEtOH | Ms | H |
| Pr-i | Me | Me | CHEtOMe | Ms | H |
| Pr-i | Me | Me | CHEtOMe | Cl | H |
| Pr-i | Me | Me | CHEtOMe | MeS | H |
| Pr-i | Me | Me | CHEtOMe | MeSO | H |
| Pr-i | Me | Me | CHEtOEt | Ms | H |
| Pr-i | Me | Me | CHEtOPr-i | Ms | H |
| Pr-i | Me | Me | CH$_2$OCH$_2$CH$_2$OMe | Ms | H |
| Pr-i | Me | Me | CH$_2$OCH$_2$CH$_2$OMe | Cl | H |
| Pr-i | Me | Me | CH$_2$OCH$_2$CH$_2$OMe | MeS | H |
| Pr-i | Me | Me | CH$_2$OCH$_2$CH$_2$OMe | MeSO | H |
| Pr-i | Me | Me | CH$_2$OCH$_2$CH$_2$OEt | Ms | H |
| Pr-i | Me | Me | CHMeOCH$_2$CH$_2$OMe | Ms | H |
| Pr-i | Me | Me | CH$_2$O—Y8 | Ms | H |
| Pr-i | Me | Me | CH$_2$O—Y9 | Ms | H |
| Pr-i | Me | Me | CH$_2$O—Y10 | Ms | H |
| Pr-i | Me | Me | CHMeO—Y8 | Ms | H |
| Pr-i | Me | Me | CHMeO—Y9 | Ms | H |
| Pr-i | Me | Me | CHMeO—Y10 | Ms | H |
| Pr-i | Me | Me | CH$_2$O—Y13 | Ms | H |
| Pr-i | Me | Me | CHMeO—Y13 | Ms | H |
| Pr-i | Me | Me | CH$_2$NMe$_2$ | Ms | H |
| Pr-i | Me | Me | CH$_2$—Y14 | Ms | H |
| Pr-i | Me | Me | CHMeNMe$_2$ | Ms | H |
| Pr-i | Me | Me | CH$_2$CH$_2$NMe$_2$ | Ms | H |
| Pr-i | Me | Me | CH$_2$OCH$_2$Ph | Ms | H |
| Pr-i | Me | Me | CHMeOCH$_2$Ph | Ms | H |
| Pr-i | Me | Me | CH$_2$OCH$_2$CO$_2$Me | Ms | H |
| Pr-i | Me | Me | CH$_2$OCH$_2$CO$_2$Et | Ms | H |
| Pr-i | Me | Me | CH$_2$OCHMeCO$_2$Me | Ms | H |
| Pr-i | Me | Me | CH$_2$CN | Ms | H |
| Pr-i | Me | Me | CHMeCN | Ms | H |
| Pr-i | Me | Me | CH$_2$SMe | Ms | H |
| Pr-i | Me | Me | CH$_2$SMe | Cl | H |
| Pr-i | Me | Me | CH$_2$SMe | MeS | H |
| Pr-i | Me | Me | CH$_2$SMe | MeSO | H |
| Pr-i | Me | Me | CH$_2$SEt | Ms | H |
| Pr-i | Me | Me | CH$_2$SEt | Cl | H |
| Pr-i | Me | Me | CH$_2$SEt | MeS | H |
| Pr-i | Me | Me | CH$_2$SEt | MeSO | H |
| Pr-i | Me | Me | CH$_2$SOMe | Ms | H |
| Pr-i | Me | Me | CH$_2$SOEt | Ms | H |
| Pr-i | Me | Me | CH$_2$SO$_2$Me | Ms | H |
| Pr-i | Me | Me | CH$_2$SO$_2$Me | Cl | H |
| Pr-i | Me | Me | CH$_2$SO$_2$Me | MeS | H |
| Pr-i | Me | Me | CH$_2$SO$_2$Me | MeSO | H |
| Pr-i | Me | Me | CH$_2$SO$_2$Et | Ms | H |
| Pr-i | Me | Me | CH$_2$SO$_2$Et | Cl | H |
| Pr-i | Me | Me | CH$_2$SO$_2$Et | MeS | H |
| Pr-i | Me | Me | CH$_2$SO$_2$Et | MeSO | H |
| Pr-i | Me | Me | CHMeSMe | Ms | H |
| Pr-i | Me | Me | CHMeSEt | Ms | H |
| Pr-i | Me | Me | CHMeSO$_2$Me | Ms | H |
| Pr-i | Me | Me | CHMeSO$_2$Et | Ms | H |
| Pr-i | Me | Me | CH$_2$SCH$_2$CH$_2$OMe | Ms | H |
| Pr-i | Me | Me | CH$_2$OCOMe | Ms | H |
| Pr-i | Me | Me | CH$_2$OCOEt | Ms | H |
| Pr-i | Me | Me | CHMeOCOMe | Ms | H |
| Pr-i | Me | Me | CH$_2$OSO$_2$Me | Ms | H |
| Pr-i | Me | Me | CH$_2$OSO$_2$Et | Ms | H |
| Pr-i | Me | Me | CHMeOSO$_2$Me | Ms | H |
| Me | Me | Cl | CH$_2$OH | Ms | H |
| Me | Me | Cl | CH$_2$OMe | Ms | H |
| Me | Me | Cl | CH$_2$OMe | Cl | H |
| Me | Me | Cl | CH$_2$OMe | MeS | H |
| Me | Me | Cl | CH$_2$OMe | MeSO | H |
| Me | Me | Cl | CH$_2$OMe | Ms | Q1 |
| Me | Me | Cl | CH$_2$OMe | Cl | Q1 |
| Me | Me | Cl | CH$_2$OMe | MeS | Q1 |
| Me | Me | Cl | CH$_2$OMe | MeSO | Q2 |
| Me | Me | Cl | CH$_2$OMe | MeS | Q2 |

-continued

| | | | | | |
|---|---|---|---|---|---|
| Me | Me | Cl | CH$_2$OMe | MeSO | Q2 |
| Me | Me | Cl | CH$_2$OMe | Ms | Q3 |
| Me | Me | Cl | CH$_2$OMe | MeS | Q3 |
| Me | Me | Cl | CH$_2$OMe | MeSO | Q3 |
| Me | Me | Cl | CH$_2$OEt | Ms | H |
| Me | Me | Cl | CH$_2$OEt | Cl | H |
| Me | Me | Cl | CH$_2$OEt | MeS | H |
| Me | Me | Cl | CH$_2$OEt | MeSO | H |
| Me | Me | Cl | CH$_2$OEt | Ms | Q1 |
| Me | Me | Cl | CH$_2$OEt | MeS | Q1 |
| Me | Me | Cl | CH$_2$OEt | MeSO | Q1 |
| Me | Me | Cl | CH$_2$OEt | Ms | Q2 |
| Me | Me | Cl | CH$_2$OEt | MeS | Q2 |
| Me | Me | Cl | CH$_2$OEt | MeSO | Q2 |
| Me | Me | Cl | CH$_2$OEt | Ms | Q3 |
| Me | Me | Cl | CH$_2$OEt | MeS | Q3 |
| Me | Me | Cl | CH$_2$OEt | MeSO | Q3 |
| Me | Me | Cl | CH$_2$OPr-i | Ms | H |
| Me | Me | Cl | CH$_2$OPr-i | Cl | H |
| Me | Me | Cl | CH$_2$OPr-i | MeS | H |
| Me | Me | Cl | CH$_2$OPr-i | MeSO | H |
| Me | Me | Cl | CH$_2$OPr-i | Ms | Q1 |
| Me | Me | Cl | CH$_2$OPr-i | Ms | Q2 |
| Me | Me | Cl | CH$_2$OPr-i | Ms | Q3 |
| Me | Me | Cl | CH$_2$OPr-n | Ms | H |
| Me | Me | Cl | CH$_2$OCH=CH$_2$ | Ms | H |
| Me | Me | Cl | CH$_2$OCH$_2$CH=CH$_2$ | Ms | H |
| Me | Me | Cl | CH$_2$OCH$_2$C≡CH | Ms | H |
| Me | Me | Cl | CH$_2$OCH$_2$CH$_2$Cl | Ms | H |
| Me | Me | Cl | CH$_2$O—Y5 | Ms | H |
| Me | Me | Cl | CHMeOH | Ms | H |
| Me | Me | Cl | CHMeOMe | Ms | H |
| Me | Me | Cl | CHMeOMe | Cl | H |
| Me | Me | Cl | CHMeOMe | MeS | H |
| Me | Me | Cl | CHMeOMe | MeSO | H |
| Me | Me | Cl | CHMeOMe | Ms | Q1 |
| Me | Me | Cl | CHMeOMe | Ms | Q2 |
| Me | Me | Cl | CHMeOMe | Ms | Q3 |
| Me | Me | Cl | CHMeOEt | Ms | H |
| Me | Me | Cl | CHMeOEt | Cl | H |
| Me | Me | Cl | CHMeOEt | MeS | H |
| Me | Me | Cl | CHMeOEt | MeSO | H |
| Me | Me | Cl | CHMeOEt | Ms | Q1 |
| Me | Me | Cl | CHMeOEt | Ms | Q2 |
| Me | Me | Cl | CHMeOEt | Ms | Q3 |
| Me | Me | Cl | CHMeOPr-i | Ms | H |
| Me | Me | Cl | CHMeOPr-i | Cl | H |
| Me | Me | Cl | CHMeOPr-i | MeS | H |
| Me | Me | Cl | CHMeOPr-i | MeSO | H |
| Me | Me | Cl | CHMeOPr-n | Ms | H |
| Me | Me | Cl | CHMeOCH=CH$_2$ | Ms | H |
| Me | Me | Cl | CHMeOCH=CH$_2$ | Ms | H |
| Me | Me | Cl | CHMeOCH$_2$CH=CH$_2$ | Ms | H |
| Me | Me | Cl | CHMeOCH$_2$C≡CH | Ms | H |
| Me | Me | Cl | CHMeOCH$_2$CH$_2$Cl | Ms | H |
| Me | Me | Cl | CHMeO—Y5 | Ms | H |
| Me | Me | Cl | CMe$_2$OH | Ms | H |
| Me | Me | Cl | CMe$_2$OMe | Ms | H |
| Me | Me | Cl | CMe$_2$OEt | Ms | H |
| Me | Me | Cl | CMe$_2$OPr-i | Ms | H |
| Me | Me | Cl | CH$_2$CH$_2$OMe | Ms | H |
| Me | Me | Cl | CH$_2$CH$_2$OEt | Ms | H |
| Me | Me | Cl | CH$_2$CH$_2$OPr-i | Ms | H |
| Me | Me | Cl | CHEtOH | Ms | H |
| Me | Me | Cl | CHEtOMe | Ms | H |
| Me | Me | Cl | CHEtOMe | Cl | H |
| Me | Me | Cl | CHEtOMe | MeS | H |
| Me | Me | Cl | CHEtOMe | MeSO | H |
| Me | Me | Cl | CHEtOEt | Ms | H |
| Me | Me | Cl | CHEtOPr-i | Ms | H |
| Me | Me | Cl | CH$_2$OCH$_2$CH$_2$OMe | Ms | H |
| Me | Me | Cl | CH$_2$OCH$_2$CH$_2$OMe | Cl | H |
| Me | Me | Cl | CH$_2$OCH$_2$CH$_2$OMe | MeS | H |
| Me | Me | Cl | CH$_2$OCH$_2$CH$_2$OMe | MeSO | H |
| Me | Me | Cl | CH$_2$OCH$_2$CH$_2$OEt | Ms | H |
| Me | Me | Cl | CHMeOCH$_2$CH$_2$OMe | Ms | H |
| Me | Me | Cl | CH$_2$O—Y8 | Ms | H |
| Me | Me | Cl | CH$_2$O—Y9 | Ms | H |
| Me | Me | Cl | CH$_2$O—Y10 | Ms | H |
| Me | Me | Cl | CHMeO—Y8 | Ms | H |
| Me | Me | Cl | CHMeO—Y9 | Ms | H |
| Me | Me | Cl | CHMeO—Y10 | Ms | H |
| Me | Me | Cl | CH$_2$O—Y13 | Ms | H |

-continued

| | | | | | |
|---|---|---|---|---|---|
| Me | Me | Cl | CHMeO—Y13 | Ms | H |
| Me | Me | Cl | CH₂NMe₂ | Ms | H |
| Me | Me | Cl | CH₂—Y14 | Ms | H |
| Me | Me | Cl | CHMeNMe₂ | Ms | H |
| Me | Me | Cl | CH₂CH₂NMe₂ | Ms | H |
| Me | Me | Cl | CH₂OCH₂Ph | Ms | H |
| Me | Me | Cl | CHMeOCH₂Ph | Ms | H |
| Me | Me | Cl | CH₂OCH₂CO₂Me | Ms | H |
| Me | Me | Cl | CH₂OCH₂CO₂Et | Ms | H |
| Me | Me | Cl | CH₂OCHMeCO₂Me | Ms | H |
| Me | Me | Cl | CH₂CN | Ms | H |
| Me | Me | Cl | CHMeCN | Ms | H |
| Me | Me | Cl | CH₂SMe | Ms | H |
| Me | Me | Cl | CH₂SMe | Cl | H |
| Me | Me | Cl | CH₂SMe | MeS | H |
| Me | Me | Cl | CH₂SMe | MeSO | H |
| Me | Me | Cl | CH₂SEt | Ms | H |
| Me | Me | Cl | CH₂SEt | Cl | H |
| Me | Me | Cl | CH₂SEt | MeS | H |
| Me | Me | Cl | CH₂SEt | MeSO | H |
| Me | Me | Cl | CH₂SOMe | Ms | H |
| Me | Me | Cl | CH₂SOEt | Ms | H |
| Me | Me | Cl | CH₂SO₂Me | Ms | H |
| Me | Me | Cl | CH₂SO₂Me | Cl | H |
| Me | Me | Cl | CH₂SO₂Me | MeS | H |
| Me | Me | Cl | CH₂SO₂Me | MeSO | H |
| Me | Me | Cl | CH₂SO₂Et | Ms | H |
| Me | Me | Cl | CH₂SO₂Et | Cl | H |
| Me | Me | Cl | CH₂SO₂Et | MeS | H |
| Me | Me | Cl | CH₂SO₂Et | MeSO | H |
| Me | Me | Cl | CHMeSMe | Ms | H |
| Me | Me | Cl | CHMeSEt | Ms | H |
| Me | Me | Cl | CHMeSO₂Me | Ms | H |
| Me | Me | Cl | CHMeSO₂Et | Ms | H |
| Me | Me | Cl | CH₂SCH₂CH₂OMe | Ms | H |
| Me | Me | Cl | CH₂OCOMe | Ms | H |
| Me | Me | Cl | CH₂OCOEt | Ms | H |
| Me | Me | Cl | CHMeOCOMe | Ms | H |
| Me | Me | Cl | CH₂OSO₂Me | Ms | H |
| Me | Me | Cl | CH₂OSO₂Et | Ms | H |
| Me | Me | Cl | CHMeOSO₂Me | Ms | H |
| Et | Me | Cl | CH₂OH | Ms | H |
| Et | Me | Cl | CH₂OMe | Ms | H |
| Et | Me | Cl | CH₂OMe | Cl | H |
| Et | Me | Cl | CH₂OMe | MeS | H |
| Et | Me | Cl | CH₂OMe | MeSO | H |
| Et | Me | Cl | CH₂OMe | Ms | Q1 |
| Et | Me | Cl | CH₂OMe | Cl | Q1 |
| Et | Me | Cl | CH₂OMe | MeS | Q1 |
| Et | Me | Cl | CH₂OMe | MeSO | Q2 |
| Et | Me | Cl | CH₂OMe | MeS | Q2 |
| Et | Me | Cl | CH₂OMe | MeSO | Q2 |
| Et | Me | Cl | CH₂OMe | Ms | Q3 |
| Et | Me | Cl | CH₂OMe | MeS | Q3 |
| Et | Me | Cl | CH₂OMe | MeSO | Q3 |
| Et | Me | Cl | CH₂OEt | Ms | H |
| Et | Me | Cl | CH₂OEt | Cl | H |
| Et | Me | Cl | CH₂OEt | MeS | H |
| Et | Me | Cl | CH₂OEt | MeSO | H |
| Et | Me | Cl | CH₂OEt | Ms | Q1 |
| Et | Me | Cl | CH₂OEt | MeS | Q1 |
| Et | Me | Cl | CH₂OEt | MeSO | Q1 |
| Et | Me | Cl | CH₂OEt | Ms | Q2 |
| Et | Me | Cl | CH₂OEt | MeS | Q2 |
| Et | Me | Cl | CH₂OEt | MeSO | Q2 |
| Et | Me | Cl | CH₂OEt | Ms | Q3 |
| Et | Me | Cl | CH₂OEt | MeS | Q3 |
| Et | Me | Cl | CH₂OEt | MeSO | Q3 |
| Et | Me | Cl | CH₂OPr-i | Ms | H |
| Et | Me | Cl | CH₂OPr-i | Cl | H |
| Et | Me | Cl | CH₂OPr-i | MeS | H |
| Et | Me | Cl | CH₂OPr-i | MeSO | H |
| Et | Me | Cl | CH₂OPr-i | Ms | Q1 |
| Et | Me | Cl | CH₂OPr-i | Ms | Q2 |
| Et | Me | Cl | CH₂OPr-i | Ms | Q3 |
| Et | Me | Cl | CH₂OPr-n | Ms | H |
| Et | Me | Cl | CH₂OCH=CH₂ | Ms | H |
| Et | Me | Cl | CH₂OCH₂CH=CH₂ | Ms | H |
| Et | Me | Cl | CH₂OCH₂C≡CH | Ms | H |
| Et | Me | Cl | CH₂OCH₂CH₂Cl | Ms | H |
| Et | Me | Cl | CH₂O—Y5 | Ms | H |
| Et | Me | Cl | CHMeOH | Ms | H |
| Et | Me | Cl | CHMeOMe | Ms | H |

-continued

| | | | | | |
|---|---|---|---|---|---|
| Et | Me | Cl | CHMeOMe | Cl | H |
| Et | Me | Cl | CHMeOMe | MeS | H |
| Et | Me | Cl | CHMeOMe | MeSO | H |
| Et | Me | Cl | CHMeOMe | Ms | Q1 |
| Et | Me | Cl | CHMeOMe | Ms | Q2 |
| Et | Me | Cl | CHMeOMe | Ms | Q3 |
| Et | Me | Cl | CHMeOEt | Ms | H |
| Et | Me | Cl | CHMeOEt | Cl | H |
| Et | Me | Cl | CHMeOEt | MeS | H |
| Et | Me | Cl | CHMeOEt | MeSO | H |
| Et | Me | Cl | CHMeOEt | Ms | Q1 |
| Et | Me | Cl | CHMeOEt | Ms | Q2 |
| Et | Me | Cl | CHMeOEt | Ms | Q3 |
| Et | Me | Cl | CHMeOPr-i | Ms | H |
| Et | Me | Cl | CHMeOPr-i | Cl | H |
| Et | Me | Cl | CHMeOPr-i | MeS | H |
| Et | Me | Cl | CHMeOPr-i | MeSO | H |
| Et | Me | Cl | CHMeOPr-n | Ms | H |
| Et | Me | Cl | CHMeOCH=CH$_2$ | Ms | H |
| Et | Me | Cl | CHMeOCH=CH$_2$ | Ms | H |
| Et | Me | Cl | CHMeOCH$_2$CH=CH$_2$ | Ms | H |
| Et | Me | Cl | CHMeOCH$_2$C≡CH | Ms | H |
| Et | Me | Cl | CHMeOCH$_2$CH$_2$Cl | Ms | H |
| Et | Me | Cl | CHMeO—Y5 | Ms | H |
| Et | Me | Cl | CMe$_2$OH | Ms | H |
| Et | Me | Cl | CMe$_2$OMe | Ms | H |
| Et | Me | Cl | CMe$_2$OEt | Ms | H |
| Et | Me | Cl | CMe$_2$OPr-i | Ms | H |
| Et | Me | Cl | CH$_2$CH$_2$OMe | Ms | H |
| Et | Me | Cl | CH$_2$CH$_2$OEt | Ms | H |
| Et | Me | Cl | CH$_2$CH$_2$OPr-i | Ms | H |
| Et | Me | Cl | CHEtOH | Ms | H |
| Et | Me | Cl | CHEtOMe | Ms | H |
| Et | Me | Cl | CHEtOMe | Cl | H |
| Et | Me | Cl | CHEtOMe | MeS | H |
| Et | Me | Cl | CHEtOMe | MeSO | H |
| Et | Me | Cl | CHEtOEt | Ms | H |
| Et | Me | Cl | CHEtOPr-i | Ms | H |
| Et | Me | Cl | CH$_2$OCH$_2$CH$_2$OMe | Ms | H |
| Et | Me | Cl | CH$_2$OCH$_2$CH$_2$OMe | Cl | H |
| Et | Me | Cl | CH$_2$OCH$_2$CH$_2$OMe | MeS | H |
| Et | Me | Cl | CH$_2$OCH$_2$CH$_2$OMe | MeSO | H |
| Et | Me | Cl | CH$_2$OCH$_2$CH$_2$OEt | Ms | H |
| Et | Me | Cl | CHMeOCH$_2$CH$_2$OMe | Ms | H |
| Et | Me | Cl | CH$_2$O—Y8 | Ms | H |
| Et | Me | Cl | CH$_2$O—Y9 | Ms | H |
| Et | Me | Cl | CH$_2$O—Y10 | Ms | H |
| Et | Me | Cl | CHMeO—Y8 | Ms | H |
| Et | Me | Cl | CHMeO—Y9 | Ms | H |
| Et | Me | Cl | CHMeO—Y10 | Ms | H |
| Et | Me | Cl | CH$_2$O—Y13 | Ms | H |
| Et | Me | Cl | CHMeO—Y13 | Ms | H |
| Et | Me | Cl | CH$_2$NMe$_2$ | Ms | H |
| Et | Me | Cl | CH$_2$—Y14 | Ms | H |
| Et | Me | Cl | CHMeNMe$_2$ | Ms | H |
| Et | Me | Cl | CH$_2$CH$_2$NMe$_2$ | Ms | H |
| Et | Me | Cl | CH$_2$OCH$_2$Ph | Ms | H |
| Et | Me | Cl | CHMeOCH$_2$Ph | Ms | H |
| Et | Me | Cl | CH$_2$OCH$_2$CO$_2$Me | Ms | H |
| Et | Me | Cl | CH$_2$OCH$_2$CO$_2$Et | Ms | H |
| Et | Me | Cl | CH$_2$OCHMeCO$_2$Me | Ms | H |
| Et | Me | Cl | CH$_2$CN | Ms | H |
| Et | Me | Cl | CHMeCN | Ms | H |
| Et | Me | Cl | CH$_2$SMe | Ms | H |
| Et | Me | Cl | CH$_2$SMe | Cl | H |
| Et | Me | Cl | CH$_2$SMe | MeS | H |
| Et | Me | Cl | CH$_2$SMe | MeSO | H |
| Et | Me | Cl | CH$_2$SEt | Ms | H |
| Et | Me | Cl | CH$_2$SEt | Cl | H |
| Et | Me | Cl | CH$_2$SEt | MeS | H |
| Et | Me | Cl | CH$_2$SEt | MeSO | H |
| Et | Me | Cl | CH$_2$SOMe | Ms | H |
| Et | Me | Cl | CH$_2$SOEt | Ms | H |
| Et | Me | Cl | CH$_2$SO$_2$Me | Ms | H |
| Et | Me | Cl | CH$_2$SO$_2$Me | Cl | H |
| Et | Me | Cl | CH$_2$SO$_2$Me | MeS | H |
| Et | Me | Cl | CH$_2$SO$_2$Me | MeSO | H |
| Et | Me | Cl | CH$_2$SO$_2$Et | Ms | H |
| Et | Me | Cl | CH$_2$SO$_2$Et | Cl | H |
| Et | Me | Cl | CH$_2$SO$_2$Et | MeS | H |
| Et | Me | Cl | CH$_2$SO$_2$Et | MeSO | H |
| Et | Me | Cl | CHMeSMe | Ms | H |
| Et | Me | Cl | CHMeSEt | Ms | H |

-continued

| | | | | | |
|---|---|---|---|---|---|
| Et | Me | Cl | CHMeSO₂Me | Ms | H |
| Et | Me | Cl | CHMeSO₂Et | Ms | H |
| Et | Me | Cl | CH₂SCH₂CH₂OMe | Ms | H |
| Et | Me | Cl | CH₂OCOMe | Ms | H |
| Et | Me | Cl | CH₂OCOEt | Ms | H |
| Et | Me | Cl | CHMeOCOMe | Ms | H |
| Et | Me | Cl | CH₂OSO₂Me | Ms | H |
| Et | Me | Cl | CH₂OSO₂Et | Ms | H |
| Et | Me | Cl | CHMeOSO₂Me | Ms | H |
| Pr-i | Me | Cl | CH₂OH | Ms | H |
| Pr-i | Me | Cl | CH₂OMe | Ms | H |
| Pr-i | Me | Cl | CH₂OMe | Cl | H |
| Pr-i | Me | Cl | CH₂OMe | MeS | H |
| Pr-i | Me | Cl | CH₂OMe | MeSO | H |
| Pr-i | Me | Cl | CH₂OMe | Ms | Q1 |
| Pr-i | Me | Cl | CH₂OMe | Cl | Q1 |
| Pr-i | Me | Cl | CH₂OMe | MeS | Q1 |
| Pr-i | Me | Cl | CH₂OMe | MeSO | Q2 |
| Pr-i | Me | Cl | CH₂OMe | MeS | Q2 |
| Pr-i | Me | Cl | CH₂OMe | MeSO | Q2 |
| Pr-i | Me | Cl | CH₂OMe | Ms | Q3 |
| Pr-i | Me | Cl | CH₂OMe | MeS | Q3 |
| Pr-i | Me | Cl | CH₂OMe | MeSO | Q3 |
| Pr-i | Me | Cl | CH₂OEt | Ms | H |
| Pr-i | Me | Cl | CH₂OEt | Cl | H |
| Pr-i | Me | Cl | CH₂OEt | MeS | H |
| Pr-i | Me | Cl | CH₂OEt | MeSO | H |
| Pr-i | Me | Cl | CH₂OEt | Ms | Q1 |
| Pr-i | Me | Cl | CH₂OEt | MeS | Q1 |
| Pr-i | Me | Cl | CH₂OEt | MeSO | Q1 |
| Pr-i | Me | Cl | CH₂OEt | Ms | Q2 |
| Pr-i | Me | Cl | CH₂OEt | MeS | Q2 |
| Pr-i | Me | Cl | CH₂OEt | MeSO | Q2 |
| Pr-i | Me | Cl | CH₂OEt | Ms | Q3 |
| Pr-i | Me | Cl | CH₂OEt | MeS | Q3 |
| Pr-i | Me | Cl | CH₂OEt | MeSO | Q3 |
| Pr-i | Me | Cl | CH₂OPr-i | Ms | H |
| Pr-i | Me | Cl | CH₂OPr-i | Cl | H |
| Pr-i | Me | Cl | CH₂OPr-i | MeS | H |
| Pr-i | Me | Cl | CH₂OPr-i | MeSO | H |
| Pr-i | Me | Cl | CH₂OPr-i | Ms | Q1 |
| Pr-i | Me | Cl | CH₂OPr-i | Ms | Q2 |
| Pr-i | Me | Cl | CH₂OPr-i | Ms | Q3 |
| Pr-i | Me | Cl | CH₂OPr-n | Ms | H |
| Pr-i | Me | Cl | CH₂OCH=CH₂ | Ms | H |
| Pr-i | Me | Cl | CH₂OCH₂CH=CH₂ | Ms | H |
| Pr-i | Me | Cl | CH₂OCH₂C≡CH | Ms | H |
| Pr-i | Me | Cl | CH₂OCH₂CH₂Cl | Ms | H |
| Pr-i | Me | Cl | CH₂O—Y5 | Ms | H |
| Pr-i | Me | Cl | CHMeOH | Ms | H |
| Pr-i | Me | Cl | CHMeOMe | Ms | H |
| Pr-i | Me | Cl | CHMeOMe | Cl | H |
| Pr-i | Me | Cl | CHMeOMe | MeS | H |
| Pr-i | Me | Cl | CHMeOMe | MeSO | H |
| Pr-i | Me | Cl | CHMeOMe | Ms | Q1 |
| Pr-i | Me | Cl | CHMeOMe | Ms | Q2 |
| Pr-i | Me | Cl | CHMeOMe | Ms | Q3 |
| Pr-i | Me | Cl | CHMeOEt | Ms | H |
| Pr-i | Me | Cl | CHMeOEt | Cl | H |
| Pr-i | Me | Cl | CHMeOEt | MeS | H |
| Pr-i | Me | Cl | CHMeOEt | MeSO | H |
| Pr-i | Me | Cl | CHMeOEt | Ms | Q1 |
| Pr-i | Me | Cl | CHMeOEt | Ms | Q2 |
| Pr-i | Me | Cl | CHMeOEt | Ms | Q3 |
| Pr-i | Me | Cl | CHMeOPr-i | Ms | H |
| Pr-i | Me | Cl | CHMeOPr-i | Cl | H |
| Pr-i | Me | Cl | CHMeOPr-i | MeS | H |
| Pr-i | Me | Cl | CHMeOPr-i | MeSO | H |
| Pr-i | Me | Cl | CHMeOPr-n | Ms | H |
| Pr-i | Me | Cl | CHMeOCH=CH₂ | Ms | H |
| Pr-i | Me | Cl | CHMeOCH=CH₂ | Ms | H |
| Pr-i | Me | Cl | CHMeOCH₂CH=CH₂ | Ms | H |
| Pr-i | Me | Cl | CHMeOCH₂C≡CH | Ms | H |
| Pr-i | Me | Cl | CHMeOCH₂CH₂Cl | Ms | H |
| Pr-i | Me | Cl | CHMeO—Y5 | Ms | H |
| Pr-i | Me | Cl | CMe₂OH | Ms | H |
| Pr-i | Me | Cl | CMe₂OMe | Ms | H |
| Pr-i | Me | Cl | CMe₂OEt | Ms | H |
| Pr-i | Me | Cl | CMe₂OPr-i | Ms | H |
| Pr-i | Me | Cl | CH₂CH₂OMe | Ms | H |
| Pr-i | Me | Cl | CH₂CH₂OEt | Ms | H |
| Pr-i | Me | Cl | CH₂CH₂OPr-i | Ms | H |
| Pr-i | Me | Cl | CHEtOH | Ms | H |

-continued

| | | | | | |
|---|---|---|---|---|---|
| Pr-i | Me | Cl | CHEtOMe | Ms | H |
| Pr-i | Me | Cl | CHEtOMe | Cl | H |
| Pr-i | Me | Cl | CHEtOMe | MeS | H |
| Pr-i | Me | Cl | CHEtOMe | MeSO | H |
| Pr-i | Me | Cl | CHEtOEt | Ms | H |
| Pr-i | Me | Cl | CHEtOPr-i | Ms | H |
| Pr-i | Me | Cl | CH$_2$OCH$_2$CH$_2$OMe | Ms | H |
| Pr-i | Me | Cl | CH$_2$OCH$_2$CH$_2$OMe | Cl | H |
| Pr-i | Me | Cl | CH$_2$OCH$_2$CH$_2$OMe | MeS | H |
| Pr-i | Me | Cl | CH$_2$OCH$_2$CH$_2$OMe | MeSO | H |
| Pr-i | Me | Cl | CH$_2$OCH$_2$CH$_2$OEt | Ms | H |
| Pr-i | Me | Cl | CHMeOCH$_2$CH$_2$OMe | Ms | H |
| Pr-i | Me | Cl | CH$_2$O—Y8 | Ms | H |
| Pr-i | Me | Cl | CH$_2$O—Y9 | Ms | H |
| Pr-i | Me | Cl | CH$_2$O—Y10 | Ms | H |
| Pr-i | Me | Cl | CHMeO—Y8 | Ms | H |
| Pr-i | Me | Cl | CHMeO—Y9 | Ms | H |
| Pr-i | Me | Cl | CHMeO—Y10 | Ms | H |
| Pr-i | Me | Cl | CH$_2$O—Y13 | Ms | H |
| Pr-i | Me | Cl | CHMeO—Y13 | Ms | H |
| Pr-i | Me | Cl | CH$_2$NMe$_2$ | Ms | H |
| Pr-i | Me | Cl | CH$_2$—Y14 | Ms | H |
| Pr-i | Me | Cl | CHMeNMe$_2$ | Ms | H |
| Pr-i | Me | Cl | CH$_2$CH$_2$NMe$_2$ | Ms | H |
| Pr-i | Me | Cl | CH$_2$OCH$_2$Ph | Ms | H |
| Pr-i | Me | Cl | CHMeOCH$_2$Ph | Ms | H |
| Pr-i | Me | Cl | CH$_2$OCH$_2$CO$_2$Me | Ms | H |
| Pr-i | Me | Cl | CH$_2$OCH$_2$CO$_2$Et | Ms | H |
| Pr-i | Me | Cl | CH$_2$OCHMeCO$_2$Me | Ms | H |
| Pr-i | Me | Cl | CH$_2$CN | Ms | H |
| Pr-i | Me | Cl | CHMeCN | Ms | H |
| Pr-i | Me | Cl | CH$_2$SMe | Ms | H |
| Pr-i | Me | Cl | CH$_2$SMe | Cl | H |
| Pr-i | Me | Cl | CH$_2$SMe | MeS | H |
| Pr-i | Me | Cl | CH$_2$SMe | MeSO | H |
| Pr-i | Me | Cl | CH$_2$SEt | Ms | H |
| Pr-i | Me | Cl | CH$_2$SEt | Cl | H |
| Pr-i | Me | Cl | CH$_2$SEt | MeS | H |
| Pr-i | Me | Cl | CH$_2$SEt | MeSO | H |
| Pr-i | Me | Cl | CH$_2$SOMe | Ms | H |
| Pr-i | Me | Cl | CH$_2$SOEt | Ms | H |
| Pr-i | Me | Cl | CH$_2$SO$_2$Me | Ms | H |
| Pr-i | Me | Cl | CH$_2$SO$_2$Me | Cl | H |
| Pr-i | Me | Cl | CH$_2$SO$_2$Me | MeS | H |
| Pr-i | Me | Cl | CH$_2$SO$_2$Me | MeSO | H |
| Pr-i | Me | Cl | CH$_2$SO$_2$Et | Ms | H |
| Pr-i | Me | Cl | CH$_2$SO$_2$Et | Cl | H |
| Pr-i | Me | Cl | CH$_2$SO$_2$Et | MeS | H |
| Pr-i | Me | Cl | CH$_2$SO$_2$Et | MeSO | H |
| Pr-i | Me | Cl | CHMeSMe | Ms | H |
| Pr-i | Me | Cl | CHMeSEt | Ms | H |
| Pr-i | Me | Cl | CHMeSO$_2$Me | Ms | H |
| Pr-i | Me | Cl | CHMeSO$_2$Et | Ms | H |
| Pr-i | Me | Cl | CH$_2$SCH$_2$CH$_2$OMe | Ms | H |
| Pr-i | Me | Cl | CH$_2$OCOMe | Ms | H |
| Pr-i | Me | Cl | CH$_2$OCOEt | Ms | H |
| Pr-i | Me | Cl | CHMeOCOMe | Ms | H |
| Pr-i | Me | Cl | CH$_2$OSO$_2$Me | Ms | H |
| Pr-i | Me | Cl | CH$_2$OSO$_2$Et | Ms | H |
| Pr-i | Me | Cl | CHMeOSO$_2$Me | Ms | H |
| Me | Me | MeO | CH$_2$OH | Ms | H |
| Me | Me | MeO | CH$_2$OMe | Ms | H |
| Me | Me | MeO | CH$_2$OMe | Cl | H |
| Me | Me | MeO | CH$_2$OMe | MeS | H |
| Me | Me | MeO | CH$_2$OMe | MeSO | H |
| Me | Me | MeO | CH$_2$OMe | Ms | Q1 |
| Me | Me | MeO | CH$_2$OMe | Cl | Q1 |
| Me | Me | MeO | CH$_2$OMe | MeS | Q1 |
| Me | Me | MeO | CH$_2$OMe | MeSO | Q2 |
| Me | Me | MeO | CH$_2$OMe | MeS | Q2 |
| Me | Me | MeO | CH$_2$OMe | MeSO | Q2 |
| Me | Me | MeO | CH$_2$OMe | Ms | Q3 |
| Me | Me | MeO | CH$_2$OMe | MeS | Q3 |
| Me | Me | MeO | CH$_2$OMe | MeSO | Q3 |
| Me | Me | MeO | CH$_2$OEt | Ms | H |
| Me | Me | MeO | CH$_2$OEt | Cl | H |
| Me | Me | MeO | CH$_2$OEt | MeS | H |
| Me | Me | MeO | CH$_2$OEt | MeSO | H |
| Me | Me | MeO | CH$_2$OEt | Ms | Q1 |
| Me | Me | MeO | CH$_2$OEt | MeS | Q1 |
| Me | Me | MeO | CH$_2$OEt | MeSO | Q1 |
| Me | Me | MeO | CH$_2$OEt | Ms | Q2 |
| Me | Me | MeO | CH$_2$OEt | MeS | Q2 |

-continued

| | | | | | |
|---|---|---|---|---|---|
| Me | Me | MeO | CH$_2$OEt | MeSO | Q2 |
| Me | Me | MeO | CH$_2$OEt | Ms | Q3 |
| Me | Me | MeO | CH$_2$OEt | MeS | Q3 |
| Me | Me | MeO | CH$_2$OEt | MeSO | Q3 |
| Me | Me | MeO | CH$_2$OPr-i | Ms | H |
| Me | Me | MeO | CH$_2$OPr-i | Cl | H |
| Me | Me | MeO | CH$_2$OPr-i | MeS | H |
| Me | Me | MeO | CH$_2$OPr-i | MeSO | H |
| Me | Me | MeO | CH$_2$OPr-i | Ms | Q1 |
| Me | Me | MeO | CH$_2$OPr-i | Ms | Q2 |
| Me | Me | MeO | CH$_2$OPr-i | Ms | Q3 |
| Me | Me | MeO | CH$_2$OPr-n | Ms | H |
| Me | Me | MeO | CH$_2$OCH=CH$_2$ | Ms | H |
| Me | Me | MeO | CH$_2$OCH$_2$CH=CH$_2$ | Ms | H |
| Me | Me | MeO | CH$_2$OCH$_2$C≡CH | Ms | H |
| Me | Me | MeO | CH$_2$OCH$_2$CH$_2$Cl | Ms | H |
| Me | Me | MeO | CH$_2$O—Y5 | Ms | H |
| Me | Me | MeO | CHMeOH | Ms | H |
| Me | Me | MeO | CHMeOMe | Ms | H |
| Me | Me | MeO | CHMeOMe | Cl | H |
| Me | Me | MeO | CHMeOMe | MeS | H |
| Me | Me | MeO | CHMeOMe | MeSO | H |
| Me | Me | MeO | CHMeOMe | Ms | Q1 |
| Me | Me | MeO | CHMeOMe | Ms | Q2 |
| Me | Me | MeO | CHMeOMe | Ms | Q3 |
| Me | Me | MeO | CHMeOEt | Ms | H |
| Me | Me | MeO | CHMeOEt | Cl | H |
| Me | Me | MeO | CHMeOEt | MeS | H |
| Me | Me | MeO | CHMeOEt | MeSO | H |
| Me | Me | MeO | CHMeOEt | Ms | Q1 |
| Me | Me | MeO | CHMeOEt | Ms | Q2 |
| Me | Me | MeO | CHMeOEt | Ms | Q3 |
| Me | Me | MeO | CHMeOPr-i | Ms | H |
| Me | Me | MeO | CHMeOPr-i | Cl | H |
| Me | Me | MeO | CHMeOPr-i | MeS | H |
| Me | Me | MeO | CHMeOPr-i | MeSO | H |
| Me | Me | MeO | CHMeOPr-n | Ms | H |
| Me | Me | MeO | CHMeOCH=CH$_2$ | Ms | H |
| Me | Me | MeO | CHMeOCH=CH$_2$ | Ms | H |
| Me | Me | MeO | CHMeOCH$_2$CH=CH$_2$ | Ms | H |
| Me | Me | MeO | CHMeOCH$_2$C≡CH | Ms | H |
| Me | Me | MeO | CHMeOCH$_2$CH$_2$Cl | Ms | H |
| Me | Me | MeO | CHMeO—Y5 | Ms | H |
| Me | Me | MeO | CMe$_2$OH | Ms | H |
| Me | Me | MeO | CMe$_2$OMe | Ms | H |
| Me | Me | MeO | CMe$_2$OEt | Ms | H |
| Me | Me | MeO | CMe$_2$OPr-i | Ms | H |
| Me | Me | MeO | CH$_2$CH$_2$OMe | Ms | H |
| Me | Me | MeO | CH$_2$CH$_2$OEt | Ms | H |
| Me | Me | MeO | CH$_2$CH$_2$OPr-i | Ms | H |
| Me | Me | MeO | CHEtOH | Ms | H |
| Me | Me | MeO | CHEtOMe | Ms | H |
| Me | Me | MeO | CHEtOMe | Cl | H |
| Me | Me | MeO | CHEtOMe | MeS | H |
| Me | Me | MeO | CHEtOMe | MeSO | H |
| Me | Me | MeO | CHEtOEt | Ms | H |
| Me | Me | MeO | CHEtOPr-i | Ms | H |
| Me | Me | MeO | CH$_2$OCH$_2$CH$_2$OMe | Ms | H |
| Me | Me | MeO | CH$_2$OCH$_2$CH$_2$OMe | Cl | H |
| Me | Me | MeO | CH$_2$OCH$_2$CH$_2$OMe | MeS | H |
| Me | Me | MeO | CH$_2$OCH$_2$CH$_2$OMe | MeSO | H |
| Me | Me | MeO | CH$_2$OCH$_2$CH$_2$OEt | Ms | H |
| Me | Me | MeO | CHMeOCH$_2$CH$_2$OMe | Ms | H |
| Me | Me | MeO | CH$_2$O—Y8 | Ms | H |
| Me | Me | MeO | CH$_2$O—Y9 | Ms | H |
| Me | Me | MeO | CH$_2$O—Y10 | Ms | H |
| Me | Me | MeO | CHMeO—Y8 | Ms | H |
| Me | Me | MeO | CHMeO—Y9 | Ms | H |
| Me | Me | MeO | CHMeO—Y10 | Ms | H |
| Me | Me | MeO | CH$_2$O—Y13 | Ms | H |
| Me | Me | MeO | CHMeO—Y13 | Ms | H |
| Me | Me | MeO | CH$_2$NMe$_2$ | Ms | H |
| Me | Me | MeO | CH$_2$—Y14 | Ms | H |
| Me | Me | MeO | CHMeNMe$_2$ | Ms | H |
| Me | Me | MeO | CH$_2$CH$_2$NMe$_2$ | Ms | H |
| Me | Me | MeO | CH$_2$OCH$_2$Ph | Ms | H |
| Me | Me | MeO | CHMeOCH$_2$Ph | Ms | H |
| Me | Me | MeO | CH$_2$OCH$_2$CO$_2$Me | Ms | H |
| Me | Me | MeO | CH$_2$OCH$_2$CO$_2$Et | Ms | H |
| Me | Me | MeO | CH$_2$OCHMeCO$_2$Me | Ms | H |
| Me | Me | MeO | CH$_2$CN | Ms | H |
| Me | Me | MeO | CHMeCN | Ms | H |
| Me | Me | MeO | CH$_2$SMe | Ms | H |

-continued

| | | | | | |
|---|---|---|---|---|---|
| Me | Me | MeO | CH$_2$SMe | Cl | H |
| Me | Me | MeO | CH$_2$SMe | MeS | H |
| Me | Me | MeO | CH$_2$SMe | MeSO | H |
| Me | Me | MeO | CH$_2$SEt | Ms | H |
| Me | Me | MeO | CH$_2$SEt | Cl | H |
| Me | Me | MeO | CH$_2$SEt | MeS | H |
| Me | Me | MeO | CH$_2$SEt | MeSO | H |
| Me | Me | MeO | CH$_2$SOMe | Ms | H |
| Me | Me | MeO | CH$_2$SOEt | Ms | H |
| Me | Me | MeO | CH$_2$SO$_2$Me | Ms | H |
| Me | Me | MeO | CH$_2$SO$_2$Me | Cl | H |
| Me | Me | MeO | CH$_2$SO$_2$Me | MeS | H |
| Me | Me | MeO | CH$_2$SO$_2$Me | MeSO | H |
| Me | Me | MeO | CH$_2$SO$_2$Et | Ms | H |
| Me | Me | MeO | CH$_2$SO$_2$Et | Cl | H |
| Me | Me | MeO | CH$_2$SO$_2$Et | MeS | H |
| Me | Me | MeO | CH$_2$SO$_2$Et | MeSO | H |
| Me | Me | MeO | CHMeSMe | Ms | H |
| Me | Me | MeO | CHMeSEt | Ms | H |
| Me | Me | MeO | CHMeSO$_2$Me | Ms | H |
| Me | Me | MeO | CHMeSO$_2$Et | Ms | H |
| Me | Me | MeO | CH$_2$SCH$_2$CH$_2$OMe | Ms | H |
| Me | Me | MeO | CH$_2$OCOMe | Ms | H |
| Me | Me | MeO | CH$_2$OCOEt | Ms | H |
| Me | Me | MeO | CHMeOCOMe | Ms | H |
| Me | Me | MeO | CH$_2$OSO$_2$Me | Ms | H |
| Me | Me | MeO | CH$_2$OSO$_2$Et | Ms | H |
| Me | Me | MeO | CHMeOSO$_2$Me | Ms | H |
| Et | Me | MeO | CH$_2$OH | Ms | H |
| Et | Me | MeO | CH$_2$OMe | Ms | H |
| Et | Me | MeO | CH$_2$OMe | Cl | H |
| Et | Me | MeO | CH$_2$OMe | MeS | H |
| Et | Me | MeO | CH$_2$OMe | MeSO | H |
| Et | Me | MeO | CH$_2$OMe | Ms | Q1 |
| Et | Me | MeO | CH$_2$OMe | Cl | Q1 |
| Et | Me | MeO | CH$_2$OMe | MeS | Q1 |
| Et | Me | MeO | CH$_2$OMe | MeSO | Q2 |
| Et | Me | MeO | CH$_2$OMe | MeS | Q2 |
| Et | Me | MeO | CH$_2$OMe | MeSO | Q2 |
| Et | Me | MeO | CH$_2$OMe | Ms | Q3 |
| Et | Me | MeO | CH$_2$OMe | MeS | Q3 |
| Et | Me | MeO | CH$_2$OMe | MeSO | Q3 |
| Et | Me | MeO | CH$_2$OEt | Ms | H |
| Et | Me | MeO | CH$_2$OEt | Cl | H |
| Et | Me | MeO | CH$_2$OEt | MeS | H |
| Et | Me | MeO | CH$_2$OEt | MeSO | H |
| Et | Me | MeO | CH$_2$OEt | Ms | Q1 |
| Et | Me | MeO | CH$_2$OEt | MeS | Q1 |
| Et | Me | MeO | CH$_2$OEt | MeSO | Q1 |
| Et | Me | MeO | CH$_2$OEt | Ms | Q2 |
| Et | Me | MeO | CH$_2$OEt | MeS | Q2 |
| Et | Me | MeO | CH$_2$OEt | MeSO | Q2 |
| Et | Me | MeO | CH$_2$OEt | Ms | Q3 |
| Et | Me | MeO | CH$_2$OEt | MeS | Q3 |
| Et | Me | MeO | CH$_2$OEt | MeSO | Q3 |
| Et | Me | MeO | CH$_2$OPr-i | Ms | H |
| Et | Me | MeO | CH$_2$OPr-i | Cl | H |
| Et | Me | MeO | CH$_2$OPr-i | MeS | H |
| Et | Me | MeO | CH$_2$OPr-i | MeSO | H |
| Et | Me | MeO | CH$_2$OPr-i | Ms | Q1 |
| Et | Me | MeO | CH$_2$OPr-i | Ms | Q2 |
| Et | Me | MeO | CH$_2$OPr-i | Ms | Q3 |
| Et | Me | MeO | CH$_2$OPr-n | Ms | H |
| Et | Me | MeO | CH$_2$OCH=CH$_2$ | Ms | H |
| Et | Me | MeO | CH$_2$OCH$_2$CH=CH$_2$ | Ms | H |
| Et | Me | MeO | CH$_2$OCH$_2$C≡CH | Ms | H |
| Et | Me | MeO | CH$_2$OCH$_2$CH$_2$Cl | Ms | H |
| Et | Me | MeO | CH$_2$O—Y5 | Ms | H |
| Et | Me | MeO | CHMeOH | Ms | H |
| Et | Me | MeO | CHMeOMe | Ms | H |
| Et | Me | MeO | CHMeOMe | Cl | H |
| Et | Me | MeO | CHMeOMe | MeS | H |
| Et | Me | MeO | CHMeOMe | MeSO | H |
| Et | Me | MeO | CHMeOMe | Ms | Q1 |
| Et | Me | MeO | CHMeOMe | Ms | Q2 |
| Et | Me | MeO | CHMeOMe | Ms | Q3 |
| Et | Me | MeO | CHMeOEt | Ms | H |
| Et | Me | MeO | CHMeOEt | Cl | H |
| Et | Me | MeO | CHMeOEt | MeS | H |
| Et | Me | MeO | CHMeOEt | MeSO | H |
| Et | Me | MeO | CHMeOEt | Ms | Q1 |
| Et | Me | MeO | CHMeOEt | Ms | Q2 |
| Et | Me | MeO | CHMeOEt | Ms | Q3 |

-continued

| | | | | | |
|---|---|---|---|---|---|
| Et | Me | MeO | CHMeOPr-i | Ms | H |
| Et | Me | MeO | CHMeOPr-i | Cl | H |
| Et | Me | MeO | CHMeOPr-i | MeS | H |
| Et | Me | MeO | CHMeOPr-i | MeSO | H |
| Et | Me | MeO | CHMeOPr-n | Ms | H |
| Et | Me | MeO | CHMeOCH=CH$_2$ | Ms | H |
| Et | Me | MeO | CHMeOCH=CH$_2$ | Ms | H |
| Et | Me | MeO | CHMeOCH$_2$CH=CH$_2$ | Ms | H |
| Et | Me | MeO | CHMeOCH$_2$C≡CH | Ms | H |
| Et | Me | MeO | CHMeOCH$_2$CH$_2$Cl | Ms | H |
| Et | Me | MeO | CHMeO—Y5 | Ms | H |
| Et | Me | MeO | CMe$_2$OH | Ms | H |
| Et | Me | MeO | CMe$_2$OMe | Ms | H |
| Et | Me | MeO | CMe$_2$OEt | Ms | H |
| Et | Me | MeO | CMe$_2$OPr-i | Ms | H |
| Et | Me | MeO | CH$_2$CH$_2$OMe | Ms | H |
| Et | Me | MeO | CH$_2$CH$_2$OEt | Ms | H |
| Et | Me | MeO | CH$_2$CH$_2$OPr-i | Ms | H |
| Et | Me | MeO | CHEtOH | Ms | H |
| Et | Me | MeO | CHEtOMe | Ms | H |
| Et | Me | MeO | CHEtOMe | Cl | H |
| Et | Me | MeO | CHEtOMe | MeS | H |
| Et | Me | MeO | CHEtOMe | MeSO | H |
| Et | Me | MeO | CHEtOEt | Ms | H |
| Et | Me | MeO | CHEtOPr-i | Ms | H |
| Et | Me | MeO | CH$_2$OCH$_2$CH$_2$OMe | Ms | H |
| Et | Me | MeO | CH$_2$OCH$_2$CH$_2$OMe | Cl | H |
| Et | Me | MeO | CH$_2$OCH$_2$CH$_2$OMe | MeS | H |
| Et | Me | MeO | CH$_2$OCH$_2$CH$_2$OMe | MeSO | H |
| Et | Me | MeO | CH$_2$OCH$_2$CH$_2$OEt | Ms | H |
| Et | Me | MeO | CHMeOCH$_2$CH$_2$OMe | Ms | H |
| Et | Me | MeO | CH$_2$O—Y8 | Ms | H |
| Et | Me | MeO | CH$_2$O—Y9 | Ms | H |
| Et | Me | MeO | CH$_2$O—Y10 | Ms | H |
| Et | Me | MeO | CHMeO—Y8 | Ms | H |
| Et | Me | MeO | CHMeO—Y9 | Ms | H |
| Et | Me | MeO | CHMeO—Y10 | Ms | H |
| Et | Me | MeO | CH$_2$O—Y13 | Ms | H |
| Et | Me | MeO | CHMeO—Y13 | Ms | H |
| Et | Me | MeO | CH$_2$NMe$_2$ | Ms | H |
| Et | Me | MeO | CH$_2$—Y14 | Ms | H |
| Et | Me | MeO | CHMeNMe$_2$ | Ms | H |
| Et | Me | MeO | CH$_2$CH$_2$NMe$_2$ | Ms | H |
| Et | Me | MeO | CH$_2$OCH$_2$Ph | Ms | H |
| Et | Me | MeO | CHMeOCH$_2$Ph | Ms | H |
| Et | Me | MeO | CH$_2$OCH$_2$CO$_2$Me | Ms | H |
| Et | Me | MeO | CH$_2$OCH$_2$CO$_2$Et | Ms | H |
| Et | Me | MeO | CH$_2$OCHMeCO$_2$Me | Ms | H |
| Et | Me | MeO | CH$_2$CN | Ms | H |
| Et | Me | MeO | CHMeCN | Ms | H |
| Et | Me | MeO | CH$_2$SMe | Ms | H |
| Et | Me | MeO | CH$_2$SMe | Cl | H |
| Et | Me | MeO | CH$_2$SMe | MeS | H |
| Et | Me | MeO | CH$_2$SMe | MeSO | H |
| Et | Me | MeO | CH$_2$SEt | Ms | H |
| Et | Me | MeO | CH$_2$SEt | Cl | H |
| Et | Me | MeO | CH$_2$SEt | MeS | H |
| Et | Me | MeO | CH$_2$SEt | MeSO | H |
| Et | Me | MeO | CH$_2$SOMe | Ms | H |
| Et | Me | MeO | CH$_2$SOEt | Ms | H |
| Et | Me | MeO | CH$_2$SO$_2$Me | Ms | H |
| Et | Me | MeO | CH$_2$SO$_2$Me | Cl | H |
| Et | Me | MeO | CH$_2$SO$_2$Me | MeS | H |
| Et | Me | MeO | CH$_2$SO$_2$Me | MeSO | H |
| Et | Me | MeO | CH$_2$SO$_2$Et | Ms | H |
| Et | Me | MeO | CH$_2$SO$_2$Et | Cl | H |
| Et | Me | MeO | CH$_2$SO$_2$Et | MeS | H |
| Et | Me | MeO | CH$_2$SO$_2$Et | MeSO | H |
| Et | Me | MeO | CHMeSMe | Ms | H |
| Et | Me | MeO | CHMeSEt | Ms | H |
| Et | Me | MeO | CHMeSO$_2$Me | Ms | H |
| Et | Me | MeO | CHMeSO$_2$Et | Ms | H |
| Et | Me | MeO | CH$_2$SCH$_2$CH$_2$OMe | Ms | H |
| Et | Me | MeO | CH$_2$OCOMe | Ms | H |
| Et | Me | MeO | CH$_2$OCOEt | Ms | H |
| Et | Me | MeO | CHMeOCOMe | Ms | H |
| Et | Me | MeO | CH$_2$OSO$_2$Me | Ms | H |
| Et | Me | MeO | CH$_2$OSO$_2$Et | Ms | H |
| Et | Me | MeO | CHMeOSO$_2$Me | Ms | H |
| Pr-i | Me | MeO | CH$_2$OH | Ms | H |
| Pr-i | Me | MeO | CH$_2$OMe | Ms | H |
| Pr-i | Me | MeO | CH$_2$OMe | Cl | H |
| Pr-i | Me | MeO | CH$_2$OMe | MeS | H |

-continued

| | | | | | |
|---|---|---|---|---|---|
| Pr-i | Me | MeO | CH₂OMe | MeSO | H |
| Pr-i | Me | MeO | CH₂OMe | Ms | Q1 |
| Pr-i | Me | MeO | CH₂OMe | Cl | Q1 |
| Pr-i | Me | MeO | CH₂OMe | MeS | Q1 |
| Pr-i | Me | MeO | CH₂OMe | MeSO | Q2 |
| Pr-i | Me | MeO | CH₂OMe | MeS | Q2 |
| Pr-i | Me | MeO | CH₂OMe | MeSO | Q2 |
| Pr-i | Me | MeO | CH₂OMe | Ms | Q3 |
| Pr-i | Me | MeO | CH₂OMe | MeS | Q3 |
| Pr-i | Me | MeO | CH₂OMe | MeSO | Q3 |
| Pr-i | Me | MeO | CH₂OEt | Ms | H |
| Pr-i | Me | MeO | CH₂OEt | Cl | H |
| Pr-i | Me | MeO | CH₂OEt | MeS | H |
| Pr-i | Me | MeO | CH₂OEt | MeSO | H |
| Pr-i | Me | MeO | CH₂OEt | Ms | Q1 |
| Pr-i | Me | MeO | CH₂OEt | MeS | Q1 |
| Pr-i | Me | MeO | CH₂OEt | MeSO | Q1 |
| Pr-i | Me | MeO | CH₂OEt | Ms | Q2 |
| Pr-i | Me | MeO | CH₂OEt | MeS | Q2 |
| Pr-i | Me | MeO | CH₂OEt | MeSO | Q2 |
| Pr-i | Me | MeO | CH₂OEt | Ms | Q3 |
| Pr-i | Me | MeO | CH₂OEt | MeS | Q3 |
| Pr-i | Me | MeO | CH₂OEt | MeSO | Q3 |
| Pr-i | Me | MeO | CH₂OPr-i | Ms | H |
| Pr-i | Me | MeO | CH₂OPr-i | Cl | H |
| Pr-i | Me | MeO | CH₂OPr-i | MeS | H |
| Pr-i | Me | MeO | CH₂OPr-i | MeSO | H |
| Pr-i | Me | MeO | CH₂OPr-i | Ms | Q1 |
| Pr-i | Me | MeO | CH₂OPr-i | Ms | Q2 |
| Pr-i | Me | MeO | CH₂OPr-i | Ms | Q3 |
| Pr-i | Me | MeO | CH₂OPr-n | Ms | H |
| Pr-i | Me | MeO | CH₂OCH=CH₂ | Ms | H |
| Pr-i | Me | MeO | CH₂OCH₂CH=CH₂ | Ms | H |
| Pr-i | Me | MeO | CH₂OCH₂C≡CH | Ms | H |
| Pr-i | Me | MeO | CH₂OCH₂CH₂Cl | Ms | H |
| Pr-i | Me | MeO | CH₂O—Y5 | Ms | H |
| Pr-i | Me | MeO | CHMeOH | Ms | H |
| Pr-i | Me | MeO | CHMeOMe | Ms | H |
| Pr-i | Me | MeO | CHMeOMe | Cl | H |
| Pr-i | Me | MeO | CHMeOMe | MeS | H |
| Pr-i | Me | MeO | CHMeOMe | MeSO | H |
| Pr-i | Me | MeO | CHMeOMe | Ms | Q1 |
| Pr-i | Me | MeO | CHMeOMe | Ms | Q2 |
| Pr-i | Me | MeO | CHMeOMe | Ms | Q3 |
| Pr-i | Me | MeO | CHMeOEt | Ms | H |
| Pr-i | Me | MeO | CHMeOEt | Cl | H |
| Pr-i | Me | MeO | CHMeOEt | MeS | H |
| Pr-i | Me | MeO | CHMeOEt | MeSO | H |
| Pr-i | Me | MeO | CHMeOEt | Ms | Q1 |
| Pr-i | Me | MeO | CHMeOEt | Ms | Q2 |
| Pr-i | Me | MeO | CHMeOEt | Ms | Q3 |
| Pr-i | Me | MeO | CHMeOPr-i | Ms | H |
| Pr-i | Me | MeO | CHMeOPr-i | Cl | H |
| Pr-i | Me | MeO | CHMeOPr-i | MeS | H |
| Pr-i | Me | MeO | CHMeOPr-i | MeSO | H |
| Pr-i | Me | MeO | CHMeOPr-n | Ms | H |
| Pr-i | Me | MeO | CHMeOCH=CH₂ | Ms | H |
| Pr-i | Me | MeO | CHMeOCH₂CH=CH₂ | Ms | H |
| Pr-i | Me | MeO | CHMeOCH₂C≡CH | Ms | H |
| Pr-i | Me | MeO | CHMeOCH₂CH₂Cl | Ms | H |
| Pr-i | Me | MeO | CHMeO—Y5 | Ms | H |
| Pr-i | Me | MeO | CMe₂OH | Ms | H |
| Pr-i | Me | MeO | CMe₂OMe | Ms | H |
| Pr-i | Me | MeO | CMe₂OEt | Ms | H |
| Pr-i | Me | MeO | CMe₂OPr-i | Ms | H |
| Pr-i | Me | MeO | CH₂CH₂OMe | Ms | H |
| Pr-i | Me | MeO | CH₂CH₂OEt | Ms | H |
| Pr-i | Me | MeO | CH₂CH₂OPr-i | Ms | H |
| Pr-i | Me | MeO | CHEtOH | Ms | H |
| Pr-i | Me | MeO | CHEtOMe | Ms | H |
| Pr-i | Me | MeO | CHEtOMe | Cl | H |
| Pr-i | Me | MeO | CHEtOMe | MeS | H |
| Pr-i | Me | MeO | CHEtOMe | MeSO | H |
| Pr-i | Me | MeO | CHEtOEt | Ms | H |
| Pr-i | Me | MeO | CHEtOPr-i | Ms | H |
| Pr-i | Me | MeO | CH₂OCH₂CH₂OMe | Ms | H |
| Pr-i | Me | MeO | CH₂OCH₂CH₂OMe | Cl | H |
| Pr-i | Me | MeO | CH₂OCH₂CH₂OMe | MeS | H |
| Pr-i | Me | MeO | CH₂OCH₂CH₂OMe | MeSO | H |
| Pr-i | Me | MeO | CH₂OCH₂CH₂OEt | Ms | H |
| Pr-i | Me | MeO | CHMeOCH₂CH₂OMe | Ms | H |
| Pr-i | Me | MeO | CH₂O—Y8 | Ms | H |

-continued

| | | | | | |
|---|---|---|---|---|---|
| Pr-i | Me | MeO | CH$_2$O—Y9 | Ms | H |
| Pr-i | Me | MeO | CH$_2$O—Y10 | Ms | H |
| Pr-i | Me | MeO | CHMeO—Y8 | Ms | H |
| Pr-i | Me | MeO | CHMeO—Y9 | Ms | H |
| Pr-i | Me | MeO | CHMeO—Y10 | Ms | H |
| Pr-i | Me | MeO | CH$_2$O—Y13 | Ms | H |
| Pr-i | Me | MeO | CHMeO—Y13 | Ms | H |
| Pr-i | Me | MeO | CH$_2$NMe$_2$ | Ms | H |
| Pr-i | Me | MeO | CH$_2$—Y14 | Ms | H |
| Pr-i | Me | MeO | CHMeNMe$_2$ | Ms | H |
| Pr-i | Me | MeO | CH$_2$CH$_2$NMe$_2$ | Ms | H |
| Pr-i | Me | MeO | CH$_2$OCH$_2$Ph | Ms | H |
| Pr-i | Me | MeO | CHMeOCH$_2$Ph | Ms | H |
| Pr-i | Me | MeO | CH$_2$OCH$_2$CO$_2$Me | Ms | H |
| Pr-i | Me | MeO | CH$_2$OCH$_2$CO$_2$Et | Ms | H |
| Pr-i | Me | MeO | CH$_2$OCHMeCO$_2$Me | Ms | H |
| Pr-i | Me | MeO | CH$_2$CN | Ms | H |
| Pr-i | Me | MeO | CHMeCN | Ms | H |
| Pr-i | Me | MeO | CH$_2$SMe | Ms | H |
| Pr-i | Me | MeO | CH$_2$SMe | Cl | H |
| Pr-i | Me | MeO | CH$_2$SMe | MeS | H |
| Pr-i | Me | MeO | CH$_2$SMe | MeSO | H |
| Pr-i | Me | MeO | CH$_2$SEt | Ms | H |
| Pr-i | Me | MeO | CH$_2$SEt | Cl | H |
| Pr-i | Me | MeO | CH$_2$SEt | MeS | H |
| Pr-i | Me | MeO | CH$_2$SEt | MeSO | H |
| Pr-i | Me | MeO | CH$_2$SOMe | Ms | H |
| Pr-i | Me | MeO | CH$_2$SOEt | Ms | H |
| Pr-i | Me | MeO | CH$_2$SO$_2$Me | Ms | H |
| Pr-i | Me | MeO | CH$_2$SO$_2$Me | Cl | H |
| Pr-i | Me | MeO | CH$_2$SO$_2$Me | MeS | H |
| Pr-i | Me | MeO | CH$_2$SO$_2$Me | MeSO | H |
| Pr-i | Me | MeO | CH$_2$SO$_2$Et | Ms | H |
| Pr-i | Me | MeO | CH$_2$SO$_2$Et | Cl | H |
| Pr-i | Me | MeO | CH$_2$SO$_2$Et | MeS | H |
| Pr-i | Me | MeO | CH$_2$SO$_2$Et | MeSO | H |
| Pr-i | Me | MeO | CHMeSMe | Ms | H |
| Pr-i | Me | MeO | CHMeSEt | Ms | H |
| Pr-i | Me | MeO | CHMeSO$_2$Me | Ms | H |
| Pr-i | Me | MeO | CHMeSO$_2$Et | Ms | H |
| Pr-i | Me | MeO | CH$_2$SCH$_2$CH$_2$OMe | Ms | H |
| Pr-i | Me | MeO | CH$_2$OCOMe | Ms | H |
| Pr-i | Me | MeO | CH$_2$OCOEt | Ms | H |
| Pr-i | Me | MeO | CHMeOCOMe | Ms | H |
| Pr-i | Me | MeO | CH$_2$OSO$_2$Me | Ms | H |
| Pr-i | Me | MeO | CH$_2$OSO$_2$Et | Ms | H |
| Pr-i | Me | MeO | CHMeOSO$_2$Me | Ms | H |
| Me | H | Br | CH$_2$OH | Ms | H |
| Me | H | Br | CH$_2$OMe | Ms | H |
| Me | H | Br | CH$_2$OMe | Cl | H |
| Me | H | Br | CH$_2$OMe | MeS | H |
| Me | H | Br | CH$_2$OMe | MeSO | H |
| Me | H | Br | CH$_2$OEt | Ms | H |
| Me | H | Br | CH$_2$OEt | Cl | H |
| Me | H | Br | CH$_2$OEt | MeS | H |
| Me | H | Br | CH$_2$OEt | MeSO | H |
| Me | H | Br | CH$_2$OPr-i | Ms | H |
| Me | H | Br | CH$_2$OPr-n | Ms | H |
| Me | H | Br | CH$_2$OCH=CH$_2$ | Ms | H |
| Me | H | Br | CH$_2$OCH$_2$CH=CH$_2$ | Ms | H |
| Me | H | Br | CH$_2$OCH$_2$C≡CH | Ms | H |
| Me | H | Br | CH$_2$OCH$_2$CH$_2$Cl | Ms | H |
| Me | H | Br | CHMeOH | Ms | H |
| Me | H | Br | CHMeOMe | Ms | H |
| Me | H | Br | CHMeOMe | Cl | H |
| Me | H | Br | CHMeOMe | MeS | H |
| Me | H | Br | CHMeOMe | MeSO | H |
| Me | H | Br | CHMeOEt | Ms | H |
| Me | H | Br | CHMeOCH=CH$_2$ | Ms | H |
| Me | H | Br | CHMeOCH=CH$_2$ | Ms | H |
| Me | H | Br | CHMeOCH$_2$CH=CH$_2$ | Ms | H |
| Me | H | Br | CHMeOCH$_2$C≡CH | Ms | H |
| Me | H | Br | CHMeOCH$_2$CH$_2$Cl | Ms | H |
| Me | H | Br | CMe$_2$OH | Ms | H |
| Me | H | Br | CMe$_2$OMe | Ms | H |
| Me | H | Br | CMe$_2$OEt | Ms | H |
| Me | H | Br | CH$_2$CH$_2$OMe | Ms | H |
| Me | H | Br | CH$_2$CH$_2$OEt | Ms | H |
| Me | H | Br | CHEtOH | Ms | H |
| Me | H | Br | CHEtOMe | Ms | H |
| Me | H | Br | CHEtOEt | Ms | H |
| Me | H | Br | CH$_2$OCH$_2$CH$_2$OMe | Ms | H |
| Me | H | Br | CHMeOCH$_2$CH$_2$OMe | Ms | H |

-continued

| | | | | | | |
|---|---|---|---|---|---|---|
| Me | H | Br | CH$_2$NMe$_2$ | Ms | H | |
| Me | H | Br | CHMeNMe$_2$ | Ms | H | |
| Me | H | Br | CH$_2$CH$_2$NMe$_2$ | Ms | H | |
| Me | H | Br | CH$_2$OCH$_2$Ph | Ms | H | |
| Me | H | Br | CHMeOCH$_2$Ph | Ms | H | |
| Me | H | Br | CH$_2$OCH$_2$CO$_2$Me | Ms | H | |
| Me | H | Br | CH$_2$OCH$_2$CO$_2$Et | Ms | H | |
| Me | H | Br | CH$_2$OCHMeCO$_2$Me | Ms | H | |
| Me | H | Br | CH$_2$CN | Ms | H | |
| Me | H | Br | CH$_2$SMe | Ms | H | |
| Me | H | Br | CH$_2$SEt | Ms | H | |
| Me | H | Br | CH$_2$SOMe | Ms | H | |
| Me | H | Br | CH$_2$SO$_2$Me | Ms | H | |
| Me | H | Br | CH$_2$SO$_2$Et | Ms | H | |
| Me | H | Br | CHMeSMe | Ms | H | |
| Me | H | Br | CHMeSO$_2$Me | Ms | H | |
| Me | H | Br | CH$_2$SCH$_2$CH$_2$OMe | Ms | H | |
| Me | H | Br | CH$_2$OCOMe | Ms | H | |
| Me | H | Br | CHMeOCOMe | Ms | H | |
| Me | H | Br | CH$_2$OSO$_2$Me | Ms | H | |
| Me | H | Br | CHMeOSO$_2$Me | Ms | H | |
| Et | H | Br | CH$_2$OH | Ms | H | |
| Et | H | Br | CH$_2$OMe | Ms | H | |
| Et | H | Br | CH$_2$OMe | Cl | H | |
| Et | H | Br | CH$_2$OMe | MeS | H | |
| Et | H | Br | CH$_2$OMe | MeSO | H | |
| Et | H | Br | CH$_2$OEt | Ms | H | |
| Et | H | Br | CH$_2$OEt | Cl | H | |
| Et | H | Br | CH$_2$OEt | MeS | H | |
| Et | H | Br | CH$_2$OEt | MeSO | H | |
| Et | H | Br | CH$_2$OPr-i | Ms | H | |
| Et | H | Br | CH$_2$OPr-n | Ms | H | |
| Et | H | Br | CH$_2$OCH=CH$_2$ | Ms | H | |
| Et | H | Br | CH$_2$OCH$_2$CH=CH$_2$ | Ms | H | |
| Et | H | Br | CH$_2$OCH$_2$C≡CH | Ms | H | |
| Et | H | Br | CH$_2$OCH$_2$CH$_2$Cl | Ms | H | |
| Et | H | Br | CHMeOH | Ms | H | |
| Et | H | Br | CHMeOMe | Ms | H | |
| Et | H | Br | CHMeOMe | Cl | H | |
| Et | H | Br | CHMeOMe | MeS | H | |
| Et | H | Br | CHMeOMe | MeSO | H | |
| Et | H | Br | CHMeOEt | Ms | H | |
| Et | H | Br | CHMeOCH=CH$_2$ | Ms | H | |
| Et | H | Br | CHMeOCH=CH$_2$ | Ms | H | |
| Et | H | Br | CHMeOCH$_2$CH=CH$_2$ | Ms | H | |
| Et | H | Br | CHMeOCH$_2$C≡CH | Ms | H | |
| Et | H | Br | CHMeOCH$_2$CH$_2$Cl | Ms | H | |
| Et | H | Br | CMe$_2$OH | Ms | H | |
| Et | H | Br | CMe$_2$OMe | Ms | H | |
| Et | H | Br | CMe$_2$OEt | Ms | H | |
| Et | H | Br | CH$_2$CH$_2$OMe | Ms | H | |
| Et | H | Br | CH$_2$CH$_2$OEt | Ms | H | |
| Et | H | Br | CHEtOH | Ms | H | |
| Et | H | Br | CHEtOMe | Ms | H | |
| Et | H | Br | CHEtOEt | Ms | H | |
| Et | H | Br | CH$_2$OCH$_2$CH$_2$OMe | Ms | H | |
| Et | H | Br | CHMeOCH$_2$CH$_2$OMe | Ms | H | |
| Et | H | Br | CH$_2$NMe$_2$ | Ms | H | |
| Et | H | Br | CHMeNMe$_2$ | Ms | H | |
| Et | H | Br | CH$_2$CH$_2$NMe$_2$ | Ms | H | |
| Et | H | Br | CH$_2$OCH$_2$Ph | Ms | H | |
| Et | H | Br | CHMeOCH$_2$Ph | Ms | H | |
| Et | H | Br | CH$_2$OCH$_2$CO$_2$Me | Ms | H | |
| Et | H | Br | CH$_2$OCH$_2$CO$_2$Et | Ms | H | |
| Et | H | Br | CH$_2$OCHMeCO$_2$Me | Ms | H | |
| Et | H | Br | CH$_2$CN | Ms | H | |
| Et | H | Br | CH$_2$SMe | Ms | H | |
| Et | H | Br | CH$_2$SEt | Ms | H | |
| Et | H | Br | CH$_2$SOMe | Ms | H | |
| Et | H | Br | CH$_2$SO$_2$Me | Ms | H | |
| Et | H | Br | CH$_2$SO$_2$Et | Ms | H | |
| Et | H | Br | CHMeSMe | Ms | H | |
| Et | H | Br | CHMeSO$_2$Me | Ms | H | |
| Et | H | Br | CH$_2$SCH$_2$CH$_2$OMe | Ms | H | |
| Et | H | Br | CH$_2$OCOMe | Ms | H | |
| Et | H | Br | CHMeOCOMe | Ms | H | |
| Et | H | Br | CH$_2$OSO$_2$Me | Ms | H | |
| Et | H | Br | CHMeOSO$_2$Me | Ms | H | |
| Pr-i | H | Br | CH$_2$OH | Ms | H | |
| Pr-i | H | Br | CH$_2$OMe | Ms | H | |
| Pr-i | H | Br | CH$_2$OMe | Cl | H | |
| Pr-i | H | Br | CH$_2$OMe | MeS | H | |
| Pr-i | H | Br | CH$_2$OMe | MeSO | H | |

-continued

| | | | | | |
|---|---|---|---|---|---|
| Pr-i | H | Br | CH$_2$OEt | Ms | H |
| Pr-i | H | Br | CH$_2$OEt | Cl | H |
| Pr-i | H | Br | CH$_2$OEt | MeS | H |
| Pr-i | H | Br | CH$_2$OEt | MeSO | H |
| Pr-i | H | Br | CH$_2$OPr-i | Ms | H |
| Pr-i | H | Br | CH$_2$OPr-n | Ms | H |
| Pr-i | H | Br | CH$_2$OCH=CH$_2$ | Ms | H |
| Pr-i | H | Br | CH$_2$OCH$_2$CH=CH$_2$ | Ms | H |
| Pr-i | H | Br | CH$_2$OCH$_2$C≡CH | Ms | H |
| Pr-i | H | Br | CH$_2$OCH$_2$CH$_2$Cl | Ms | H |
| Pr-i | H | Br | CHMeOH | Ms | H |
| Pr-i | H | Br | CHMeOMe | Ms | H |
| Pr-i | H | Br | CHMeOMe | Cl | H |
| Pr-i | H | Br | CHMeOMe | MeS | H |
| Pr-i | H | Br | CHMeOMe | MeSO | H |
| Pr-i | H | Br | CHMeOEt | Ms | H |
| Pr-i | H | Br | CHMeOCH=CH$_2$ | Ms | H |
| Pr-i | H | Br | CHMeOCH=CH$_2$ | Ms | H |
| Pr-i | H | Br | CHMeOCH$_2$CH=CH$_2$ | Ms | H |
| Pr-i | H | Br | CHMeOCH$_2$C≡CH | Ms | H |
| Pr-i | H | Br | CHMeOCH$_2$CH$_2$Cl | Ms | H |
| Pr-i | H | Br | CMe$_2$OH | Ms | H |
| Pr-i | H | Br | CMe$_2$OMe | Ms | H |
| Pr-i | H | Br | CMe$_2$OEt | Ms | H |
| Pr-i | H | Br | CH$_2$CH$_2$OMe | Ms | H |
| Pr-i | H | Br | CH$_2$CH$_2$OEt | Ms | H |
| Pr-i | H | Br | CHEtOH | Ms | H |
| Pr-i | H | Br | CHEtOMe | Ms | H |
| Pr-i | H | Br | CHEtOEt | Ms | H |
| Pr-i | H | Br | CH$_2$OCH$_2$CH$_2$OMe | Ms | H |
| Pr-i | H | Br | CHMeOCH$_2$CH$_2$OMe | Ms | H |
| Pr-i | H | Br | CH$_2$NMe$_2$ | Ms | H |
| Pr-i | H | Br | CHMeNMe$_2$ | Ms | H |
| Pr-i | H | Br | CH$_2$CH$_2$NMe$_2$ | Ms | H |
| Pr-i | H | Br | CH$_2$OCH$_2$Ph | Ms | H |
| Pr-i | H | Br | CHMeOCH$_2$Ph | Ms | H |
| Pr-i | H | Br | CH$_2$OCH$_2$CO$_2$Me | Ms | H |
| Pr-i | H | Br | CH$_2$OCH$_2$CO$_2$Et | Ms | H |
| Pr-i | H | Br | CH$_2$OCHMeCO$_2$Me | Ms | H |
| Pr-i | H | Br | CH$_2$CN | Ms | H |
| Pr-i | H | Br | CH$_2$SMe | Ms | H |
| Pr-i | H | Br | CH$_2$SEt | Ms | H |
| Pr-i | H | Br | CH$_2$SOMe | Ms | H |
| Pr-i | H | Br | CH$_2$SO$_2$Me | Ms | H |
| Pr-i | H | Br | CH$_2$SO$_2$Et | Ms | H |
| Pr-i | H | Br | CHMeSMe | Ms | H |
| Pr-i | H | Br | CHMeSO$_2$Me | Ms | H |
| Pr-i | H | Br | CH$_2$SCH$_2$CH$_2$OMe | Ms | H |
| Pr-i | H | Br | CH$_2$OCOMe | Ms | H |
| Pr-i | H | Br | CHMeOCOMe | Ms | H |
| Pr-i | H | Br | CH$_2$OSO$_2$Me | Ms | H |
| Pr-i | H | Br | CHMeOSO$_2$Me | Ms | H |
| Me | H | I | CH$_2$OH | Ms | H |
| Me | H | I | CH$_2$OMe | Ms | H |
| Me | H | I | CH$_2$OMe | Cl | H |
| Me | H | I | CH$_2$OMe | MeS | H |
| Me | H | I | CH$_2$OMe | MeSO | H |
| Me | H | I | CH$_2$OEt | Ms | H |
| Me | H | I | CH$_2$OEt | Cl | H |
| Me | H | I | CH$_2$OEt | MeS | H |
| Me | H | I | CH$_2$OEt | MeSO | H |
| Me | H | I | CH$_2$OPr-i | Ms | H |
| Me | H | I | CH$_2$OPr-n | Ms | H |
| Me | H | I | CH$_2$OCH=CH$_2$ | Ms | H |
| Me | H | I | CH$_2$OCH$_2$CH=CH$_2$ | Ms | H |
| Me | H | I | CH$_2$OCH$_2$C≡CH | Ms | H |
| Me | H | I | CH$_2$OCH$_2$CH$_2$Cl | Ms | H |
| Me | H | I | CHMeOH | Ms | H |
| Me | H | I | CHMeOMe | Ms | H |
| Me | H | I | CHMeOMe | Cl | H |
| Me | H | I | CHMeOMe | MeS | H |
| Me | H | I | CHMeOMe | MeSO | H |
| Me | H | I | CHMeOEt | Ms | H |
| Me | H | I | CHMeOCH=CH$_2$ | Ms | H |
| Me | H | I | CHMeOCH=CH$_2$ | Ms | H |
| Me | H | I | CHMeOCH$_2$CH=CH$_2$ | Ms | H |
| Me | H | I | CHMeOCH$_2$C≡CH | Ms | H |
| Me | H | I | CHMeOCH$_2$CH$_2$Cl | Ms | H |
| Me | H | I | CMe$_2$OH | Ms | H |
| Me | H | I | CMe$_2$OMe | Ms | H |
| Me | H | I | CMe$_2$OEt | Ms | H |
| Me | H | I | CH$_2$CH$_2$OMe | Ms | H |
| Me | H | I | CH$_2$CH$_2$OEt | Ms | H |

-continued

| | | | | | |
|---|---|---|---|---|---|
| Me | H | I | CHEtOH | Ms | H |
| Me | H | I | CHEtOMe | Ms | H |
| Me | H | I | CHEtOEt | Ms | H |
| Me | H | I | CH$_2$OCH$_2$CH$_2$OMe | Ms | H |
| Me | H | I | CHMeOCH$_2$CH$_2$OMe | Ms | H |
| Me | H | I | CH$_2$NMe$_2$ | Ms | H |
| Me | H | I | CHMeNMe$_2$ | Ms | H |
| Me | H | I | CH$_2$CH$_2$NMe$_2$ | Ms | H |
| Me | H | I | CH$_2$OCH$_2$Ph | Ms | H |
| Me | H | I | CHMeOCH$_2$Ph | Ms | H |
| Me | H | I | CH$_2$OCH$_2$CO$_2$Me | Ms | H |
| Me | H | I | CH$_2$OCH$_2$CO$_2$Et | Ms | H |
| Me | H | I | CH$_2$OCHMeCO$_2$Me | Ms | H |
| Me | H | I | CH$_2$CN | Ms | H |
| Me | H | I | CH$_2$SMe | Ms | H |
| Me | H | I | CH$_2$SEt | Ms | H |
| Me | H | I | CH$_2$SOMe | Ms | H |
| Me | H | I | CH$_2$SO$_2$Me | Ms | H |
| Me | H | I | CH$_2$SO$_2$Et | Ms | H |
| Me | H | I | CHMeSMe | Ms | H |
| Me | H | I | CHMeSO$_2$Me | Ms | H |
| Me | H | I | CH$_2$SCH$_2$CH$_2$OMe | Ms | H |
| Me | H | I | CH$_2$OCOMe | Ms | H |
| Me | H | I | CHMeOCOMe | Ms | H |
| Me | H | I | CH$_2$OSO$_2$Me | Ms | H |
| Me | H | I | CHMeOSO$_2$Me | Ms | H |
| Et | H | I | CH$_2$OH | Ms | H |
| Et | H | I | CH$_2$OMe | Ms | H |
| Et | H | I | CH$_2$OMe | Cl | H |
| Et | H | I | CH$_2$OMe | MeS | H |
| Et | H | I | CH$_2$OMe | MeSO | H |
| Et | H | I | CH$_2$OEt | Ms | H |
| Et | H | I | CH$_2$OEt | Cl | H |
| Et | H | I | CH$_2$OEt | MeS | H |
| Et | H | I | CH$_2$OEt | MeSO | H |
| Et | H | I | CH$_2$OPr-i | Ms | H |
| Et | H | I | CH$_2$OPr-n | Ms | H |
| Et | H | I | CH$_2$OCH=CH$_2$ | Ms | H |
| Et | H | I | CH$_2$OCH$_2$CH=CH$_2$ | Ms | H |
| Et | H | I | CH$_2$OCH$_2$C≡CH | Ms | H |
| Et | H | I | CH$_2$OCH$_2$CH$_2$Cl | Ms | H |
| Et | H | I | CHMeOH | Ms | H |
| Et | H | I | CHMeOMe | Ms | H |
| Et | H | I | CHMeOMe | Cl | H |
| Et | H | I | CHMeOMe | MeS | H |
| Et | H | I | CHMeOMe | MeSO | H |
| Et | H | I | CHMeOEt | Ms | H |
| Et | H | I | CHMeOCH=CH$_2$ | Ms | H |
| Et | H | I | CHMeOCH=CH$_2$ | Ms | H |
| Et | H | I | CHMeOCH$_2$CH=CH$_2$ | Ms | H |
| Et | H | I | CHMeOCH$_2$C≡CH | Ms | H |
| Et | H | I | CHMeOCH$_2$CH$_2$Cl | Ms | H |
| Et | H | I | CMe$_2$OH | Ms | H |
| Et | H | I | CMe$_2$OMe | Ms | H |
| Et | H | I | CMe$_2$OEt | Ms | H |
| Et | H | I | CH$_2$CH$_2$OMe | Ms | H |
| Et | H | I | CH$_2$CH$_2$OEt | Ms | H |
| Et | H | I | CHEtOH | Ms | H |
| Et | H | I | CHEtOMe | Ms | H |
| Et | H | I | CHEtOEt | Ms | H |
| Et | H | I | CH$_2$OCH$_2$CH$_2$OMe | Ms | H |
| Et | H | I | CHMeOCH$_2$CH$_2$OMe | Ms | H |
| Et | H | I | CH$_2$NMe$_2$ | Ms | H |
| Et | H | I | CHMeNMe$_2$ | Ms | H |
| Et | H | I | CH$_2$CH$_2$NMe$_2$ | Ms | H |
| Et | H | I | CH$_2$OCH$_2$Ph | Ms | H |
| Et | H | I | CHMeOCH$_2$Ph | Ms | H |
| Et | H | I | CH$_2$OCH$_2$CO$_2$Me | Ms | H |
| Et | H | I | CH$_2$OCH$_2$CO$_2$Et | Ms | H |
| Et | H | I | CH$_2$OCHMeCO$_2$Me | Ms | H |
| Et | H | I | CH$_2$CN | Ms | H |
| Et | H | I | CH$_2$SMe | Ms | H |
| Et | H | I | CH$_2$SEt | Ms | H |
| Et | H | I | CH$_2$SOMe | Ms | H |
| Et | H | I | CH$_2$SO$_2$Me | Ms | H |
| Et | H | I | CH$_2$SO$_2$Et | Ms | H |
| Et | H | I | CHMeSMe | Ms | H |
| Et | H | I | CHMeSO$_2$Me | Ms | H |
| Et | H | I | CH$_2$SCH$_2$CH$_2$OMe | Ms | H |
| Et | H | I | CH$_2$OCOMe | Ms | H |
| Et | H | I | CHMeOCOMe | Ms | H |
| Et | H | I | CH$_2$OSO$_2$Me | Ms | H |
| Et | H | I | CHMeOSO$_2$Me | Ms | H |

-continued

| | | | | | |
|---|---|---|---|---|---|
| Pr-i | H | I | CH₂OH | Ms | H |
| Pr-i | H | I | CH₂OMe | Ms | H |
| Pr-i | H | I | CH₂OMe | Cl | H |
| Pr-i | H | I | CH₂OMe | MeS | H |
| Pr-i | H | I | CH₂OMe | MeSO | H |
| Pr-i | H | I | CH₂OEt | Ms | H |
| Pr-i | H | I | CH₂OEt | Cl | H |
| Pr-i | H | I | CH₂OEt | MeS | H |
| Pr-i | H | I | CH₂OEt | MeSO | H |
| Pr-i | H | I | CH₂OPr-i | Ms | H |
| Pr-i | H | I | CH₂OPr-n | Ms | H |
| Pr-i | H | I | CH₂OCH=CH₂ | Ms | H |
| Pr-i | H | I | CH₂OCH₂CH=CH₂ | Ms | H |
| Pr-i | H | I | CH₂OCH₂C≡CH | Ms | H |
| Pr-i | H | I | CH₂OCH₂CH₂Cl | Ms | H |
| Pr-i | H | I | CHMeOH | Ms | H |
| Pr-i | H | I | CHMeOMe | Ms | H |
| Pr-i | H | I | CHMeOMe | Cl | H |
| Pr-i | H | I | CHMeOMe | MeS | H |
| Pr-i | H | I | CHMeOMe | MeSO | H |
| Pr-i | H | I | CHMeOEt | Ms | H |
| Pr-i | H | I | CHMeOCH=CH₂ | Ms | H |
| Pr-i | H | I | CHMeOCH=CH₂ | Ms | H |
| Pr-i | H | I | CHMeOCH₂CH=CH₂ | Ms | H |
| Pr-i | H | I | CHMeOCH₂C≡CH | Ms | H |
| Pr-i | H | I | CHMeOCH₂CH₂Cl | Ms | H |
| Pr-i | H | I | CMe₂OH | Ms | H |
| Pr-i | H | I | CMe₂OMe | Ms | H |
| Pr-i | H | I | CMe₂OEt | Ms | H |
| Pr-i | H | I | CH₂CH₂OMe | Ms | H |
| Pr-i | H | I | CH₂CH₂OEt | Ms | H |
| Pr-i | H | I | CHEtOH | Ms | H |
| Pr-i | H | I | CHEtOMe | Ms | H |
| Pr-i | H | I | CHEtOEt | Ms | H |
| Pr-i | H | I | CH₂OCH₂CH₂OMe | Ms | H |
| Pr-i | H | I | CHMeOCH₂CH₂OMe | Ms | H |
| Pr-i | H | I | CH₂NMe₂ | Ms | H |
| Pr-i | H | I | CHMeNMe₂ | Ms | H |
| Pr-i | H | I | CH₂CH₂NMe₂ | Ms | H |
| Pr-i | H | I | CH₂OCH₂Ph | Ms | H |
| Pr-i | H | I | CHMeOCH₂Ph | Ms | H |
| Pr-i | H | I | CH₂OCH₂CO₂Me | Ms | H |
| Pr-i | H | I | CH₂OCH₂CO₂Et | Ms | H |
| Pr-i | H | I | CH₂OCHMeCO₂Me | Ms | H |
| Pr-i | H | I | CH₂CN | Ms | H |
| Pr-i | H | I | CH₂SMe | Ms | H |
| Pr-i | H | I | CH₂SEt | Ms | H |
| Pr-i | H | I | CH₂SOMe | Ms | H |
| Pr-i | H | I | CH₂SO₂Me | Ms | H |
| Pr-i | H | I | CH₂SO₂Et | Ms | H |
| Pr-i | H | I | CHMeSMe | Ms | H |
| Pr-i | H | I | CHMeSO₂Me | Ms | H |
| Pr-i | H | I | CH₂SCH₂CH₂OMe | Ms | H |
| Pr-i | H | I | CH₂OCOMe | Ms | H |
| Pr-i | H | I | CHMeOCOMe | Ms | H |
| Pr-i | H | I | CH₂OSO₂Me | Ms | H |
| Pr-i | H | I | CHMeOSO₂Me | Ms | H |
| Me | H | Et | CH₂OH | Ms | H |
| Me | H | Et | CH₂OMe | Ms | H |
| Me | H | Et | CH₂OMe | Cl | H |
| Me | H | Et | CH₂OMe | MeS | H |
| Me | H | Et | CH₂OMe | MeSO | H |
| Me | H | Et | CH₂OEt | Ms | H |
| Me | H | Et | CH₂OEt | Cl | H |
| Me | H | Et | CH₂OEt | MeS | H |
| Me | H | Et | CH₂OEt | MeSO | H |
| Me | H | Et | CH₂OPr-i | Ms | H |
| Me | H | Et | CH₂OPr-n | Ms | H |
| Me | H | Et | CH₂OCH=CH₂ | Ms | H |
| Me | H | Et | CH₂OCH₂CH=CH₂ | Ms | H |
| Me | H | Et | CH₂OCH₂C≡CH | Ms | H |
| Me | H | Et | CH₂OCH₂CH₂Cl | Ms | H |
| Me | H | Et | CHMeOH | Ms | H |
| Me | H | Et | CHMeOMe | Ms | H |
| Me | H | Et | CHMeOMe | Cl | H |
| Me | H | Et | CHMeOMe | MeS | H |
| Me | H | Et | CHMeOMe | MeSO | H |
| Me | H | Et | CHMeOEt | Ms | H |
| Me | H | Et | CHMeOCH=CH₂ | Ms | H |
| Me | H | Et | CHMeOCH=CH₂ | Ms | H |
| Me | H | Et | CHMeOCH₂CH=CH₂ | Ms | H |
| Me | H | Et | CHMeOCH₂C≡CH | Ms | H |
| Me | H | Et | CHMeOCH₂CH₂Cl | Ms | H |

5,175,299

-continued

| | | | | | |
|---|---|---|---|---|---|
| Me | H | Et | CMe₂OH | Ms | H |
| Me | H | Et | CMe₂OMe | Ms | H |
| Me | H | Et | CMe₂OEt | Ms | H |
| Me | H | Et | CH₂CH₂OMe | Ms | H |
| Me | H | Et | CH₂CH₂OEt | Ms | H |
| Me | H | Et | CHEtOH | Ms | H |
| Me | H | Et | CHEtOMe | Ms | H |
| Me | H | Et | CHEtOEt | Ms | H |
| Me | H | Et | CH₂OCH₂CH₂OMe | Ms | H |
| Me | H | Et | CHMeOCH₂CH₂OMe | Ms | H |
| Me | H | Et | CH₂NMe₂ | Ms | H |
| Me | H | Et | CHMeNMe₂ | Ms | H |
| Me | H | Et | CH₂CH₂NMe₂ | Ms | H |
| Me | H | Et | CH₂OCH₂Ph | Ms | H |
| Me | H | Et | CHMeOCH₂Ph | Ms | H |
| Me | H | Et | CH₂OCH₂CO₂Me | Ms | H |
| Me | H | Et | CH₂OCH₂CO₂Et | Ms | H |
| Me | H | Et | CH₂OCHMeCO₂Me | Ms | H |
| Me | H | Et | CH₂CN | Ms | H |
| Me | H | Et | CH₂SMe | Ms | H |
| Me | H | Et | CH₂SEt | Ms | H |
| Me | H | Et | CH₂SOMe | Ms | H |
| Me | H | Et | CH₂SO₂Me | Ms | H |
| Me | H | Et | CH₂SO₂Et | Ms | H |
| Me | H | Et | CHMeSMe | Ms | H |
| Me | H | Et | CHMeSO₂Me | Ms | H |
| Me | H | Et | CH₂SCH₂CH₂OMe | Ms | H |
| Me | H | Et | CH₂OCOMe | Ms | H |
| Me | H | Et | CHMeOCOMe | Ms | H |
| Me | H | Et | CH₂OSO₂Me | Ms | H |
| Me | H | Et | CHMeOSO₂Me | Ms | H |
| Et | H | Et | CH₂OH | Ms | H |
| Et | H | Et | CH₂OMe | Ms | H |
| Et | H | Et | CH₂OMe | Cl | H |
| Et | H | Et | CH₂OMe | MeS | H |
| Et | H | Et | CH₂OMe | MeSO | H |
| Et | H | Et | CH₂OEt | Ms | H |
| Et | H | Et | CH₂OEt | Cl | H |
| Et | H | Et | CH₂OEt | MeS | H |
| Et | H | Et | CH₂OEt | MeSO | H |
| Et | H | Et | CH₂OPr-i | Ms | H |
| Et | H | Et | CH₂OPr-n | Ms | H |
| Et | H | Et | CH₂OCH=CH₂ | Ms | H |
| Et | H | Et | CH₂OCH₂CH=CH₂ | Ms | H |
| Et | H | Et | CH₂OCH₂C≡CH | Ms | H |
| Et | H | Et | CH₂OCH₂CH₂Cl | Ms | H |
| Et | H | Et | CHMeOH | Ms | H |
| Et | H | Et | CHMeOMe | Ms | H |
| Et | H | Et | CHMeOMe | Cl | H |
| Et | H | Et | CHMeOMe | MeS | H |
| Et | H | Et | CHMeOMe | MeSO | H |
| Et | H | Et | CHMeOEt | Ms | H |
| Et | H | Et | CHMeOCH=CH₂ | Ms | H |
| Et | H | Et | CHMeOCH=CH₂ | Ms | H |
| Et | H | Et | CHMeOCH₂CH=CH₂ | Ms | H |
| Et | H | Et | CHMeOCH₂C≡CH | Ms | H |
| Et | H | Et | CHMeOCH₂CH₂Cl | Ms | H |
| Et | H | Et | CMe₂OH | Ms | H |
| Et | H | Et | CMe₂OMe | Ms | H |
| Et | H | Et | CMe₂OEt | Ms | H |
| Et | H | Et | CH₂CH₂OMe | Ms | H |
| Et | H | Et | CH₂CH₂OEt | Ms | H |
| Et | H | Et | CHEtOH | Ms | H |
| Et | H | Et | CHEtOMe | Ms | H |
| Et | H | Et | CHEtOEt | Ms | H |
| Et | H | Et | CH₂OCH₂CH₂OMe | Ms | H |
| Et | H | Et | CHMeOCH₂CH₂OMe | Ms | H |
| Et | H | Et | CH₂NMe₂ | Ms | H |
| Et | H | Et | CHMeNMe₂ | Ms | H |
| Et | H | Et | CH₂CH₂NMe₂ | Ms | H |
| Et | H | Et | CH₂OCH₂Ph | Ms | H |
| Et | H | Et | CHMeOCH₂Ph | Ms | H |
| Et | H | Et | CH₂OCH₂CO₂Me | Ms | H |
| Et | H | Et | CH₂OCH₂CO₂Et | Ms | H |
| Et | H | Et | CH₂OCHMeCO₂Me | Ms | H |
| Et | H | Et | CH₂CN | Ms | H |
| Et | H | Et | CH₂SMe | Ms | H |
| Et | H | Et | CH₂SEt | Ms | H |
| Et | H | Et | CH₂SOMe | Ms | H |
| Et | H | Et | CH₂SO₂Me | Ms | H |
| Et | H | Et | CH₂SO₂Et | Ms | H |
| Et | H | Et | CHMeSMe | Ms | H |
| Et | H | Et | CHMeSO₂Me | Ms | H |

-continued

| | | | | | |
|---|---|---|---|---|---|
| Et | H | Et | CH$_2$SCH$_2$CH$_2$OMe | Ms | H |
| Et | H | Et | CH$_2$OCOMe | Ms | H |
| Et | H | Et | CHMeOCOMe | Ms | H |
| Et | H | Et | CH$_2$OSO$_2$Me | Ms | H |
| Et | H | Et | CHMeOSO$_2$Me | Ms | H |
| Pr-i | H | Et | CH$_2$OH | Ms | H |
| Pr-i | H | Et | CH$_2$OMe | Ms | H |
| Pr-i | H | Et | CH$_2$OMe | Cl | H |
| Pr-i | H | Et | CH$_2$OMe | MeS | H |
| Pr-i | H | Et | CH$_2$OMe | MeSO | H |
| Pr-i | H | Et | CH$_2$OEt | Ms | H |
| Pr-i | H | Et | CH$_2$OEt | Cl | H |
| Pr-i | H | Et | CH$_2$OEt | MeS | H |
| Pr-i | H | Et | CH$_2$OEt | MeSO | H |
| Pr-i | H | Et | CH$_2$OPr-i | Ms | H |
| Pr-i | H | Et | CH$_2$OPr-n | Ms | H |
| Pr-i | H | Et | CH$_2$OCH=CH$_2$ | Ms | H |
| Pr-i | H | Et | CH$_2$OCH$_2$CH=CH$_2$ | Ms | H |
| Pr-i | H | Et | CH$_2$OCH$_2$C≡CH | Ms | H |
| Pr-i | H | Et | CH$_2$OCH$_2$CH$_2$Cl | Ms | H |
| Pr-i | H | Et | CHMeOH | Ms | H |
| Pr-i | H | Et | CHMeOMe | Ms | H |
| Pr-i | H | Et | CHMeOMe | Cl | H |
| Pr-i | H | Et | CHMeOMe | MeS | H |
| Pr-i | H | Et | CHMeOMe | MeSO | H |
| Pr-i | H | Et | CHMeOEt | Ms | H |
| Pr-i | H | Et | CHMeOCH=CH$_2$ | Ms | H |
| Pr-i | H | Et | CHMeOCH=CH$_2$ | Ms | H |
| Pr-i | H | Et | CHMeOCH$_2$CH=CH$_2$ | Ms | H |
| Pr-i | H | Et | CHMeOCH$_2$C≡CH | Ms | H |
| Pr-i | H | Et | CHMeOCH$_2$CH$_2$Cl | Ms | H |
| Pr-i | H | Et | CMe$_2$OH | Ms | H |
| Pr-i | H | Et | CMe$_2$OMe | Ms | H |
| Pr-i | H | Et | CMe$_2$OEt | Ms | H |
| Pr-i | H | Et | CH$_2$CH$_2$OMe | Ms | H |
| Pr-i | H | Et | CH$_2$CH$_2$OEt | Ms | H |
| Pr-i | H | Et | CHEtOH | Ms | H |
| Pr-i | H | Et | CHEtOMe | Ms | H |
| Pr-i | H | Et | CHEtOEt | Ms | H |
| Pr-i | H | Et | CH$_2$OCH$_2$CH$_2$OMe | Ms | H |
| Pr-i | H | Et | CHMeOCH$_2$CH$_2$OMe | Ms | H |
| Pr-i | H | Et | CH$_2$NMe$_2$ | Ms | H |
| Pr-i | H | Et | CHMeNMe$_2$ | Ms | H |
| Pr-i | H | Et | CH$_2$CH$_2$NMe$_2$ | Ms | H |
| Pr-i | H | Et | CH$_2$OCH$_2$Ph | Ms | H |
| Pr-i | H | Et | CHMeOCH$_2$Ph | Ms | H |
| Pr-i | H | Et | CH$_2$OCH$_2$CO$_2$Me | Ms | H |
| Pr-i | H | Et | CH$_2$OCH$_2$CO$_2$Et | Ms | H |
| Pr-i | H | Et | CH$_2$OCHMeCO$_2$Me | Ms | H |
| Pr-i | H | Et | CH$_2$CN | Ms | H |
| Pr-i | H | Et | CH$_2$SMe | Ms | H |
| Pr-i | H | Et | CH$_2$SEt | Ms | H |
| Pr-i | H | Et | CH$_2$SOMe | Ms | H |
| Pr-i | H | Et | CH$_2$SO$_2$Me | Ms | H |
| Pr-i | H | Et | CH$_2$SO$_2$Et | Ms | H |
| Pr-i | H | Et | CHMeSMe | Ms | H |
| Pr-i | H | Et | CHMeSO$_2$Me | Ms | H |
| Pr-i | H | Et | CH$_2$SCH$_2$CH$_2$OMe | Ms | H |
| Pr-i | H | Et | CH$_2$OCOMe | Ms | H |
| Pr-i | H | Et | CHMeOCOMe | Ms | H |
| Pr-i | H | Et | CH$_2$OSO$_2$Me | Ms | H |
| Pr-i | H | Et | CHMeOSO$_2$Me | Ms | H |
| Me | Me | Br | CH$_2$OH | Ms | H |
| Me | Me | Br | CH$_2$OMe | Ms | H |
| Me | Me | Br | CH$_2$OMe | Cl | H |
| Me | Me | Br | CH$_2$OMe | MeS | H |
| Me | Me | Br | CH$_2$OMe | MeSO | H |
| Me | Me | Br | CH$_2$OEt | Ms | H |
| Me | Me | Br | CH$_2$OEt | Cl | H |
| Me | Me | Br | CH$_2$OEt | MeS | H |
| Me | Me | Br | CH$_2$OEt | MeSO | H |
| Me | Me | Br | CH$_2$OPr-i | Ms | H |
| Me | Me | Br | CH$_2$OPr-n | Ms | H |
| Me | Me | Br | CH$_2$OCH=CH$_2$ | Ms | H |
| Me | Me | Br | CH$_2$OCH$_2$CH=CH$_2$ | Ms | H |
| Me | Me | Br | CH$_2$OCH$_2$C≡CH | Ms | H |
| Me | Me | Br | CH$_2$OCH$_2$CH$_2$Cl | Ms | H |
| Me | Me | Br | CHMeOH | Ms | H |
| Me | Me | Br | CHMeOMe | Ms | H |
| Me | Me | Br | CHMeOMe | Cl | H |
| Me | Me | Br | CHMeOMe | MeS | H |
| Me | Me | Br | CHMeOMe | MeSO | H |
| Me | Me | Br | CHMeOEt | Ms | H |

-continued

| | | | | | |
|---|---|---|---|---|---|
| Me | Me | Br | CH$_2$CH$_2$OMe | Ms | H |
| Me | Me | Br | CH$_2$CH$_2$OEt | Ms | H |
| Me | Me | Br | CHEtOH | Ms | H |
| Me | Me | Br | CHEtOMe | Ms | H |
| Me | Me | Br | CHEtOEt | Ms | H |
| Me | Me | Br | CH$_2$OCH$_2$CH$_2$OMe | Ms | H |
| Me | Me | Br | CH$_2$NMe$_2$ | Ms | H |
| Me | Me | Br | CH$_2$OCH$_2$Ph | Ms | H |
| Me | Me | Br | CH$_2$OCH$_2$CO$_2$Me | Ms | H |
| Me | Me | Br | CH$_2$OCH$_2$CO$_2$Et | Ms | H |
| Me | Me | Br | CH$_2$OCHMeCO$_2$Me | Ms | H |
| Me | Me | Br | CH$_2$CN | Ms | H |
| Me | Me | Br | CH$_2$SMe | Ms | H |
| Me | Me | Br | CH$_2$SEt | Ms | H |
| Me | Me | Br | CH$_2$SO$_2$Me | Ms | H |
| Me | Me | Br | CH$_2$SO$_2$Et | Ms | H |
| Me | Me | Br | CH$_2$SCH$_2$CH$_2$OMe | Ms | H |
| Me | Me | Br | CH$_2$OCOMe | Ms | H |
| Me | Me | Br | CHMeOCOMe | Ms | H |
| Me | Me | Br | CH$_2$OSO$_2$Me | Ms | H |
| Me | Me | Br | CHMeOSO$_2$Me | Ms | H |
| Et | Me | Br | CH$_2$OH | Ms | H |
| Et | Me | Br | CH$_2$OMe | Ms | H |
| Et | Me | Br | CH$_2$OMe | Cl | H |
| Et | Me | Br | CH$_2$OMe | MeS | H |
| Et | Me | Br | CH$_2$OMe | MeSO | H |
| Et | Me | Br | CH$_2$OEt | Ms | H |
| Et | Me | Br | CH$_2$OEt | Cl | H |
| Et | Me | Br | CH$_2$OEt | MeS | H |
| Et | Me | Br | CH$_2$OEt | MeSO | H |
| Et | Me | Br | CH$_2$OPr-i | Ms | H |
| Et | Me | Br | CH$_2$OPr-n | Ms | H |
| Et | Me | Br | CH$_2$OCH=CH$_2$ | Ms | H |
| Et | Me | Br | CH$_2$OCH$_2$CH=CH$_2$ | Ms | H |
| Et | Me | Br | CH$_2$OCH$_2$C≡CH | Ms | H |
| Et | Me | Br | CH$_2$OCH$_2$CH$_2$Cl | Ms | H |
| Et | Me | Br | CHMeOH | Ms | H |
| Et | Me | Br | CHMeOMe | Ms | H |
| Et | Me | Br | CHMeOMe | Cl | H |
| Et | Me | Br | CHMeOMe | MeS | H |
| Et | Me | Br | CHMeOMe | MeSO | H |
| Et | Me | Br | CHMeOEt | Ms | H |
| Et | Me | Br | CH$_2$CH$_2$OMe | Ms | H |
| Et | Me | Br | CH$_2$CH$_2$OEt | Ms | H |
| Et | Me | Br | CHEtOH | Ms | H |
| Et | Me | Br | CHEtOMe | Ms | H |
| Et | Me | Br | CHEtOEt | Ms | H |
| Et | Me | Br | CH$_2$OCH$_2$CH$_2$OMe | Ms | H |
| Et | Me | Br | CH$_2$NMe$_2$ | Ms | H |
| Et | Me | Br | CH$_2$OCH$_2$Ph | Ms | H |
| Et | Me | Br | CH$_2$OCH$_2$CO$_2$Me | Ms | H |
| Et | Me | Br | CH$_2$OCH$_2$CO$_2$Et | Ms | H |
| Et | Me | Br | CH$_2$OCHMeCO$_2$Me | Ms | H |
| Et | Me | Br | CH$_2$CN | Ms | H |
| Et | Me | Br | CH$_2$SMe | Ms | H |
| Et | Me | Br | CH$_2$SEt | Ms | H |
| Et | Me | Br | CH$_2$SO$_2$Me | Ms | H |
| Et | Me | Br | CH$_2$SO$_2$Et | Ms | H |
| Et | Me | Br | CH$_2$SCH$_2$CH$_2$OMe | Ms | H |
| Et | Me | Br | CH$_2$OCOMe | Ms | H |
| Et | Me | Br | CHMeOCOMe | Ms | H |
| Et | Me | Br | CH$_2$OSO$_2$Me | Ms | H |
| Et | Me | Br | CHMeOSO$_2$Me | Ms | H |
| Pr-i | Me | Br | CH$_2$OH | Ms | H |
| Pr-i | Me | Br | CH$_2$OMe | Ms | H |
| Pr-i | Me | Br | CH$_2$OMe | Cl | H |
| Pr-i | Me | Br | CH$_2$OMe | MeS | H |
| Pr-i | Me | Br | CH$_2$OMe | MeSO | H |
| Pr-i | Me | Br | CH$_2$OEt | Ms | H |
| Pr-i | Me | Br | CH$_2$OEt | Cl | H |
| Pr-i | Me | Br | CH$_2$OEt | MeS | H |
| Pr-i | Me | Br | CH$_2$OEt | MeSO | H |
| Pr-i | Me | Br | CH$_2$OPr-i | Ms | H |
| Pr-i | Me | Br | CH$_2$OPr-n | Ms | H |
| Pr-i | Me | Br | CH$_2$OCH=CH$_2$ | Ms | H |
| Pr-i | Me | Br | CH$_2$OCH$_2$CH=CH$_2$ | Ms | H |
| Pr-i | Me | Br | CH$_2$OCH$_2$C≡CH | Ms | H |
| Pr-i | Me | Br | CH$_2$OCH$_2$CH$_2$Cl | Ms | H |
| Pr-i | Me | Br | CHMeOH | Ms | H |
| Pr-i | Me | Br | CHMeOMe | Ms | H |
| Pr-i | Me | Br | CHMeOMe | Cl | H |
| Pr-i | Me | Br | CHMeOMe | MeS | H |
| Pr-i | Me | Br | CHMeOMe | MeSO | H |

-continued

| | | | | | |
|---|---|---|---|---|---|
| Pr-i | Me | Br | CHMeOEt | Ms | H |
| Pr-i | Me | Br | CH$_2$CH$_2$OMe | Ms | H |
| Pr-i | Me | Br | CH$_2$CH$_2$OEt | Ms | H |
| Pr-i | Me | Br | CHEtOH | Ms | H |
| Pr-i | Me | Br | CHEtOMe | Ms | H |
| Pr-i | Me | Br | CHEtOEt | Ms | H |
| Pr-i | Me | Br | CH$_2$OCH$_2$CH$_2$OMe | Ms | H |
| Pr-i | Me | Br | CH$_2$NMe$_2$ | Ms | H |
| Pr-i | Me | Br | CH$_2$OCH$_2$Ph | Ms | H |
| Pr-i | Me | Br | CH$_2$OCH$_2$CO$_2$Me | Ms | H |
| Pr-i | Me | Br | CH$_2$OCH$_2$CO$_2$Et | Ms | H |
| Pr-i | Me | Br | CH$_2$OCHMeCO$_2$Me | Ms | H |
| Pr-i | Me | Br | CH$_2$CN | Ms | H |
| Pr-i | Me | Br | CH$_2$SMe | Ms | H |
| Pr-i | Me | Br | CH$_2$SEt | Ms | H |
| Pr-i | Me | Br | CH$_2$SO$_2$Me | Ms | H |
| Pr-i | Me | Br | CH$_2$SO$_2$Et | Ms | H |
| Pr-i | Me | Br | CH$_2$SCH$_2$CH$_2$OMe | Ms | H |
| Pr-i | Me | Br | CH$_2$OCOMe | Ms | H |
| Pr-i | Me | Br | CHMeOCOMe | Ms | H |
| Pr-i | Me | Br | CH$_2$OSO$_2$Me | Ms | H |
| Pr-i | Me | Br | CHMeOSO$_2$Me | Ms | H |
| Me | Me | I | CH$_2$OH | Ms | H |
| Me | Me | I | CH$_2$OMe | Ms | H |
| Me | Me | I | CH$_2$OMe | Cl | H |
| Me | Me | I | CH$_2$OMe | MeS | H |
| Me | Me | I | CH$_2$OMe | MeSO | H |
| Me | Me | I | CH$_2$OEt | Ms | H |
| Me | Me | I | CH$_2$OEt | Cl | H |
| Me | Me | I | CH$_2$OEt | MeS | H |
| Me | Me | I | CH$_2$OEt | MeSO | H |
| Me | Me | I | CH$_2$OPr-i | Ms | H |
| Me | Me | I | CH$_2$OPr-n | Ms | H |
| Me | Me | I | CH$_2$OCH=CH$_2$ | Ms | H |
| Me | Me | I | CH$_2$OCH$_2$CH=CH$_2$ | Ms | H |
| Me | Me | I | CH$_2$OCH$_2$C≡CH | Ms | H |
| Me | Me | I | CH$_2$OCH$_2$CH$_2$Cl | Ms | H |
| Me | Me | I | CHMeOH | Ms | H |
| Me | Me | I | CHMeOMe | Ms | H |
| Me | Me | I | CHMeOMe | Cl | H |
| Me | Me | I | CHMeOMe | MeS | H |
| Me | Me | I | CHMeOMe | MeSO | H |
| Me | Me | I | CHMeOEt | Ms | H |
| Me | Me | I | CH$_2$CH$_2$OMe | Ms | H |
| Me | Me | I | CH$_2$CH$_2$OEt | Ms | H |
| Me | Me | I | CHEtOH | Ms | H |
| Me | Me | I | CHEtOMe | Ms | H |
| Me | Me | I | CHEtOEt | Ms | H |
| Me | Me | I | CH$_2$OCH$_2$CH$_2$OMe | Ms | H |
| Me | Me | I | CH$_2$NMe$_2$ | Ms | H |
| Me | Me | I | CH$_2$OCH$_2$Ph | Ms | H |
| Me | Me | I | CH$_2$OCH$_2$CO$_2$Me | Ms | H |
| Me | Me | I | CH$_2$OCH$_2$CO$_2$Et | Ms | H |
| Me | Me | I | CH$_2$OCHMeCO$_2$Me | Ms | H |
| Me | Me | I | CH$_2$CN | Ms | H |
| Me | Me | I | CH$_2$SMe | Ms | H |
| Me | Me | I | CH$_2$SEt | Ms | H |
| Me | Me | I | CH$_2$SO$_2$Me | Ms | H |
| Me | Me | I | CH$_2$SO$_2$Et | Ms | H |
| Me | Me | I | CH$_2$SCH$_2$CH$_2$OMe | Ms | H |
| Me | Me | I | CH$_2$OCOMe | Ms | H |
| Me | Me | I | CHMeOCOMe | Ms | H |
| Me | Me | I | CH$_2$OSO$_2$Me | Ms | H |
| Me | Me | I | CHMeOSO$_2$Me | Ms | H |
| Et | Me | I | CH$_2$OH | Ms | H |
| Et | Me | I | CH$_2$OMe | Ms | H |
| Et | Me | I | CH$_2$OMe | Cl | H |
| Et | Me | I | CH$_2$OMe | MeS | H |
| Et | Me | I | CH$_2$OMe | MeSO | H |
| Et | Me | I | CH$_2$OEt | Ms | H |
| Et | Me | I | CH$_2$OEt | Cl | H |
| Et | Me | I | CH$_2$OEt | MeS | H |
| Et | Me | I | CH$_2$OEt | MeSO | H |
| Et | Me | I | CH$_2$OPr-i | Ms | H |
| Et | Me | I | CH$_2$OPr-n | Ms | H |
| Et | Me | I | CH$_2$OCH=CH$_2$ | Ms | H |
| Et | Me | I | CH$_2$OCH$_2$CH=CH$_2$ | Ms | H |
| Et | Me | I | CH$_2$OCH$_2$C≡CH | Ms | H |
| Et | Me | I | CH$_2$OCH$_2$CH$_2$Cl | Ms | H |
| Et | Me | I | CHMeOH | Ms | H |
| Et | Me | I | CHMeOMe | Ms | H |
| Et | Me | I | CHMeOMe | Cl | H |
| Et | Me | I | CHMeOMe | MeS | H |

-continued

| | | | | | |
|---|---|---|---|---|---|
| Et | Me | I | CHMeOMe | MeSO | H |
| Et | Me | I | CHMeOEt | Ms | H |
| Et | Me | I | CH$_2$CH$_2$OMe | Ms | H |
| Et | Me | I | CH$_2$CH$_2$OEt | Ms | H |
| Et | Me | I | CHEtOH | Ms | H |
| Et | Me | I | CHEtOMe | Ms | H |
| Et | Me | I | CHEtOEt | Ms | H |
| Et | Me | I | CH$_2$OCH$_2$CH$_2$OMe | Ms | H |
| Et | Me | I | CH$_2$NMe$_2$ | Ms | H |
| Et | Me | I | CH$_2$OCH$_2$Ph | Ms | H |
| Et | Me | I | CH$_2$OCH$_2$CO$_2$Me | Ms | H |
| Et | Me | I | CH$_2$OCH$_2$CO$_2$Et | Ms | H |
| Et | Me | I | CH$_2$OCHMeCO$_2$Me | Ms | H |
| Et | Me | I | CH$_2$CN | Ms | H |
| Et | Me | I | CH$_2$SMe | Ms | H |
| Et | Me | I | CH$_2$SEt | Ms | H |
| Et | Me | I | CH$_2$SO$_2$Me | Ms | H |
| Et | Me | I | CH$_2$SO$_2$Et | Ms | H |
| Et | Me | I | CH$_2$SCH$_2$CH$_2$OMe | Ms | H |
| Et | Me | I | CH$_2$OCOMe | Ms | H |
| Et | Me | I | CHMeOCOMe | Ms | H |
| Et | Me | I | CH$_2$OSO$_2$Me | Ms | H |
| Et | Me | I | CHMeOSO$_2$Me | Ms | H |
| Pr-i | Me | I | CH$_2$OH | Ms | H |
| Pr-i | Me | I | CH$_2$OMe | Ms | H |
| Pr-i | Me | I | CH$_2$OMe | Cl | H |
| Pr-i | Me | I | CH$_2$OMe | MeS | H |
| Pr-i | Me | I | CH$_2$OMe | MeSO | H |
| Pr-i | Me | I | CH$_2$OEt | Ms | H |
| Pr-i | Me | I | CH$_2$OEt | Cl | H |
| Pr-i | Me | I | CH$_2$OEt | MeS | H |
| Pr-i | Me | I | CH$_2$OEt | MeSO | H |
| Pr-i | Me | I | CH$_2$OPr-i | Ms | H |
| Pr-i | Me | I | CH$_2$OPr-n | Ms | H |
| Pr-i | Me | I | CH$_2$OCH=CH$_2$ | Ms | H |
| Pr-i | Me | I | CH$_2$OCH$_2$CH=CH$_2$ | Ms | H |
| Pr-i | Me | I | CH$_2$OCH$_2$C≡CH | Ms | H |
| Pr-i | Me | I | CH$_2$OCH$_2$CH$_2$Cl | Ms | H |
| Pr-i | Me | I | CHMeOH | Ms | H |
| Pr-i | Me | I | CHMeOMe | Ms | H |
| Pr-i | Me | I | CHMeOMe | Cl | H |
| Pr-i | Me | I | CHMeOMe | MeS | H |
| Pr-i | Me | I | CHMeOMe | MeSO | H |
| Pr-i | Me | I | CHMeOEt | Ms | H |
| Pr-i | Me | I | CH$_2$CH$_2$OMe | Ms | H |
| Pr-i | Me | I | CH$_2$CH$_2$OEt | Ms | H |
| Pr-i | Me | I | CHEtOH | Ms | H |
| Pr-i | Me | I | CHEtOMe | Ms | H |
| Pr-i | Me | I | CHEtOEt | Ms | H |
| Pr-i | Me | I | CH$_2$OCH$_2$CH$_2$OMe | Ms | H |
| Pr-i | Me | I | CH$_2$NMe$_2$ | Ms | H |
| Pr-i | Me | I | CH$_2$OCH$_2$Ph | Ms | H |
| Pr-i | Me | I | CH$_2$OCH$_2$CO$_2$Me | Ms | H |
| Pr-i | Me | I | CH$_2$OCH$_2$CO$_2$Et | Ms | H |
| Pr-i | Me | I | CH$_2$OCHMeCO$_2$Me | Ms | H |
| Pr-i | Me | I | CH$_2$CN | Ms | H |
| Pr-i | Me | I | CH$_2$SMe | Ms | H |
| Pr-i | Me | I | CH$_2$SEt | Ms | H |
| Pr-i | Me | I | CH$_2$SO$_2$Me | Ms | H |
| Pr-i | Me | I | CH$_2$SO$_2$Et | Ms | H |
| Pr-i | Me | I | CH$_2$SCH$_2$CH$_2$OMe | Ms | H |
| Pr-i | Me | I | CH$_2$OCOMe | Ms | H |
| Pr-i | Me | I | CHMeOCOMe | Ms | H |
| Pr-i | Me | I | CH$_2$OSO$_2$Me | Ms | H |
| Pr-i | Me | I | CHMeOSO$_2$Me | Ms | H |
| Me | Me | Et | CH$_2$OH | Ms | H |
| Me | Me | Et | CH$_2$OMe | Ms | H |
| Me | Me | Et | CH$_2$OMe | Cl | H |
| Me | Me | Et | CH$_2$OMe | MeS | H |
| Me | Me | Et | CH$_2$OMe | MeSO | H |
| Me | Me | Et | CH$_2$OEt | Ms | H |
| Me | Me | Et | CH$_2$OEt | Cl | H |
| Me | Me | Et | CH$_2$OEt | MeS | H |
| Me | Me | Et | CH$_2$OEt | MeSO | H |
| Me | Me | Et | CH$_2$OPr-i | Ms | H |
| Me | Me | Et | CH$_2$OPr-n | Ms | H |
| Me | Me | Et | CH$_2$OCH=CH$_2$ | Ms | H |
| Me | Me | Et | CH$_2$OCH$_2$CH=CH$_2$ | Ms | H |
| Me | Me | Et | CH$_2$OCH$_2$C≡CH | Ms | H |
| Me | Me | Et | CH$_2$OCH$_2$CH$_2$Cl | Ms | H |
| Me | Me | Et | CHMeOH | Ms | H |
| Me | Me | Et | CHMeOMe | Ms | H |
| Me | Me | Et | CHMeOMe | Cl | H |

-continued

| | | | | | |
|---|---|---|---|---|---|
| Me | Me | Et | CHMeOMe | MeS | H |
| Me | Me | Et | CHMeOMe | MeSO | H |
| Me | Me | Et | CHMeOEt | Ms | H |
| Me | Me | Et | CH$_2$CH$_2$OMe | Ms | H |
| Me | Me | Et | CH$_2$CH$_2$OEt | Ms | H |
| Me | Me | Et | CHEtOH | Ms | H |
| Me | Me | Et | CHEtOMe | Ms | H |
| Me | Me | Et | CHEtOEt | Ms | H |
| Me | Me | Et | CH$_2$OCH$_2$CH$_2$OMe | Ms | H |
| Me | Me | Et | CH$_2$NMe$_2$ | Ms | H |
| Me | Me | Et | CH$_2$OCH$_2$Ph | Ms | H |
| Me | Me | Et | CH$_2$OCH$_2$CO$_2$Me | Ms | H |
| Me | Me | Et | CH$_2$OCH$_2$CO$_2$Et | Ms | H |
| Me | Me | Et | CH$_2$OCHMeCO$_2$Me | Ms | H |
| Me | Me | Et | CH$_2$CN | Ms | H |
| Me | Me | Et | CH$_2$SMe | Ms | H |
| Me | Me | Et | CH$_2$SEt | Ms | H |
| Me | Me | Et | CH$_2$SO$_2$Me | Ms | H |
| Me | Me | Et | CH$_2$SO$_2$Et | Ms | H |
| Me | Me | Et | CH$_2$SCH$_2$CH$_2$OMe | Ms | H |
| Me | Me | Et | CH$_2$OCOMe | Ms | H |
| Me | Me | Et | CHMeOCOMe | Ms | H |
| Me | Me | Et | CH$_2$OSO$_2$Me | Ms | H |
| Me | Me | Et | CHMeOSO$_2$Me | Ms | H |
| Et | Me | Et | CH$_2$OH | Ms | H |
| Et | Me | Et | CH$_2$OMe | Ms | H |
| Et | Me | Et | CH$_2$OMe | Cl | H |
| Et | Me | Et | CH$_2$OMe | MeS | H |
| Et | Me | Et | CH$_2$OMe | MeSO | H |
| Et | Me | Et | CH$_2$OEt | Ms | H |
| Et | Me | Et | CH$_2$OEt | Cl | H |
| Et | Me | Et | CH$_2$OEt | MeS | H |
| Et | Me | Et | CH$_2$OEt | MeSO | H |
| Et | Me | Et | CH$_2$OPr-i | Ms | H |
| Et | Me | Et | CH$_2$OPr-n | Ms | H |
| Et | Me | Et | CH$_2$OCH=CH$_2$ | Ms | H |
| Et | Me | Et | CH$_2$OCH$_2$CH=CH$_2$ | Ms | H |
| Et | Me | Et | CH$_2$OCH$_2$C≡CH | Ms | H |
| Et | Me | Et | CH$_2$OCH$_2$CH$_2$Cl | Ms | H |
| Et | Me | Et | CHMeOH | Ms | H |
| Et | Me | Et | CHMeOMe | Ms | H |
| Et | Me | Et | CHMeOMe | Cl | H |
| Et | Me | Et | CHMeOMe | MeS | H |
| Et | Me | Et | CHMeOMe | MeSO | H |
| Et | Me | Et | CHMeOEt | Ms | H |
| Et | Me | Et | CH$_2$CH$_2$OMe | Ms | H |
| Et | Me | Et | CH$_2$CH$_2$OEt | Ms | H |
| Et | Me | Et | CHEtOH | Ms | H |
| Et | Me | Et | CHEtOMe | Ms | H |
| Et | Me | Et | CHEtOEt | Ms | H |
| Et | Me | Et | CH$_2$OCH$_2$CH$_2$OMe | Ms | H |
| Et | Me | Et | CH$_2$NMe$_2$ | Ms | H |
| Et | Me | Et | CH$_2$OCH$_2$Ph | Ms | H |
| Et | Me | Et | CH$_2$OCH$_2$CO$_2$Me | Ms | H |
| Et | Me | Et | CH$_2$OCH$_2$CO$_2$Et | Ms | H |
| Et | Me | Et | CH$_2$OCHMeCO$_2$Me | Ms | H |
| Et | Me | Et | CH$_2$CN | Ms | H |
| Et | Me | Et | CH$_2$SMe | Ms | H |
| Et | Me | Et | CH$_2$SEt | Ms | H |
| Et | Me | Et | CH$_2$SO$_2$Me | Ms | H |
| Et | Me | Et | CH$_2$SO$_2$Et | Ms | H |
| Et | Me | Et | CH$_2$SCH$_2$CH$_2$OMe | Ms | H |
| Et | Me | Et | CH$_2$OCOMe | Ms | H |
| Et | Me | Et | CHMeOCOMe | Ms | H |
| Et | Me | Et | CH$_2$OSO$_2$Me | Ms | H |
| Et | Me | Et | CHMeOSO$_2$Me | Ms | H |
| Pr-i | Me | Et | CH$_2$OH | Ms | H |
| Pr-i | Me | Et | CH$_2$OMe | Ms | H |
| Pr-i | Me | Et | CH$_2$OMe | Cl | H |
| Pr-i | Me | Et | CH$_2$OMe | MeS | H |
| Pr-i | Me | Et | CH$_2$OMe | MeSO | H |
| Pr-i | Me | Et | CH$_2$OEt | Ms | H |
| Pr-i | Me | Et | CH$_2$OEt | Cl | H |
| Pr-i | Me | Et | CH$_2$OEt | MeS | H |
| Pr-i | Me | Et | CH$_2$OEt | MeSO | H |
| Pr-i | Me | Et | CH$_2$OPr-i | Ms | H |
| Pr-i | Me | Et | CH$_2$OPr-n | Ms | H |
| Pr-i | Me | Et | CH$_2$OCH=CH$_2$ | Ms | H |
| Pr-i | Me | Et | CH$_2$OCH$_2$CH=CH$_2$ | Ms | H |
| Pr-i | Me | Et | CH$_2$OCH$_2$C≡CH | Ms | H |
| Pr-i | Me | Et | CH$_2$OCH$_2$CH$_2$Cl | Ms | H |
| Pr-i | Me | Et | CHMeOH | Ms | H |
| Pr-i | Me | Et | CHMeOMe | Ms | H |

-continued

| | | | | | |
|---|---|---|---|---|---|
| Pr-i | Me | Et | CHMeOMe | Cl | H |
| Pr-i | Me | Et | CHMeOMe | MeS | H |
| Pr-i | Me | Et | CHMeOMe | MeSO | H |
| Pr-i | Me | Et | CHMeOEt | Ms | H |
| Pr-i | Me | Et | CH$_2$CH$_2$OMe | Ms | H |
| Pr-i | Me | Et | CH$_2$CH$_2$OEt | Ms | H |
| Pr-i | Me | Et | CHEtOH | Ms | H |
| Pr-i | Me | Et | CHEtOMe | Ms | H |
| Pr-i | Me | Et | CHEtOEt | Ms | H |
| Pr-i | Me | Et | CH$_2$OCH$_2$CH$_2$OMe | Ms | H |
| Pr-i | Me | Et | CH$_2$NMe$_2$ | Ms | H |
| Pr-i | Me | Et | CH$_2$OCH$_2$Ph | Ms | H |
| Pr-i | Me | Et | CH$_2$OCH$_2$CO$_2$Me | Ms | H |
| Pr-i | Me | Et | CH$_2$OCH$_2$CO$_2$Et | Ms | H |
| Pr-i | Me | Et | CH$_2$OCHMeCO$_2$Me | Ms | H |
| Pr-i | Me | Et | CH$_2$CN | Ms | H |
| Pr-i | Me | Et | CH$_2$SMe | Ms | H |
| Pr-i | Me | Et | CH$_2$SEt | Ms | H |
| Pr-i | Me | Et | CH$_2$SO$_2$Me | Ms | H |
| Pr-i | Me | Et | CH$_2$SO$_2$Et | Ms | H |
| Pr-i | Me | Et | CH$_2$SCH$_2$CH$_2$OMe | Ms | H |
| Pr-i | Me | Et | CH$_2$OCOMe | Ms | H |
| Pr-i | Me | Et | CHMeOCOMe | Ms | H |
| Pr-i | Me | Et | CH$_2$OSO$_2$Me | Ms | H |
| Pr-i | Me | Et | CHMeOSO$_2$Me | Ms | H |
| CH$_2$CH=CH$_2$ | H | Me | CH$_2$OH | Ms | H |
| CH$_2$CH=CH$_2$ | H | Me | CH$_2$OMe | Ms | H |
| CH$_2$CH=CH$_2$ | H | Me | CH$_2$OMe | Cl | H |
| CH$_2$CH=CH$_2$ | H | Me | CH$_2$OMe | MeS | H |
| CH$_2$CH=CH$_2$ | H | Me | CH$_2$OMe | MeSO | H |
| CH$_2$CH=CH$_2$ | H | Me | CH$_2$OEt | Ms | H |
| CH$_2$CH=CH$_2$ | H | Me | CH$_2$OEt | Cl | H |
| CH$_2$CH=CH$_2$ | H | Me | CH$_2$OEt | MeS | H |
| CH$_2$CH=CH$_2$ | H | Me | CH$_2$OEt | MeSO | H |
| CH$_2$CH=CH$_2$ | H | Me | CH$_2$OPr-i | Ms | H |
| CH$_2$CH=CH$_2$ | H | Me | CH$_2$OPr-n | Ms | H |
| CH$_2$CH=CH$_2$ | H | Me | CH$_2$OCH=CH$_2$ | Ms | H |
| CH$_2$CH=CH$_2$ | H | Me | CH$_2$OCH$_2$CH=CH$_2$ | Ms | H |
| CH$_2$CH=CH$_2$ | H | Me | CH$_2$OCH$_2$C≡CH | Ms | H |
| CH$_2$CH=CH$_2$ | H | Me | CH$_2$OCH$_2$CH$_2$Cl | Ms | H |
| CH$_2$CH=CH$_2$ | H | Me | CHMeOH | Ms | H |
| CH$_2$CH=CH$_2$ | H | Me | CHMeOMe | Ms | H |
| CH$_2$CH=CH$_2$ | H | Me | CHMeOMe | Cl | H |
| CH$_2$CH=CH$_2$ | H | Me | CHMeOMe | MeS | H |
| CH$_2$CH=CH$_2$ | H | Me | CHMeOMe | MeSO | H |
| CH$_2$CH=CH$_2$ | H | Me | CHMeOEt | Ms | H |
| CH$_2$CH=CH$_2$ | H | Me | CHMeOCH=CH$_2$ | Ms | H |
| CH$_2$CH=CH$_2$ | H | Me | CHMeOCH=CH$_2$ | Ms | H |
| CH$_2$CH=CH$_2$ | H | Me | CHMeOCH$_2$CH=CH$_2$ | Ms | H |
| CH$_2$CH=CH$_2$ | H | Me | CHMeOCH$_2$C≡CH | Ms | H |
| CH$_2$CH=CH$_2$ | H | Me | CHMeOCH$_2$CH$_2$Cl | Ms | H |
| CH$_2$CH=CH$_2$ | H | Me | CMe$_2$OH | Ms | H |
| CH$_2$CH=CH$_2$ | H | Me | CMe$_2$OMe | Ms | H |
| CH$_2$CH=CH$_2$ | H | Me | CMe$_2$OEt | Ms | H |
| CH$_2$CH=CH$_2$ | H | Me | CH$_2$CH$_2$OMe | Ms | H |
| CH$_2$CH=CH$_2$ | H | Me | CH$_2$CH$_2$OEt | Ms | H |
| CH$_2$CH=CH$_2$ | H | Me | CHEtOH | Ms | H |
| CH$_2$CH=CH$_2$ | H | Me | CHEtOMe | Ms | H |
| CH$_2$CH=CH$_2$ | H | Me | CHEtOEt | Ms | H |
| CH$_2$CH=CH$_2$ | H | Me | CH$_2$OCH$_2$CH$_2$OMe | Ms | H |
| CH$_2$CH=CH$_2$ | H | Me | CHMeOCH$_2$CH$_2$OMe | Ms | H |
| CH$_2$CH=CH$_2$ | H | Me | CH$_2$NMe$_2$ | Ms | H |
| CH$_2$CH=CH$_2$ | H | Me | CHMeNMe$_2$ | Ms | H |
| CH$_2$CH=CH$_2$ | H | Me | CH$_2$CH$_2$NMe$_2$ | Ms | H |
| CH$_2$CH=CH$_2$ | H | Me | CH$_2$OCH$_2$Ph | Ms | H |
| CH$_2$CH=CH$_2$ | H | Me | CHMeOCH$_2$Ph | Ms | H |
| CH$_2$CH=CH$_2$ | H | Me | CH$_2$OCH$_2$CO$_2$Me | Ms | H |
| CH$_2$CH=CH$_2$ | H | Me | CH$_2$OCH$_2$CO$_2$Et | Ms | H |
| CH$_2$CH=CH$_2$ | H | Me | CH$_2$OCHMeCO$_2$Me | Ms | H |
| CH$_2$CH=CH$_2$ | H | Me | CH$_2$CN | Ms | H |
| CH$_2$CH=CH$_2$ | H | Me | CH$_2$SMe | Ms | H |
| CH$_2$CH=CH$_2$ | H | Me | CH$_2$SEt | Ms | H |
| CH$_2$CH=CH$_2$ | H | Me | CH$_2$SOMe | Ms | H |
| CH$_2$CH=CH$_2$ | H | Me | CH$_2$SO$_2$Me | Ms | H |
| CH$_2$CH=CH$_2$ | H | Me | CH$_2$SO$_2$Et | Ms | H |
| CH$_2$CH=CH$_2$ | H | Me | CHMeSMe | Ms | H |
| CH$_2$CH=CH$_2$ | H | Me | CHMeSO$_2$Me | Ms | H |
| CH$_2$CH=CH$_2$ | H | Me | CH$_2$SCH$_2$CH$_2$OMe | Ms | H |
| CH$_2$CH=CH$_2$ | H | Me | CH$_2$OCOMe | Ms | H |
| CH$_2$CH=CH$_2$ | H | Me | CHMeOCOMe | Ms | H |
| CH$_2$CH=CH$_2$ | H | Me | CH$_2$OSO$_2$Me | Ms | H |
| CH$_2$CH=CH$_2$ | H | Me | CHMeOSO$_2$Me | Ms | H |
| CH$_2$C≡CH | H | Me | CH$_2$OH | Ms | H |

-continued

| | | | | | |
|---|---|---|---|---|---|
| CH$_2$C≡CH | H | Me | CH$_2$OMe | Ms | H |
| CH$_2$C≡CH | H | Me | CH$_2$OMe | Cl | H |
| CH$_2$C≡CH | H | Me | CH$_2$OMe | MeS | H |
| CH$_2$C≡CH | H | Me | CH$_2$OMe | MeSO | H |
| CH$_2$C≡CH | H | Me | CH$_2$OEt | Ms | H |
| CH$_2$C≡CH | H | Me | CH$_2$OEt | Cl | H |
| CH$_2$C≡CH | H | Me | CH$_2$OEt | MeS | H |
| CH$_2$C≡CH | H | Me | CH$_2$OEt | MeSO | H |
| CH$_2$C≡CH | H | Me | CH$_2$OPr-i | Ms | H |
| CH$_2$C≡CH | H | Me | CH$_2$OPr-n | Ms | H |
| CH$_2$C≡CH | H | Me | CH$_2$OCH=CH$_2$ | Ms | H |
| CH$_2$C≡CH | H | Me | CH$_2$OCH$_2$CH=CH$_2$ | Ms | H |
| CH$_2$C≡CH | H | Me | CH$_2$OCH$_2$C≡CH | Ms | H |
| CH$_2$C≡CH | H | Me | CH$_2$OCH$_2$CH$_2$Cl | Ms | H |
| CH$_2$C≡CH | H | Me | CHMeOH | Ms | H |
| CH$_2$C≡CH | H | Me | CHMeOMe | Ms | H |
| CH$_2$C≡CH | H | Me | CHMeOMe | Cl | H |
| CH$_2$C≡CH | H | Me | CHMeOMe | MeS | H |
| CH$_2$C≡CH | H | Me | CHMeOMe | MeSO | H |
| CH$_2$C≡CH | H | Me | CHMeOEt | Ms | H |
| CH$_2$C≡CH | H | Me | CHMeOCH=CH$_2$ | Ms | H |
| CH$_2$C≡CH | H | Me | CHMeOCH=CH$_2$ | Ms | H |
| CH$_2$C≡CH | H | Me | CHMeOCH$_2$CH=CH$_2$ | Ms | H |
| CH$_2$C≡CH | H | Me | CHMeOCH$_2$C≡CH | Ms | H |
| CH$_2$C≡CH | H | Me | CHMeOCH$_2$CH$_2$Cl | Ms | H |
| CH$_2$C≡CH | H | Me | CMe$_2$OH | Ms | H |
| CH$_2$C≡CH | H | Me | CMe$_2$OMe | Ms | H |
| CH$_2$C≡CH | H | Me | CMe$_2$OEt | Ms | H |
| CH$_2$C≡CH | H | Me | CH$_2$CH$_2$OMe | Ms | H |
| CH$_2$C≡CH | H | Me | CH$_2$CH$_2$OEt | Ms | H |
| CH$_2$C≡CH | H | Me | CHEtOH | Ms | H |
| CH$_2$C≡CH | H | Me | CHEtOMe | Ms | H |
| CH$_2$C≡CH | H | Me | CHEtOEt | Ms | H |
| CH$_2$C≡CH | H | Me | CH$_2$OCH$_2$CH$_2$OMe | Ms | H |
| CH$_2$C≡CH | H | Me | CHMeOCH$_2$CH$_2$OMe | Ms | H |
| CH$_2$C≡CH | H | Me | CH$_2$NMe$_2$ | Ms | H |
| CH$_2$C≡CH | H | Me | CHMeNMe$_2$ | Ms | H |
| CH$_2$C≡CH | H | Me | CH$_2$CH$_2$NMe$_2$ | Ms | H |
| CH$_2$C≡CH | H | Me | CH$_2$OCH$_2$Ph | Ms | H |
| CH$_2$C≡CH | H | Me | CHMeOCH$_2$Ph | Ms | H |
| CH$_2$C≡CH | H | Me | CH$_2$OCH$_2$CO$_2$Me | Ms | H |
| CH$_2$C≡CH | H | Me | CH$_2$OCH$_2$CO$_2$Et | Ms | H |
| CH$_2$C≡CH | H | Me | CH$_2$OCHMeCO$_2$Me | Ms | H |
| CH$_2$C≡CH | H | Me | CH$_2$CN | Ms | H |
| CH$_2$C≡CH | H | Me | CH$_2$SMe | Ms | H |
| CH$_2$C≡CH | H | Me | CH$_2$SEt | Ms | H |
| CH$_2$C≡CH | H | Me | CH$_2$SOMe | Ms | H |
| CH$_2$C≡CH | H | Me | CH$_2$SO$_2$Me | Ms | H |
| CH$_2$C≡CH | H | Me | CH$_2$SO$_2$Et | Ms | H |
| CH$_2$C≡CH | H | Me | CHMeSMe | Ms | H |
| CH$_2$C≡CH | H | Me | CHMeSO$_2$Me | Ms | H |
| CH$_2$C≡CH | H | Me | CH$_2$SCH$_2$CH$_2$OMe | Ms | H |
| CH$_2$C≡CH | H | Me | CH$_2$OCOMe | Ms | H |
| CH$_2$C≡CH | H | Me | CHMeOCOMe | Ms | H |
| CH$_2$C≡CH | H | Me | CH$_2$OSO$_2$Me | Ms | H |
| CH$_2$C≡CH | H | Me | CHMeOSO$_2$Me | Ms | H |
| CH$_2$CH=CH$_2$ | H | Cl | CH$_2$OH | Ms | H |
| CH$_2$CH=CH$_2$ | H | Cl | CH$_2$OMe | Ms | H |
| CH$_2$CH=CH$_2$ | H | Cl | CH$_2$OMe | Cl | H |
| CH$_2$CH=CH$_2$ | H | Cl | CH$_2$OMe | MeS | H |
| CH$_2$CH=CH$_2$ | H | Cl | CH$_2$OMe | MeSO | H |
| CH$_2$CH=CH$_2$ | H | Cl | CH$_2$OEt | Ms | H |
| CH$_2$CH=CH$_2$ | H | Cl | CH$_2$OEt | Cl | H |
| CH$_2$CH=CH$_2$ | H | Cl | CH$_2$OEt | MeS | H |
| CH$_2$CH=CH$_2$ | H | Cl | CH$_2$OEt | MeSO | H |
| CH$_2$CH=CH$_2$ | H | Cl | CH$_2$OPr-i | Ms | H |
| CH$_2$CH=CH$_2$ | H | Cl | CH$_2$OPr-n | Ms | H |
| CH$_2$CH=CH$_2$ | H | Cl | CH$_2$OCH=CH$_2$ | Ms | H |
| CH$_2$CH=CH$_2$ | H | Cl | CH$_2$OCH$_2$CH=CH$_2$ | Ms | H |
| CH$_2$CH=CH$_2$ | H | Cl | CH$_2$OCH$_2$C≡CH | Ms | H |
| CH$_2$CH=CH$_2$ | H | Cl | CH$_2$OCH$_2$CH$_2$Cl | Ms | H |
| CH$_2$CH=CH$_2$ | H | Cl | CHMeOH | Ms | H |
| CH$_2$CH=CH$_2$ | H | Cl | CHMeOMe | Ms | H |
| CH$_2$CH=CH$_2$ | H | Cl | CHMeOMe | Cl | H |
| CH$_2$CH=CH$_2$ | H | Cl | CHMeOMe | MeS | H |
| CH$_2$CH=CH$_2$ | H | Cl | CHMeOMe | MeSO | H |
| CH$_2$CH=CH$_2$ | H | Cl | CHMeOEt | Ms | H |
| CH$_2$CH=CH$_2$ | H | Cl | CHMeOCH=CH$_2$ | Ms | H |
| CH$_2$CH=CH$_2$ | H | Cl | CHMeOCH=CH$_2$ | Ms | H |
| CH$_2$CH=CH$_2$ | H | Cl | CHMeOCH$_2$CH=CH$_2$ | Ms | H |
| CH$_2$CH=CH$_2$ | H | Cl | CHMeOCH$_2$C≡CH | Ms | H |
| CH$_2$CH=CH$_2$ | H | Cl | CHMeOCH$_2$CH$_2$Cl | Ms | H |
| CH$_2$CH=CH$_2$ | H | Cl | CMe$_2$OH | Ms | H |

-continued

| | | | | | |
|---|---|---|---|---|---|
| CH₂CH=CH₂ | H | Cl | CMe₂OMe | Ms | H |
| CH₂CH=CH₂ | H | Cl | CMe₂OEt | Ms | H |
| CH₂CH=CH₂ | H | Cl | CH₂CH₂OMe | Ms | H |
| CH₂CH=CH₂ | H | Cl | CH₂CH₂OEt | Ms | H |
| CH₂CH=CH₂ | H | Cl | CHEtOH | Ms | H |
| CH₂CH=CH₂ | H | Cl | CHEtOMe | Ms | H |
| CH₂CH=CH₂ | H | Cl | CHEtOEt | Ms | H |
| CH₂CH=CH₂ | H | Cl | CH₂OCH₂CH₂OMe | Ms | H |
| CH₂CH=CH₂ | H | Cl | CHMeOCH₂CH₂OMe | Ms | H |
| CH₂CH=CH₂ | H | Cl | CH₂NMe₂ | Ms | H |
| CH₂CH=CH₂ | H | Cl | CHMeNMe₂ | Ms | H |
| CH₂CH=CH₂ | H | Cl | CH₂CH₂NMe₂ | Ms | H |
| CH₂CH=CH₂ | H | Cl | CH₂OCH₂Ph | Ms | H |
| CH₂CH=CH₂ | H | Cl | CHMeOCH₂Ph | Ms | H |
| CH₂CH=CH₂ | H | Cl | CH₂OCH₂CO₂Me | Ms | H |
| CH₂CH=CH₂ | H | Cl | CH₂OCH₂CO₂Et | Ms | H |
| CH₂CH=CH₂ | H | Cl | CH₂OCHMeCO₂Me | Ms | H |
| CH₂CH=CH₂ | H | Cl | CH₂CN | Ms | H |
| CH₂CH=CH₂ | H | Cl | CH₂SMe | Ms | H |
| CH₂CH=CH₂ | H | Cl | CH₂SEt | Ms | H |
| CH₂CH=CH₂ | H | Cl | CH₂SOMe | Ms | H |
| CH₂CH=CH₂ | H | Cl | CH₂SO₂Me | Ms | H |
| CH₂CH=CH₂ | H | Cl | CH₂SO₂Et | Ms | H |
| CH₂CH=CH₂ | H | Cl | CHMeSMe | Ms | H |
| CH₂CH=CH₂ | H | Cl | CHMeSO₂Me | Ms | H |
| CH₂CH=CH₂ | H | Cl | CH₂SCH₂CH₂OMe | Ms | H |
| CH₂CH=CH₂ | H | Cl | CH₂OCOMe | Ms | H |
| CH₂CH=CH₂ | H | Cl | CHMeOCOMe | Ms | H |
| CH₂CH=CH₂ | H | Cl | CH₂OSO₂Me | Ms | H |
| CH₂CH=CH₂ | H | Cl | CHMeOSO₂Me | Ms | H |
| CH₂C≡CH | H | Cl | CH₂OH | Ms | H |
| CH₂C≡CH | H | Cl | CH₂OMe | Ms | H |
| CH₂C≡CH | H | Cl | CH₂OMe | Cl | H |
| CH₂C≡CH | H | Cl | CH₂OMe | MeS | H |
| CH₂C≡CH | H | Cl | CH₂OMe | MeSO | H |
| CH₂C≡CH | H | Cl | CH₂OEt | Ms | H |
| CH₂C≡CH | H | Cl | CH₂OEt | Cl | H |
| CH₂C≡CH | H | Cl | CH₂OEt | MeS | H |
| CH₂C≡CH | H | Cl | CH₂OEt | MeSO | H |
| CH₂C≡CH | H | Cl | CH₂OPr-i | Ms | H |
| CH₂C≡CH | H | Cl | CH₂OPr-n | Ms | H |
| CH₂C≡CH | H | Cl | CH₂OCH=CH₂ | Ms | H |
| CH₂C≡CH | H | Cl | CH₂OCH₂CH=CH₂ | Ms | H |
| CH₂C≡CH | H | Cl | CH₂OCH₂C≡CH | Ms | H |
| CH₂C≡CH | H | Cl | CH₂OCH₂CH₂Cl | Ms | H |
| CH₂C≡CH | H | Cl | CHMeOH | Ms | H |
| CH₂C≡CH | H | Cl | CHMeOMe | Ms | H |
| CH₂C≡CH | H | Cl | CHMeOMe | Cl | H |
| CH₂C≡CH | H | Cl | CHMeOMe | MeS | H |
| CH₂C≡CH | H | Cl | CHMeOMe | MeSO | H |
| CH₂C≡CH | H | Cl | CHMeOEt | Ms | H |
| CH₂C≡CH | H | Cl | CHMeOCH=CH₂ | Ms | H |
| CH₂C≡CH | H | Cl | CHMeOCH=CH₂ | Ms | H |
| CH₂C≡CH | H | Cl | CHMeOCH₂CH=CH₂ | Ms | H |
| CH₂C≡CH | H | Cl | CHMeOCH₂C≡CH | Ms | H |
| CH₂C≡CH | H | Cl | CHMeOCH₂CH₂Cl | Ms | H |
| CH₂C≡CH | H | Cl | CMe₂OH | Ms | H |
| CH₂C≡CH | H | Cl | CMe₂OMe | Ms | H |
| CH₂C≡CH | H | Cl | CMe₂OEt | Ms | H |
| CH₂C≡CH | H | Cl | CH₂CH₂OMe | Ms | H |
| CH₂C≡CH | H | Cl | CH₂CH₂OEt | Ms | H |
| CH₂C≡CH | H | Cl | CHEtOH | Ms | H |
| CH₂C≡CH | H | Cl | CHEtOMe | Ms | H |
| CH₂C≡CH | H | Cl | CHEtOEt | Ms | H |
| CH₂C≡CH | H | Cl | CH₂OCH₂CH₂OMe | Ms | H |
| CH₂C≡CH | H | Cl | CHMeOCH₂CH₂OMe | Ms | H |
| CH₂C≡CH | H | Cl | CH₂NMe₂ | Ms | H |
| CH₂C≡CH | H | Cl | CHMeNMe₂ | Ms | H |
| CH₂C≡CH | H | Cl | CH₂CH₂NMe₂ | Ms | H |
| CH₂C≡CH | H | Cl | CH₂OCH₂Ph | Ms | H |
| CH₂C≡CH | H | Cl | CHMeOCH₂Ph | Ms | H |
| CH₂C≡CH | H | Cl | CH₂OCH₂CO₂Me | Ms | H |
| CH₂C≡CH | H | Cl | CH₂OCH₂CO₂Et | Ms | H |
| CH₂C≡CH | H | Cl | CH₂OCHMeCO₂Me | Ms | H |
| CH₂C≡CH | H | Cl | CH₂CN | Ms | H |
| CH₂C≡CH | H | Cl | CH₂SMe | Ms | H |
| CH₂C≡CH | H | Cl | CH₂SEt | Ms | H |
| CH₂C≡CH | H | Cl | CH₂SOMe | Ms | H |
| CH₂C≡CH | H | Cl | CH₂SO₂Me | Ms | H |
| CH₂C≡CH | H | Cl | CH₂SO₂Et | Ms | H |
| CH₂C≡CH | H | Cl | CHMeSMe | Ms | H |
| CH₂C≡CH | H | Cl | CHMeSO₂Me | Ms | H |
| CH₂C≡CH | H | Cl | CH₂SCH₂CH₂OMe | Ms | H |

-continued

| | | | | | |
|---|---|---|---|---|---|
| CH₂C≡CH | H | Cl | CH₂OCOMe | Ms | H |
| CH₂C≡CH | H | Cl | CHMeOCOMe | Ms | H |
| CH₂C≡CH | H | Cl | CH₂OSO₂Me | Ms | H |
| CH₂C≡CH | H | Cl | CHMeOSO₂Me | Ms | H |
| CH₂CH=CH₂ | H | MeO | CH₂OH | Ms | H |
| CH₂CH=CH₂ | H | MeO | CH₂OMe | Ms | H |
| CH₂CH=CH₂ | H | MeO | CH₂OMe | Cl | H |
| CH₂CH=CH₂ | H | MeO | CH₂OMe | MeS | H |
| CH₂CH=CH₂ | H | MeO | CH₂OMe | MeSO | H |
| CH₂CH=CH₂ | H | MeO | CH₂OEt | Ms | H |
| CH₂CH=CH₂ | H | MeO | CH₂OEt | Cl | H |
| CH₂CH=CH₂ | H | MeO | CH₂OEt | MeS | H |
| CH₂CH=CH₂ | H | MeO | CH₂OEt | MeSO | H |
| CH₂CH=CH₂ | H | MeO | CH₂OPr-i | Ms | H |
| CH₂CH=CH₂ | H | MeO | CH₂OPr-n | Ms | H |
| CH₂CH=CH₂ | H | MeO | CH₂OCH=CH₂ | Ms | H |
| CH₂CH=CH₂ | H | MeO | CH₂OCH₂CH=CH₂ | Ms | H |
| CH₂CH=CH₂ | H | MeO | CH₂OCH₂C≡CH | Ms | H |
| CH₂CH=CH₂ | H | MeO | CH₂OCH₂CH₂Cl | Ms | H |
| CH₂CH=CH₂ | H | MeO | CHMeOH | Ms | H |
| CH₂CH=CH₂ | H | MeO | CHMeOMe | Ms | H |
| CH₂CH=CH₂ | H | MeO | CHMeOMe | Cl | H |
| CH₂CH=CH₂ | H | MeO | CHMeOMe | MeS | H |
| CH₂CH=CH₂ | H | MeO | CHMeOMe | MeSO | H |
| CH₂CH=CH₂ | H | MeO | CHMeOEt | Ms | H |
| CH₂CH=CH₂ | H | MeO | CHMeOCH=CH₂ | Ms | H |
| CH₂CH=CH₂ | H | MeO | CHMeOCH=CH₂ | Ms | H |
| CH₂CH=CH₂ | H | MeO | CHMeOCH₂CH=CH₂ | Ms | H |
| CH₂CH=CH₂ | H | MeO | CHMeOCH₂C≡CH | Ms | H |
| CH₂CH=CH₂ | H | MeO | CHMeOCH₂CH₂Cl | Ms | H |
| CH₂CH=CH₂ | H | MeO | CMe₂OH | Ms | H |
| CH₂CH=CH₂ | H | MeO | CMe₂OMe | Ms | H |
| CH₂CH=CH₂ | H | MeO | CMe₂OEt | Ms | H |
| CH₂CH=CH₂ | H | MeO | CH₂CH₂OMe | Ms | H |
| CH₂CH=CH₂ | H | MeO | CH₂CH₂OEt | Ms | H |
| CH₂CH=CH₂ | H | MeO | CHEtOH | Ms | H |
| CH₂CH=CH₂ | H | MeO | CHEtOMe | Ms | H |
| CH₂CH=CH₂ | H | MeO | CHEtOEt | Ms | H |
| CH₂CH=CH₂ | H | MeO | CH₂OCH₂CH₂OMe | Ms | H |
| CH₂CH=CH₂ | H | MeO | CHMeOCH₂CH₂OMe | Ms | H |
| CH₂CH=CH₂ | H | MeO | CH₂NMe₂ | Ms | H |
| CH₂CH=CH₂ | H | MeO | CHMeNMe₂ | Ms | H |
| CH₂CH=CH₂ | H | MeO | CH₂CH₂NMe₂ | Ms | H |
| CH₂CH=CH₂ | H | MeO | CH₂OCH₂Ph | Ms | H |
| CH₂CH=CH₂ | H | MeO | CHMeOCH₂Ph | Ms | H |
| CH₂CH=CH₂ | H | MeO | CH₂OCH₂CO₂Me | Ms | H |
| CH₂CH=CH₂ | H | MeO | CH₂OCH₂CO₂Et | Ms | H |
| CH₂CH=CH₂ | H | MeO | CH₂OCHMeCO₂Me | Ms | H |
| CH₂CH=CH₂ | H | MeO | CH₂CN | Ms | H |
| CH₂CH=CH₂ | H | MeO | CH₂SMe | Ms | H |
| CH₂CH=CH₂ | H | MeO | CH₂SEt | Ms | H |
| CH₂CH=CH₂ | H | MeO | CH₂SOMe | Ms | H |
| CH₂CH=CH₂ | H | MeO | CH₂SO₂Me | Ms | H |
| CH₂CH=CH₂ | H | MeO | CH₂SO₂Et | Ms | H |
| CH₂CH=CH₂ | H | MeO | CHMeSMe | Ms | H |
| CH₂CH=CH₂ | H | MeO | CHMeSO₂Me | Ms | H |
| CH₂CH=CH₂ | H | MeO | CH₂SCH₂CH₂OMe | Ms | H |
| CH₂CH=CH₂ | H | MeO | CH₂OCOMe | Ms | H |
| CH₂CH=CH₂ | H | MeO | CHMeOCOMe | Ms | H |
| CH₂CH=CH₂ | H | MeO | CH₂OSO₂Me | Ms | H |
| CH₂CH=CH₂ | H | MeO | CHMeOSO₂Me | Ms | H |
| CH₂C≡CH | H | MeO | CH₂OH | Ms | H |
| CH₂C≡CH | H | MeO | CH₂OMe | Ms | H |
| CH₂C≡CH | H | MeO | CH₂OMe | Cl | H |
| CH₂C≡CH | H | MeO | CH₂OMe | MeS | H |
| CH₂C≡CH | H | MeO | CH₂OMe | MeSO | H |
| CH₂C≡CH | H | MeO | CH₂OEt | Ms | H |
| CH₂C≡CH | H | MeO | CH₂OEt | Cl | H |
| CH₂C≡CH | H | MeO | CH₂OEt | MeS | H |
| CH₂C≡CH | H | MeO | CH₂OEt | MeSO | H |
| CH₂C≡CH | H | MeO | CH₂OPr-i | Ms | H |
| CH₂C≡CH | H | MeO | CH₂OPr-n | Ms | H |
| CH₂C≡CH | H | MeO | CH₂OCH=CH₂ | Ms | H |
| CH₂C≡CH | H | MeO | CH₂OCH₂CH=CH₂ | Ms | H |
| CH₂C≡CH | H | MeO | CH₂OCH₂C≡CH | Ms | H |
| CH₂C≡CH | H | MeO | CH₂OCH₂CH₂Cl | Ms | H |
| CH₂C≡CH | H | MeO | CHMeOH | Ms | H |
| CH₂C≡CH | H | MeO | CHMeOMe | Ms | H |
| CH₂C≡CH | H | MeO | CHMeOMe | Cl | H |
| CH₂C≡CH | H | MeO | CHMeOMe | MeS | H |
| CH₂C≡CH | H | MeO | CHMeOMe | MeSO | H |
| CH₂C≡CH | H | MeO | CHMeOEt | Ms | H |
| CH₂C≡CH | H | MeO | CHMeOCH=CH₂ | Ms | H |

-continued

| | | | | | |
|---|---|---|---|---|---|
| CH₂C≡CH | H | MeO | CHMeOCH=CH₂ | Ms | H |
| CH₂C≡CH | H | MeO | CHMeOCH₂CH=CH₂ | Ms | H |
| CH₂C≡CH | H | MeO | CHMeOCH₂C≡CH | Ms | H |
| CH₂C≡CH | H | MeO | CHMeOCH₂CH₂Cl | Ms | H |
| CH₂C≡CH | H | MeO | CMe₂OH | Ms | H |
| CH₂C≡CH | H | MeO | CMe₂OMe | Ms | H |
| CH₂C≡CH | H | MeO | CMe₂OEt | Ms | H |
| CH₂C≡CH | H | MeO | CH₂CH₂OMe | Ms | H |
| CH₂C≡CH | H | MeO | CH₂CH₂OEt | Ms | H |
| CH₂C≡CH | H | MeO | CHEtOH | Ms | H |
| CH₂C≡CH | H | MeO | CHEtOMe | Ms | H |
| CH₂C≡CH | H | MeO | CHEtOEt | Ms | H |
| CH₂C≡CH | H | MeO | CH₂OCH₂CH₂OMe | Ms | H |
| CH₂C≡CH | H | MeO | CHMeOCH₂CH₂OMe | Ms | H |
| CH₂C≡CH | H | MeO | CH₂NMe₂ | Ms | H |
| CH₂C≡CH | H | MeO | CHMeNMe₂ | Ms | H |
| CH₂C≡CH | H | MeO | CH₂CH₂NMe₂ | Ms | H |
| CH₂C≡CH | H | MeO | CH₂OCH₂Ph | Ms | H |
| CH₂C≡CH | H | MeO | CHMeOCH₂Ph | Ms | H |
| CH₂C≡CH | H | MeO | CH₂OCH₂CO₂Me | Ms | H |
| CH₂C≡CH | H | MeO | CH₂OCH₂CO₂Et | Ms | H |
| CH₂C≡CH | H | MeO | CH₂OCHMeCO₂Me | Ms | H |
| CH₂C≡CH | H | MeO | CH₂CN | Ms | H |
| CH₂C≡CH | H | MeO | CH₂SMe | Ms | H |
| CH₂C≡CH | H | MeO | CH₂SEt | Ms | H |
| CH₂C≡CH | H | MeO | CH₂SOMe | Ms | H |
| CH₂C≡CH | H | MeO | CH₂SO₂Me | Ms | H |
| CH₂C≡CH | H | MeO | CH₂SO₂Et | Ms | H |
| CH₂C≡CH | H | MeO | CHMeSMe | Ms | H |
| CH₂C≡CH | H | MeO | CHMeSO₂Me | Ms | H |
| CH₂C≡CH | H | MeO | CH₂SCH₂CH₂OMe | Ms | H |
| CH₂C≡CH | H | MeO | CH₂OCOMe | Ms | H |
| CH₂C≡CH | H | MeO | CHMeOCOMe | Ms | H |
| CH₂C≡CH | H | MeO | CH₂OSO₂Me | Ms | H |
| CH₂C≡CH | H | MeO | CHMeOSO₂Me | Ms | H |
| CH₂CH=CH₂ | Me | Me | CH₂OH | Ms | H |
| CH₂CH=CH₂ | Me | Me | CH₂OMe | Ms | H |
| CH₂CH=CH₂ | Me | Me | CH₂OMe | Cl | H |
| CH₂CH=CH₂ | Me | Me | CH₂OMe | MeS | H |
| CH₂CH=CH₂ | Me | Me | CH₂OMe | MeSO | H |
| CH₂CH=CH₂ | Me | Me | CH₂OEt | Ms | H |
| CH₂CH=CH₂ | Me | Me | CH₂OEt | Cl | H |
| CH₂CH=CH₂ | Me | Me | CH₂OEt | MeS | H |
| CH₂CH=CH₂ | Me | Me | CH₂OEt | MeSO | H |
| CH₂CH=CH₂ | Me | Me | CH₂OPr-i | Ms | H |
| CH₂CH=CH₂ | Me | Me | CH₂OPr-n | Ms | H |
| CH₂CH=CH₂ | Me | Me | CH₂OCH=CH₂ | Ms | H |
| CH₂CH=CH₂ | Me | Me | CH₂OCH₂CH=CH₂ | Ms | H |
| CH₂CH=CH₂ | Me | Me | CH₂OCH₂C≡CH | Ms | H |
| CH₂CH=CH₂ | Me | Me | CH₂OCH₂CH₂Cl | Ms | H |
| CH₂CH=CH₂ | Me | Me | CHMeOH | Ms | H |
| CH₂CH=CH₂ | Me | Me | CHMeOMe | Ms | H |
| CH₂CH=CH₂ | Me | Me | CHMeOMe | Cl | H |
| CH₂CH=CH₂ | Me | Me | CHMeOMe | MeS | H |
| CH₂CH=CH₂ | Me | Me | CHMeOMe | MeSO | H |
| CH₂CH=CH₂ | Me | Me | CHMeOEt | Ms | H |
| CH₂CH=CH₂ | Me | Me | CH₂CH₂OMe | Ms | H |
| CH₂CH=CH₂ | Me | Me | CH₂CH₂OEt | Ms | H |
| CH₂CH=CH₂ | Me | Me | CHEtOH | Ms | H |
| CH₂CH=CH₂ | Me | Me | CHEtOMe | Ms | H |
| CH₂CH=CH₂ | Me | Me | CHEtOEt | Ms | H |
| CH₂CH=CH₂ | Me | Me | CH₂OCH₂CH₂OMe | Ms | H |
| CH₂CH=CH₂ | Me | Me | CH₂NMe₂ | Ms | H |
| CH₂CH=CH₂ | Me | Me | CH₂OCH₂Ph | Ms | H |
| CH₂CH=CH₂ | Me | Me | CH₂OCH₂CO₂Me | Ms | H |
| CH₂CH=CH₂ | Me | Me | CH₂OCH₂CO₂Et | Ms | H |
| CH₂CH=CH₂ | Me | Me | CH₂OCHMeCO₂Me | Ms | H |
| CH₂CH=CH₂ | Me | Me | CH₂CN | Ms | H |
| CH₂CH=CH₂ | Me | Me | CH₂SMe | Ms | H |
| CH₂CH=CH₂ | Me | Me | CH₂SEt | Ms | H |
| CH₂CH=CH₂ | Me | Me | CH₂SO₂Me | Ms | H |
| CH₂CH=CH₂ | Me | Me | CH₂SO₂Et | Ms | H |
| CH₂CH=CH₂ | Me | Me | CH₂SCH₂CH₂OMe | Ms | H |
| CH₂CH=CH₂ | Me | Me | CH₂OCOMe | Ms | H |
| CH₂CH=CH₂ | Me | Me | CHMeOCOMe | Ms | H |
| CH₂CH=CH₂ | Me | Me | CH₂OSO₂Me | Ms | H |
| CH₂CH=CH₂ | Me | Me | CHMeOSO₂Me | Ms | H |
| CH₂C≡CH | Me | Me | CH₂OH | Ms | H |
| CH₂C≡CH | Me | Me | CH₂OMe | Ms | H |
| CH₂C≡CH | Me | Me | CH₂OMe | Cl | H |
| CH₂C≡CH | Me | Me | CH₂OMe | MeS | H |
| CH₂C≡CH | Me | Me | CH₂OMe | MeSO | H |
| CH₂C≡CH | Me | Me | CH₂OEt | Ms | H |

-continued

| | | | | | |
|---|---|---|---|---|---|
| CH$_2$C≡CH | Me | Me | CH$_2$OEt | Cl | H |
| CH$_2$C≡CH | Me | Me | CH$_2$OEt | MeS | H |
| CH$_2$C≡CH | Me | Me | CH$_2$OEt | MeSO | H |
| CH$_2$C≡CH | Me | Me | CH$_2$OPr-i | Ms | H |
| CH$_2$C≡CH | Me | Me | CH$_2$OPr-n | Ms | H |
| CH$_2$C≡CH | Me | Me | CH$_2$OCH=CH$_2$ | Ms | H |
| CH$_2$C≡CH | Me | Me | CH$_2$OCH$_2$CH=CH$_2$ | Ms | H |
| CH$_2$C≡CH | Me | Me | CH$_2$OCH$_2$C≡CH | Ms | H |
| CH$_2$C≡CH | Me | Me | CH$_2$OCH$_2$CH$_2$Cl | Ms | H |
| CH$_2$C≡CH | Me | Me | CHMeOH | Ms | H |
| CH$_2$C≡CH | Me | Me | CHMeOMe | Ms | H |
| CH$_2$C≡CH | Me | Me | CHMeOMe | Cl | H |
| CH$_2$C≡CH | Me | Me | CHMeOMe | MeS | H |
| CH$_2$C≡CH | Me | Me | CHMeOMe | MeSO | H |
| CH$_2$C≡CH | Me | Me | CHMeOEt | Ms | H |
| CH$_2$C≡CH | Me | Me | CH$_2$CH$_2$OMe | Ms | H |
| CH$_2$C≡CH | Me | Me | CH$_2$CH$_2$OEt | Ms | H |
| CH$_2$C≡CH | Me | Me | CHEtOH | Ms | H |
| CH$_2$C≡CH | Me | Me | CHEtOMe | Ms | H |
| CH$_2$C≡CH | Me | Me | CHEtOEt | Ms | H |
| CH$_2$C≡CH | Me | Me | CH$_2$OCH$_2$CH$_2$OMe | Ms | H |
| CH$_2$C≡CH | Me | Me | CH$_2$NMe$_2$ | Ms | H |
| CH$_2$C≡CH | Me | Me | CH$_2$OCH$_2$Ph | Ms | H |
| CH$_2$C≡CH | Me | Me | CH$_2$OCH$_2$CO$_2$Me | Ms | H |
| CH$_2$C≡CH | Me | Me | CH$_2$OCH$_2$CO$_2$Et | Ms | H |
| CH$_2$C≡CH | Me | Me | CH$_2$OCHMeCO$_2$Me | Ms | H |
| CH$_2$C≡CH | Me | Me | CH$_2$CN | Ms | H |
| CH$_2$C≡CH | Me | Me | CH$_2$SMe | Ms | H |
| CH$_2$C≡CH | Me | Me | CH$_2$SEt | Ms | H |
| CH$_2$C≡CH | Me | Me | CH$_2$SO$_2$Me | Ms | H |
| CH$_2$C≡CH | Me | Me | CH$_2$SO$_2$Et | Ms | H |
| CH$_2$C≡CH | Me | Me | CH$_2$SCH$_2$CH$_2$OMe | Ms | H |
| CH$_2$C≡CH | Me | Me | CH$_2$OCOMe | Ms | H |
| CH$_2$C≡CH | Me | Me | CHMeOCOMe | Ms | H |
| CH$_2$C≡CH | Me | Me | CH$_2$OSO$_2$Me | Ms | H |
| CH$_2$C≡CH | Me | Me | CHMeOSO$_2$Me | Ms | H |
| CH$_2$CH=CH$_2$ | Me | Cl | CH$_2$OH | Ms | H |
| CH$_2$CH=CH$_2$ | Me | Cl | CH$_2$OMe | Ms | H |
| CH$_2$CH=CH$_2$ | Me | Cl | CH$_2$OMe | Cl | H |
| CH$_2$CH=CH$_2$ | Me | Cl | CH$_2$OMe | MeS | H |
| CH$_2$CH=CH$_2$ | Me | Cl | CH$_2$OMe | MeSO | H |
| CH$_2$CH=CH$_2$ | Me | Cl | CH$_2$OEt | Ms | H |
| CH$_2$CH=CH$_2$ | Me | Cl | CH$_2$OEt | Cl | H |
| CH$_2$CH=CH$_2$ | Me | Cl | CH$_2$OEt | MeS | H |
| CH$_2$CH=CH$_2$ | Me | Cl | CH$_2$OEt | MeSO | H |
| CH$_2$CH=CH$_2$ | Me | Cl | CH$_2$OPr-i | Ms | H |
| CH$_2$CH=CH$_2$ | Me | Cl | CH$_2$OPr-n | Ms | H |
| CH$_2$CH=CH$_2$ | Me | Cl | CH$_2$OCH=CH$_2$ | Ms | H |
| CH$_2$CH=CH$_2$ | Me | Cl | CH$_2$OCH$_2$CH=CH$_2$ | Ms | H |
| CH$_2$CH=CH$_2$ | Me | Cl | CH$_2$OCH$_2$C≡CH | Ms | H |
| CH$_2$CH=CH$_2$ | Me | Cl | CH$_2$OCH$_2$CH$_2$Cl | Ms | H |
| CH$_2$CH=CH$_2$ | Me | Cl | CHMeOH | Ms | H |
| CH$_2$CH=CH$_2$ | Me | Cl | CHMeOMe | Ms | H |
| CH$_2$CH=CH$_2$ | Me | Cl | CHMeOMe | Cl | H |
| CH$_2$CH=CH$_2$ | Me | Cl | CHMeOMe | MeS | H |
| CH$_2$CH=CH$_2$ | Me | Cl | CHMeOMe | MeSO | H |
| CH$_2$CH=CH$_2$ | Me | Cl | CHMeOEt | Ms | H |
| CH$_2$CH=CH$_2$ | Me | Cl | CH$_2$CH$_2$OMe | Ms | H |
| CH$_2$CH=CH$_2$ | Me | Cl | CH$_2$CH$_2$OEt | Ms | H |
| CH$_2$CH=CH$_2$ | Me | Cl | CHEtOH | Ms | H |
| CH$_2$CH=CH$_2$ | Me | Cl | CHEtOMe | Ms | H |
| CH$_2$CH=CH$_2$ | Me | Cl | CHEtOEt | Ms | H |
| CH$_2$CH=CH$_2$ | Me | Cl | CH$_2$OCH$_2$CH$_2$OMe | Ms | H |
| CH$_2$CH=CH$_2$ | Me | Cl | CH$_2$NMe$_2$ | Ms | H |
| CH$_2$CH=CH$_2$ | Me | Cl | CH$_2$OCH$_2$Ph | Ms | H |
| CH$_2$CH=CH$_2$ | Me | Cl | CH$_2$OCH$_2$CO$_2$Me | Ms | H |
| CH$_2$CH=CH$_2$ | Me | Cl | CH$_2$OCH$_2$CO$_2$Et | Ms | H |
| CH$_2$CH=CH$_2$ | Me | Cl | CH$_2$OCHMeCO$_2$Me | Ms | H |
| CH$_2$CH=CH$_2$ | Me | Cl | CH$_2$CN | Ms | H |
| CH$_2$CH=CH$_2$ | Me | Cl | CH$_2$SMe | Ms | H |
| CH$_2$CH=CH$_2$ | Me | Cl | CH$_2$SEt | Ms | H |
| CH$_2$CH=CH$_2$ | Me | Cl | CH$_2$SO$_2$Me | Ms | H |
| CH$_2$CH=CH$_2$ | Me | Cl | CH$_2$SO$_2$Et | Ms | H |
| CH$_2$CH=CH$_2$ | Me | Cl | CH$_2$SCH$_2$CH$_2$OMe | Ms | H |
| CH$_2$CH=CH$_2$ | Me | Cl | CH$_2$OCOMe | Ms | H |
| CH$_2$CH=CH$_2$ | Me | Cl | CHMeOCOMe | Ms | H |
| CH$_2$CH=CH$_2$ | Me | Cl | CH$_2$OSO$_2$Me | Ms | H |
| CH$_2$CH=CH$_2$ | Me | Cl | CHMeOSO$_2$Me | Ms | H |
| CH$_2$C≡CH | Me | Cl | CH$_2$OH | Ms | H |
| CH$_2$C≡CH | Me | Cl | CH$_2$OMe | Ms | H |
| CH$_2$C≡CH | Me | Cl | CH$_2$OMe | Cl | H |
| CH$_2$C≡CH | Me | Cl | CH$_2$OMe | MeS | H |
| CH$_2$C≡CH | Me | Cl | CH$_2$OMe | MeSO | H |

-continued

| | | | | | |
|---|---|---|---|---|---|
| CH$_2$C≡CH | Me | Cl | CH$_2$OEt | Ms | H |
| CH$_2$C≡CH | Me | Cl | CH$_2$OEt | Cl | H |
| CH$_2$C≡CH | Me | Cl | CH$_2$OEt | MeS | H |
| CH$_2$C≡CH | Me | Cl | CH$_2$OEt | MeSO | H |
| CH$_2$C≡CH | Me | Cl | CH$_2$OPr-i | Ms | H |
| CH$_2$C≡CH | Me | Cl | CH$_2$OPr-n | Ms | H |
| CH$_2$C≡CH | Me | Cl | CH$_2$OCH=CH$_2$ | Ms | H |
| CH$_2$C≡CH | Me | Cl | CH$_2$OCH$_2$CH=CH$_2$ | Ms | H |
| CH$_2$C≡CH | Me | Cl | CH$_2$OCH$_2$C≡CH | Ms | H |
| CH$_2$C≡CH | Me | Cl | CH$_2$OCH$_2$CH$_2$Cl | Ms | H |
| CH$_2$C≡CH | Me | Cl | CHMeOH | Ms | H |
| CH$_2$C≡CH | Me | Cl | CHMeOMe | Ms | H |
| CH$_2$C≡CH | Me | Cl | CHMeOMe | Cl | H |
| CH$_2$C≡CH | Me | Cl | CHMeOMe | MeS | H |
| CH$_2$C≡CH | Me | Cl | CHMeOMe | MeSO | H |
| CH$_2$C≡CH | Me | Cl | CHMeOEt | Ms | H |
| CH$_2$C≡CH | Me | Cl | CH$_2$CH$_2$OMe | Ms | H |
| CH$_2$C≡CH | Me | Cl | CH$_2$CH$_2$OEt | Ms | H |
| CH$_2$C≡CH | Me | Cl | CHEtOH | Ms | H |
| CH$_2$C≡CH | Me | Cl | CHEtOMe | Ms | H |
| CH$_2$C≡CH | Me | Cl | CHEtOEt | Ms | H |
| CH$_2$C≡CH | Me | Cl | CH$_2$OCH$_2$CH$_2$OMe | Ms | H |
| CH$_2$C≡CH | Me | Cl | CH$_2$NMe$_2$ | Ms | H |
| CH$_2$C≡CH | Me | Cl | CH$_2$OCH$_2$Ph | Ms | H |
| CH$_2$C≡CH | Me | Cl | CH$_2$OCH$_2$CO$_2$Me | Ms | H |
| CH$_2$C≡CH | Me | Cl | CH$_2$OCH$_2$CO$_2$Et | Ms | H |
| CH$_2$C≡CH | Me | Cl | CH$_2$OCHMeCO$_2$Me | Ms | H |
| CH$_2$C≡CH | Me | Cl | CH$_2$CN | Ms | H |
| CH$_2$C≡CH | Me | Cl | CH$_2$SMe | Ms | H |
| CH$_2$C≡CH | Me | Cl | CH$_2$SEt | Ms | H |
| CH$_2$C≡CH | Me | Cl | CH$_2$SO$_2$Me | Ms | H |
| CH$_2$C≡CH | Me | Cl | CH$_2$SO$_2$Et | Ms | H |
| CH$_2$C≡CH | Me | Cl | CH$_2$SCH$_2$CH$_2$OMe | Ms | H |
| CH$_2$C≡CH | Me | Cl | CH$_2$OCOMe | Ms | H |
| CH$_2$C≡CH | Me | Cl | CHMeOCOMe | Ms | H |
| CH$_2$C≡CH | Me | Cl | CH$_2$OSO$_2$Me | Ms | H |
| CH$_2$C≡CH | Me | Cl | CHMeOSO$_2$Me | Ms | H |
| CH$_2$CH=CH$_2$ | Me | MeO | CH$_2$OH | Ms | H |
| CH$_2$CH=CH$_2$ | Me | MeO | CH$_2$OMe | Ms | H |
| CH$_2$CH=CH$_2$ | Me | MeO | CH$_2$OMe | Cl | H |
| CH$_2$CH=CH$_2$ | Me | MeO | CH$_2$OMe | MeS | H |
| CH$_2$CH=CH$_2$ | Me | MeO | CH$_2$OMe | MeSO | H |
| CH$_2$CH=CH$_2$ | Me | MeO | CH$_2$OEt | Ms | H |
| CH$_2$CH=CH$_2$ | Me | MeO | CH$_2$OEt | Cl | H |
| CH$_2$CH=CH$_2$ | Me | MeO | CH$_2$OEt | MeS | H |
| CH$_2$CH=CH$_2$ | Me | MeO | CH$_2$OEt | MeSO | H |
| CH$_2$CH=CH$_2$ | Me | MeO | CH$_2$OPr-i | Ms | H |
| CH$_2$CH=CH$_2$ | Me | MeO | CH$_2$OPr-n | Ms | H |
| CH$_2$CH=CH$_2$ | Me | MeO | CH$_2$OCH=CH$_2$ | Ms | H |
| CH$_2$CH=CH$_2$ | Me | MeO | CH$_2$OCH$_2$CH=CH$_2$ | Ms | H |
| CH$_2$CH=CH$_2$ | Me | MeO | CH$_2$OCH$_2$C≡CH | Ms | H |
| CH$_2$CH=CH$_2$ | Me | MeO | CH$_2$OCH$_2$CH$_2$Cl | Ms | H |
| CH$_2$CH=CH$_2$ | Me | MeO | CHMeOH | Ms | H |
| CH$_2$CH=CH$_2$ | Me | MeO | CHMeOMe | Ms | H |
| CH$_2$CH=CH$_2$ | Me | MeO | CHMeOMe | Cl | H |
| CH$_2$CH=CH$_2$ | Me | MeO | CHMeOMe | MeS | H |
| CH$_2$CH=CH$_2$ | Me | MeO | CHMeOMe | MeSO | H |
| CH$_2$CH=CH$_2$ | Me | MeO | CHMeOEt | Ms | H |
| CH$_2$CH=CH$_2$ | Me | MeO | CH$_2$CH$_2$OMe | Ms | H |
| CH$_2$CH=CH$_2$ | Me | MeO | CH$_2$CH$_2$OEt | Ms | H |
| CH$_2$CH=CH$_2$ | Me | MeO | CHEtOH | Ms | H |
| CH$_2$CH=CH$_2$ | Me | MeO | CHEtOMe | Ms | H |
| CH$_2$CH=CH$_2$ | Me | MeO | CHEtOEt | Ms | H |
| CH$_2$CH=CH$_2$ | Me | MeO | CH$_2$OCH$_2$CH$_2$OMe | Ms | H |
| CH$_2$CH=CH$_2$ | Me | MeO | CH$_2$NMe$_2$ | Ms | H |
| CH$_2$CH=CH$_2$ | Me | MeO | CH$_2$OCH$_2$Ph | Ms | H |
| CH$_2$CH=CH$_2$ | Me | MeO | CH$_2$OCH$_2$CO$_2$Me | Ms | H |
| CH$_2$CH=CH$_2$ | Me | MeO | CH$_2$OCH$_2$CO$_2$Et | Ms | H |
| CH$_2$CH=CH$_2$ | Me | MeO | CH$_2$OCHMeCO$_2$Me | Ms | H |
| CH$_2$CH=CH$_2$ | Me | MeO | CH$_2$CN | Ms | H |
| CH$_2$CH=CH$_2$ | Me | MeO | CH$_2$SMe | Ms | H |
| CH$_2$CH=CH$_2$ | Me | MeO | CH$_2$SEt | Ms | H |
| CH$_2$CH=CH$_2$ | Me | MeO | CH$_2$SO$_2$Me | Ms | H |
| CH$_2$CH=CH$_2$ | Me | MeO | CH$_2$SO$_2$Et | Ms | H |
| CH$_2$CH=CH$_2$ | Me | MeO | CH$_2$SCH$_2$CH$_2$OMe | Ms | H |
| CH$_2$CH=CH$_2$ | Me | MeO | CH$_2$OCOMe | Ms | H |
| CH$_2$CH=CH$_2$ | Me | MeO | CHMeOCOMe | Ms | H |
| CH$_2$CH=CH$_2$ | Me | MeO | CH$_2$OSO$_2$Me | Ms | H |
| CH$_2$CH=CH$_2$ | Me | MeO | CHMeOSO$_2$Me | Ms | H |
| CH$_2$C≡CH | Me | MeO | CH$_2$OH | Ms | H |
| CH$_2$C≡CH | Me | MeO | CH$_2$OMe | Ms | H |
| CH$_2$C≡CH | Me | MeO | CH$_2$OMe | Cl | H |
| CH$_2$C≡CH | Me | MeO | CH$_2$OMe | MeS | H |

-continued

| | | | | | |
|---|---|---|---|---|---|
| CH$_2$C≡CH | Me | MeO | CH$_2$OMe | MeSO | H |
| CH$_2$C≡CH | Me | MeO | CH$_2$OEt | Ms | H |
| CH$_2$C≡CH | Me | MeO | CH$_2$OEt | Cl | H |
| CH$_2$C≡CH | Me | MeO | CH$_2$OEt | MeS | H |
| CH$_2$C≡CH | Me | MeO | CH$_2$OEt | MeSO | H |
| CH$_2$C≡CH | Me | MeO | CH$_2$OPr-i | Ms | H |
| CH$_2$C≡CH | Me | MeO | CH$_2$OPr-n | Ms | H |
| CH$_2$C≡CH | Me | MeO | CH$_2$OCH=CH$_2$ | Ms | H |
| CH$_2$C≡CH | Me | MeO | CH$_2$OCH$_2$CH=CH$_2$ | Ms | H |
| CH$_2$C≡CH | Me | MeO | CH$_2$OCH$_2$C≡CH | Ms | H |
| CH$_2$C≡CH | Me | MeO | CH$_2$OCH$_2$CH$_2$Cl | Ms | H |
| CH$_2$C≡CH | Me | MeO | CHMeOH | Ms | H |
| CH$_2$C≡CH | Me | MeO | CHMeOMe | Ms | H |
| CH$_2$C≡CH | Me | MeO | CHMeOMe | Cl | H |
| CH$_2$C≡CH | Me | MeO | CHMeOMe | MeS | H |
| CH$_2$C≡CH | Me | MeO | CHMeOMe | MeSO | H |
| CH$_2$C≡CH | Me | MeO | CHMeOEt | Ms | H |
| CH$_2$C≡CH | Me | MeO | CH$_2$CH$_2$OMe | Ms | H |
| CH$_2$C≡CH | Me | MeO | CH$_2$CH$_2$OEt | Ms | H |
| CH$_2$C≡CH | Me | MeO | CHEtOH | Ms | H |
| CH$_2$C≡CH | Me | MeO | CHEtOMe | Ms | H |
| CH$_2$C≡CH | Me | MeO | CHEtOEt | Ms | H |
| CH$_2$C≡CH | Me | MeO | CH$_2$OCH$_2$CH$_2$OMe | Ms | H |
| CH$_2$C≡CH | Me | MeO | CH$_2$NMe$_2$ | Ms | H |
| CH$_2$C≡CH | Me | MeO | CH$_2$OCH$_2$Ph | Ms | H |
| CH$_2$C≡CH | Me | MeO | CH$_2$OCH$_2$CO$_2$Me | Ms | H |
| CH$_2$C≡CH | Me | MeO | CH$_2$OCH$_2$CO$_2$Et | Ms | H |
| CH$_2$C≡CH | Me | MeO | CH$_2$OCHMeCO$_2$Me | Ms | H |
| CH$_2$C≡CH | Me | MeO | CH$_2$CN | Ms | H |
| CH$_2$C≡CH | Me | MeO | CH$_2$SMe | Ms | H |
| CH$_2$C≡CH | Me | MeO | CH$_2$SEt | Ms | H |
| CH$_2$C≡CH | Me | MeO | CH$_2$SO$_2$Me | Ms | H |
| CH$_2$C≡CH | Me | MeO | CH$_2$SO$_2$Et | Ms | H |
| CH$_2$C≡CH | Me | MeO | CH$_2$SCH$_2$CH$_2$OMe | Ms | H |
| CH$_2$C≡CH | Me | MeO | CH$_2$OCOMe | Ms | H |
| CH$_2$C≡CH | Me | MeO | CHMeOCOMe | Ms | H |
| CH$_2$C≡CH | Me | MeO | CH$_2$OSO$_2$Me | Ms | H |
| CH$_2$C≡CH | Me | Me | CHMeOSO$_2$Me | Ms | H |
| Me | CF$_3$ | Me | CH$_2$OMe | Ms | H |
| Me | CF$_3$ | Me | CH$_2$OEt | Ms | H |
| Me | CF$_3$ | Me | CHMeOMe | Ms | H |
| Me | CF$_3$ | Me | CHMeOEt | Ms | H |
| Me | CF$_3$ | Me | CH$_2$CH$_2$OMe | Ms | H |
| Me | CF$_3$ | Me | CH$_2$CH$_2$OEt | Ms | H |
| Me | CF$_3$ | Me | CHEtOMe | Ms | H |
| Me | CF$_3$ | Me | CHEtOEt | Ms | H |
| Me | CF$_3$ | Me | CH$_2$OCH$_2$CO$_2$Me | Ms | H |
| Me | CF$_3$ | Me | CH$_2$SMe | Ms | H |
| Me | CF$_3$ | Me | CH$_2$SEt | Ms | H |
| Me | CF$_3$ | Me | CH$_2$SO$_2$Me | Ms | H |
| Me | CF$_3$ | Me | CH$_2$OCOMe | Ms | H |
| Me | CF$_3$ | Me | CHMeOCOMe | Ms | H |
| Me | CF$_3$ | Me | CH$_2$OSO$_2$Me | Ms | H |
| Me | CF$_3$ | Me | CHMeOSO$_2$Me | Ms | H |
| Et | CF$_3$ | Me | CH$_2$OMe | Ms | H |
| Et | CF$_3$ | Me | CH$_2$OEt | Ms | H |
| Et | CF$_3$ | Me | CHMeOMe | Ms | H |
| Et | CF$_3$ | Me | CHMeOEt | Ms | H |
| Et | CF$_3$ | Me | CH$_2$CH$_2$OMe | Ms | H |
| Et | CF$_3$ | Me | CH$_2$CH$_2$OEt | Ms | H |
| Et | CF$_3$ | Me | CHEtOMe | Ms | H |
| Et | CF$_3$ | Me | CHEtOEt | Ms | H |
| Et | CF$_3$ | Me | CH$_2$OCH$_2$CO$_2$Me | Ms | H |
| Et | CF$_3$ | Me | CH$_2$SMe | Ms | H |
| Et | CF$_3$ | Me | CH$_2$SEt | Ms | H |
| Et | CF$_3$ | Me | CH$_2$SO$_2$Me | Ms | H |
| Et | CF$_3$ | Me | CH$_2$OCOMe | Ms | H |
| Et | CF$_3$ | Me | CHMeOCOMe | Ms | H |
| Et | CF$_3$ | Me | CH$_2$OSO$_2$Me | Ms | H |
| Et | CF$_3$ | Me | CHMeOSO$_2$Me | Ms | H |
| Pr-i | CF$_3$ | Me | CH$_2$OMe | Ms | H |
| Pr-i | CF$_3$ | Me | CH$_2$OEt | Ms | H |
| Pr-i | CF$_3$ | Me | CHMeOMe | Ms | H |
| Pr-i | CF$_3$ | Me | CHMeOEt | Ms | H |
| Pr-i | CF$_3$ | Me | CH$_2$CH$_2$OMe | Ms | H |
| Pr-i | CF$_3$ | Me | CH$_2$CH$_2$OEt | Ms | H |
| Pr-i | CF$_3$ | Me | CHEtOMe | Ms | H |
| Pr-i | CF$_3$ | Me | CHEtOEt | Ms | H |
| Pr-i | CF$_3$ | Me | CH$_2$OCH$_2$CO$_2$Me | Ms | H |
| Pr-i | CF$_3$ | Me | CH$_2$SMe | Ms | H |

-continued

| | | | | | |
|---|---|---|---|---|---|
| Pr-i | CF$_3$ | Me | CH$_2$SEt | Ms | H |
| Pr-i | CF$_3$ | Me | CH$_2$SO$_2$Me | Ms | H |
| Pr-i | CF$_3$ | Me | CH$_2$OCOMe | Ms | H |
| Pr-i | CF$_3$ | Me | CHMeOCOMe | Ms | H |
| Pr-i | CF$_3$ | Me | CH$_2$OSO$_2$Me | Ms | H |
| Pr-i | CF$_3$ | Me | CHMeOSO$_2$Me | Ms | H |
| Me | CF$_3$ | Cl | CH$_2$OMe | Ms | H |
| Me | CF$_3$ | Cl | CH$_2$OEt | Ms | H |
| Me | CF$_3$ | Cl | CHMeOMe | Ms | H |
| Me | CF$_3$ | Cl | CHMeOEt | Ms | H |
| Me | CF$_3$ | Cl | CH$_2$CH$_2$OMe | Ms | H |
| Me | CF$_3$ | Cl | CH$_2$CH$_2$OEt | Ms | H |
| Me | CF$_3$ | Cl | CHEtOMe | Ms | H |
| Me | CF$_3$ | Cl | CHEtOEt | Ms | H |
| Me | CF$_3$ | Cl | CH$_2$OCH$_2$CO$_2$Me | Ms | H |
| Me | CF$_3$ | Cl | CH$_2$SMe | Ms | H |
| Me | CF$_3$ | Cl | CH$_2$SEt | Ms | H |
| Me | CF$_3$ | Cl | CH$_2$SO$_2$Me | Ms | H |
| Me | CF$_3$ | Cl | CH$_2$OCOMe | Ms | H |
| Me | CF$_3$ | Cl | CHMeOCOMe | Ms | H |
| Me | CF$_3$ | Cl | CH$_2$OSO$_2$Me | Ms | H |
| Me | CF$_3$ | Cl | CHMeOSO$_2$Me | Ms | H |
| Et | CF$_3$ | Cl | CH$_2$OMe | Ms | H |
| Et | CF$_3$ | Cl | CH$_2$OEt | Ms | H |
| Et | CF$_3$ | Cl | CHMeOMe | Ms | H |
| Et | CF$_3$ | Cl | CHMeOEt | Ms | H |
| Et | CF$_3$ | Cl | CH$_2$CH$_2$OMe | Ms | H |
| Et | CF$_3$ | Cl | CH$_2$CH$_2$OEt | Ms | H |
| Et | CF$_3$ | Cl | CHEtOMe | Ms | H |
| Et | CF$_3$ | Cl | CHEtOEt | Ms | H |
| Et | CF$_3$ | Cl | CH$_2$OCH$_2$CH$_2$Me | Ms | H |
| Et | CF$_3$ | Cl | CH$_2$SMe | Ms | H |
| Et | CF$_3$ | Cl | CH$_2$SEt | Ms | H |
| Et | CF$_3$ | Cl | CH$_2$SO$_2$Me | Ms | H |
| Et | CF$_3$ | Cl | CH$_2$OCOMe | Ms | H |
| Et | CF$_3$ | Cl | CHMeOCOMe | Ms | H |
| Et | CF$_3$ | Cl | CH$_2$OSO$_2$Me | Ms | H |
| Et | CF$_3$ | Cl | CHMeOSO$_2$Me | Ms | H |
| Pr-i | CF$_3$ | Cl | CH$_2$OMe | Ms | H |
| Pr-i | CF$_3$ | Cl | CH$_2$OEt | Ms | H |
| Pr-i | CF$_3$ | Cl | CHMeOMe | Ms | H |
| Pr-i | CF$_3$ | Cl | CHMeOEt | Ms | H |
| Pr-i | CF$_3$ | Cl | CH$_2$CH$_2$OMe | Ms | H |
| Pr-i | CF$_3$ | Cl | CH$_2$CH$_2$OEt | Ms | H |
| Pr-i | CF$_3$ | Cl | CHEtOMe | Ms | H |
| Pr-i | CF$_3$ | Cl | CHEtOEt | Ms | H |
| Pr-i | CF$_3$ | Cl | CH$_2$OCH$_2$CO$_2$Me | Ms | H |
| Pr-i | CF$_3$ | Cl | CH$_2$SMe | Ms | H |
| Pr-i | CF$_3$ | Cl | CH$_2$SEt | Ms | H |
| Pr-i | CF$_3$ | Cl | CH$_2$SO$_2$Me | Ms | H |
| Pr-i | CF$_3$ | Cl | CH$_2$OCOMe | Ms | H |
| Pr-i | CF$_3$ | Cl | CHMeOCOMe | Ms | H |
| Pr-i | CF$_3$ | Cl | CH$_2$OSO$_2$Me | Ms | H |
| Pr-i | CF$_3$ | Cl | CHMeOSO$_2$Me | Ms | H |
| Me | Et | Me | CH$_2$OMe | Ms | H |
| Me | Et | Me | CH$_2$OEt | Ms | H |
| Me | Et | Me | CHMeOMe | Ms | H |
| Me | Et | Me | CHMeOEt | Ms | H |
| Me | Et | Me | CH$_2$CH$_2$OMe | Ms | H |
| Me | Et | Me | CH$_2$CH$_2$OEt | Ms | H |
| Me | Et | Me | CHEtOMe | Ms | H |
| Me | Et | Me | CHEtOEt | Ms | H |
| Me | Et | Me | CH$_2$OCH$_2$CO$_2$Me | Ms | H |
| Me | Et | Me | CH$_2$SMe | Ms | H |
| Me | Et | Me | CH$_2$SEt | Ms | H |
| Me | Et | Me | CH$_2$SO$_2$Me | Ms | H |
| Me | Et | Me | CH$_2$OCOMe | Ms | H |
| Me | Et | Me | CHMeOCOMe | Ms | H |
| Me | Et | Me | CH$_2$OSO$_2$Me | Ms | H |
| Me | Et | Me | CHMeOSO$_2$Me | Ms | H |
| Et | Et | Me | CH$_2$OMe | Ms | H |
| Et | Et | Me | CH$_2$OEt | Ms | H |
| Et | Et | Me | CHMeOMe | Ms | H |
| Et | Et | Me | CHMeOEt | Ms | H |
| Et | Et | Me | CH$_2$CH$_2$OMe | Ms | H |
| Et | Et | Me | CH$_2$CH$_2$OEt | Ms | H |
| Et | Et | Me | CHEtOMe | Ms | H |
| Et | Et | Me | CHEtOEt | Ms | H |
| Et | Et | Me | CH$_2$OCH$_2$CO$_2$Me | Ms | H |
| Et | Et | Me | CH$_2$SMe | Ms | H |
| Et | Et | Me | CH$_2$SEt | Ms | H |
| Et | Et | Me | CH$_2$SO$_2$Me | Ms | H |
| Et | Et | Me | CH$_2$OCOMe | Ms | H |

-continued

| | | | | | |
|---|---|---|---|---|---|
| Et | Et | Me | CHMeOCOMe | Ms | H |
| Et | Et | Me | CH$_2$OSO$_2$Me | Ms | H |
| Pr-i | Et | Me | CHMeOSO$_2$Me | Ms | H |
| Pr-i | Et | Me | CH$_2$OMe | Ms | H |
| Pr-i | Et | Me | CH$_2$OEt | Ms | H |
| Pr-i | Et | Me | CHMeOMe | Ms | H |
| Pr-i | Et | Me | CHMeOEt | Ms | H |
| Pr-i | Et | Me | CH$_2$CH$_2$OMe | Ms | H |
| Pr-i | Et | Me | CH$_2$CH$_2$OEt | Ms | H |
| Pr-i | Et | Me | CHEtOMe | Ms | H |
| Pr-i | Et | Me | CHEtOEt | Ms | H |
| Pr-i | Et | Me | CH$_2$OCH$_2$CO$_2$Me | Ms | H |
| Pr-i | Et | Me | CH$_2$SMe | Ms | H |
| Pr-i | Et | Me | CH$_2$SEt | Ms | H |
| Pr-i | Et | Me | CH$_2$SO$_2$Me | Ms | H |
| Pr-i | Et | Me | CH$_2$OCOMe | Ms | H |
| Pr-i | Et | Me | CHMeOCOMe | Ms | H |
| Pr-i | Et | Me | CH$_2$OSO$_2$Me | Ms | H |
| Pr-i | Et | Me | CHMeOSO$_2$Me | Ms | H |
| Me | Et | Cl | CH$_2$OMe | Ms | H |
| Me | Et | Cl | CH$_2$OEt | Ms | H |
| Me | Et | Cl | CHMeOMe | Ms | H |
| Me | Et | Cl | CHMeOEt | Ms | H |
| Me | Et | Cl | CH$_2$CH$_2$OMe | Ms | H |
| Me | Et | Cl | CH$_2$CH$_2$OEt | Ms | H |
| Me | Et | Cl | CHEtOMe | Ms | H |
| Me | Et | Cl | CHEtOEt | Ms | H |
| Me | Et | Cl | CH$_2$OCH$_2$CO$_2$Me | Ms | H |
| Me | Et | Cl | CH$_2$SMe | Ms | H |
| Me | Et | Cl | CH$_2$SEt | Ms | H |
| Me | Et | Cl | CH$_2$SO$_2$Me | Ms | H |
| Me | Et | Cl | CH$_2$OCOMe | Ms | H |
| Me | Et | Cl | CHMeOCOMe | Ms | H |
| Me | Et | Cl | CH$_2$OSO$_2$Me | Ms | H |
| Me | Et | Cl | CHMeOSO$_2$Me | Ms | H |
| Et | Et | Cl | CH$_2$OMe | Ms | H |
| Et | Et | Cl | CH$_2$OEt | Ms | H |
| Et | Et | Cl | CHMeOMe | Ms | H |
| Et | Et | Cl | CHMeOEt | Ms | H |
| Et | Et | Cl | CH$_2$CH$_2$OMe | Ms | H |
| Et | Et | Cl | CH$_2$CH$_2$OEt | Ms | H |
| Et | Et | Cl | CHEtOMe | Ms | H |
| Et | Et | Cl | CHEtOEt | Ms | H |
| Et | Et | Cl | CH$_2$OCH$_2$CO$_2$Me | Ms | H |
| Et | Et | Cl | CH$_2$SMe | Ms | H |
| Et | Et | Cl | CH$_2$SEt | Ms | H |
| Et | Et | Cl | CH$_2$SO$_2$Me | Ms | H |
| Et | Et | Cl | CH$_2$OCOMe | Ms | H |
| Et | Et | Cl | CHMeOCOMe | Ms | H |
| Et | Et | Cl | CH$_2$OSO$_2$Me | Ms | H |
| Et | Et | Cl | CHMeOSO$_2$Me | Ms | H |
| Et | Et | Cl | CH$_2$OMe | Ms | H |
| Pr-i | Et | Cl | CH$_2$OEt | Ms | H |
| Pr-i | Et | Cl | CHMeOMe | Ms | H |
| Pr-i | Et | Cl | CHMeOEt | Ms | H |
| Pr-i | Et | Cl | CH$_2$CH$_2$OMe | Ms | H |
| Pr-i | Et | Cl | CH$_2$CH$_2$OEt | Ms | H |
| Pr-i | Et | Cl | CHEtOMe | Ms | H |
| Pr-i | Et | Cl | CHEtOEt | Ms | H |
| Pr-i | Et | Cl | CH$_2$OCH$_2$CO$_2$Me | Ms | H |
| Pr-i | Et | Cl | CH$_2$SMe | Ms | H |
| Pr-i | Et | Cl | CH$_2$SEt | Ms | H |
| Pr-i | Et | Cl | CH$_2$SO$_2$Me | Ms | H |
| Pr-i | Et | Cl | CH$_2$OCOMe | Ms | H |
| Pr-i | Et | Cl | CHMeOCOMe | Ms | H |
| Pr-i | Et | Cl | CH$_2$OSO$_2$Me | Ms | H |
| Pr-i | Et | Cl | CHMeOSO$_2$Me | Ms | H |
| Me | CH$_2$OMe | Me | CH$_2$OMe | Ms | H |
| Me | CH$_2$OMe | Me | CH$_2$OEt | Ms | H |
| Me | CH$_2$OMe | Me | CHMeOMe | Ms | H |
| Me | CH$_2$OMe | Me | CHMeOEt | Ms | H |
| Me | CH$_2$OMe | Me | CH$_2$CH$_2$OMe | Ms | H |
| Me | CH$_2$OMe | Me | CH$_2$CH$_2$OEt | Ms | H |
| Me | CH$_2$OMe | Me | CHEtOMe | Ms | H |
| Me | CH$_2$OMe | Me | CHEtOEt | Ms | H |
| Me | CH$_2$OMe | Me | CH$_2$OCH$_2$CO$_2$Me | Ms | H |
| Me | CH$_2$OMe | Me | CH$_2$SMe | Ms | H |
| Me | CH$_2$OMe | Me | CH$_2$SEt | Ms | H |
| Me | CH$_2$OMe | Me | CH$_2$SO$_2$Me | Ms | H |
| Me | CH$_2$OMe | Me | CH$_2$OCOMe | Ms | H |
| Me | CH$_2$OMe | Me | CHMeOCOMe | Ms | H |
| Me | CH$_2$OMe | Me | CH$_2$OSO$_2$Me | Ms | H |
| Me | CH$_2$OMe | Me | CHMeOSO$_2$Me | Ms | H |

-continued

| | | | | | |
|---|---|---|---|---|---|
| Et | CH$_2$OMe | Me | CH$_2$OMe | Ms | H |
| Et | CH$_2$OMe | Me | CH$_2$OEt | Ms | H |
| Et | CH$_2$OMe | Me | CHMeOMe | Ms | H |
| Et | CH$_2$OMe | Me | CHMeOEt | Ms | H |
| Et | CH$_2$OMe | Me | CH$_2$CH$_2$OMe | Ms | H |
| Et | CH$_2$OMe | Me | CH$_2$CH$_2$OEt | Ms | H |
| Et | CH$_2$OMe | Me | CHEtOMe | Ms | H |
| Et | CH$_2$OMe | Me | CHEtOEt | Ms | H |
| Et | CH$_2$OMe | Me | CH$_2$OCH$_2$CO$_2$Me | Ms | H |
| Et | CH$_2$OMe | Me | CH$_2$SMe | Ms | H |
| Et | CH$_2$OMe | Me | CH$_2$SEt | Ms | H |
| Et | CH$_2$OMe | Me | CH$_2$SO$_2$Me | Ms | H |
| Et | CH$_2$OMe | Me | CH$_2$OCOMe | Ms | H |
| Et | CH$_2$OMe | Me | CHMeOCOMe | Ms | H |
| Et | CH$_2$OMe | Me | CH$_2$OSO$_2$Me | Ms | H |
| Et | CH$_2$OMe | Me | CHMeOSO$_2$Me | Ms | H |
| Pr-i | CH$_2$OMe | Me | CH$_2$OMe | Ms | H |
| Pr-i | CH$_2$OMe | Me | CH$_2$OEt | Ms | H |
| Pr-i | CH$_2$OMe | Me | CHMeOMe | Ms | H |
| Pr-i | CH$_2$OMe | Me | CHMeOEt | Ms | H |
| Pr-i | CH$_2$OMe | Me | CH$_2$CH$_2$OMe | Ms | H |
| Pr-i | CH$_2$OMe | Me | CH$_2$CH$_2$OEt | Ms | H |
| Pr-i | CH$_2$OMe | Me | CHEtOMe | Ms | H |
| Pr-i | CH$_2$OMe | Me | CHEtOEt | Ms | H |
| Pr-i | CH$_2$OMe | Me | CH$_2$OCH$_2$CO$_2$Me | Ms | H |
| Pr-i | CH$_2$OMe | Me | CH$_2$SMe | Ms | H |
| Pr-i | CH$_2$OMe | Me | CH$_2$SEt | Ms | H |
| Pr-i | CH$_2$OMe | Me | CH$_2$SO$_2$Me | Ms | H |
| Pr-i | CH$_2$OMe | Me | CH$_2$OCOMe | Ms | H |
| Pr-i | CH$_2$OMe | Me | CHMeOCOMe | Ms | H |
| Pr-i | CH$_2$OMe | Me | CH$_2$OSO$_2$Me | Ms | H |
| Pr-i | CH$_2$OMe | Me | CHMeOSO$_2$Me | Ms | H |
| Me | CH$_2$OMe | Cl | CH$_2$OMe | Ms | H |
| Me | CH$_2$OMe | Cl | CH$_2$OEt | Ms | H |
| Me | CH$_2$OMe | Cl | CHMeOMe | Ms | H |
| Me | CH$_2$OMe | Cl | CHMeOEt | Ms | H |
| Me | CH$_2$OMe | Cl | CH$_2$CH$_2$OMe | Ms | H |
| Me | CH$_2$OMe | Cl | CH$_2$CH$_2$OEt | Ms | H |
| Me | CH$_2$OMe | Cl | CHEtOMe | Ms | H |
| Me | CH$_2$OMe | Cl | CHEtOEt | Ms | H |
| Me | CH$_2$OMe | Cl | CH$_2$OCH$_2$CO$_2$Me | Ms | H |
| Me | CH$_2$OMe | Cl | CH$_2$SMe | Ms | H |
| Me | CH$_2$OMe | Cl | CH$_2$SEt | Ms | H |
| Me | CH$_2$OMe | Cl | CH$_2$SO$_2$Me | Ms | H |
| Me | CH$_2$OMe | Cl | CH$_2$OCOMe | Ms | H |
| Me | CH$_2$OMe | Cl | CHMeOCOMe | Ms | H |
| Me | CH$_2$OMe | Cl | CH$_2$OSO$_2$Me | Ms | H |
| Me | CH$_2$OMe | Cl | CHMeOSO$_2$Me | Ms | H |
| Et | CH$_2$OMe | Cl | CH$_2$OMe | Ms | H |
| Et | CH$_2$OMe | Cl | CH$_2$OEt | Ms | H |
| Et | CH$_2$OMe | Cl | CHMeOMe | Ms | H |
| Et | CH$_2$OMe | Cl | CHMeOEt | Ms | H |
| Et | CH$_2$OMe | Cl | CH$_2$CH$_2$OMe | Ms | H |
| Et | CH$_2$OMe | Cl | CH$_2$CH$_2$OEt | Ms | H |
| Et | CH$_2$OMe | Cl | CHEtOMe | Ms | H |
| Et | CH$_2$OMe | Cl | CHEtOEt | Ms | H |
| Et | CH$_2$OMe | Cl | CH$_2$OCH$_2$CO$_2$Me | Ms | H |
| Et | CH$_2$OMe | Cl | CH$_2$SMe | Ms | H |
| Et | CH$_2$OMe | Cl | CH$_2$SEt | Ms | H |
| Et | CH$_2$OMe | Cl | CH$_2$SO$_2$Me | Ms | H |
| Et | CH$_2$OMe | Cl | CH$_2$OCOMe | Ms | H |
| Et | CH$_2$OMe | Cl | CHMeOCOMe | Ms | H |
| Et | CH$_2$OMe | Cl | CH$_2$OSO$_2$Me | Ms | H |
| Et | CH$_2$OMe | Cl | CHMeOSO$_2$Me | Ms | H |
| Pr-i | CH$_2$OMe | Cl | CH$_2$OMe | Ms | H |
| Pr-i | CH$_2$OMe | Cl | CH$_2$OEt | Ms | H |
| Pr-i | CH$_2$OMe | Cl | CHMeOMe | Ms | H |
| Pr-i | CH$_2$OMe | Cl | CHMeOEt | Ms | H |
| Pr-i | CH$_2$OMe | Cl | CH$_2$CH$_2$OMe | Ms | H |
| Pr-i | CH$_2$OMe | Cl | CH$_2$CH$_2$OEt | Ms | H |
| Pr-i | CH$_2$OMe | Cl | CHEtOMe | Ms | H |
| Pr-i | CH$_2$OMe | Cl | CHEtOEt | Ms | H |
| Pr-i | CH$_2$OMe | Cl | CH$_2$OCH$_2$CO$_2$Me | Ms | H |
| Pr-i | CH$_2$OMe | Cl | CH$_2$SMe | Ms | H |
| Pr-i | CH$_2$OMe | Cl | CH$_2$SEt | Ms | H |
| Pr-i | CH$_2$OMe | Cl | CH$_2$SO$_2$Me | Ms | H |
| Pr-i | CH$_2$OMe | Cl | CH$_2$OCOMe | Ms | H |
| Pr-i | CH$_2$OMe | Cl | CHMeOCOMe | Ms | H |
| Pr-i | CH$_2$OMe | Cl | CH$_2$OSO$_2$Me | Ms | H |
| Pr-i | CH$_2$OMe | Cl | CHMeOSO$_2$Me | Ms | H |
| Me | OMe | Me | CH$_2$OMe | Ms | H |
| Me | OMe | Me | CH$_2$OEt | Ms | H |
| Me | OMe | Me | CHMeOMe | Ms | H |

-continued

| | | | | | |
|---|---|---|---|---|---|
| Me | OMe | Me | CHMeOEt | Ms | H |
| Me | OMe | Me | CH$_2$CH$_2$OMe | Ms | H |
| Me | OMe | Me | CH$_2$CH$_2$OEt | Ms | H |
| Me | OMe | Me | CHEtOMe | Ms | H |
| Me | OMe | Me | CHEtOEt | Ms | H |
| Me | OMe | Me | CH$_2$OCH$_2$CH$_2$Me | Ms | H |
| Me | OMe | Me | CH$_2$SMe | Ms | H |
| Me | OMe | Me | CH$_2$SEt | Ms | H |
| Me | OMe | Me | CH$_2$SO$_2$Me | Ms | H |
| Me | OMe | Me | CH$_2$OCOMe | Ms | H |
| Me | OMe | Me | CHMeOCOMe | Ms | H |
| Me | OMe | Me | CH$_2$OSO$_2$Me | Ms | H |
| Me | OMe | Me | CHMeOSO$_2$Me | Ms | H |
| Et | OMe | Me | CH$_2$OMe | Ms | H |
| Et | OMe | Me | CH$_2$OEt | Ms | H |
| Et | OMe | Me | CHMeOMe | Ms | H |
| Et | OMe | Me | CHMeOEt | Ms | H |
| Et | OMe | Me | CH$_2$CH$_2$OMe | Ms | H |
| Et | OMe | Me | CH$_2$CH$_2$OEt | Ms | H |
| Et | OMe | Me | CHEtOMe | Ms | H |
| Et | OMe | Me | CHEtOEt | Ms | H |
| Et | OMe | Cl | CH$_2$OCH$_2$CO$_2$Me | Ms | H |
| Et | OMe | Cl | CH$_2$SMe | Ms | H |
| Et | OMe | Cl | CH$_2$SEt | Ms | H |
| Et | OMe | Cl | CH$_2$SO$_2$Me | Ms | H |
| Et | OMe | Cl | CH$_2$OCOMe | Ms | H |
| Et | OMe | Cl | CHMeOCOMe | Ms | H |
| Et | OMe | Cl | CH$_2$OSO$_2$Me | Ms | H |
| Et | OMe | Cl | CHMeOSO$_2$Me | Ms | H |
| Pr-i | OMe | Cl | CH$_2$OMe | Ms | H |
| Pr-i | OMe | Cl | CH$_2$OEt | Ms | H |
| Pr-i | OMe | Cl | CHMeOMe | Ms | H |
| Pr-i | OMe | Cl | CHMeOEt | Ms | H |
| Pr-i | OMe | Cl | CH$_2$CH$_2$OMe | Ms | H |
| Pr-i | OMe | Cl | CH$_2$CH$_2$OEt | Ms | H |
| Pr-i | OMe | Cl | CHEtOMe | Ms | H |
| Pr-i | OMe | Cl | CHEtOEt | Ms | H |
| Pr-i | OMe | Cl | CH$_2$OCH$_2$CO$_2$Me | Ms | H |
| Pr-i | OMe | Cl | CH$_2$SMe | Ms | H |
| Pr-i | OMe | Cl | CH$_2$SEt | Ms | H |
| Pr-i | OMe | Cl | CH$_2$SO$_2$Me | Ms | H |
| Pr-i | OMe | Cl | CH$_2$OCOMe | Ms | H |
| Pr-i | OMe | Cl | CHMeOCOMe | Ms | H |
| Pr-i | OMe | Cl | CH$_2$OSO$_2$Me | Ms | H |
| Pr-i | OMe | Cl | CHMeOSO$_2$Me | Ms | H |
| Me | SMe | Me | CH$_2$OMe | Ms | H |
| Me | SMe | Me | CH$_2$OEt | Ms | H |
| Me | SMe | Me | CHMeOMe | Ms | H |
| Me | SMe | Me | CHMeOEt | Ms | H |
| Me | SMe | Me | CHEtOMe | Ms | H |
| Me | SMe | Me | CHEtOEt | Ms | H |
| Me | SMe | Cl | CH$_2$OMe | Ms | H |
| Me | SMe | Cl | CH$_2$OEt | Ms | H |
| Me | SMe | Cl | CHMeOMe | Ms | H |
| Me | SMe | Cl | CHMeOEt | Ms | H |
| Et | SMe | Me | CH$_2$OMe | Ms | H |
| Et | SMe | Me | CH$_2$OEt | Ms | H |
| Et | SMe | Me | CHMeOMe | Ms | H |
| Et | SMe | Me | CHMeOEt | Ms | H |
| Et | SMe | Me | CHEtOMe | Ms | H |
| Et | SMe | Me | CHEtOEt | Ms | H |
| Et | SMe | Cl | CH$_2$OMe | Ms | H |
| Et | SMe | Cl | CH$_2$OEt | Ms | H |
| Et | SMe | Cl | CHMeOMe | Ms | H |
| Et | SMe | Cl | CHMeOEt | Ms | H |
| Pr-i | SMe | Me | CH$_2$OMe | Ms | H |
| Pr-i | SMe | Me | CH$_2$OEt | Ms | H |
| Pr-i | SMe | Me | CHMeOMe | Ms | H |
| Pr-i | SMe | Me | CHMeOEt | Ms | H |
| Pr-i | SMe | Me | CHEtOMe | Ms | H |
| Pr-i | SMe | Me | CHEtOEt | Ms | H |
| Pr-i | SMe | Cl | CH$_2$OMe | Ms | H |
| Pr-i | SMe | Cl | CH$_2$OEt | Ms | H |
| Pr-i | SMe | Cl | CHMeOMe | Ms | H |
| Pr-i | SMe | Cl | CHMeOEt | Ms | H |
| Me | CH$_2$SMe | Me | CH$_2$OMe | Ms | H |
| Me | CH$_2$SMe | Me | CH$_2$OEt | Ms | H |
| Me | CH$_2$SMe | Me | CHMeOMe | Ms | H |
| Me | CH$_2$SMe | Me | CHMeOEt | Ms | H |
| Me | CH$_2$SMe | Me | CHEtOMe | Ms | H |
| Me | CH$_2$SMe | Me | CHEtOEt | Ms | H |
| Me | CH$_2$SMe | Cl | CH$_2$OMe | Ms | H |
| Me | CH$_2$SMe | Cl | CH$_2$OEt | Ms | H |

-continued

| | | | | | |
|---|---|---|---|---|---|
| Me | CH₂SMe | Cl | CHMeOMe | Ms | H |
| Me | CH₂SMe | Cl | CHMeOEt | Ms | H |
| Et | CH₂SMe | Me | CH₂OMe | Ms | H |
| Et | CH₂SMe | Me | CH₂OEt | Ms | H |
| Et | CH₂SMe | Me | CHMeOMe | Ms | H |
| Et | CH₂SMe | Me | CHMeOEt | Ms | H |
| Et | CH₂SMe | Me | CHEtOMe | Ms | H |
| Et | CH₂SMe | Me | CHEtOEt | Ms | H |
| Et | CH₂SMe | Cl | CH₂OMe | Ms | H |
| Et | CH₂SMe | Cl | CH₂OEt | Ms | H |
| Et | CH₂SMe | Cl | CHMeOMe | Ms | H |
| Et | CH₂SMe | Cl | CHMeOEt | Ms | H |
| Pr-i | CH₂SMe | Me | CH₂OMe | Ms | H |
| Pr-i | CH₂SMe | Me | CH₂OEt | Ms | H |
| Pr-i | CH₂SMe | Me | CHMeOMe | Ms | H |
| Pr-i | CH₂SMe | Me | CHMeOEt | Ms | H |
| Pr-i | CH₂SMe | Me | CHEtOMe | Ms | H |
| Pr-i | CH₂SMe | Me | CHEtOEt | Ms | H |
| Pr-i | CH₂SMe | Cl | CH₂OMe | Ms | H |
| Pr-i | CH₂SMe | Cl | CH₂OEt | Ms | H |
| Pr-i | CH₂SMe | Cl | CHMeOMe | Ms | H |
| Pr-i | CH₂SMe | Cl | CHMeOEt | Ms | H |
| Me | CH₂Cl | Me | CH₂OMe | Ms | H |
| Me | CH₂Cl | Me | CH₂OEt | Ms | H |
| Me | CH₂Cl | Me | CHMeOMe | Ms | H |
| Me | CH₂Cl | Me | CHMeOEt | Ms | H |
| Me | CH₂Cl | Me | CHEtOMe | Ms | H |
| Me | CH₂Cl | Me | CHEtOEt | Ms | H |
| Me | CH₂Cl | Cl | CH₂OMe | Ms | H |
| Me | CH₂Cl | Cl | CH₂OEt | Ms | H |
| Me | CH₂Cl | Cl | CHMeOMe | Ms | H |
| Me | CH₂Cl | Cl | CHMeOEt | Ms | H |
| Et | Ch₂Cl | Me | CH₂OMe | Ms | H |
| Et | Ch₂Cl | Me | CH₂OEt | Ms | H |
| Et | Ch₂Cl | Me | CHMeOMe | Ms | H |
| Et | Ch₂Cl | Me | CHMeOEt | Ms | H |
| Et | Ch₂Cl | Me | CHEtOMe | Ms | H |
| Et | Ch₂Cl | Me | CHEtOEt | Ms | H |
| Et | Ch₂Cl | Cl | CH₂OMe | Ms | H |
| Et | Ch₂Cl | Cl | CH₂OEt | Ms | H |
| Et | Ch₂Cl | Cl | CHMeOMe | Ms | H |
| Et | Ch₂Cl | Cl | CHMeOEt | Ms | H |
| Pr-i | CH₂Cl | Me | CH₂OMe | Ms | H |
| Pr-i | CH₂Cl | Me | CH₂OEt | Ms | H |
| Pr-i | CH₂Cl | Me | CHMeOMe | Ms | H |
| Pr-i | CH₂Cl | Me | CHMeOEt | Ms | H |
| Pr-i | CH₂Cl | Me | CHEtOMe | Ms | H |
| Pr-i | CH₂Cl | Me | CHEtOEt | Ms | H |
| Pr-i | CH₂Cl | Cl | CH₂OMe | Ms | H |
| Pr-i | CH₂Cl | Cl | CH₂OEt | Ms | H |
| Pr-i | CH₂Cl | Cl | CHMeOMe | Ms | H |
| Pr-i | CH₂Cl | Cl | CHMeOEt | Ms | H |
| Me | H | CH₂OMe | CH₂OH | Ms | H |
| Me | H | CH₂OMe | CH₂OMe | MS | H |
| Me | H | CH₂OMe | CH₂OMe | Cl | H |
| Me | H | CH₂OMe | CH₂OMe | MeS | H |
| Me | H | CH₂OMe | CH₂OMe | MeSO | H |
| Me | H | CH₂OMe | CH₂OEt | Ms | H |
| Me | H | CH₂OMe | CH₂OEt | Cl | H |
| Me | H | CH₂OMe | CH₂OEt | MeS | H |
| Me | H | CH₂OMe | CH₂OEt | MeSO | H |
| Me | H | CH₂OMe | CH₂OPr-i | Ms | H |
| Me | H | CH₂OMe | CH₂OPr-n | Ms | H |
| Me | H | CH₂OMe | CH₂OCH=CH₂ | Ms | H |
| Me | H | CH₂OMe | CH₂OCH₂CH=CH₂ | Ms | H |
| Me | H | CH₂OMe | CH₂OCH₂C≡CH | Ms | H |
| Me | H | CH₂OMe | CH₂OCH₂CH₂Cl | Ms | H |
| Me | H | CH₂OMe | CHMeOH | Ms | H |
| Me | H | CH₂OMe | CHMeOMe | Ms | H |
| Me | H | CH₂OMe | CHMeOMe | Cl | H |
| Me | H | CH₂OMe | CHMeOMe | MeS | H |
| Me | H | CH₂OMe | CHMeOMe | MeSO | H |
| Me | H | CH₂OMe | CHMeOEt | Ms | H |
| Me | H | CH₂OMe | CHMeOCH=CH₂ | Ms | H |
| Me | H | CH₂OMe | CHMeOCH=CH₂ | Ms | H |
| Me | H | CH₂OMe | CHMeOCH₂CH=CH₂ | Ms | H |
| Me | H | CH₂OMe | CHMeOCH₂C≡CH | Ms | H |
| Me | H | CH₂OMe | CHMeOCH₂CH₂Cl | Ms | H |
| Me | H | CH₂OMe | CMe₂OH | Ms | H |
| Me | H | CH₂OMe | CMe₂OMe | Ms | H |
| Me | H | CH₂OMe | CMe₂OEt | Ms | H |
| Me | H | CH₂OMe | CH₂CH₂OMe | Ms | H |
| Me | H | CH₂OMe | CH₂Ch₂OEt | Ms | H |

-continued

| | | | | | |
|---|---|---|---|---|---|
| Me | H | CH₂OMe | CHEtOH | Ms | H |
| Me | H | CH₂OMe | CHEtOMe | Ms | H |
| Me | H | CH₂OMe | CHEtOEt | Ms | H |
| Me | H | CH₂OMe | CH₂OCH₂CH₂OMe | Ms | H |
| Me | H | CH₂OMe | CHMeOCH₂CH₂OMe | Ms | H |
| Me | H | CH₂OMe | CH₂NMe₂ | Ms | H |
| Me | H | CH₂OMe | CHMeNMe₂ | Ms | H |
| Me | H | CH₂OMe | CH₂CH₂NMe₂ | Ms | H |
| Me | H | CH₂OMe | CH₂OCH₂Ph | Ms | H |
| Me | H | CH₂OMe | CHMeOCH₂Ph | Ms | H |
| Me | H | CH₂OMe | CH₂OCH₂CO₂Me | Ms | H |
| Me | H | CH₂OMe | CH₂OCH₂CO₂Et | Ms | H |
| Me | H | CH₂OMe | CH₂OCHMeCO₂Me | Ms | H |
| Me | H | CH₂OMe | CH₂CN | Ms | H |
| Me | H | CH₂OMe | CH₂SMe | Ms | H |
| Me | H | CH₂OMe | CH₂SEt | Ms | H |
| Me | H | CH₂OMe | CH₂SOMe | Ms | H |
| Me | H | CH₂OMe | CH₂SO₂Me | Ms | H |
| Me | H | CH₂OMe | CH₂SO₂Et | Ms | H |
| Me | H | CH₂OMe | CHMeSMe | Ms | H |
| Me | H | CH₂OMe | CHMeSO₂Me | Ms | H |
| Me | H | CH₂OMe | CH₂SCH₂CH₂OMe | Ms | H |
| Me | H | CH₂OMe | CH₂OCOMe | Ms | H |
| Me | H | CH₂OMe | CHMeOCOMe | Ms | H |
| Me | H | CH₂OMe | CH₂OSO₂Me | Ms | H |
| Me | H | CH₂OMe | CHMeOSO₂Me | Ms | H |
| Et | H | CH₂OMe | CH₂OH | Ms | H |
| Et | H | CH₂OMe | CH₂OMe | Ms | H |
| Et | H | CH₂OMe | CH₂OMe | Cl | H |
| Et | H | CH₂OMe | CH₂OMe | MeS | H |
| Et | H | CH₂OMe | CH₂OMe | MeSO | H |
| Et | H | CH₂OMe | CH₂OEt | Ms | H |
| Et | H | CH₂OMe | CH₂OEt | Cl | H |
| Et | H | CH₂OMe | CH₂OEt | MeS | H |
| Et | H | CH₂OMe | CH₂OEt | MeSO | H |
| Et | H | CH₂OMe | CH₂OPr-i | Ms | H |
| Et | H | CH₂OMe | CH₂OPr-n | Ms | H |
| Et | H | CH₂OMe | CH₂OCH=CH₂ | Ms | H |
| Et | H | CH₂OMe | CH₂OCH₂CH=CH₂ | Ms | H |
| Et | H | CH₂OMe | CH₂OCH₂C≡CH | Ms | H |
| Et | H | CH₂OMe | CH₂OCH₂CH₂Cl | Ms | H |
| Et | H | CH₂OMe | CHMeOH | Ms | H |
| Et | H | CH₂OMe | CHMeOMe | Ms | H |
| Et | H | CH₂OMe | CHMeOMe | Cl | H |
| Et | H | CH₂OMe | CHMeOMe | MeS | H |
| Et | H | CH₂OMe | CHMeOMe | MeSO | H |
| Et | H | CH₂OMe | CHMeOEt | Ms | H |
| Et | H | CH₂OMe | CHMeOCH=CH₂ | Ms | H |
| Et | H | CH₂OMe | CHMeOCH=CH₂ | Ms | H |
| Et | H | CH₂OMe | CHMeOCH₂CH=CH₂ | Ms | H |
| Et | H | CH₂OMe | CHMeOCH₂C≡CH | Ms | H |
| Et | H | CH₂OMe | CHMeOCH₂CH₂Cl | Ms | H |
| Et | H | CH₂OMe | CMe₂OH | Ms | H |
| Et | H | CH₂OMe | CMe₂OMe | Ms | H |
| Et | H | CH₂OMe | CMe₂OEt | Ms | H |
| Et | H | CH₂OMe | CH₂CH₂OMe | Ms | H |
| Et | H | CH₂OMe | CH₂CH₂OEt | Ms | H |
| Et | H | CH₂OMe | CHEtOH | Ms | H |
| Et | H | CH₂OMe | CHEtOMe | Ms | H |
| Et | H | CH₂OMe | CHEtOEt | Ms | H |
| Et | H | CH₂OMe | CH₂OCH₂CH₂OMe | Ms | H |
| Et | H | CH₂OMe | CHMeOCH₂CH₂OMe | Ms | H |
| Et | H | CH₂OMe | CH₂NMe₂ | Ms | H |
| Et | H | CH₂OMe | CHMeNMe₂ | Ms | H |
| Et | H | CH₂OMe | CH₂CH₂NMe₂ | Ms | H |
| Et | H | CH₂OMe | CH₂OCH₂Ph | Ms | H |
| Et | H | CH₂OMe | CHMeOCH₂Ph | Ms | H |
| Et | H | CH₂OMe | CH₂OCH₂CO₂Me | Ms | H |
| Et | H | CH₂OMe | CH₂OCH₂CO₂Et | Ms | H |
| Et | H | CH₂OMe | CH₂OCHMeCO₂Me | Ms | H |
| Et | H | CH₂OMe | CH₂CN | Ms | H |
| Et | H | CH₂OMe | CH₂SMe | Ms | H |
| Et | H | CH₂OMe | CH₂SEt | Ms | H |
| Et | H | CH₂OMe | CH₂SOMe | Ms | H |
| Et | H | CH₂OMe | CH₂SO₂Me | Ms | H |
| Et | H | CH₂OMe | CH₂SO₂Et | Ms | H |
| Et | H | CH₂OMe | CHMeSMe | Ms | H |
| Et | H | CH₂OMe | CHMeSO₂Me | Ms | H |
| Et | H | CH₂OMe | CH₂SCH₂CH₂OMe | Ms | H |
| Et | H | CH₂OMe | CH₂OCOMe | Ms | H |
| Et | H | CH₂OMe | CHMeOCOMe | Ms | H |
| Et | H | CH₂OMe | CH₂OSO₂Me | Ms | H |
| Et | H | CH₂OMe | CHMeOSO₂Me | Ms | H |

-continued

| | | | | | |
|---|---|---|---|---|---|
| Pr-i | H | CH$_2$OMe | CH$_2$OH | Ms | H |
| Pr-i | H | CH$_2$OMe | CH$_2$OMe | Ms | H |
| Pr-i | H | CH$_2$OMe | CH$_2$OMe | Cl | H |
| Pr-i | H | CH$_2$OMe | CH$_2$OMe | MeS | H |
| Pr-i | H | CH$_2$OMe | CH$_2$OMe | MeSO | H |
| Pr-i | H | CH$_2$OMe | CH$_2$OEt | Ms | H |
| Pr-i | H | CH$_2$OMe | CH$_2$OEt | Cl | H |
| Pr-i | H | CH$_2$OMe | CH$_2$OEt | MeS | H |
| Pr-i | H | CH$_2$OMe | CH$_2$OEt | MeSO | H |
| Pr-i | H | CH$_2$OMe | CH$_2$OPr-i | Ms | H |
| Pr-i | H | CH$_2$OMe | CH$_2$OPr-n | Ms | H |
| Pr-i | H | CH$_2$OMe | CH$_2$OCH=CH$_2$ | Ms | H |
| Pr-i | H | CH$_2$OMe | CH$_2$OCH$_2$CH=CH$_2$ | Ms | H |
| Pr-i | H | CH$_2$OMe | CH$_2$OCH$_2$C≡CH | Ms | H |
| Pr-i | H | CH$_2$OMe | CH$_2$OCH$_2$CH$_2$Cl | Ms | H |
| Pr-i | H | CH$_2$OMe | CHMeOH | Ms | H |
| Pr-i | H | CH$_2$OMe | CHMeOMe | Ms | H |
| Pr-i | H | CH$_2$OMe | CHMeOMe | Cl | H |
| Pr-i | H | CH$_2$OMe | CHMeOMe | MeS | H |
| Pr-i | H | CH$_2$OMe | CHMeOMe | MeSO | H |
| Pr-i | H | CH$_2$OMe | CHMeOEt | Ms | H |
| Pr-i | H | CH$_2$OMe | CHMeOCH=CH$_2$ | Ms | H |
| Pr-i | H | CH$_2$OMe | CHMeOCH=CH$_2$ | Ms | H |
| Pr-i | H | CH$_2$OMe | CHMeOCH$_2$CH=CH$_2$ | Ms | H |
| Pr-i | H | CH$_2$OMe | CHMeOCH$_2$C≡CH$_2$ | Ms | H |
| Pr-i | H | CH$_2$OMe | CHMeOCH$_2$CH$_2$Cl | Ms | H |
| Pr-i | H | CH$_2$OMe | CMe$_2$OH | Ms | H |
| Pr-i | H | CH$_2$OMe | CMe$_2$OMe | Ms | H |
| Pr-i | H | CH$_2$OMe | CMe$_2$OEt | Ms | H |
| Pr-i | H | CH$_2$OMe | CH$_2$CH$_2$OMe | Ms | H |
| Pr-i | H | CH$_2$OMe | CH$_2$CH$_2$OEt | Ms | H |
| Pr-i | H | CH$_2$OMe | CHEtOH | Ms | H |
| Pr-i | H | CH$_2$OMe | CHEtOMe | Ms | H |
| Pr-i | H | CH$_2$OMe | CHEtOEt | Ms | H |
| Pr-i | H | CH$_2$OMe | CH$_2$OCH$_2$CH$_2$OMe | Ms | H |
| Pr-i | H | CH$_2$OMe | CHMeOCH$_2$CH$_2$OMe | Ms | H |
| Pr-i | H | CH$_2$OMe | CH$_2$NMe$_2$ | Ms | H |
| Pr-i | H | CH$_2$OMe | CHMeNMe$_2$ | Ms | H |
| Pr-i | H | CH$_2$OMe | CH$_2$CH$_2$NMe$_2$ | Ms | H |
| Pr-i | H | CH$_2$OMe | CH$_2$OCH$_2$Ph | Ms | H |
| Pr-i | H | CH$_2$OMe | CHMeOCH$_2$Ph | Ms | H |
| Pr-i | H | CH$_2$OMe | CH$_2$OCH$_2$CO$_2$Me | Ms | H |
| Pr-i | H | CH$_2$OMe | CH$_2$OCH$_2$CO$_2$Et | Ms | H |
| Pr-i | H | CH$_2$OMe | CH$_2$OCHMeCO$_2$Me | Ms | H |
| Pr-i | H | CH$_2$OMe | CH$_2$CN | Ms | H |
| Pr-i | H | CH$_2$OMe | CH$_2$SMe | Ms | H |
| Pr-i | H | CH$_2$OMe | CH$_2$SEt | Ms | H |
| Pr-i | H | CH$_2$OMe | CH$_2$SOMe | Ms | H |
| Pr-i | H | CH$_2$OMe | CH$_2$SO$_2$Me | Ms | H |
| Pr-i | H | CH$_2$OMe | CH$_2$SO$_2$Et | Ms | H |
| Pr-i | H | CH$_2$OMe | CHMeSMe | Ms | H |
| Pr-i | H | CH$_2$OMe | CHMeSO$_2$Me | Ms | H |
| Pr-i | H | CH$_2$OMe | CH$_2$SCH$_2$CH$_2$OMe | Ms | H |
| Pr-i | H | CH$_2$OMe | CH$_2$OCOMe | Ms | H |
| Pr-i | H | CH$_2$OMe | CHMeOCOMe | Ms | H |
| Pr-i | H | CH$_2$OMe | CH$_2$OSO$_2$Me | Ms | H |
| Pr-i | H | CH$_2$OMe | CHMeOSO$_2$Me | Ms | H |
| Me | Me | CH$_2$OMe | CH$_2$OH | Ms | H |
| Me | Me | CH$_2$OMe | CH$_2$OMe | Ms | H |
| Me | Me | CH$_2$OMe | CH$_2$OMe | Cl | H |
| Me | Me | CH$_2$OMe | CH$_2$OMe | MeS | H |
| Me | Me | CH$_2$OMe | CH$_2$OMe | MeSO | H |
| Me | Me | CH$_2$OMe | CH$_2$OEt | Ms | H |
| Me | Me | CH$_2$OMe | CH$_2$OEt | Cl | H |
| Me | Me | CH$_2$OMe | CH$_2$OEt | MeS | H |
| Me | Me | CH$_2$OMe | CH$_2$OEt | MeSO | H |
| Me | Me | CH$_2$OMe | CH$_2$OPr-i | Ms | H |
| Me | Me | CH$_2$OMe | CH$_2$OPr-n | Ms | H |
| Me | Me | CH$_2$OMe | CH$_2$OCH=CH$_2$ | Ms | H |
| Me | Me | CH$_2$OMe | CH$_2$OCH$_2$CH=CH$_2$ | Ms | H |
| Me | Me | CH$_2$OMe | CH$_2$OCH$_2$C≡CH | Ms | H |
| Me | Me | CH$_2$OMe | CH$_2$OCH$_2$CH$_2$Cl | Ms | H |
| Me | Me | CH$_2$OMe | CHMeOH | Ms | H |
| Me | Me | CH$_2$OMe | CHMeOMe | Ms | H |
| Me | Me | CH$_2$OMe | CHMeOMe | Ms | H |
| Me | Me | CH$_2$OMe | CHMeOMe | Ms | H |
| Me | Me | CH$_2$OMe | CHMeOEt | Ms | H |
| Me | Me | CH$_2$OMe | CH$_2$CH$_2$OMe | Ms | H |
| Me | Me | CH$_2$OMe | CH$_2$CH$_2$OEt | Ms | H |
| Me | Me | CH$_2$OMe | CHEtOH | Ms | H |
| Me | Me | CH$_2$OMe | CHEtOMe | Ms | H |
| Me | Me | CH$_2$OMe | CHEtOEt | Ms | H |

-continued

| | | | | | |
|---|---|---|---|---|---|
| Me | Me | CH$_2$OMe | CH$_2$OCH$_2$CH$_2$OMe | Ms | H |
| Me | Me | CH$_2$OMe | CH$_2$NMe$_2$ | Ms | H |
| Me | Me | CH$_2$OMe | CH$_2$OCH$_2$Ph | Ms | H |
| Me | Me | CH$_2$OMe | CH$_2$OCH$_2$CO$_2$Me | Ms | H |
| Me | Me | CH$_2$OMe | CH$_2$OCH$_2$CO$_2$Et | Ms | H |
| Me | Me | CH$_2$OMe | CH$_2$OCHMeCO$_2$Me | Ms | H |
| Me | Me | CH$_2$OMe | CH$_2$CN | Ms | H |
| Me | Me | CH$_2$OMe | CH$_2$SMe | Ms | H |
| Me | Me | CH$_2$OMe | CH$_2$SEt | Ms | H |
| Me | Me | CH$_2$OMe | CH$_2$SO$_2$Me | Ms | H |
| Me | Me | CH$_2$OMe | CH$_2$SO$_2$Et | Ms | H |
| Me | Me | CH$_2$OMe | CH$_2$SCH$_2$CH$_2$OMe | Ms | H |
| Me | Me | CH$_2$OMe | CH$_2$OCOMe | Ms | H |
| Me | Me | CH$_2$OMe | CHMeOCOMe | Ms | H |
| Me | Me | CH$_2$OMe | CH$_2$OSO$_2$Me | Ms | H |
| Et | Me | Ch$_2$OMe | CHMeOSO$_2$Me | MS | H |
| Et | Me | CH$_2$OMe | CH$_2$OH | MS | H |
| Et | Me | Ch$_2$OMe | CH$_2$OMe | Ms | H |
| Et | Me | Ch$_2$OMe | CH$_2$OMe | Cl | H |
| Et | Me | Ch$_2$OMe | CH$_2$OMe | MeS | H |
| Et | Me | Ch$_2$OMe | CH$_2$OMe | MeSO | H |
| Et | Me | Ch$_2$OMe | CH$_2$OEt | Ms | H |
| Et | Me | Ch$_2$OMe | CH$_2$OEt | Cl | H |
| Et | Me | Ch$_2$OMe | CH$_2$OEt | MeS | H |
| Et | Me | Ch$_2$OMe | CH$_2$OEt | MeSO | H |
| Et | Me | Ch$_2$OMe | CH$_2$OPr-i | Ms | H |
| Et | Me | Ch$_2$OMe | CH$_2$OPr-n | Ms | H |
| Et | Me | Ch$_2$OMe | CH$_2$OCH=CH$_2$ | Ms | H |
| Et | Me | Ch$_2$OMe | CH$_2$OCH$_2$CH=CH$_2$ | Ms | H |
| Et | Me | Ch$_2$OMe | CH$_2$OCH$_2$C≡CH | Ms | H |
| Et | Me | Ch$_2$OMe | CH$_2$OCH$_2$CH$_2$Cl | Ms | H |
| Et | Me | Ch$_2$OMe | CHMeOH | Ms | H |
| Et | Me | Ch$_2$OMe | CHMeOMe | Ms | H |
| Et | Me | Ch$_2$OMe | CHMeOMe | Cl | H |
| Et | Me | Ch$_2$OMe | CHMeOMe | MeS | H |
| Et | Me | Ch$_2$OMe | CHMeOMe | MeSO | H |
| Et | Me | Ch$_2$OMe | CHMeOEt | Ms | H |
| Et | Me | Ch$_2$OMe | CH$_2$CH$_2$OMe | Ms | H |
| Et | Me | Ch$_2$OMe | CH$_2$CH$_2$OEt | Ms | H |
| Et | Me | Ch$_2$OMe | CHEtOH | Ms | H |
| Et | Me | Ch$_2$OMe | CHEtOMe | Ms | H |
| Et | Me | Ch$_2$OMe | CHEtOEt | Ms | H |
| Et | Me | Ch$_2$OMe | CH$_2$OCH$_2$CH$_2$OMe | Ms | H |
| Et | Me | Ch$_2$OMe | CH$_2$NMe$_2$ | Ms | H |
| Et | Me | Ch$_2$OMe | CH$_2$OCH$_2$Ph | Ms | H |
| Et | Me | Ch$_2$OMe | CH$_2$OCH$_2$CO$_2$Me | Ms | H |
| Et | Me | Ch$_2$OMe | CH$_2$OCH$_2$CO$_2$Et | Ms | H |
| Et | Me | Ch$_2$OMe | CH$_2$OCHMeCO$_2$Me | Ms | H |
| Et | Me | Ch$_2$OMe | CH$_2$CN | Ms | H |
| Et | Me | Ch$_2$OMe | CH$_2$SMe | Ms | H |
| Et | Me | Ch$_2$OMe | CH$_2$SEt | Ms | H |
| Et | Me | Ch$_2$OMe | CH$_2$SO$_2$Me | Ms | H |
| Et | Me | Ch$_2$OMe | CH$_2$SO$_2$Et | Ms | H |
| Et | Me | Ch$_2$OMe | CH$_2$SCH$_2$CH$_2$OMe | Ms | H |
| Et | Me | Ch$_2$OMe | CH$_2$OCOMe | Ms | H |
| Et | Me | Ch$_2$OMe | CHMeOCOMe | Ms | H |
| Et | Me | Ch$_2$OMe | CH$_2$OSO$_2$Me | Ms | H |
| Et | Me | Ch$_2$OMe | CHMeOSO$_2$Me | Ms | H |
| Pr-i | Me | Ch$_2$OME | CH$_2$OH | Ms | H |
| Pr-i | Me | Ch$_2$OME | CH$_2$OMe | Ms | H |
| Pr-i | Me | Ch$_2$OME | CH$_2$OMe | Cl | H |
| Pr-i | Me | Ch$_2$OME | CH$_2$OMe | MeS | H |
| Pr-i | Me | Ch$_2$OME | CH$_2$OMe | MeSO | H |
| Pr-i | Me | Ch$_2$OME | CH$_2$OEt | Ms | H |
| Pr-i | Me | Ch$_2$OME | CH$_2$OEt | Cl | H |
| Pr-i | Me | Ch$_2$OME | CH$_2$OEt | MeS | H |
| Pr-i | Me | Ch$_2$OME | CH$_2$OEt | MeSO | H |
| Pr-i | Me | Ch$_2$OME | CH$_2$OPr-i | Ms | H |
| Pr-i | Me | Ch$_2$OME | CH$_2$OPr-n | Ms | H |
| Pr-i | Me | Ch$_2$OME | CH$_2$OCH=CH$_2$ | Ms | H |
| Pr-i | Me | Ch$_2$OME | CH$_2$OCH$_2$CH=CH$_2$ | Ms | H |
| Pr-i | Me | Ch$_2$OME | CH$_2$OCH$_2$C≡CH | Ms | H |
| Pr-i | Me | Ch$_2$OME | CH$_2$OCH$_2$CH$_2$Cl | Ms | H |
| Pr-i | Me | Ch$_2$OME | CHMeOH | Ms | H |
| Pr-i | Me | Ch$_2$OME | CHMeOMe | Ms | H |
| Pr-i | Me | Ch$_2$OME | CHMeOMe | Cl | H |
| Pr-i | Me | Ch$_2$OME | CHMeOMe | MeS | H |
| Pr-i | Me | Ch$_2$OME | CHMeOMe | MeSO | H |
| Pr-i | Me | Ch$_2$OME | CHMeOEt | Ms | H |
| Pr-i | Me | Ch$_2$OME | CH$_2$CH$_2$OMe | Ms | H |
| Pr-i | Me | Ch$_2$OME | CH$_2$CH$_2$OEt | Ms | H |
| Pr-i | Me | Ch$_2$OME | CHEtOH | Ms | H |
| Pr-i | Me | Ch$_2$OME | CHEtOMe | Ms | H |

-continued

| | | | | | |
|---|---|---|---|---|---|
| Pr-i | Me | Ch$_2$OME | CHEtOEt | Ms | H |
| Pr-i | Me | Ch$_2$OME | CH$_2$OCH$_2$CH$_2$OMe | Ms | H |
| Pr-i | Me | Ch$_2$OME | CH$_2$NMe$_2$ | Ms | H |
| Pr-i | Me | Ch$_2$OME | CH$_2$OCH$_2$Ph | Ms | H |
| Pr-i | Me | Ch$_2$OME | CH$_2$OCH$_2$CO$_2$Me | Ms | H |
| Pr-i | Me | Ch$_2$OME | CH$_2$PL OCH2CO$_2$Et | Ms | H |
| Pr-i | Me | Ch$_2$OME | CH$_2$OCHMeCO$_2$Me | Ms | H |
| Pr-i | Me | Ch$_2$OME | CH$_2$CN | Ms | H |
| Pr-i | Me | Ch$_2$OME | CH$_2$SMe | Ms | H |
| Pr-i | Me | Ch$_2$OME | CH$_2$SEt | Ms | H |
| Pr-i | Me | Ch$_2$OME | CH$_2$SO$_2$Me | Ms | H |
| Pr-i | Me | Ch$_2$OME | CH$_2$SO$_2$Et | Ms | H |
| Pr-i | Me | Ch$_2$OME | CH$_2$SCH$_2$CH$_2$OMe | Ms | H |
| Pr-i | Me | Ch$_2$OME | CH$_2$OCOMe | Ms | H |
| Pr-i | Me | Ch$_2$OME | CHMeOCOME | Ms | H |
| Pr-i | Me | Ch$_2$OME | CH$_2$OSO$_2$Me | Ms | H |
| Pr-i | Me | Ch$_2$OME | CHMeOSO$_2$Me | Ms | H |
| Me | H | Pr-i | CH$_2$OMe | Ms | H |
| Me | H | Pr-i | CH$_2$OEt | Ms | H |
| Me | H | Pr-i | CHMeOMe | Ms | H |
| Me | H | Pr-i | CHMeOEt | Ms | H |
| Me | H | Pr-i | CHEtOMe | Ms | H |
| Me | H | Pr-i | CHEtOEt | Ms | H |
| Me | H | Pr-i | CH$_2$SMe | Ms | H |
| Me | H | Pr-i | CH$_2$SEt | Ms | H |
| Me | H | Pr-i | CH$_2$SO$_2$Me | Ms | H |
| Me | H | Pr-i | CH$_2$OCOMe | Ms | H |
| Me | H | Pr-i | CHMeOCOMe | Ms | H |
| Me | H | Pr-i | CH$_2$OSO$_2$Me | Ms | H |
| Me | H | Pr-i | CHMeOSO$_2$Me | Ms | H |
| Et | H | Pr-i | CH$_2$OMe | Ms | H |
| Et | H | Pr-i | CH$_2$OEt | Ms | H |
| Et | H | Pr-i | CHMeOMe | Ms | H |
| Et | H | Pr-i | CHMeOEt | Ms | H |
| Et | H | Pr-i | CHEtOMe | Ms | H |
| Et | H | Pr-i | CHEtOEt | Ms | H |
| Et | H | Pr-i | CH$_2$SMe | Ms | H |
| Et | H | Pr-i | CH$_2$SEt | Ms | H |
| Et | H | Pr-i | CH$_2$SO$_2$Me | Ms | H |
| Et | H | Pr-i | CH$_2$OCOMe | Ms | H |
| Et | H | Pr-i | CHMeOCOMe | Ms | H |
| Et | H | Pr-i | CH$_2$OSO$_2$Me | Ms | H |
| Et | H | Pr-i | CHMeOSO$_2$Me | Ms | H |
| Pr-i | H | Pr-i | CH$_2$OMe | Ms | H |
| Pr-i | H | Pr-i | CH$_2$OEt | Ms | H |
| Pr-i | H | Pr-i | CHMeOMe | Ms | H |
| Pr-i | H | Pr-i | CHMeOEt | Ms | H |
| Pr-i | H | Pr-i | CHEtOMe | Ms | H |
| Pr-i | H | Pr-i | CHEtOEt | Ms | H |
| Pr-i | H | Pr-i | CH$_2$SMe | Ms | H |
| Pr-i | H | Pr-i | CH$_2$SEt | Ms | H |
| Pr-i | H | Pr-i | CH$_2$SO$_2$Me | Ms | H |
| Pr-i | H | Pr-i | CH$_2$OCOMe | Ms | H |
| Pr-i | H | Pr-i | CHMeOCOMe | Ms | H |
| Pr-i | H | Pr-i | CH$_2$OSO$_2$Me | Ms | H |
| Pr-i | H | Pr-i | CHMeOSO$_2$Me | Ms | H |
| Me | Me | Pr-i | CH$_2$OMe | Ms | H |
| Me | Me | Pr-i | CH$_2$OEt | Ms | H |
| Me | Me | Pr-i | CHMeOMe | Ms | H |
| Me | Me | Pr-i | CHMeOEt | Ms | H |
| Me | Me | Pr-i | CH$_2$SMe | Ms | H |
| Me | Me | Pr-i | CH$_2$SO$_2$Me | Ms | H |
| Et | Me | Pr-i | CH$_2$OMe | Ms | H |
| Et | Me | Pr-i | CH$_2$OEt | Ms | H |
| Et | Me | Pr-i | CHMeOMe | Ms | H |
| Et | Me | Pr-i | CHMeOEt | Ms | H |
| Et | Me | Pr-i | CH$_2$SME | Ms | H |
| Et | Me | Pr-i | CH$_2$SO$_2$Me | Ms | H |
| Pr-i | Me | Pr-i | CH$_2$OMe | Ms | H |
| Pr-i | Me | Pr-i | CH$_2$OEt | Ms | H |
| Pr-i | Me | Pr-i | CHMeOMe | Ms | H |
| Pr-i | Me | Pr-i | CHMeOEt | Ms | H |
| Pr-i | Me | Pr-i | CH$_2$SMe | Ms | H |
| Pr-i | Me | Pr-i | CH$_2$SO$_2$Me | Ms | H |
| Me | H | F | CH$_2$OMe | Ms | H |
| Me | H | F | CH$_2$OEt | Ms | H |
| Me | H | F | CHMeOMe | Ms | H |
| Et | H | F | CH$_2$OMe | Ms | H |
| Et | H | F | CH$_2$OEt | Ms | H |
| Et | H | F | CHMeOMe | Ms | H |
| Et | H | F | CHMeOEt | Ms | H |
| Pr-i | H | F | CH$_2$OMe | Ms | H |
| Pr-i | H | F | CH$_2$OEt | Ms | H |

-continued

| | | | | | |
|---|---|---|---|---|---|
| Pr-i | H | F | CHMeOMe | Ms | H |
| Me | Me | F | CH$_2$OMe | Ms | H |
| Me | Me | F | CH$_2$OEt | Ms | H |
| Et | Me | F | CH$_2$OMe | Ms | H |
| Et | Me | F | CH$_2$OEt | Ms | H |
| Et | Me | F | CHMeOMe | Ms | H |
| Pr-i | Me | F | CH$_2$OMe | Ms | H |
| Pr-i | Me | F | CH$_2$OEt | Ms | H |
| Me | H | NO$_2$ | CH$_2$OMe | Ms | H |
| Me | H | NO$_2$ | CH$_2$OEt | Ms | H |
| Me | H | NO$_2$ | CHMeOMe | Ms | H |
| Et | H | NO$_2$ | CH$_2$OMe | Ms | H |
| Et | H | NO$_2$ | CH$_2$OEt | Ms | H |
| Et | H | NO$_2$ | CHMeOMe | Ms | H |
| Et | H | NO$_2$ | CHMeOEt | Ms | H |
| Pr-i | H | NO$_2$ | CH$_2$OMe | Ms | H |
| Pr-i | H | NO$_2$ | CH$_2$OEt | Ms | H |
| Pr-i | H | NO$_2$ | CHMeOMe | Ms | H |
| Me | Me | NO$_2$ | CH$_2$OMe | Ms | H |
| Me | Me | NO$_2$ | CH$_2$OEt | Ms | H |
| Et | Me | NO$_2$ | CH$_2$OMe | Ms | H |
| Et | Me | NO$_2$ | CH$_2$OEt | Ms | H |
| Et | Me | NO$_2$ | CHMeOMe | Ms | H |
| Pr-i | Me | NO$_2$ | CH$_2$OMe | Ms | H |
| Pr-i | Me | NO$_2$ | CH$_2$OEt | Ms | H |
| Me | H | CF$_3$ | CH$_2$OMe | Ms | H |
| Me | H | CF$_3$ | CH$_2$OEt | Ms | H |
| Me | H | CF$_3$ | CHMeOMe | Ms | H |
| Et | H | CF$_3$ | CH$_2$OMe | Ms | H |
| Et | H | CF$_3$ | CH$_2$OEt | Ms | H |
| Et | H | CF$_3$ | CHMeOMe | Ms | H |
| Et | H | CF$_3$ | CHMeOEt | Ms | H |
| Pr-i | H | CF$_3$ | CH$_2$OMe | Ms | H |
| Pr-i | H | CF$_3$ | CH$_2$OEt | Ms | H |
| Pr-i | H | CF$_3$ | CHMeOMe | Ms | H |
| Me | Me | CF$_3$ | CH$_2$OMe | Ms | H |
| Me | Me | CF$_3$ | CH$_2$OEt | Ms | H |
| Et | Me | CF$_3$ | CH$_2$OMe | Ms | H |
| Et | Me | CF$_3$ | CH$_2$OEt | Ms | H |
| Et | Me | CF$_3$ | CHMeOMe | Ms | H |
| Pr-i | Me | CF$_3$ | CH$_2$OMe | Ms | H |
| Pr-i | Me | CF$_3$ | CH$_2$OEt | Ms | H |
| Me | H | COCH$_3$ | CH$_2$OMe | Ms | H |
| Me | H | COCH$_3$ | CH$_2$OEt | Ms | H |
| Et | H | COCH$_3$ | CH$_2$OMe | Ms | H |
| Et | H | COCH$_3$ | CH$_2$OEt | Ms | H |
| Et | H | COCH$_3$ | CHMeOMe | Ms | H |
| Pr-i | H | COCH$_3$ | CH$_2$OMe | Ms | H |
| Pr-i | H | COCH$_3$ | CH$_2$OEt | Ms | H |
| Me | Me | COCH$_3$ | CH$_2$OMe | Ms | H |
| Et | Me | COCH$_3$ | CH$_2$OMe | Ms | H |
| Et | Me | COCH$_3$ | CH$_2$OEt | Ms | H |
| Pr-i | Me | COCH$_3$ | CH$_2$OMe | Ms | H |
| Me | H | SCH$_3$ | CH$_2$OMe | MS | H |
| Me | H | SCH$_3$ | CH$_2$OEt | Ms | H |
| Et | H | SCH$_3$ | CH$_2$OMe | Ms | H |
| Et | H | SCH$_3$ | CH$_2$OEt | Ms | H |
| Et | H | SCH$_3$ | CHMeOEt | Ms | H |
| Pr-i | H | SCH$_3$ | CH$_2$OMe | Ms | H |
| Me | Me | SCH$_3$ | CH$_2$OMe | Ms | H |
| Et | Me | SCH$_3$ | CH$_2$OMe | Ms | H |
| Et | Me | SCH$_3$ | CH$_2$OEt | Ms | H |
| Pr-i | Me | SCH$_3$ | CH$_2$OMe | Ms | H |
| Me | H | OCHF$_2$ | CH$_2$OMe | Ms | H |
| Me | H | OCHF$_2$ | CH$_2$OEt | Ms | H |
| Et | H | OCHF$_2$ | CH$_2$OMe | Ms | H |
| Et | H | OCHF$_2$ | CH$_2$OEt | Ms | H |
| Et | H | OCHF$_2$ | CHMeOEt | MS | H |
| Pr-i | H | OCHF$_2$ | CH$_2$OMe | Ms | H |
| Pr-i | H | OCHF$_2$ | CH$_2$OEt | Ms | H |
| Me | Me | OCHF$_2$ | CH$_2$OMe | Ms | H |
| Me | Me | OCHF$_2$ | CH$_2$OEt | Ms | H |
| Et | Me | OCHF$_2$ | CH$_2$OMe | Ms | H |
| Et | Me | OCHF$_2$ | CH$_2$OEt | Ms | H |
| Pr-i | Me | OCHF$_2$ | CH$_2$OMe | Ms | H |
| Pr-i | Me | OCHF$_2$ | CH$_2$OEt | Ms | H |
| Me | H | OCF$_3$ | CH$_2$OMe | Ms | H |
| Me | H | OCF$_3$ | CH$_2$OEt | Ms | H |
| Et | H | OCF$_3$ | CH$_2$OMe | Ms | H |
| Et | H | OCF$_3$ | CH$_2$OEt | Ms | H |
| Et | H | OCF$_3$ | CHMeOEt | Ms | H |
| Pr-i | H | OCF$_3$ | CH$_2$OMe | Ms | H |
| Pr-i | H | OCF$_3$ | CH$_2$OEt | Ms | H |

-continued

| | | | | | |
|---|---|---|---|---|---|
| Me | Me | OCF₃ | CH₂OMe | Ms | H |
| Et | Me | OCF₃ | CH₂OMe | Ms | H |
| Et | Me | OCF₃ | CH₂OEt | Ms | H |
| Pr-i | Me | OCF₃ | CH₂OMe | Ms | H |
| Me | H | CH₂SMe | CH₂OMe | MS | H |
| Et | H | CH₂SMe | CH₂OMe | Ms | H |
| Et | H | CH₂SMe | CH₂OEt | Ms | H |
| Et | H | CH₂SMe | CHMeOEt | Ms | H |
| Pr-i | H | CH₂SMe | CH₂OMe | Ms | H |
| Pr-i | H | CH₂SMe | CHMeOMe | Ms | H |
| Me | Me | CH₂SMe | CH₂OMe | MS | H |
| Et | Me | CH₂SMe | CH₂OMe | Ms | H |
| Et | Me | CH₂SMe | CH₂OEt | Ms | H |
| Pr-i | Me | CH₂SMe | CH₂OMe | Ms | H |
| Me | H | CN | CH₂OMe | Ms | H |
| Et | H | CN | CH₂OMe | Ms | H |
| Et | H | CN | CH₂OEt | Ms | H |
| Pr-i | H | CN | CH₂OMe | Ms | H |
| Me | Me | CN | CH₂OMe | Ms | H |
| Et | Me | CN | CH₂OMe | Ms | H |
| Pr-i | Me | CN | CH₂OMe | Ms | H |
| Me | H | CO₂Me | CH₂OMe | Ms | H |
| Et | H | CO₂Me | CH₂OMe | Ms | H |
| Et | H | CO₂Me | CH₂OEt | Ms | H |
| Pr-i | H | CO₂Me | CH₂OMe | Ms | H |
| Me | Me | CO₂Me | CH₂OMe | Ms | H |
| Et | Me | CO₂Me | CH₂OMe | Ms | H |
| Pr-i | Me | CO₂Me | CH₂OMe | Ms | H |
| Me | H | CONMe₂ | CH₂OMe | Ms | H |
| Et | H | CONMe₂ | CH₂OMe | Ms | H |
| Pr-i | H | CONMe₂ | CH₂OMe | Ms | H |
| Me | H | Me | CH₂OMe | NO₂ | H |
| Me | H | Me | CH₂OEt | NO₂ | H |
| Et | H | Me | CH₂OMe | NO₂ | H |
| Et | H | Me | CH₂OEt | NO₂ | H |
| Et | H | Me | CHMeOMe | NO₂ | H |
| Pr-i | H | Me | CH₂OMe | NO₂ | H |
| Pr-i | H | Me | CH₂OEt | NO₂ | H |
| Me | H | Cl | CH₂OMe | NO₂ | H |
| Me | H | Cl | CH₂OEt | NO₂ | H |
| Et | H | Cl | CH₂OMe | NO₂ | H |
| Et | H | Cl | CH₂OEt | NO₂ | H |
| Et | H | Cl | CHMeOMe | NO₂ | H |
| Pr-i | H | Cl | CH₂OMe | NO₂ | H |
| Pr-i | H | Cl | CH₂OEt | NO₂ | H |
| Me | Me | Me | CH₂OMe | NO₂ | H |
| Et | Me | Me | CH₂OMe | NO₂ | H |
| Et | Me | Me | CH₂OEt | NO₂ | H |
| Pr-i | Me | Me | CH₂OMe | NO₂ | H |
| Me | Me | Cl | CH₂OMe | NO₂ | H |
| Et | Me | Cl | CH₂OMe | NO₂ | H |
| Et | Me | Cl | CH₂OEt | NO₂ | H |
| Et | Me | Cl | CHMeOMe | NO₂ | H |
| Pr-i | Me | Cl | CH₂OMe | NO₂ | H |
| Me | H | Me | CH₂OMe | CF₃ | H |
| Me | H | Me | CH₂OEt | CF₃ | H |
| Et | H | Me | CH₂OMe | CF₃ | H |
| Et | H | Me | CH₂OEt | CF₃ | H |
| Et | H | Me | CHMeOMe | CF₃ | H |
| Pr-i | H | Me | CH₂OMe | CF₃ | H |
| Pr-i | H | Me | CH₂OEt | CF₃ | H |
| Me | H | Cl | CH₂OMe | CF₃ | H |
| Me | H | Cl | CH₂OEt | CF₃ | H |
| Et | H | Cl | CH₂OMe | CF₃ | H |
| Et | H | Cl | CH₂OEt | CF₃ | H |
| Et | H | Cl | CHMeOMe | CF₃ | H |
| Pr-i | H | Cl | CH₂OMe | CF₃ | H |
| Pr-i | H | Cl | CH₂OEt | CF₃ | H |
| Me | Me | Me | CH₂OMe | CF₃ | H |
| Et | Me | Me | CH₂OMe | CF₃ | H |
| Et | Me | Me | CH₂OEt | CF₃ | H |
| Pr-i | Me | Me | CH₂OMe | CF₃ | H |
| Me | Me | Cl | CH₂OMe | CF₃ | H |
| Et | Me | Cl | CH₂OMe | CF₃ | H |
| Et | Me | Cl | CH₂OEt | CF₃ | H |
| Et | Me | Cl | CHMeOMe | CF₃ | H |
| Pr-i | Me | Cl | CH₂OMe | CF₃ | H |
| Me | H | Me | CH₂OMe | CN | H |
| Me | H | Me | CH₂OEt | CN | H |
| Et | H | Me | CH₂OMe | CN | H |
| Et | H | Me | CH₂OEt | CN | H |
| Et | H | Me | CHMeOMe | CN | H |
| Pr-i | H | Me | CH₂OMe | CN | H |

-continued

| | | | | | |
|---|---|---|---|---|---|
| Pr-i | H | Me | CH₂OEt | CN | H |
| Me | H | Cl | CH₂OMe | CN | H |
| Me | H | Cl | CH₂OEt | CN | H |
| Et | H | Cl | CH₂OMe | CN | H |
| Et | H | Cl | CH₂OEt | CN | H |
| Et | H | Cl | CHMeOMe | CN | H |
| Pr-i | H | Cl | CH₂OMe | CN | H |
| Pr-i | H | Cl | CH₂OEt | CN | H |
| Me | Me | Me | CH₂OMe | CN | H |
| Et | Me | Me | CH₂OMe | CN | H |
| Et | Me | Me | CH₂OEt | CN | H |
| Pr-i | Me | Me | CH₂OMe | CN | H |
| Me | Me | Cl | CH₂OMe | CN | H |
| Et | Me | Cl | CH₂OMe | CN | H |
| Et | Me | Cl | CH₂OEt | CN | H |
| Et | Me | Cl | CHMeOMe | CN | H |
| Pr-i | Me | Cl | CH₂OMe | CN | H |
| Me | H | Me | CH₂OMe | OMe | H |
| Me | H | Me | CH₂OEt | OMe | H |
| Et | H | Me | CH₂OMe | OMe | H |
| Et | H | Me | CH₂OEt | OMe | H |
| Et | H | Me | CHMeOMe | OMe | H |
| Pr-i | H | Me | CH₂OMe | OMe | H |
| Pr-i | H | Me | CH₂OEt | OMe | H |
| Me | H | Cl | CH₂OMe | OMe | H |
| Me | H | Cl | CH₂OEt | OMe | H |
| Et | H | Cl | CH₂OMe | OMe | H |
| Et | H | Cl | CH₂OEt | OMe | H |
| Et | H | Cl | CHMeOMe | OMe | H |
| Pr-i | H | Cl | CH₂OMe | OMe | H |
| Pr-i | H | Cl | CH₂OEt | OMe | H |
| Me | Me | Me | CH₂OMe | OMe | H |
| Et | Me | Me | CH₂OMe | OMe | H |
| Et | Me | Me | CH₂OEt | OMe | H |
| Pr-i | Me | Me | CH₂OMe | OMe | H |
| Me | Me | Cl | CH₂OMe | OMe | H |
| Et | Me | Cl | CH₂OMe | OMe | H |
| Et | Me | Cl | CH₂OEt | OMe | H |
| Et | Me | Cl | CHMeOMe | OMe | H |
| Pr-i | Me | Cl | CH₂OMe | OMe | H |
| Me | H | Me | CH₂OMe | Br | H |
| Me | H | Me | CH₂OEt | Br | H |
| Et | H | Me | CH₂OMe | Br | H |
| Et | H | Me | CH₂OEt | Br | H |
| Et | H | Me | CHMeOMe | Br | H |
| Pr-i | H | Me | CH₂OMe | Br | H |
| Pr-i | H | Me | CH₂OEt | Br | H |
| Me | H | Cl | CH₂OMe | Br | H |
| Me | H | Cl | CH₂OEt | Br | H |
| Et | H | Cl | CH₂OMe | Br | H |
| Et | H | Cl | CH₂OEt | Br | H |
| Et | H | Cl | CHMeOMe | Br | H |
| Pr-i | H | Cl | CH₂OMe | Br | H |
| Pr-i | H | Cl | CH₂OEt | Br | H |
| Me | Me | Me | CH₂OMe | Br | H |
| Et | Me | Me | CH₂OMe | Br | H |
| Et | Me | Me | CH₂OEt | Br | H |
| Pr-i | Me | Me | CH₂OMe | Br | H |
| Me | Me | Cl | CH₂OMe | Br | H |
| Et | Me | Cl | CH₂OMe | Br | H |
| Et | Me | Cl | CH₂OEt | Br | H |
| Et | Me | Cl | CHMeOMe | Br | H |
| Pr-i | Me | Cl | CH₂OMe | Br | H |
| Me | H | Me | CH₂OMe | I | H |
| Me | H | Me | CH₂OEt | I | H |
| Et | H | Me | CH₂OMe | I | H |
| Et | H | Me | CH₂OEt | I | H |
| Et | H | Me | CHMeOMe | I | H |
| Pr-i | H | Me | CH₂OMe | I | H |
| Pr-i | H | Me | CH₂OEt | I | H |
| Me | H | Cl | CH₂OMe | I | H |
| Me | H | Cl | CH₂OEt | I | H |
| Et | H | Cl | CH₂OMe | I | H |
| Et | H | Cl | CH₂OEt | I | H |
| Et | H | Cl | CHMeOMe | I | H |
| Pr-i | H | Cl | CH₂OMe | I | H |
| Pr-i | H | Me | CH₂OEt | I | H |
| Me | Me | Me | CH₂OMe | I | H |
| Et | Me | Me | CH₂OMe | I | H |
| Et | Me | Me | CH₂OEt | I | H |
| Pr-i | Me | Me | CH₂OMe | I | H |
| Me | Me | Cl | CH₂OMe | I | H |
| Et | Me | Cl | CH₂OMe | I | H |

-continued

| | | | | | |
|---|---|---|---|---|---|
| Et | Me | Cl | CH₂OEt | I | H |
| Et | Me | Cl | CHMeOMe | I | H |
| Pr-i | Me | Cl | CH₂OMe | I | H |
| Me | H | Me | CH₂OMe | SCF₃ | H |
| Me | H | Me | CH₂OEt | SCF₃ | H |
| Et | H | Me | CH₂OMe | SCF₃ | H |
| Et | H | Me | CH₂OEt | SCF₃ | H |
| Et | H | Me | CHMeOMe | SCF₃ | H |
| Pr-i | H | Me | CH₂OMe | SCF₃ | H |
| Pr-i | H | Me | CH₂OEt | SCF₃ | H |
| Me | H | Cl | CH₂OMe | SCF₃ | H |
| Me | H | Cl | CH₂OEt | SCF₃ | H |
| Et | H | Cl | CH₂OMe | SCF₃ | H |
| Et | H | Cl | CH₂OEt | SCF₃ | H |
| Et | H | Cl | CHMeOMe | SCF₃ | H |
| Pr-i | H | Cl | CH₂OMe | SCF₃ | H |
| Pr-i | H | Cl | CH₂OEt | SCF₃ | H |
| Me | Me | Me | CH₂OMe | SCF₃ | H |
| Et | Me | Me | CH₂OMe | SCF₃ | H |
| Et | Me | Me | CH₂OEt | SCF₃ | H |
| Pr-i | Me | Me | CH₂OMe | SCF₃ | H |
| Me | Me | Cl | CH₂OMe | SCF₃ | H |
| Et | Me | Cl | CH₂OMe | SCF₃ | H |
| Et | Me | Cl | CH₂OEt | SCF₃ | H |
| Et | Me | Cl | CHMeOMe | SCF₃ | H |
| Pr-i | Me | Cl | CH₂OMe | SCF₃ | H |
| Me | H | Me | CH₂OMe | SO₂CF₃ | H |
| Me | H | Me | CH₂OEt | SO₂CF₃ | H |
| Et | H | Me | CH₂OMe | SO₂CF₃ | H |
| Et | H | Me | CH₂OEt | SO₂CF₃ | H |
| Et | H | Me | CHMeOMe | SO₂CF₃ | H |
| Pr-i | H | Me | CH₂OMe | SO₂CF₃ | H |
| Pr-i | H | Me | CH₂OEt | SO₂CF₃ | H |
| Me | H | Cl | CH₂OMe | SO₂CF₃ | H |
| Me | H | Cl | CH₂OEt | SO₂CF₃ | H |
| Et | H | Cl | CH₂OMe | SO₂CF₃ | H |
| Et | H | Cl | CH₂OEt | SO₂CF₃ | H |
| Et | H | Cl | CHMeOMe | SO₂CF₃ | H |
| Pr-i | H | Cl | CH₂OMe | SO₂CF₃ | H |
| Pr-i | H | Cl | CH₂OEt | SO₂CF₃ | H |
| Me | Me | Me | CH₂OMe | SO₂CF₃ | H |
| Et | Me | Me | CH₂OMe | SO₂CF₃ | H |
| Et | Me | Me | CH₂OEt | SO₂CF₃ | H |
| Pr-i | Me | Me | CH₂OMe | SO₂CF₃ | H |
| Me | Me | Cl | CH₂OMe | SO₂CF₃ | H |
| Et | Me | Cl | CH₂OMe | SO₂CF₃ | H |
| Et | Me | Cl | CH₂OEt | SO₂CF₃ | H |
| Et | Me | Cl | CHMeOMe | SO₂CF₃ | H |
| Pr-i | Me | Cl | CH₂OMe | SO₂CF₃ | H |
| Me | H | Me | COOMe | Ms | Na |
| Me | H | Me | COOMe | Ms | K |
| Me | H | Me | COOMe | Ms | Ca½ |
| Me | H | Me | COOMe | Ms | Mg½ |
| Me | H | Me | COOMe | Ms | EtN⁺H₃ |
| Me | H | Me | COOMe | Ms | i-PrN⁺H₃ |
| Me | H | Me | COOMe | Ms | Et₂N⁺H₂ |
| Me | H | Me | COOMe | Ms | Me₃N⁺CH₂CH₂OH |
| Et | H | Me | COOMe | Ms | Na |
| Et | H | Me | COOMe | Ms | K |
| Et | H | Me | COOMe | Ms | Ca½ |
| Et | H | Me | COOMe | Ms | Mg½ |
| Et | H | Me | COOMe | Ms | EtN⁺H₃ |
| Et | H | Me | COOMe | Ms | i-PrN⁺H₃ |
| Et | H | Me | COOMe | Ms | Et₂N⁺H₂ |
| Et | H | Me | COOMe | Ms | Me₃N⁺CH₂CH₂OH |
| i-Pr | H | Me | COOMe | Ms | Na |
| i-Pr | H | Me | COOMe | Ms | K |
| i-Pr | H | Me | COOMe | Ms | Ca½ |
| i-Pr | H | Me | COOMe | Ms | Mg½ |
| i-Pr | H | Me | COOMe | Ms | EtN⁺H₃ |
| i-Pr | H | Me | COOMe | Ms | i-PrN⁺H₃ |
| i-Pr | H | Me | COOMe | Ms | Et₂N⁺H₂ |
| i-Pr | H | Me | COOMe | Ms | Me₃N⁺CH₂CH₂OH |
| Me | Me | Me | COOMe | Ms | i-PrN⁺H₃ |
| Et | Me | Me | COOMe | Ms | Na |
| Et | Me | Me | COOMe | Ms | i-PrN⁺H₃ |
| i-Pr | Me | Me | COOMe | Ms | i-PrN⁺H₃ |
| Me | H | Cl | COOMe | Ms | Na |
| Me | H | Cl | COOMe | Ms | K |
| Me | H | Cl | COOMe | Ms | Ca½ |
| Me | H | Cl | COOMe | Ms | Mg½ |
| Me | H | Cl | COOMe | Ms | EtN⁺H₃ |
| Me | H | Cl | COOMe | Ms | i-PrN⁺H₃ |

-continued

| | | | | | |
|---|---|---|---|---|---|
| Me | H | Cl | COOMe | Ms | $Et_2N^+H_2$ |
| Me | H | Cl | COOMe | Ms | $Me_3N^+CH_2CH_2OH$ |
| Et | H | Cl | COOMe | Ms | Na |
| Et | H | Cl | COOMe | Ms | K |
| Et | H | Cl | COOMe | Ms | $Ca_{\frac{1}{2}}$ |
| Et | H | Cl | COOMe | Ms | $Mg_{\frac{1}{2}}$ |
| Et | H | Cl | COOMe | Ms | $EtN^+H_3$ |
| Et | H | Cl | COOMe | Ms | $i\text{-}PrN^+H_3$ |
| Et | H | Cl | COOMe | Ms | $Et_2N^+H_2$ |
| Et | H | Cl | COOMe | Ms | $Me_3N^+CH_2CH_2OH$ |
| i-Pr | H | Cl | COOMe | Ms | Na |
| i-Pr | H | Cl | COOMe | Ms | K |
| i-Pr | H | Cl | COOMe | Ms | $Ca_{\frac{1}{2}}$ |
| i-Pr | H | Cl | COOMe | Ms | $Mg_{\frac{1}{2}}$ |
| i-Pr | H | Cl | COOMe | Ms | $EtN^+H_3$ |
| i-Pr | H | Cl | COOMe | Ms | $i\text{-}PrN^+H_3$ |
| i-Pr | H | Cl | COOMe | Ms | $Et_2N^+H_2$ |
| i-Pr | H | Cl | COOMe | Ms | $Me_3N^+CH_2CH_2OH$ |
| Me | Me | Cl | COOMe | Ms | $i\text{-}PrN^+H_3$ |
| Et | Me | Cl | COOMe | Ms | Na |
| Et | Me | Cl | COOMe | Ms | $i\text{-}PrN^+H_3$ |
| i-Pr | Me | Cl | COOMe | Ms | $i\text{-}PrN^+H_3$ |
| Me | H | OMe | COOMe | Ms | Na |
| Me | H | OMe | COOMe | Ms | K |
| Me | H | OMe | COOMe | Ms | $Ca_{\frac{1}{2}}$ |
| Me | H | OMe | COOMe | Ms | $Mg_{\frac{1}{2}}$ |
| Me | H | OMe | COOMe | Ms | $EtN^+H_3$ |
| Me | H | OMe | COOMe | Ms | $i\text{-}PrN^+H_3$ |
| Me | H | OMe | COOMe | Ms | $Et_2N^+H_2$ |
| Me | H | OMe | COOMe | Ms | $Me_3N^+CH_2CH_2OH$ |
| Et | H | OMe | COOMe | Ms | Na |
| Et | H | OMe | COOMe | Ms | K |
| Et | H | OMe | COOMe | Ms | $Ca_{\frac{1}{2}}$ |
| Et | H | OMe | COOMe | Ms | $Mg_{\frac{1}{2}}$ |
| Et | H | OMe | COOMe | Ms | $EtN^+H_3$ |
| Et | H | OMe | COOMe | Ms | $i\text{-}PrN^+H_3$ |
| Et | H | OMe | COOMe | Ms | $Et_2N^+H_2$ |
| Et | H | OMe | COOMe | Ms | $Me_3N^+CH_2CH_2OH$ |
| i-Pr | H | OMe | COOMe | Ms | Na |
| i-Pr | H | OMe | COOMe | Ms | K |
| i-Pr | H | OMe | COOMe | Ms | $Ca_{\frac{1}{2}}$ |
| i-Pr | H | OMe | COOMe | Ms | $Mg_{\frac{1}{2}}$ |
| i-Pr | H | OMe | COOMe | Ms | $EtN^+H_3$ |
| i-Pr | H | OMe | COOMe | Ms | $i\text{-}PrN^+H_3$ |
| i-Pr | H | OMe | COOMe | Ms | $Et_2N^+H_2$ |
| i-Pr | H | OMe | COOMe | Ms | $Me_3N^+CH_2CH_2OH$ |
| Et | Me | OMe | COOMe | Ms | $i\text{-}PrN^+H_3$ |
| Me | H | Me | COOEt | Ms | Na |
| Me | H | Me | COOEt | Ms | K |
| Me | H | Me | COOEt | Ms | $Ca_{\frac{1}{2}}$ |
| Me | H | Me | COOEt | Ms | $Mg_{\frac{1}{2}}$ |
| Me | H | Me | COOEt | Ms | $EtN^+H_3$ |
| Me | H | Me | COOEt | Ms | $i\text{-}PrN^+H_3$ |
| Me | H | Me | COOEt | Ms | $Et_2N^+H_2$ |
| Me | H | Me | COOEt | Ms | $Me_3N^+CH_2CH_2OH$ |
| Et | H | Me | COOEt | Ms | Na |
| Et | H | Me | COOEt | Ms | K |
| Et | H | Me | COOEt | Ms | $Ca_{\frac{1}{2}}$ |
| Et | H | Me | COOEt | Ms | $Mg_{\frac{1}{2}}$ |
| Et | H | Me | COOEt | Ms | $EtN^+H_3$ |
| Et | H | Me | COOEt | Ms | $i\text{-}PrN^+H_3$ |
| Et | H | Me | COOEt | Ms | $Et_2N^+H_2$ |
| Et | H | Me | COOEt | Ms | $Me_3N^+CH_2CH_2OH$ |
| i-Pr | H | Me | COOEt | Ms | Na |
| i-Pr | H | Me | COOEt | Ms | K |
| i-Pr | H | Me | COOEt | Ms | $Ca_{\frac{1}{2}}$ |
| i-Pr | H | Me | COOEt | Ms | $Mg_{\frac{1}{2}}$ |
| i-Pr | H | Me | COOEt | Ms | $EtN^+H_3$ |
| i-Pr | H | Me | COOEt | Ms | $i\text{-}PrN^+H_3$ |
| i-Pr | H | Me | COOEt | Ms | $Et_2N^+H_2$ |
| i-Pr | H | Me | COOEt | Ms | $Me_3N^+CH_2CH_2OH$ |
| Me | Me | Me | COOEt | Ms | $i\text{-}PrN^+H_3$ |
| Et | Me | Me | COOEt | Ms | Na |
| Et | Me | Me | COOEt | Ms | $i\text{-}PrN^+H_3$ |
| i-Pr | Me | Me | COOEt | Ms | $i\text{-}PrN^+H_3$ |
| Me | H | Cl | COOEt | Ms | Na |
| Me | H | Cl | COOEt | Ms | K |
| Me | H | Cl | COOEt | Ms | $Ca_{\frac{1}{2}}$ |
| Me | H | Cl | COOEt | Ms | $Mg_{\frac{1}{2}}$ |
| Me | H | Cl | COOEt | Ms | $EtN^+H_3$ |
| Me | H | Cl | COOEt | Ms | $i\text{-}PrN^+H_3$ |
| Me | H | Cl | COOEt | Ms | $Et_2N^+H_2$ |
| Me | H | Cl | COOEt | Ms | $Me_3N^+CH_2CH_2OH$ |

-continued

| | | | | | |
|---|---|---|---|---|---|
| Et | H | Cl | COOEt | Ms | Na |
| Et | H | Cl | COOEt | Ms | K |
| Et | H | Cl | COOEt | Ms | Ca$_{\frac{1}{2}}$ |
| Et | H | Cl | COOEt | Ms | Mg$_{\frac{1}{2}}$ |
| Et | H | Cl | COOEt | Ms | EtN$^+$H$_3$ |
| Et | H | Cl | COOEt | Ms | i-PrN$^+$H$_3$ |
| Et | H | Cl | COOEt | Ms | Et$_2$N$^+$H$_2$ |
| Et | H | Cl | COOEt | Ms | Me$_3$N$^+$CH$_2$CH$_2$OH |
| i-Pr | H | Cl | COOEt | Ms | Na |
| i-Pr | H | Cl | COOEt | Ms | K |
| i-Pr | H | Cl | COOEt | Ms | Ca$_{\frac{1}{2}}$ |
| i-Pr | H | Cl | COOEt | Ms | Mg$_{\frac{1}{2}}$ |
| i-Pr | H | Cl | COOEt | Ms | EtN$^+$H$_3$ |
| i-Pr | H | Cl | COOEt | Ms | i-PrN$^+$H$_3$ |
| i-Pr | H | Cl | COOEt | Ms | Et$_2$N$^+$H$_2$ |
| i-Pr | H | Cl | COOEt | Ms | Me$_3$N$^+$CH$_2$CH$_2$OH |
| Me | Me | Cl | COOEt | Ms | i-PrN$^+$H$_3$ |
| Et | Me | Cl | COOEt | Ms | Na |
| Et | Me | Cl | COOEt | Ms | i-PrN$^+$H$_3$ |
| i-Pr | Me | Cl | COOEt | Ms | i-PrN$^+$H$_3$ |
| Me | Me | OMe | COOEt | Ms | Na |
| Me | Me | OMe | COOEt | Ms | K |
| Me | H | OMe | COOEt | Ms | Ca$_{\frac{1}{2}}$ |
| Me | H | OMe | COOEt | Ms | Mg$_{\frac{1}{2}}$ |
| Me | H | OMe | COOEt | Ms | EtN$^+$H$_3$ |
| Me | H | OMe | COOEt | Ms | i-PrN$^+$H$_3$ |
| Me | H | OMe | COOEt | Ms | Et$_2$N$^+$H$_2$ |
| Me | H | OMe | COOEt | Ms | Me$_3$N$^+$CH$_2$CH$_2$OH |
| Me | H | OMe | COOEt | Ms | Na |
| Me | H | OMe | COOEt | Ms | K |
| Et | H | OMe | COOEt | Ms | Ca$_{\frac{1}{2}}$ |
| Et | H | OMe | COOEt | Ms | Mg$_{\frac{1}{2}}$ |
| Et | H | OMe | COOEt | Ms | EtN$^+$H$_3$ |
| Et | H | OMe | COOEt | Ms | i-PrN$^+$H$_3$ |
| Et | H | OMe | COOEt | Ms | Et$_2$N$^+$H$_2$ |
| Et | H | OMe | COOEt | Ms | Me$_3$N$^+$CH$_2$CH$_2$OH |
| i-Pr | H | OMe | COOEt | Ms | Na |
| i-Pr | H | OMe | COOEt | Ms | K |
| i-Pr | H | OMe | COOEt | Ms | Ca$_{\frac{1}{2}}$ |
| i-Pr | H | OMe | COOEt | Ms | Mg$_{\frac{1}{2}}$ |
| i-Pr | H | OMe | COOEt | Ms | EtN$^+$H$_3$ |
| i-Pr | H | OMe | COOEt | Ms | i-PrN$^+$H$_3$ |
| i-Pr | H | OMe | COOEt | Ms | Et$_2$N$^+$H$_2$ |
| i-Pr | H | OMe | COOEt | Ms | Me$_3$N$^+$CH$_2$CH$_2$OH |
| Et | Me | OMe | COOEt | Ms | i-PrN$^+$H$_3$ |
| Me | H | Me | COOPr-i | Ms | Na |
| Me | H | Me | COOPr-i | Ms | K |
| Me | H | Me | COOPr-i | Ms | Ca$_{\frac{1}{2}}$ |
| Me | H | Me | COOPr-i | Ms | Mg$_{\frac{1}{2}}$ |
| Me | H | Me | COOPr-i | Ms | EtN$^+$H$_3$ |
| Me | H | Me | COOPr-i | Ms | i-PrN$^+$H$_3$ |
| Me | H | Me | COOPr-i | Ms | Et$_2$N$^+$H$_2$ |
| Me | H | Me | COOPr-i | Ms | Me$_3$N$^+$CH$_2$CH$_2$OH |
| Et | H | Me | COOPr-i | Ms | Na |
| Et | H | Me | COOPr-i | Ms | K |
| Et | H | Me | COOPr-i | Ms | Ca$_{\frac{1}{2}}$ |
| Et | H | Me | COOPr-i | Ms | Mg$_{\frac{1}{2}}$ |
| Et | H | Me | COOPr-i | Ms | EtN$^+$H$_3$ |
| Et | H | Me | COOPr-i | Ms | i-PrN$^+$H$_3$ |
| Et | H | Me | COOPr-i | Ms | Et$_2$N$^+$H$_2$ |
| Et | H | Me | COOPr-i | Ms | Me$_3$N$^+$CH$_2$CH$_2$OH |
| i-Pr | H | Me | COOPr-i | Ms | Na |
| i-Pr | H | Me | COOPr-i | Ms | K |
| i-Pr | H | Me | COOPr-i | Ms | Ca$_{\frac{1}{2}}$ |
| i-Pr | H | Me | COOPr-i | Ms | Mg$_{\frac{1}{2}}$ |
| i-Pr | H | Me | COOPr-i | Ms | EtN$^+$H$_3$ |
| i-Pr | H | Me | COOPr-i | Ms | i-PrN$^+$H$_3$ |
| i-Pr | H | Me | COOPr-i | Ms | Et$_2$N$^+$H$_2$ |
| i-Pr | H | Me | COOPr-i | Ms | Me$_3$N$^+$CH$_2$CH$_2$OH |
| Me | Me | Me | COOPr-i | Ms | i-PrN$^+$H$_3$ |
| Et | Me | Me | COOPr-i | Ms | Na |
| Et | Me | Me | COOPr-i | Ms | i-PrN$^+$H$_3$ |
| i-Pr | Me | Me | COOPr-i | Ms | i-PrN$^+$H$_3$ |
| Me | H | Cl | COOPr-i | Ms | Na |
| Me | H | Cl | COOPr-i | Ms | K |
| Me | H | Cl | COOPr-i | Ms | Ca$_{\frac{1}{2}}$ |
| Me | H | Cl | COOPr-i | Ms | Mg$_{\frac{1}{2}}$ |
| Me | H | Cl | COOPr-i | Ms | EtN$^+$H$_3$ |
| Me | H | Cl | COOPr-i | Ms | i-PrN$^+$H$_3$ |
| Me | H | Cl | COOPr-i | Ms | Et$_2$N$^+$H$_2$ |
| Me | H | Cl | COOPr-i | Ms | Me$_3$N$^+$CH$_2$CH$_2$OH |
| Et | H | Cl | COOPr-i | Ms | Na |
| Et | H | Cl | COOPr-i | Ms | K |

-continued

| | | | | | |
|---|---|---|---|---|---|
| Et | H | Cl | COOPr-i | Ms | Ca$_{\frac{1}{2}}$ |
| Et | H | Cl | COOPr-i | Ms | Mg$_{\frac{1}{2}}$ |
| Et | H | Cl | COOPr-i | Ms | EtN$^+$H$_3$ |
| Et | H | Cl | COOPr-i | Ms | i-PrN$^+$H$_3$ |
| Et | H | Cl | COOPr-i | Ms | Et$_2$N$^+$H$_2$ |
| Et | H | Cl | COOPr-i | Ms | Me$_3$N$^+$CH$_2$CH$_2$OH |
| i-Pr | H | Cl | COOPr-i | Ms | Na |
| i-Pr | H | Cl | COOPr-i | Ms | K |
| i-Pr | H | Cl | COOPr-i | Ms | Ca$_{\frac{1}{2}}$ |
| i-Pr | H | Cl | COOPr-i | Ms | Mg$_{\frac{1}{2}}$ |
| i-Pr | H | Cl | COOPr-i | Ms | EtN$^+$H$_3$ |
| i-Pr | H | Cl | COOPr-i | Ms | i-PrN$^+$H$_3$ |
| i-Pr | H | Cl | COOPr-i | Ms | Et$_2$N$^+$H$_2$ |
| i-Pr | H | Cl | COOPr-i | Ms | Me$_3$N$^+$CH$_2$CH$_2$OH |
| Me | Me | Cl | COOPr-i | Ms | i-PrN$^+$H$_3$ |
| Et | Me | Cl | COOPr-i | Ms | Na |
| Et | Me | Cl | COOPr-i | Ms | i-PrN$^+$H$_3$ |
| i-Pr | Me | Cl | COOPr-i | Ms | i-PrN$^+$H$_3$ |
| Me | H | OMe | COOPr-i | Ms | Na |
| Me | H | OMe | COOPr-i | Ms | K |
| Me | H | OMe | COOPr-i | Ms | Ca$_{\frac{1}{2}}$ |
| Me | H | OMe | COOPr-i | Ms | Mg$_{\frac{1}{2}}$ |
| Me | H | OMe | COOPr-i | Ms | EtN$^+$H$_3$ |
| Me | H | OMe | COOPr-i | Ms | i-PrN$^+$H$_3$ |
| Me | H | OMe | COOPr-i | Ms | Et$_2$N$^+$H$_2$ |
| Me | H | OMe | COOPr-i | Ms | Me$_3$N$^+$CH$_2$CH$_2$OH |
| Et | H | OMe | COOPr-i | Ms | Na |
| Et | H | OMe | COOPr-i | Ms | K |
| Et | H | OMe | COOPr-i | Ms | Ca$_{\frac{1}{2}}$ |
| Et | H | OMe | COOPr-i | Ms | Mg$_{\frac{1}{2}}$ |
| Et | H | OMe | COOPr-i | Ms | EtN$^+$H$_3$ |
| Et | H | OMe | COOPr-i | Ms | i-PrN$^+$H$_3$ |
| Et | H | OMe | COOPr-i | Ms | Et$_2$N$^+$H$_2$ |
| Et | H | OMe | COOPr-i | Ms | Me$_3$N$^+$CH$_2$CH$_2$OH |
| i-Pr | H | OMe | COOPr-i | Ms | Na |
| i-Pr | H | OMe | COOPr-i | Ms | K |
| i-Pr | H | OMe | COOPr-i | Ms | Ca$_{\frac{1}{2}}$ |
| i-Pr | H | OMe | COOPr-i | Ms | Mg$_{\frac{1}{2}}$ |
| i-Pr | H | OMe | COOPr-i | Ms | EtN$^+$H$_3$ |
| i-Pr | H | OMe | COOPr-i | Ms | i-PrN$^+$H$_3$ |
| i-Pr | H | OMe | COOPr-i | Ms | Et$_2$N$^+$H$_2$ |
| i-Pr | H | OMe | COOPr-i | Ms | Me$_3$N$^+$CH$_2$CH$_2$OH |
| Et | Me | OMe | COOPr-i | Ms | i-PrN$^+$H$_3$ |
| Me | H | Me | COOCH$_2$CH$_2$OMe | Ms | Na |
| Me | H | Me | COOCH$_2$CH$_2$OMe | Ms | K |
| Me | H | Me | COOCH$_2$CH$_2$OMe | Ms | Ca$_{\frac{1}{2}}$ |
| Me | H | Me | COOCH$_2$CH$_2$OMe | Ms | Mg$_{\frac{1}{2}}$ |
| Me | H | Me | COOCH$_2$CH$_2$OMe | Ms | EtN$^+$H$_3$ |
| Me | H | Me | COOCH$_2$CH$_2$OMe | Ms | i-PrN$^+$H$_3$ |
| Me | H | Me | COOCH$_2$CH$_2$OMe | Ms | Et$_2$N$^+$H$_2$ |
| Me | H | Me | COOCH$_2$CH$_2$OMe | Ms | Me$_3$N$^+$CH$_2$CH$_2$OH |
| Et | H | Me | COOCH$_2$CH$_2$OMe | Ms | Na |
| Et | H | Me | COOCH$_2$CH$_2$OMe | Ms | K |
| Et | H | Me | COOCH$_2$CH$_2$OMe | Ms | Ca$_{\frac{1}{2}}$ |
| Et | H | Me | COOCH$_2$CH$_2$OMe | Ms | Mg$_{\frac{1}{2}}$ |
| Et | H | Me | COOCH$_2$CH$_2$OMe | Ms | EtN$^+$H$_3$ |
| Et | H | Me | COOCH$_2$CH$_2$OMe | Ms | i-PrN$^+$H$_3$ |
| Et | H | Me | COOCH$_2$CH$_2$OMe | Ms | Et$_2$N$^+$H$_2$ |
| Et | H | Me | COOCH$_2$CH$_2$OMe | Ms | Me$_3$N$^+$CH$_2$CH$_2$OH |
| i-Pr | H | Me | COOCH$_2$CH$_2$OMe | Ms | Na |
| i-Pr | H | Me | COOCH$_2$CH$_2$OMe | Ms | K |
| i-Pr | H | Me | COOCH$_2$CH$_2$OMe | Ms | Ca$_{\frac{1}{2}}$ |
| i-Pr | H | Me | COOCH$_2$CH$_2$OMe | Ms | Mg$_{\frac{1}{2}}$ |
| i-Pr | H | Me | COOCH$_2$CH$_2$OMe | Ms | EtN$^+$H$_2$ |
| i-Pr | H | Me | COOCH$_2$CH$_2$OMe | Ms | Me$_3$N$^+$CH$_2$CH$_2$OH |
| Me | Me | Me | COOCH$_2$CH$_2$OMe | Ms | i-PrN$^+$H$_3$ |
| Et | Me | Me | COOCH$_2$CH$_2$OMe | Ms | Na |
| Et | Me | Me | COOCH$_2$CH$_2$OMe | Ms | i-PrN$^+$H$_3$ |
| i-Pr | Me | Me | COOCH$_2$CH$_2$OMe | Ms | i-Pr$^+$H$_3$ |
| Me | H | Cl | COOCH$_2$CH$_2$OMe | Ms | Na |
| Me | H | Cl | COOCH$_2$CH$_2$OMe | Ms | K |
| Me | H | Cl | COOCH$_2$CH$_2$OMe | Ms | Ca$_{\frac{1}{2}}$ |
| Me | H | Cl | COOCH$_2$CH$_2$OMe | Ms | Mg$_{\frac{1}{2}}$ |
| Me | H | Cl | COOCH$_2$CH$_2$OMe | Ms | EtN$^+$H$_3$ |
| Me | H | Cl | COOCH$_2$CH$_2$OMe | Ms | i-PrN$^+$H$_3$ |
| Me | H | Cl | COOCH$_2$CH$_2$OMe | Ms | Et$_2$N$^+$H$_2$ |
| Me | H | Cl | COOCH$_2$CH$_2$OMe | Ms | Me$_3$N$^+$CH$_2$CH$_2$OH |
| Et | H | Cl | COOCH$_2$CH$_2$OMe | Ms | Na |
| Et | H | Cl | COOCH$_2$CH$_2$OMe | Ms | K |
| Et | H | Cl | COOCH$_2$CH$_2$OMe | Ms | Ca$_{\frac{1}{2}}$ |
| Et | H | Cl | COOCH$_2$CH$_2$OMe | Ms | Mg$_{\frac{1}{2}}$ |
| Et | H | Cl | COOCH$_2$CH$_2$OMe | Ms | EtN$^+$H$_3$ |
| Et | H | Cl | COOCH$_2$CH$_2$OMe | Ms | i-PrN$^+$H$_3$ |

-continued

| | | | | | |
|---|---|---|---|---|---|
| Et | H | Cl | COOCH$_2$CH$_2$OMe | Ms | Et$_2$N$^+$H$_2$ |
| Et | H | Cl | COOCH$_2$CH$_2$OMe | Ms | Me$_3$N$^+$CH$_2$CH$_2$OH |
| i-Pr | H | Cl | COCH$_2$CH$_2$OMe | Ms | Na |
| i-Pr | H | Cl | COOCH$_2$CH$_2$OMe | Ms | K |
| i-Pr | H | Cl | COOCH$_2$CH$_2$OMe | Ms | Ca$_\frac{1}{2}$ |
| i-Pr | H | Cl | COOCH$_2$CH$_2$OMe | Ms | Mg$_\frac{1}{2}$ |
| i-Pr | H | Cl | COOCH$_2$CH$_2$OMe | Ms | EtN$^+$H$_3$ |
| i-Pr | H | Cl | COOCH$_2$CH$_2$OMe | Ms | i-PrN$^+$H$_3$ |
| i-Pr | H | Cl | COOCH$_2$CH$_2$OMe | Ms | Et$_2$N$^+$H$_2$ |
| i-Pr | H | Cl | COOCH$_2$CH$_2$OMe | Ms | Me$_3$N$^+$CH$_2$CH$_2$OH |
| Me | Me | Cl | COOCH$_2$CH$_2$OMe | Ms | i-PrN$^+$H$_3$ |
| Et | Me | Cl | COOCH$_2$CH$_2$OMe | Ms | Na |
| Et | Me | Cl | COOCH$_2$CH$_2$OMe | Ms | i-PrN$^+$H$_3$ |
| i-Pr | Me | Cl | COOCH$_2$CH$_2$OMe | Ms | i-PrN$^+$H$_3$ |
| Me | H | OMe | COOCH$_2$CH$_2$OMe | Ms | Na |
| Me | H | OMe | COOCH$_2$CH$_2$OMe | Ms | K |
| Me | H | OMe | COOCH$_2$CH$_2$OMe | Ms | Ca$_\frac{1}{2}$ |
| Me | H | OMe | COOCH$_2$CH$_2$OMe | Ms | Mg$_\frac{1}{2}$ |
| Me | H | OMe | COOCH$_2$CH$_2$OMe | Ms | EtN$^+$H$_3$ |
| Me | H | OMe | COOCH$_2$CH$_2$OMe | Ms | i-PrN$^+$H$_3$ |
| Me | H | OMe | COOCH$_2$CH$_2$OMe | Ms | Et$_2$N$^+$H$_2$ |
| Me | H | OMe | COOCH$_2$CH$_2$OMe | Ms | Me$_3$N$^+$CH$_2$CH$_2$OH |
| Et | H | OMe | COOCH$_2$CH$_2$OMe | Ms | Na |
| Et | H | OMe | COOCH$_2$CH$_2$OMe | Ms | K |
| Et | H | OMe | COOCH$_2$CH$_2$OMe | Ms | Ca$_\frac{1}{2}$ |
| Et | H | OMe | COOCH$_2$CH$_2$OMe | Ms | Mg$_\frac{1}{2}$ |
| Et | H | OMe | COOCH$_2$CH$_2$OMe | Ms | EtN$^+$H$_3$ |
| Et | H | OMe | COOCH$_2$CH$_2$OMe | Ms | i-PrN$^+$H$_3$ |
| Et | H | OMe | COOCH$_2$CH$_2$OMe | Ms | Et$_2$N$^+$H$_2$ |
| Et | H | OMe | COOCH$_2$CH$_2$OMe | Ms | Me$_3$N$^+$CH$_2$CH$_2$OH |
| i-Pr | H | OMe | COOCH$_3$CH$_2$OMe | Ms | Na |
| i-Pr | H | OMe | COOCH$_2$CH$_2$OMe | Ms | K |
| i-Pr | H | OMe | COOCH$_2$CH$_2$OMe | Ms | Ca$_\frac{1}{2}$ |
| i-Pr | H | OMe | COOCH$_2$CH$_2$OMe | Ms | Mg$_\frac{1}{2}$ |
| i-Pr | H | OMe | COOCH$_2$CH$_2$OMe | Ms | EtN$^+$H$_3$ |
| i-Pr | H | OMe | COOCH$_2$CH$_2$OMe | Ms | i-PrN$^+$H$_3$ |
| i-Pr | H | OMe | COOCH$_2$CH$_2$OMe | Ms | Et$_2$N$^+$H$_2$ |
| i-Pr | H | OMe | COOCH$_2$CH$_2$OMe | Ms | Me$_3$N$^+$CH$_2$CH$_2$OH |
| Et | Me | OMe | COOCH$_2$CH$_2$OMe | Ms | i-PrN$^+$H$_3$ |
| Me | H | Me | CH$_2$OMe | Ms | Na |
| Me | H | Me | CH$_2$OMe | Ms | K |
| Me | H | Me | CH$_2$OMe | Ms | Ca$_\frac{1}{2}$ |
| Me | H | Me | CH$_2$OMe | Ms | Mg$_\frac{1}{2}$ |
| Me | H | Me | CH$_2$OMe | Ms | EtN$^+$H$_3$ |
| Me | H | Me | CH$_2$OMe | Ms | i-PrN$^+$H$_3$ |
| Me | H | Me | CH$_2$OMe | Ms | Et$_2$N$^+$H$_2$ |
| Me | H | Me | CH$_2$OMe | Ms | Me$_3$N$^+$CH$_2$CH$_2$OH |
| Et | H | Me | CH$_2$OMe | Ms | Na |
| Et | H | Me | CH$_2$OMe | Ms | K |
| Et | H | Me | CH$_2$OMe | Ms | Ca$_\frac{1}{2}$ |
| Et | H | Me | CH$_2$OMe | Ms | Mg$_\frac{1}{2}$ |
| Et | H | Me | CH$_2$OMe | Ms | EtN$^+$H$_3$ |
| Et | H | Me | CH$_2$OMe | Ms | i-PrN$^+$H$_3$ |
| Et | H | Me | CH$_2$OMe | Ms | Et$_2$N$^+$H$_2$ |
| Et | H | Me | CH$_2$OMe | Ms | Me$_3$N$^+$CH$_2$CH$_2$OH |
| i-Pr | H | Me | CH$_2$OMe | Ms | Na |
| i-Pr | H | Me | CH$_2$OMe | Ms | K |
| i-Pr | H | Me | CH$_2$OMe | Ms | Ca$_\frac{1}{2}$ |
| i-Pr | H | Me | CH$_2$OMe | Ms | Mg$_\frac{1}{2}$ |
| i-Pr | H | Me | CH$_2$OMe | Ms | EtN$^+$H$_3$ |
| i-Pr | H | Me | CH$_2$OMe | Ms | i-PrN$^+$H$_3$ |
| i-Pr | H | Me | CH$_2$OMe | Ms | Et$_2$N$^+$H$_2$ |
| i-Pr | H | Me | CH$_2$OMe | Ms | Me$_3$N$^+$CH$_2$CH$_2$OH |
| Me | Me | Me | CH$_2$OMe | Ms | i-PrN$^+$H$_3$ |
| Et | Me | Me | CH$_2$OMe | Ms | Na |
| Et | Me | Me | CH$_2$OMe | Ms | i-PrN$^+$H$_3$ |
| i-Pr | Me | Me | CH$_2$OMe | Ms | i-PrN$^+$H$_3$ |
| Me | H | Cl | CH$_2$OMe | Ms | Na |
| Me | H | Cl | CH$_2$OMe | Ms | K |
| Me | H | Cl | CH$_2$OMe | Ms | Ca$_\frac{1}{2}$ |
| Me | H | Cl | CH$_2$OMe | Ms | Mg$_\frac{1}{2}$ |
| Me | H | Cl | CH$_2$OMe | Ms | EtN$^+$H$_3$ |
| Me | H | Cl | CH$_2$OMe | Ms | i-PrN$^+$H$_3$ |
| Me | H | Cl | CH$_2$OMe | Ms | Et$_2$N$^+$H$_2$ |
| Me | H | Cl | CH$_2$OMe | Ms | Me$_3$N$^+$CH$_2$CH$_2$OH |
| Et | H | Cl | CH$_2$OMe | Ms | Na |
| Et | H | Cl | CH$_2$OMe | Ms | K |
| Et | H | Cl | CH$_2$OMe | Ms | Ca$_\frac{1}{2}$ |
| Et | H | Cl | CH$_2$OMe | Ms | Mg$_\frac{1}{2}$ |
| Et | H | Cl | CH$_2$OMe | Ms | EtN$^+$H$_3$ |
| Et | H | Cl | CH$_2$OMe | Ms | i-PrN$^+$H$_3$ |
| Et | H | Cl | CH$_2$OMe | Ms | Et$_2$N$^+$H$_2$ |
| Et | H | Cl | CH$_2$OMe | Ms | Me$_3$N$^+$CH$_2$CH$_2$OH |

-continued

| | | | | | |
|---|---|---|---|---|---|
| i-Pr | H | Cl | CH$_2$OMe | Ms | Na |
| i-Pr | H | Cl | CH$_2$OMe | Ms | K |
| i-Pr | H | Cl | CH$_2$OMe | Ms | Ca$_{\frac{1}{2}}$ |
| i-Pr | H | Cl | CH$_2$OMe | Ms | Mg$_{\frac{1}{2}}$ |
| i-Pr | H | Cl | CH$_2$OMe | Ms | EtN$^+$H$_3$ |
| i-Pr | H | Cl | CH$_2$OMe | Ms | i-PrN$^+$H$_3$ |
| i-Pr | H | Cl | CH$_2$OMe | Ms | Et$_2$N$^+$H$_2$ |
| i-Pr | H | Cl | CH$_2$OMe | Ms | Me$_3$N$^+$CH$_2$CH$_2$OH |
| Me | Me | Cl | CH$_2$OMe | Ms | i-PrN$^+$H$_3$ |
| Et | Me | Cl | CH$_2$OMe | Ms | Na |
| Et | Me | Cl | CH$_2$OMe | Ms | i-PrN$^+$H$_3$ |
| i-Pr | Me | Cl | CH$_2$OMe | Ms | i-PrN$^+$H$_3$ |
| Me | H | OMe | CH$_2$OMe | Ms | Na |
| Me | H | OMe | CH$_2$OMe | Ms | K |
| Me | H | OMe | CH$_2$OMe | Ms | Ca$_{\frac{1}{2}}$ |
| Me | H | OMe | CH$_2$OMe | Ms | Mg$_{\frac{1}{2}}$ |
| Me | H | OMe | CH$_2$OMe | Ms | EtN$^+$H$_3$ |
| Me | H | OMe | CH$_2$OMe | Ms | i-PrN$^+$H$_3$ |
| Me | H | OMe | CH$_2$OMe | Ms | Et$_2$N$^+$H$_2$ |
| Me | H | OMe | CH$_2$OMe | Ms | Me$_3$N$^+$CH$_2$CH$_2$OH |
| Et | H | OMe | CH$_2$OMe | Ms | Na |
| Et | H | OMe | CH$_2$OMe | Ms | K |
| Et | H | OMe | CH$_2$OMe | Ms | Ca$_{\frac{1}{2}}$ |
| Et | H | OMe | CH$_2$OMe | Ms | Mg$_{\frac{1}{2}}$ |
| Et | H | OMe | CH$_2$OMe | Ms | EtN$^+$H$_3$ |
| Et | H | OMe | CH$_2$OMe | Ms | i-PrN$^+$H$_3$ |
| Et | H | OMe | CH$_2$OMe | Ms | Et$_2$N$^+$H$_2$ |
| Et | H | OMe | CH$_2$OMe | Ms | Me$_3$N$^+$CH$_2$CH$_2$OH |
| i-Pr | H | OMe | CH$_2$OMe | Ms | Na |
| i-Pr | H | OMe | CH$_2$OMe | Ms | K |
| i-Pr | H | OMe | CH$_2$OMe | Ms | Ca$_{\frac{1}{2}}$ |
| i-Pr | H | OMe | CH$_2$OMe | Ms | Mg$_{\frac{1}{2}}$ |
| i-Pr | H | OMe | CH$_2$OMe | Ms | EtN$^+$H$_3$ |
| i-Pr | H | OMe | CH$_2$OMe | Ms | i-PrN$^+$H$_3$ |
| i-Pr | H | OMe | CH$_2$OMe | Ms | Et$_2$N$^+$H$_2$ |
| i-Pr | H | OMe | CH$_2$OMe | Ms | Me$_3$N$^+$CH$_2$CH$_2$OH |
| Et | Me | OMe | CH$_2$OMe | Ms | i-PrN$^+$H$_3$ |
| Me | H | Me | CH$_2$OEt | Ms | Na |
| Me | H | Me | CH$_2$OEt | Ms | K |
| Me | H | Me | CH$_2$OEt | Ms | Ca$_{\frac{1}{2}}$ |
| Me | H | Me | CH$_2$OEt | Ms | Mg$_{\frac{1}{2}}$ |
| Me | H | Me | CH$_2$OEt | Ms | EtN$^+$H$_3$ |
| Me | H | Me | CH$_2$OEt | Ms | i-PrN$^+$H$_3$ |
| Me | H | Me | CH$_2$OEt | Ms | Et$_2$N$^+$H$_2$ |
| Me | H | Me | CH$_2$OEt | Ms | Me$_3$N$^+$CH$_2$CH$_2$OH |
| Et | H | Me | CH$_2$OEt | Ms | Na |
| Et | H | Me | CH$_2$OEt | Ms | K |
| Et | H | Me | CH$_2$OEt | Ms | Ca$_{\frac{1}{2}}$ |
| Et | H | Me | CH$_2$OEt | Ms | Mg$_{\frac{1}{2}}$ |
| Et | H | Me | CH$_2$OEt | Ms | EtN$^+$H$_3$ |
| Et | H | Me | CH$_2$OEt | Ms | i-PrN$^+$H$_3$ |
| Et | H | Me | CH$_2$OEt | Ms | Et$_2$N$^+$H$_2$ |
| Et | H | Me | CH$_2$OEt | Ms | Me$_3$N$^+$CH$_2$CH$_2$OH |
| i-Pr | H | Me | CH$_2$OEt | Ms | Na |
| i-Pr | H | Me | CH$_2$OEt | Ms | K |
| i-Pr | H | Me | CH$_2$OEt | Ms | Ca$_{\frac{1}{2}}$ |
| i-Pr | H | Me | CH$_2$OEt | Ms | Mg$_{\frac{1}{2}}$ |
| i-Pr | H | Me | CH$_2$OEt | Ms | EtN$^+$H$_3$ |
| i-Pr | H | Me | CH$_2$OEt | Ms | i-PrN$^+$H$_3$ |
| i-Pr | H | Me | CH$_2$OEt | Ms | Et$_2$N$^+$H$_2$ |
| i-Pr | H | Me | CH$_2$OEt | Ms | Me$_3$N$^+$CH$_2$CH$_2$OH |
| Me | Me | Me | CH$_2$OEt | Ms | i-PrN$^+$H$_3$ |
| Et | Me | Me | CH$_2$OEt | Ms | Na |
| Et | Me | Me | CH$_2$OEt | Ms | i-PrN$^+$H$_3$ |
| i-Pr | Me | Me | CH$_2$OEt | Ms | i-PrN$^+$H$_3$ |
| Me | H | Cl | CH$_2$OEt | Ms | Na |
| Me | H | Cl | CH$_2$OEt | Ms | K |
| Me | H | Cl | CH$_2$OEt | Ms | Ca$_{\frac{1}{2}}$ |
| Me | H | Cl | CH$_2$OEt | Ms | Mg$_{\frac{1}{2}}$ |
| Me | H | Cl | CH$_2$OEt | Ms | EtN$^+$H$_3$ |
| Me | H | Cl | CH$_2$OEt | Ms | i-PrN$^+$H$_3$ |
| Me | H | Cl | CH$_2$OEt | Ms | Et$_2$N$^+$H$_2$ |
| Me | H | Cl | CH$_2$OEt | Ms | Me$_3$N$^+$CH$_2$CH$_2$OH |
| Et | H | Cl | CH$_2$OEt | Ms | Na |
| Et | H | Cl | CH$_2$OEt | Ms | K |
| Et | H | Cl | CH$_2$OEt | Ms | Ca$_{\frac{1}{2}}$ |
| Et | H | Cl | CH$_2$OEt | Ms | Mg$_{\frac{1}{2}}$ |
| Et | H | Cl | CH$_2$OEt | Ms | EtN$^+$H$_3$ |
| Et | H | Cl | CH$_2$OEt | Ms | i-PrN$^+$H$_3$ |
| Et | H | Cl | CH$_2$OEt | Ms | Et$_2$N$^+$H$_2$ |
| Et | H | Cl | CH$_2$OEt | Ms | Me$_3$N$^+$CH$_2$CH$_2$OH |
| i-Pr | H | Cl | CH$_2$OEt | Ms | Na |
| i-Pr | H | Cl | CH$_2$OEt | Ms | K |

-continued

| | | | | | |
|---|---|---|---|---|---|
| i-Pr | H | Cl | CH$_2$OEt | Ms | Ca$_{\frac{1}{2}}$ |
| i-Pr | H | Cl | CH$_2$OEt | Ms | Mg$_{\frac{1}{2}}$ |
| i-Pr | H | Cl | CH$_2$OEt | Ms | EtN$^+$H$_3$ |
| i-Pr | H | Cl | CH$_2$OEt | Ms | i-PrN$^+$H$_3$ |
| i-Pr | H | Cl | CH$_2$OEt | Ms | Et$_2$N$^+$H$_2$ |
| i-Pr | H | Cl | CH$_2$OEt | Ms | Me$_3$N$^+$CH$_2$CH$_2$OH |
| Me | Me | Cl | CHMeOEt | Ms | i-PrN$^+$H$_3$ |
| Et | Me | Cl | CHMeOEt | Ms | Na |
| Et | Me | Cl | CH$_2$OEt | Ms | i-PrN$^+$H$_3$ |
| i-Pr | Me | Cl | CH$_2$OEt | Ms | i-PrN$^+$H$_3$ |
| Me | H | OMe | CH$_2$OEt | Ms | Na |
| Me | H | OMe | CH$_2$OEt | Ms | K |
| Me | H | OMe | CH$_2$OEt | Ms | Ca$_{\frac{1}{2}}$ |
| Me | H | OMe | CH$_2$OEt | Ms | Mg$_{\frac{1}{2}}$ |
| Me | H | OMe | CH$_2$OEt | Ms | EtN$^+$H$_3$ |
| Me | H | OMe | CH$_2$OEt | Ms | i-PrN$^+$H$_3$ |
| Me | H | OMe | CH$_2$OEt | Ms | Et$_2$N$^+$H$_2$ |
| Me | H | OMe | CH$_2$OEt | Ms | Me$_3$N$^+$CH$_2$CH$_2$OH |
| Et | H | OMe | CH$_2$OEt | Ms | Na |
| Et | H | OMe | CH$_2$OEt | Ms | K |
| Et | H | OMe | CH$_2$OEt | Ms | Ca$_{\frac{1}{2}}$ |
| Et | H | OMe | CH$_2$OEt | Ms | Mg$_{\frac{1}{2}}$ |
| Et | H | OMe | CH$_2$OEt | Ms | EtN$^+$H$_3$ |
| Et | H | OMe | CH$_2$OEt | Ms | i-PrN$^+$H$_3$ |
| Et | H | OMe | CH$_2$OEt | Ms | Et$_2$N$^+$H$_2$ |
| Et | H | OMe | CH$_2$OEt | Ms | Me$_3$N$^+$CH$_2$CH$_2$OH |
| i-Pr | H | OMe | CH$_2$OEt | Ms | Na |
| i-Pr | H | OMe | CH$_2$OEt | Ms | K |
| i-Pr | H | OMe | CH$_2$OEt | Ms | Ca$_{\frac{1}{2}}$ |
| i-Pr | H | OMe | CH$_2$OEt | Ms | Mg$_{\frac{1}{2}}$ |
| i-Pr | H | OMe | CH$_2$OEt | Ms | EtN$^+$H$_3$ |
| i-Pr | H | OMe | CH$_2$OEt | Ms | i-PrN$^+$H$_3$ |
| i-Pr | H | OMe | CH$_2$OEt | Ms | Et$_2$N$^+$H$_2$ |
| i-Pr | H | OMe | CH$_2$OEt | Ms | Me$_3$N$^+$CH$_2$CH$_2$OH |
| Et | Me | OMe | CH$_2$OEt | Ms | i-PrN$^+$H$_3$ |
| Me | H | Me | CHMeOMe | Ms | Na |
| Me | H | Me | CHMeOMe | Ms | K |
| Me | H | Me | CHMeOMe | Ms | Ca$_{\frac{1}{2}}$ |
| Me | H | Me | CHMeOMe | Ms | Mg$_{\frac{1}{2}}$ |
| Me | H | Me | CHMeOMe | Ms | EtN$^+$H$_3$ |
| Me | H | Me | CHMeOMe | Ms | i-PrN$^+$H$_3$ |
| Me | H | Me | CHMeOMe | Ms | Et$_2$N$^+$H$_2$ |
| Me | H | Me | CHMeOMe | Ms | Me$_3$N$^+$CH$_2$CH$_2$OH |
| Et | H | Me | CHMeOMe | Ms | Na |
| Et | H | Me | CHMeOMe | Ms | K |
| Et | H | Me | CHMeOMe | Ms | Ca$_{\frac{1}{2}}$ |
| Et | H | Me | CHMeOMe | Ms | Mg$_{\frac{1}{2}}$ |
| Et | H | Cl | CHMeOMe | Ms | EtN$^+$H$_3$ |
| Et | H | Cl | CHMeOMe | Ms | i-PrN$^+$H$_3$ |
| Et | H | Cl | CHMeOMe | Ms | Et$_2$N$^+$H$_2$ |
| Et | H | Cl | CHMeOMe | Ms | Me$_3$N$^+$CH$_2$CH$_2$OH |
| i-Pr | H | Cl | CHMeOMe | Ms | Na |
| i-Pr | H | Cl | CHMeOMe | Ms | K |
| i-Pr | H | Cl | CHMeOMe | Ms | Ca$_{\frac{1}{2}}$ |
| i-Pr | H | Cl | CHMeOMe | Ms | Mg$_{\frac{1}{2}}$ |
| i-Pr | H | Cl | CHMeOMe | Ms | EtN$^+$H$_3$ |
| i-Pr | H | Cl | CHMeOMe | Ms | i-PrN$^+$H$_3$ |
| i-Pr | H | Cl | CHMeOMe | Ms | Et$_2$N$^+$H$_2$ |
| i-Pr | H | Cl | CHMeOMe | Ms | Me$_3$N$^+$CH$_2$CH$_2$OH |
| Me | Me | Cl | CHMeOMe | Ms | i-PrN$^+$H$_3$ |
| Et | Me | Cl | CHMeOMe | Ms | Na |
| Et | Me | Cl | CHMeOMe | Ms | i-PrN$^+$H$_3$ |
| i-Pr | Me | Cl | CHMeOMe | Ms | i-PrN$^+$H$_3$ |
| Me | H | OMe | CHMeOMe | Ms | Na |
| Me | H | OMe | CHMeOMe | Ms | K |
| Me | H | OMe | CHMeOMe | Ms | Ca$_{\frac{1}{2}}$ |
| Me | H | OMe | CHMeOMe | Ms | Mg$_{\frac{1}{2}}$ |
| Me | H | OMe | CHMeOMe | Ms | EtN$^+$H$_3$ |
| Me | H | OMe | CHMeOMe | Ms | i-PrN$^+$H$_3$ |
| Me | H | OMe | CHMeOMe | Ms | Et$_2$N$^+$H$_2$ |
| Me | H | OMe | CHMeOMe | Ms | Me$_3$N$^+$CH$_2$CH$_2$OH |
| Et | H | OMe | CHMeOMe | Ms | Na |
| Et | H | OMe | CHMeOMe | Ms | K |
| Et | H | OMe | CHMeOMe | Ms | Ca$_{\frac{1}{2}}$ |
| Et | H | OMe | CHMeOMe | Ms | Mg$_{\frac{1}{2}}$ |
| Et | H | OMe | CHMeOMe | Ms | EtN$^+$H$_3$ |
| Et | H | OMe | CHMeOMe | Ms | i-PrN$^+$H$_3$ |
| Et | H | OMe | CHMeOMe | Ms | Et$_2$N$^+$H$_2$ |
| Et | H | OMe | CHMeOMe | Ms | Me$_3$N$^+$CH$_2$CH$_2$OH |
| i-Pr | H | OMe | CHMeOMe | Ms | Na |
| i-Pr | H | OMe | CHMeOMe | Ms | K |
| i-Pr | H | OMe | CHMeOMe | Ms | Ca$_{\frac{1}{2}}$ |
| i-Pr | H | OMe | CHMeOMe | Ms | Mg$_{\frac{1}{2}}$ |

-continued

| | | | | | |
|---|---|---|---|---|---|
| i-Pr | H | OMe | CHMeOMe | Ms | EtN$^+$H$_3$ |
| i-Pr | H | OMe | CHMeOMe | Ms | i-PrN$^+$H$_3$ |
| i-Pr | H | OMe | CHMeOMe | Ms | Et$_2$N$^+$H$_2$ |
| i-Pr | H | OMe | CHMeOMe | Ms | Me$_3$N$^+$CH$_2$CH$_2$OH |
| Et | Me | OMe | CHMeOMe | Ms | i-PrN$^+$H$_3$ |
| Me | H | Me | CHMeOEt | Ms | Na |
| Me | H | Me | CHMeOEt | Ms | K |
| Me | H | Me | CHMeOEt | Ms | Ca$_{\frac{1}{2}}$ |
| Me | H | Me | CHMeOEt | Ms | Mg$_{\frac{1}{2}}$ |
| Me | H | Me | CHMeOEt | Ms | EtN$^+$H$_3$ |
| Me | H | Me | CHMeOEt | Ms | i-PrN$^+$H$_3$ |
| Me | H | Me | CHMeOEt | Ms | Et$_2$N$^+$H$_2$ |
| Me | H | Me | CHMeOEt | Ms | Me$_3$N$^+$CH$_2$CH$_2$OH |
| Et | H | Me | CHMeOEt | Ms | Na |
| Et | H | Me | CHMeOEt | Ms | K |
| Et | H | Me | CHMeOEt | Ms | Ca$_{\frac{1}{2}}$ |
| Et | H | Me | CHMeOEt | Ms | Mg$_{\frac{1}{2}}$ |
| Et | H | Me | CHMeOEt | Ms | EtN$^+$H$_3$ |
| Et | H | Me | CHMeOEt | Ms | i-PrN$^+$H$_3$ |
| Et | H | Me | CHMeOEt | Ms | Et$_2$N$^+$H$_2$ |
| Et | H | Me | CHMeOEt | Ms | Me$_3$N$^+$CH$_2$CH$_2$OH |
| i-Pr | H | Me | CHMeOEt | Ms | Na |
| i-Pr | H | Me | CHMeOEt | Ms | K |
| i-Pr | H | Me | CHMeOEt | Ms | Ca$_{\frac{1}{2}}$ |
| i-Pr | H | Me | CHMeOEt | Ms | Mg$_{\frac{1}{2}}$ |
| i-Pr | H | Me | CHMeOEt | Ms | EtN$^+$H$_3$ |
| i-Pr | H | Me | CHMeOEt | Ms | i-PrN$^+$H$_3$ |
| i-Pr | H | Me | CHMeOEt | Ms | Et$_2$N$^+$H$_2$ |
| i-Pr | H | Me | CHMeOEt | Ms | Me$_3$N$^+$CH$_2$CH$_2$OH |
| Me | Me | Me | CHMeOEt | Ms | i-PrN$^+$H$_3$ |
| Et | Me | Me | CHMeOEt | Ms | Na |
| Et | Me | Me | CHMeOEt | Ms | i-PrN$^+$H$_3$ |
| i-Pr | Me | Me | CHMeOEt | Ms | i-PrN$^+$H$_3$ |
| Me | H | Cl | CHMeOEt | Ms | Na |
| Me | H | Cl | CHMeOEt | Ms | K |
| Me | H | Cl | CHMeOEt | Ms | Ca$_{\frac{1}{2}}$ |
| Me | H | Cl | CHMeOEt | Ms | Mg$_{\frac{1}{2}}$ |
| Me | H | Cl | CHMeOEt | Ms | EtN$^+$H$_3$ |
| Me | H | Cl | CHMeOEt | Ms | i-PrN$^+$H$_3$ |
| Me | H | Cl | CHMeOEt | Ms | Et$_2$N$^+$H$_2$ |
| Me | H | Cl | CHMeOEt | Ms | Me$_3$N$^+$CH$_2$CH$_2$OH |
| Et | H | Cl | CHMeOEt | Ms | Na |
| Et | H | Cl | CHMeOEt | Ms | K |
| Et | H | Cl | CHMeOEt | Ms | Ca$_{\frac{1}{2}}$ |
| Et | H | Cl | CHMeOEt | Ms | Mg$_{\frac{1}{2}}$ |
| Et | H | Cl | CHMeOEt | Ms | EtN$^+$H$_3$ |
| Et | H | Cl | CHMeOEt | Ms | i-PrN$^+$H$_3$ |
| Et | H | Cl | CHMeOEt | Ms | Et$_2$N$^+$H$_2$ |
| Et | H | Cl | CHMeOEt | Ms | Me$_3$N$^+$CH$_2$CH$_2$OH |
| i-Pr | H | Cl | CHMeOEt | Ms | Na |
| i-Pr | H | Cl | CHMeOEt | Ms | K |
| i-Pr | H | Cl | CHMeOEt | Ms | Ca$_{\frac{1}{2}}$ |
| i-Pr | H | Cl | CHMeOEt | Ms | Mg$_{\frac{1}{2}}$ |
| i-Pr | H | Cl | CHMeOEt | Ms | EtN$^+$H$_3$ |
| i-Pr | H | Cl | CHMeOEt | Ms | i-PrN$^+$H$_3$ |
| i-Pr | H | Cl | CHMeOEt | Ms | Et$_2$N$^+$H$_2$ |
| i-Pr | H | Cl | CHMeOEt | Ms | Me$_3$N$^+$CH$_2$CH$_2$OH |
| Me | Me | Cl | CHMeOEt | Ms | i-PrN$^+$H$_3$ |
| Et | Me | Cl | CHMeOEt | Ms | Na |
| Et | Me | Cl | CHMeOEt | Ms | i-PrN$^+$H$_3$ |
| i-Pr | Me | Cl | CHMeOEt | Ms | i-PrN$^+$H$_3$ |
| Me | H | OMe | CHMeOEt | Ms | Na |
| Me | H | OMe | CHMeOEt | Ms | K |
| Me | H | OMe | CHMeOEt | Ms | Ca$_{\frac{1}{2}}$ |
| Me | H | OMe | CHMeOEt | Ms | Mg$_{\frac{1}{2}}$ |
| Me | H | OMe | CHMeOEt | Ms | EtN$^+$H$_3$ |
| Me | H | OMe | CHMeOEt | Ms | i-PrN$^+$H$_3$ |
| Me | H | OMe | CHMeOEt | Ms | Et$_2$N$^+$H$_2$ |
| Me | H | OMe | CHMeOEt | Ms | Me$_3$N$^+$CH$_2$CH$_2$OH |
| Et | H | OMe | CHMeOEt | Ms | Na |
| Et | H | OMe | CHMeOEt | Ms | K |
| Et | H | OMe | CHMeOEt | Ms | Ca$_{\frac{1}{2}}$ |
| Et | H | OMe | CHMeOEt | Ms | Mg$_{\frac{1}{2}}$ |
| Et | H | OMe | CHMeOEt | Ms | EtN$^+$H$_3$ |
| Et | H | OMe | CHMeOEt | Ms | i-PrN$^+$H$_3$ |
| Et | H | OMe | CHMeOEt | Ms | Et$_2$N$^+$H$_2$ |
| Et | H | OMe | CHMeOEt | Ms | Me$_3$N$^+$CH$_2$CH$_2$OH |
| i-Pr | H | OMe | CHMeOEt | Ms | Na |
| i-Pr | H | OMe | CHMeOEt | Ms | K |
| i-Pr | H | OMe | CHMeOEt | Ms | Ca$_{\frac{1}{2}}$ |
| i-Pr | H | OMe | CHMeOEt | Ms | Mg$_{\frac{1}{2}}$ |
| i-Pr | H | OMe | CHMeOEt | Ms | EtN$^+$H$_3$ |
| i-Pr | H | OMe | CHMeOEt | Ms | i-PrN$^+$H$_3$ |

-continued

| | | | | | |
|---|---|---|---|---|---|
| i-Pr | H | OMe | CHMeOEt | Ms | $Et_2N^+ H_2$ |
| i-Pr | H | OMe | CHMeOEt | Ms | $Me_3N^+ CH_2CH_2OH$ |
| Et | Me | OMe | CHMeOEt | Ms | $i\text{-}PrN^+ H_3$ |
| Me | H | Me | $CHM_2CO_2Me$ | Ms | H |
| Et | H | Me | $CH_2CO_2Me$ | Ms | H |
| i-Pr | H | Me | $CH_2CO_2Me$ | Ms | H |
| Me | H | Me | $CH_2CO_2Me$ | Ms | H |
| Et | H | Me | $CH_2CO_2Me$ | Ms | H |
| i-Pr | H | Me | $CH_2CO_2Me$ | Ms | H |
| Me | H | Me | $CH_2CO_2Pr\text{-}i$ | Ms | H |
| Et | H | Me | $CH_2CO_2Pr\text{-}i$ | Ms | H |
| i-Pr | H | Me | $CH_2CO_2Pr\text{-}i$ | Ms | H |
| Me | H | Me | $CHMeCO_2Me$ | Ms | H |
| Et | H | Me | $CHMeCO_2Me$ | Ms | H |
| i-Pr | H | Me | $CHMeCO_2Me$ | Ms | H |
| Me | H | Me | $CHMeCO_2Et$ | Ms | H |
| Et | H | Me | $CHMeCO_2Et$ | Ms | H |
| i-Pr | H | Me | $CHMeCO_2Et$ | Ms | H |
| Me | H | Me | $CHMeCO_2Pr\text{-}i$ | Ms | H |
| Et | H | Me | $CHMeCO_2Pr\text{-}i$ | Ms | H |
| i-Pr | H | Me | $CHMeCO_2Pr\text{-}i$ | Ms | H |
| Me | H | Me | $CH_2CH_2CO_2Me$ | Ms | H |
| Et | H | Me | $CH_2CH_2CO_2Me$ | Ms | H |
| i-Pr | H | Me | $CH_2CH_2CO_2Me$ | Ms | H |
| Me | H | Me | $CH_2CH_2CO_2Et$ | Ms | H |
| Et | H | Me | $CH_2CH_2CO_2Et$ | Ms | H |
| i-Pr | H | Me | $CH_2CH_2CO_2Et$ | Ms | H |
| Me | H | Me | $CH_2CH_2CO_2Pr\text{-}i$ | Ms | H |
| Et | H | Me | $CH_2CH_2CO_2Pr\text{-}i$ | Ms | H |
| i-Pr | H | Me | $CH_2CH_2CO_2Pr\text{-}i$ | Ms | H |
| Me | H | Me | CH=CHOMe | Ms | H |
| Et | H | Me | CH=CHOMe | Ms | H |
| i-Pr | H | Me | CH=CHOMe | Ms | H |
| Me | H | Me | CH=CHOEt | Ms | H |
| Et | H | Me | CH=CHOEt | Ms | H |
| i-Pr | H | Me | CH=CHOEt | Ms | H |
| Me | H | Me | CH=CHOPr-i | Ms | H |
| Et | H | Me | CH=CHOPr-i | Ms | H |
| i-Pr | H | Me | CH=CHOPr-i | Ms | H |
| Me | H | Me | $CH_2CO_2Me$ | Ms | H |
| Et | H | Me | $CH_2CO_2Me$ | Ms | H |
| i-Pr | H | Me | $CH_2CO_2Me$ | Ms | H |
| Me | H | Me | $CH_2CO_2Et$ | Ms | H |
| Et | H | Me | $CH_2CO_2Et$ | Ms | H |
| i-Pr | H | Cl | $CH_2CO_2Et$ | Ms | H |
| Me | H | Cl | $CH_2CO_2Pr\text{-}i$ | Ms | H |
| Et | H | Cl | $CH_2CO_2Pr\text{-}i$ | Ms | H |
| i-Pr | H | Cl | $CH_2CO_2Pr\text{-}i$ | Ms | H |
| Me | H | Cl | $CHMeCO_2Me$ | Ms | H |
| Et | H | Cl | $CHMeCO_2Me$ | Ms | H |
| i-Pr | H | Cl | $CHMeCO_2Me$ | Ms | H |
| Me | H | Cl | $CHMeCO_2Et$ | Ms | H |
| Et | H | Cl | $CHMeCO_2Et$ | Ms | H |
| i-Pr | H | Cl | $CHMeCO_2Et$ | Ms | H |
| Me | H | Cl | $CHMeCO_2Pr\text{-}i$ | Ms | H |
| Et | H | Cl | $CHMeCO_2Pr\text{-}i$ | Ms | H |
| i-Pr | H | Cl | $CHMeCO_2Pr\text{-}i$ | Ms | H |
| Me | H | Cl | $CH_2CH_2CO_2Me$ | M | H |
| Et | H | Cl | $CH_2CH_2CO_2Me$ | M | H |
| i-Pr | H | Cl | $CH_2CH_2CO_2Me$ | M | H |
| Me | H | Cl | $CH_2CH_2CO_2Et$ | M | H |
| Et | H | Cl | $CH_2CH_2CO_2Et$ | M | H |
| i-Pr | H | Cl | $CH_2CH_2CO_2Et$ | M | H |
| Me | H | Cl | $CH_2CH_2CO_2Pr\text{-}i$ | M | H |
| Et | H | Cl | $CH_2CH_2CO_2Pr\text{-}i$ | M | H |
| i-Pr | H | Cl | $CH_2CH_2CO_2Pr\text{-}i$ | M | H |
| Me | H | Cl | CH=CHOMe | Ms | H |
| Et | H | Cl | CH=CHOMe | Ms | H |
| i-Pr | H | Cl | CH=CHOMe | Ms | H |
| Me | H | Cl | CH=CHOEt | Ms | H |
| Et | H | Cl | CH=CHOEt | Ms | H |
| i-Pr | H | Cl | CH=CHOEt | Ms | H |
| Me | H | Cl | CH=CHOPr-i | Ms | H |
| Et | H | Cl | CH=CHOPr-i | Ms | H |
| i-Pr | H | Cl | CH=CHOPr-i | Ms | H |

When the compound of the present invention is to be used as an agricultural or horticultural herbicide, it is usually mixed with a suitable carrier, for instance, a solid carrier such as clay, talc, bentonite or diatomaceous earth, or a liquid carrier such as water, an alcohol (such as methanol or ethanol), an aromatic hydrocarbon (such as benzene, toluene or xylene), a chlorinated hydrocarbon, an ether, a ketone, an ester (such as ethyl acetate) or an acid amide (such as dimethylformamide). If desired, an emulsifier, a dispersing agent, a suspending agent, a penetrating agent, a spreader or a stabilizer may be added to prepare an optional formulation such as a liquid formulation, an emulsifiable concentrate, a wettable powder, a dust, a granule or a flowable.

Further, if desired, other herbicides, various insecticides, bacteriocides, plant regulating agents or synergism agents may be combined at the time of the preparation of the formulations or at a time of the application of the herbicides.

As other herbicides to be combined with the herbicide of the present invention, there may be mentioned, for instance, compounds disclosed in Farm Chemicals Handbook, the 73rd Edition (1987). Among them, there may be mentioned, for example, atrazine, cyanazine, alachlor, metolachlor, EPTC, 2,4-D, butylate, dicamba, bromoxynil and tridiphane. Further, N-[(4,6-dimethoxypyrimidin-2-yl)-aminocarbonyl]-3-chloro-4-methoxycarbonyl-1-methylpyrazole-5-sulfonamide or N-[(4,6-dimethoxypyrimidin-2-yl)aminocarbonyl]-3-bromo-4-methoxycarbonyl-1-methylpyrazole-5-sulfonamide as disclosed in U.S. Pat. No. 4,668,277 may also be combined with the herbicide of the present invention.

The dose varies depending upon the application site, the season for application, the method for application, the type of the crop plant, etc. In general, however, the dose is usually within a range of from 0.001 to 10 kg per hectare as the amount of the active ingredient.

Now, Formulation Examples of the herbicides containing the compounds of the present invention as active ingredients, will be given. However, it should be understood that the present invention is by no means restricted to such specific Examples. In the following Formulation Examples, "parts" means "parts by weight".

| FORMULATION EXAMPLE 1: Wettable powder | |
|---|---|
| Compound No. 3 of the present invention | 60 parts |
| Zeeklite PFP (tradename for a kaolin-type clay, manufactured by Zeeklite Industries, Co., Ltd.) | 33 parts |
| Sorpol 5039 (tradename for a mixture of a nonionic surfactant and an anionic surfactant, manufactured by Toho Chemical Co., Ltd.) | 5 parts |
| Carplex (tradename for a coagulation-preventing agent composed of a mixture of a surfactant and fine silica powder, manufactured by Shionogi Pharmaceutical Co., Ltd.) | 2 parts |

The above ingredients are homogeneously pulverized and mixed to form a wettable powder.

| FORMULATION EXAMPLE 2: Wettable powder | |
|---|---|
| Compound No. 7 of the present invention | 60 parts |
| Zeeklite PFP (tradename for a kaolin-type clay, manufactured by Zeeklite Industries, Co., Ltd.) | 33 parts |
| Sorpol 5039 (tradename for a mixture of a nonionic surfactant and an anionic surfactant, manufactured by Toho Chemical Co., Ltd.) | 5 parts |
| Carplex (tradename for a coagulation-preventing agent composed of a mixture of a surfactant and fine silica powder, manufactured by Shionogi Pharmaceutical Co., Ltd.) | 2 parts |

| FORMULATION EXAMPLE 3: Wettable powder | |
|---|---|
| Compound No. 15 of the present invention | 60 parts |
| Zeeklite PFP (tradename for a kaolin-type clay, manufactured by Zeeklite Industries, Co., Ltd.) | 33 parts |
| Sorpol 5039 (tradename for a mixture of a nonionic surfactant and an anionic surfactant, manufactured by Toho Chemical Co., Ltd.) | 5 parts |
| Carplex (tradename for a coagulation-preventing agent composed of a mixture of a surfactant and fine silica powder, manufactured by Shionogi Pharmaceutical Co., Ltd.) | 2 parts |

| FORMULATION EXAMPLE 4: Wettable powder | |
|---|---|
| Compound No. 21 of the present invention | 60 parts |
| Zeeklite PFP (tradename for a kaolin-type clay, manufactured by Zeeklite Industries, Co., Ltd.) | 33 parts |
| Sorpol 5039 (tradename for a mixture of a nonionic surfactant and an anionic surfactant, manufactured by Toho Chemical Co., Ltd.) | 5 parts |
| Carplex (tradename for a coagulation-preventing agent composed of a mixture of a surfactant and fine silica powder, manufactured by Shionogi Pharmaceutical Co., Ltd.) | 2 parts |

| FORMULATION EXAMPLE 5: Wettable powder | |
|---|---|
| Compound No. 25 of the present invention | 60 parts |
| Zeeklite PFP (tradename for a kaolin-type clay, manufactured by Zeeklite Industries, Co., Ltd.) | 33 parts |
| Sorpol 5039 (tradename for a mixture of a nonionic surfactant and an anionic surfactant, manufactured by Toho Chemical Co., Ltd.) | 5 parts |
| Carplex (tradename for a coagulation-preventing agent composed of a mixture of a surfactant and fine silica powder, manufactured by Shionogi Pharmaceutical Co., Ltd.) | 2 parts |

| FORMULATION EXAMPLE 6: Wettable powder | |
|---|---|
| Compound No. 35 of the present invention | 60 parts |
| Zeeklite PFP (tradename for a kaolin-type clay, manufactured by Zeeklite Industries, Co., Ltd.) | 33 parts |
| Sorpol 5039 (tradename for a mixture of a nonionic surfactant and an anionic surfactant, manufactured by Toho Chemical Co., Ltd.) | 5 parts |
| Carplex (tradename for a coagulation-preventing agent composed of a mixture of a surfactant and fine silica powder, manufactured by Shionogi Pharmaceutical Co., Ltd.) | 2 parts |

| FORMULATION EXAMPLE 7: Emulsifiable concentrate | |
|---|---|
| Compound No. 3 of the present invention | 1.5 parts |
| Xylene | 78.5 parts |
| N,N-dimethylformamide | 15 parts |
| Sorpol 2680 (tradename for a mixture of a nonionic surfactant and an anionic surfactant, manufactured by Toho Chemical Co., Ltd.) | 5 parts |

The above ingredients are homogeneously mixed to obtain an emulsifiable concentrate.

| FORMULATION EXAMPLE 8: Emulsifiable concentrate | |
|---|---|
| Compound No. 11 of the present invention | 1.5 parts |
| Xylene | 78.5 parts |
| N,N-dimethylformamide | 15 parts |
| Sorpol 2680 (tradename for a mixture of a nonionic surfactant and an anionic surfactant, manufactured by Toho Chemical Co., Ltd.) | 5 parts |

| FORMULATION EXAMPLE 9: Flowable | |
|---|---|
| Compound No. 3 of the present invention | 40 parts |
| Agrizole B-710 (tradename for a nonionic surfactant, manufactured by Kao Corporation) | 10 parts |
| Runox 1000C (tradename for an anionic surfactant, manufactured by Toho Chemical Co., Ltd.) | 0.5 part |
| 1% Rodopol water (tradename for a thickener, manufactured by Rhone-Poulenc) | 20 parts |
| Water | 29.5 parts |

The above ingredients are homogeneously mixed to form a flowable.

| FORMULATION EXAMPLE 10: Flowable | |
|---|---|
| Compound No. 10 of the present invention | 40 parts |
| Agrizole B-710 (tradename for a nonionic | 10 parts |

-continued

| | |
|---|---|
| surfactant, manufactured by Kao Corporation) | |
| Runox 1000C (tradename for an anionic surfactant, manufactured by Toho Chemical Co., Ltd.) | 0.5 part |
| 1% Rodopol water (tradename for a thickener, manufactured by Rhone-Poulenc) | 20 parts |
| Water | 29.5 parts |
| FORMULATION EXAMPLE 11: Liquid formulation | |
| Compound No. 39 of the present invention | 30 parts |
| Nippol (tradename for a nonionic surfactant, manufactured by Nissan Chemical Industries, Ltd.) | 10 parts |
| Water | 60 parts |
| The above ingredients are homogeneously mixed to obtain a liquid formulation. | |
| FORMULATION EXAMPLE 12: Liquid formulation | |
| Compound No. 40 of the present invention | 30 parts |
| Nippol (tradename for a nonionic surfactant, manufactured by Nissan Chemical Industries, Ltd.) | 10 parts |
| Water | 60 parts |
| FORMULATION EXAMPLE 13: Liquid formulation | |
| Compound No. 46 of the present invention | 30 parts |
| Nippol (tradename for a nonionic surfactant, manufactured by Nissan Chemical Industries, Ltd.) | 10 parts |
| Water | 60 parts |
| FORMULATION EXAMPLE 14: Liquid formulation | |
| Compound No. 41 of the present invention | 10 parts |
| Sorpol W-150 (tradename for a nonionic surfactant, manufactured by Toho Chemical Co., Ltd.) | 10 parts |
| Water | 80 parts |

The above ingredients are homogeneously mixed to form a liquid formulation.

In their use, the above wettable powders, emulsifiable concentrates, flowables or liquid formulations are diluted with water from 50 to 1,000 times and applied so that the respective active ingredients will be from 0.001 to 5 kg per hectare.

The compounds of the present invention are applicable not only to agricultural and horticultural fields such as upland fields, paddy fields and orchards, but to non-agricultural fields such as athletic fields, vacant fields and railway sides for the control of various weeds. The dose in their application varies depending upon the application site, the season for application, the type of crop plants, etc. However, it is usually within a range of from 0.001 to 5 kg per hectare.

Now, the herbicidal activities of the compounds of the present invention will be described with respect to specific Test Examples.

TEST EXAMPLE 1

Test on the herbicidal effects in soil treatment

A plastic box having a length of 15 cm, a width of 22 cm and a depth of 6 cm was filled with a sterilized diluvium soil, and seeds Echinochloa crus-galli, Setaria viridis, Eleusine indica, Digitaria adscendens, Panicum dichotomiflorum, Abutilon theophrasti, Amaranthus lividus, Polygonum longisetum and Zea mays were sown, and tubers of Cyperus esculentus were further planted. The soil was covered thereon in the thickness of about 1.5 cm, and then a herbicide solution was applied onto the surface of the soil uniformly so that the active ingredient is distributed at a predetermined concentration. The herbicide solution was prepared by diluting a wettable powder, an emulsifiable concentrate, a liquid formulation or a flowable with water and applied onto the entire soil surface by means of a small spray. Three weeks after the application of the herbicidal solution, the herbicidal effects against each weed were determined on the basis of the following standard ratings. The results thereby obtained are shown in Table 6. The Compound Nos. correspond to the Compound Nos. in Table 3.

Standard ratings:
- 5: Growth control rate of more than 90% (almost completely withered)
- 4: Growth control rate of from 70 to 90%
- 3: Growth control rate of from 40 to 70%
- 2: Growth control rate of from 20 to 40%
- 1: Growth control rate of from 5 to 20%
- 0: Growth control rate of less than 5% (almost non-effective)

The above growth control rates were calculated by the following equation:

$$\text{Growth control rate (\%)} = \left(1 - \frac{T}{N}\right) \times 100$$

where
T: Weight of the weed growth above the soil surface of the treated area
N: Weight of the weed grown above the soil surface of the non-treated area

TEST EXAMPLE 2

Test on the herbicidal effects in foliage treatment

A plastic box having a length of 15 cm, a width of 22 cm and a depth of 6 cm was filled with a sterilized diluvium soil, and seeds of Echinochloa crus-galli, Setaria viridis, Eleusine indica, Digitaria adscendens, Panicum dichotomiflorum, Xanthium strumarium, Abutilon theophrasti, Amaranthus lividus, Polygonum longisetum and Zea mays were spot-wisely sown, and tubers of Cyperus esculentus were further planted. Then, the soil was covered thereon in a thickness of about 1.5 cm. When the various weeds and crops grew to the 2 or 3 leaf stage, a herbicidal solution was uniformly sprayed on the foliages so that the active ingredient is applied in a predetermined concentration.

The herbicidal solution was prepared by diluting the wettable powder, the emulsifiable concentrate, the liquid formulation or the flowable as described in the above Formulation Examples with water and applied onto the entire surface of the foliages of the weeds and the crop plants by a small spray. Two weeks after the application of the herbicide solution, the herbicidal effects against each weed were determined on the basis of the standard ratings described in Test Example 1, and the phytotoxicity against each crop plant was determined on the basis of the standard ratings in Test Example 1. The results are shown in Table 7. The Compound Nos. in Table 7 correspond to the Compound Nos. in Table 3.

In Tables 6 and 7, the following abbreviations are used:
- Dose: Dose of active ingredient (g/are)
- EC: Echinochloa crus-galli (barnyardgrass)
- SE: Setaria viridis (green foxtail)
- EL: Eleusine indica (goosegrass)
- DI: Digitaria adscendens (large crabgrass)
- PA: Panicum dichotomiflorum (fall panicum)
- AB: Abutilon theophrasti (velvet leaf)
- AM: Amaranthus lividus (livid amaranth)

PO: *Polygonum longisetum* (persicaria blumei gross)
XA: *Xanthium strumarium* (cocklebur)
CY: *Cyperus esculentus* (yellow nutsedge)
ZE: *Zea mays* (corn)

TABLE 6

| Compound No. | Dose | EC | SE | EL | DI | PA | AB | AM | PO | CY | ZE |
|---|---|---|---|---|---|---|---|---|---|---|---|
| 1 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 2 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 3 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 4 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 6 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 7 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 8 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 9 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 10 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 11 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 12 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 13 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 14 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 15 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 16 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 17 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 18 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 19 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 20 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 21 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 22 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 23 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 24 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 25 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 26 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |

TABLE 6-continued

| Compound No. | Dose | EC | SE | EL | DI | PA | AB | AM | PO | CY | ZE |
|---|---|---|---|---|---|---|---|---|---|---|---|
| 27 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 28 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 29 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 30 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 34 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 35 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 36 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 37 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 39 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 40 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 41 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 42 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 43 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 44 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 45 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 46 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 47 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 48 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 49 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 50 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 56 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 58 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 61 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 63 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 64 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 65 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 66 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |

TABLE 6-continued

| Compound No. | Dose | EC | SE | EL | DI | PA | AB | AM | PO | CY | ZE |
|---|---|---|---|---|---|---|---|---|---|---|---|
| | 2 | 5 | 5 | 5 | 5 | 5 | 5 | 5 | 5 | 5 | 0 |
| 67 | 0.5 | 5 | 5 | 5 | 5 | 5 | 5 | 5 | 5 | 5 | 0 |
| | 1 | 5 | 5 | 5 | 5 | 5 | 5 | 5 | 5 | 5 | 0 |
| | 2 | 5 | 5 | 5 | 5 | 5 | 5 | 5 | 5 | 5 | 0 |
| 68 | 0.5 | 5 | 5 | 5 | 5 | 5 | 5 | 5 | 5 | 5 | 0 |
| | 1 | 5 | 5 | 5 | 5 | 5 | 5 | 5 | 5 | 5 | 0 |
| | 2 | 5 | 5 | 5 | 5 | 5 | 5 | 5 | 5 | 5 | 0 |
| Reference Example A | 4 | 3 | 1 | 3 | 3 | 1 | 4 | 5 | 5 | 0 | 0 |
| | 8 | 4 | 2 | 4 | 4 | 2 | 5 | 5 | 5 | 0 | 0 |
| | 16 | 5 | 3 | 5 | 5 | 3 | 5 | 5 | 5 | 1 | 1 |
| Reference Example B | 4 | 5 | 5 | 5 | 5 | 5 | 1 | 1 | 1 | 2 | 0 |
| | 8 | 5 | 5 | 5 | 5 | 5 | 2 | 2 | 2 | 3 | 0 |
| | 16 | 5 | 5 | 5 | 5 | 5 | 3 | 3 | 3 | 4 | 1 |

TABLE 7

| Compound No. | Dose | EC | SE | EL | DI | PA | AB | AM | PO | XA | CY | ZE |
|---|---|---|---|---|---|---|---|---|---|---|---|---|
| 1 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 2 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 3 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 4 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 6 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 7 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 8 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 9 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 10 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 11 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 12 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 13 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 14 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 15 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 16 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 17 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 18 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 19 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 20 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |
| 21 | 0.5 | 5 | 5 | 5 | 5 | 5 | 5 | 5 | 5 | 5 | 5 | 0 |
| | 1 | 5 | 5 | 5 | 5 | 5 | 5 | 5 | 5 | 5 | 5 | 0 |
| | 2 | 5 | 5 | 5 | 5 | 5 | 5 | 5 | 5 | 5 | 5 | 0 |

TABLE 7-continued

| Compound No. | Dose | EC | SE | EL | DI | PA | AB | AM | PO | XA | CY | ZE |
|---|---|---|---|---|---|---|---|---|---|---|---|---|
| 22 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 23 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 24 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 25 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 26 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 27 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 28 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 29 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 30 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 34 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 35 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 36 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 37 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 39 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 40 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 41 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 42 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 43 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 44 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 45 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 46 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 47 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 48 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 49 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 50 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 56 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 58 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |

TABLE 7-continued

| Compound No. | Dose | EC | SE | EL | DI | PA | AB | AM | PO | XA | CY | ZE |
|---|---|---|---|---|---|---|---|---|---|---|---|---|
|  | 2 | 5 | 5 | 5 | 5 | 5 | 5 | 5 | 5 | 5 | 5 | 0 |
| 61 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 63 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 64 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 65 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 66 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 67 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| 68 | 0.5 | 5 | 5 | 5 | 5 | 5 | 5 | 5 | 5 | 5 | 5 | 0 |
|  | 1 | 5 | 5 | 5 | 5 | 5 | 5 | 5 | 5 | 5 | 5 | 0 |
|  | 2 | 5 | 5 | 5 | 5 | 5 | 5 | 5 | 5 | 5 | 5 | 0 |
| Reference Example A | 4 | 3 | 1 | 2 | 3 | 0 | 3 | 5 | 5 | 4 | 0 | 0 |
|  | 8 | 4 | 2 | 3 | 4 | 1 | 5 | 5 | 5 | 5 | 0 | 1 |
|  | 16 | 5 | 3 | 4 | 5 | 2 | 5 | 5 | 5 | 5 | 1 | 2 |
| Reference Example B | 4 | 4 | 3 | 3 | 4 | 3 | 0 | 2 | 2 | 0 | 1 | 0 |
|  | 8 | 4 | 4 | 4 | 4 | 4 | 1 | 3 | 3 | 1 | 2 | 1 |
|  | 16 | 5 | 5 | 5 | 5 | 5 | 2 | 4 | 4 | 2 | 3 | 2 |

In Table 6 and 7, the Comparative Compounds are as follows:

Comparative Compound A: Atrazine

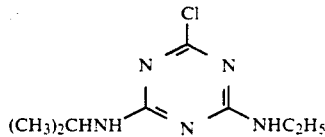

Comparative Compound B: Alachlor

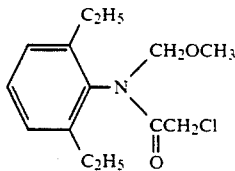

What is claimed is:

1. A benzoic acid of the formula

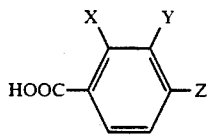

wherein:
X is an alkyl group having from 1 to 6 carbon atoms, an alkoxy group having from 1 to 6 carbon atoms or a halogen atom;
Z is Cl, —SR or —SO$_2$R wherein R is an alkyl group of 1 to 6 carbon atoms; and
Y is —COOR; wherein R' is an alkyl group having from 1 to 6 carbon atoms, an alkyl group having from 1 to 6 carbon atoms substituted by an alkoxy or alkyl alkoxy which may be a halogenated group having from 1 to 6 carbon atoms, a haloalkyl group having from 1 to 6 carbon atoms or a cyclohexyl group,
an alkyl group having from 1 to 6 carbon atoms substituted by thioalkyl wherein the alkyl group has from 1 to 6 carbon atoms;
an alkyl group having from 1 to 6 carbon atoms substituted by hydroxy;
an alkyl group having from 1 to 6 carbon atoms substituted by —CN;
an alkyl group having from 1 to 6 carbon atoms substituted by acyloxy having from 1 to 6 carbon atoms;
an alkyl group having from 1 to 6 carbon atoms substituted by a piperidine group;
an alkyl group having from 1 to 6 carbon atoms substituted by an alkynyloxy group having from 1 to 6 carbon atoms;
an alkyl group having from 1 to 6 carbon atoms substituted by an alkenyloxy group having from 1 to 6 carbon atoms;
an alkenyl radical having from 1 to 6 carbon atoms substituted by an alkoxy group having from 1 to 6 carbon atoms;
or a dialkyl amide radical wherein the alkyl radicals have from 1 to 6 carbon atoms.

2. A benzoic acid of the formula

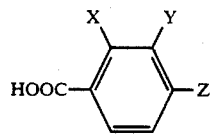

wherein:
X is —CH$_3$, Cl or —OCH$_3$,
Z is Cl, —SCH$_3$ or —SO$_2$CH$_3$, and
Y is —CH$_2$OCH$_3$, —COOCH$_3$, —CH$_2$OC$_2$H$_5$, —CH(CH$_3$)OCH$_3$, —COOi—Pr, —CH$_2$Oi—Pr, —COOCH$_2$CH$_2$OCH$_3$, —CH$_2$SC$_2$H$_5$,
—COOC$_2$H$_5$, —CH$_2$OCH$_2$CH$_2$OCH$_3$,

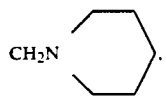

—COO—cyclohexyl, —COOnPr, —CH$_2$OH, —CH(C$_2$H$_5$)OCH$_3$, —CH(CH$_3$)OC$_2$H$_5$, —CH$_2$OCH$_2$C≡CH, —CH$_2$OCH$_2$CH=CH$_2$, —CH$_2$O-nAm, —COOiAm, —CH$_2$OCH$_2$CF$_3$, —COOCH$_2$CH$_2$Cl, —CH$_2$CN, —CH$_2$OOCH$_3$, —CH=CHOCH$_3$ or —CON(C$_2$H$_5$)$_2$.

3. A benzoic acid according to claim 2, wherein
X is —CH$_3$
Y is —CH$_2$OCH$_3$, and
Z is —SCH$_3$.

4. A benzoic acid according to claim 2, wherein
X is —CH$_3$
Y is —CH$_2$OCH$_3$, and
Z is —SO$_2$CH$_3$.

5. A benzoic acid according to claim 2, wherein
X is —CH$_3$
Y is —CO$_2$CH$_3$, and
Z is —SCH$_3$.

6. A benzoic acid according to claim 2, wherein
X is —CH$_3$
Y is —CO$_2$CH$_3$, and
Z is —SO$_2$CH$_3$.

7. A benzoic acid according to claim 2, wherein
X is —CH$_3$
Y is —CH$_2$OC$_2$H$_5$, and
Z is —SCH$_3$.

8. A benzoic acid according to claim 2, wherein
X is —CH$_3$
Y is —CH$_2$OC$_2$H$_5$, and
Z is —SO$_2$CH$_3$.

9. A benzoic acid according to claim 2, wherein
X is —Cl
Y is —CO$_2$CH$_3$, and
Z is —Cl.

10. A benzoic acid according to claim 2, wherein
X is —CH$_3$
Y is —CHCH$_3$OCH$_3$, and
Z is —SCH$_3$.

11. A benzoic acid according to claim 2, wherein
X is —CH$_3$
Y is —CHCH$_3$OCH$_3$, and
Z is —SO$_2$CH$_3$.

12. A benzoic acid according to claim 2, wherein
X is —CH$_3$
Y is —CO$_2$Pr—i, and
Z is —SCH$_3$.

13. A benzoic acid according to claim 2, wherein
X is —CH$_3$
Y is —CO$_2$Pr—i, and
Z is —SO$_2$CH$_3$.

14. A benzoic acid according to claim 2, wherein
X is Cl
Y is —CH$_2$OCH$_3$, and
Z is —SO$_2$CH$_3$.

15. A benzoic acid according to claim 2, wherein
X is —CH$_3$
Y is —CH$_2$OPr—i, and
Z is —SCH$_3$.

16. A benzoic acid according to claim 2, wherein
X is —CH$_3$
Y is —CH$_2$OPr—i, and
Z is —SO$_2$CH$_3$.

17. A benzoic acid according to claim 2, wherein
X is —CH$_3$
Y is —CO$_2$CH$_2$CH$_2$OCH$_3$, and
Z is —SCH$_3$.

18. A benzoic acid according to claim 2, wherein
X is —CH$_3$
Y is —CO$_2$CH$_2$CH$_2$OCH$_3$, and
Z is —SO$_2$CH$_3$.

19. A benzoic acid according to claim 2, wherein
X is —Cl
Y is —CH$_2$SC$_2$H$_5$, and
Z is —SO$_2$CH$_3$.

20. A benzoic acid according to claim 2, wherein
X is —CH$_3$
Y is —CO$_2$C$_2$H$_5$, and
Z is —SCH$_3$.

21. A benzoic acid according to claim 2, wherein
X is —CH$_3$
Y is —CO$_2$C$_2$H$_5$, and
Z is —SO$_2$CH$_3$.

22. A benzoic acid according to claim 2, wherein
X is —Cl
Y is —CH$_2$OCH$_2$CH$_2$OCH$_3$, and
Z is —SO$_2$CH$_3$.

23. A benzoic acid according to claim 2, wherein
X is —Cl
Y is

and
Z is —SO$_2$CH$_3$.

24. A benzoic acid according to claim 2, wherein
X is —CH$_3$
Y is

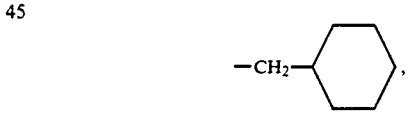

and
Z is —SCH$_3$.

25. A benzoic acid according to claim 2, wherein
X is —CH$_3$
Y is

and
Z is —SO$_2$CH$_3$.

26. A benzoic acid according to claim 2, wherein
X is —CH$_3$
Y is —CO$_2$Pr—n, and
Z is —SCH$_3$.

27. A benzoic acid according to claim 2, wherein
X is —CH$_3$
Y is —CO$_2$Pr—n, and
Z is —SO$_2$CH$_3$.

28. A benzoic acid according to claim 2, wherein
X is —Cl
Y is —CH$_2$OH, and
Z is —SO$_2$CH$_3$.

29. A benzoic acid according to claim 2, wherein
X is —Cl
Y is —CO$_2$CH$_3$, and
Z is —SCH$_3$.

30. A benzoic acid according to claim 2, wherein
X is —Cl
Y is —CO$_2$CH$_3$, and
Z is —SO$_2$CH$_3$.

31. A benzoic acid according to claim 2, wherein
X is —Cl
Y is —CO$_2$Pr—i, and
Z is —SCH$_3$.

32. A benzoic acid according to claim 2, wherein
X is —Cl
Y is —CO$_2$Pr—i, and
Z is —SO$_2$CH$_3$.

33. A benzoic acid according to claim 2, wherein
X is —OCH$_3$
Y is —CO$_2$CH$_3$, and
Z is —SCH$_3$.

34. A benzoic acid according to claim 2, wherein
X is —OCH$_3$
Y is —CO$_2$CH$_3$, and
Z is —SO$_2$CH$_3$.

35. A benzoic acid according to claim 2, wherein
X is —CH$_3$
Y is —CHC$_2$H$_5$OCH$_3$, and
Z is —SCH$_3$.

36. A benzoic acid according to claim 2, wherein
X is —CH$_3$
Y is —CHC$_2$H$_5$OCH$_3$, and
Z is —SO$_2$CH$_3$.

37. A benzoic acid according to claim 2, wherein
X is —CH$_3$
Y is —CHCH$_3$OC$_2$H$_5$, and
Z is —SCH$_3$.

38. A benzoic acid according to claim 2, wherein
X is —CH$_3$
Y is —CHCH$_3$OC$_2$H$_5$, and
Z is —SO$_2$CH$_3$.

39. A benzoic acid according to claim 2, wherein
X is —Cl
Y is —CH$_2$OCH$_2$C≡CH, and
Z is —SO$_2$CH$_3$.

40. A benzoic acid according to claim 2, wherein
X is —Cl
Y is —CH$_2$OCH$_2$CH=CH$_2$, and
Z is —SO$_2$CH$_3$.

41. A benzoic acid according to claim 2, wherein
X is —Cl
Y is —CH$_2$OAm—n, and
Z is —SO$_2$CH$_3$.

42. A benzoic acid according to claim 2, wherein
X is —CH$_3$
Y is —CO$_2$Am—i, and
Z is —SCH$_3$.

43. A benzoic acid according to claim 2, wherein
X is —CH$_3$
Y is —CO$_2$Am—i, and
Z is —SO$_2$CH$_3$.

44. A benzoic acid according to claim 2, wherein
X is —Cl
Y is —CH$_2$OCH$_2$CF$_3$, and
Z is —SO$_2$CH$_3$.

45. A benzoic acid according to claim 2, wherein
X is —OCH$_3$
Y is —CH$_{OCH_3}$, and
Z is —SCH$_3$.

46. A benzoic acid according to claim 2, wherein
X is —OCH$_3$
Y is —CH$_2$OCH$_3$, and
Z is —SO$_2$CH$_3$.

47. A benzoic acid according to claim 2, wherein
X is —CH$_3$
Y is —CO$_2$CH$_2$CH$_2$Cl, and
Z is —SCH$_3$.

48. A benzoic acid according to claim 2, wherein
X is —CH$_3$
Y is —CO$_2$CH$_2$CH$_2$Cl, and
Z is —SO$_2$CH$_3$.

49. A benzoic acid according to claim 2, wherein
X is —Cl
Y is —CH$_2$CN, and
Z is —SO$_2$CH$_3$.

50. A benzoic acid according to claim 2, wherein
X is —Cl
Y is —CH$_2$OAc, and
Z is —SO$_2$CH$_3$.

51. A benzoic acid according to claim 2, wherein
X is —Cl
Y is —CH$_2$OCH$_3$, and
Z is —Cl.

52. A benzoic acid according to claim 2, wherein
X is —Cl
Y is —CO$_2$C$_2$H$_5$, and
Z is —SO$_2$CH$_3$.

53. A benzoic acid according to claim 2, wherein
X is —Cl
Y is —CH=CHOCH$_3$, and
Z is —SO$_2$CH$_3$.

54. A benzoic acid according to claim 2, wherein
X is —Cl
Y is —CON(C$_2$H$_5$)$_2$, and
Z is —SO$_2$CH$_3$.

* * * * *

UNITED STATES PATENT AND TRADEMARK OFFICE
CERTIFICATE OF CORRECTION

PATENT NO. : 5,175,299
DATED : December 29, 1992
INVENTOR(S) : Masatoshi Baba, et al It is certified that error appears in the above-indentified patent and that said Letters Patent is hereby corrected as shown below:

Column 2, line 64, "$-CON-(CH_2)_n$" should read -- $-CON-(CH_2)_n$ --. (circled)

Column 3, line 30, "$-COO-N=C-(CH_2)_n$" should read -- $-COO-N=C-(CH_2)_n$ --. (circled)

Column 7, line 48, "$COOCH_2CH_2CH_2Cn$" should read -- $COOCH_2CH_2CH_2CN$ --.

Column 10, line 30, "invention" should read --inventors--.

Column 25, line 46, "stireed" should read --stirred--.

Column 207, lines 33-42, second column from the left, "$Ch_2C$" should read --$CH_2Cl$--

UNITED STATES PATENT AND TRADEMARK OFFICE
CERTIFICATE OF CORRECTION

PATENT NO. : 5,175,299
DATED : December 29, 1992
INVENTOR(S) : Masatoshi Baba, et al Page 2 of 3

It is certified that error appears in the above-indentified patent and that said Letters Patent is hereby corrected as shown below:

Column 207, line 44, third column from the left, "Ch$_2$OMe" should read --CH$_2$OMe.

Column 213, lines 16-58, third column from the left, "Ch$_2$OMe" should read --CH$_2$OMe--;
lines 59-83, third column from the left, "Ch$_2$OME" should read --CH$_2$OMe--.

Column 215, lines 1-17, third column from the left, "Ch$_2$OMI" should read --CH$_2$OMe--.

Column 230, line 51, "Me$_3$N$^+$CH$_2$Ch$_2$OH" should read --Me$_3$N$^+$CH$_2$CH$_2$OH--;
line 59, "Me$_3$N$^+$CH$_2$Ch$_2$OH" should read --Me$_3$N$^+$CH$_2$CH$_2$OH--;
line 77, "Me$_3$N$^+$CH$_2$Ch$_2$OH" should read --Me$_3$N$^+$CH$_2$CH$_2$OH--.

Column 253, line 64, Claim 1, "-COOR;" should read -- -COOR,--.

UNITED STATES PATENT AND TRADEMARK OFFICE
CERTIFICATE OF CORRECTION

PATENT NO. : 5,175,299
DATED : December 29, 1992
INVENTOR(S) : Masatoshi Baba, et al It is certified that error appears in the above-indentified patent and that said Letters Patent is hereby corrected as shown below:

Column 254, line 32, Claim 1, "group," should read --group;--.

Column 258, line 19, Claim 45, "Y is $-CH_{OCH3}$, and" should read --Y is $-CH_2OCH_3$, and--.

Signed and Sealed this

Twelfth Day of April, 1994

BRUCE LEHMAN

Attest:

Attesting Officer

Commissioner of Patents and Trademarks